US012612440B2

(12) United States Patent
Hays Putnam et al.

(10) Patent No.: US 12,612,440 B2
(45) Date of Patent: Apr. 28, 2026

(54) MODIFIED BOVINE G-CSF POLYPEPTIDES AND THEIR USES

(71) Applicants: Ambrx, Inc., La Jolla, CA (US); Elanco US Inc., Greenfield, IN (US)

(72) Inventors: Anna-Maria A. Hays Putnam, San Diego, CA (US); Nick Knudsen, San Diego, CA (US); Thea Norman, San Diego, CA (US); Alan Koder, San Diego, CA (US); Vadim Kraynov, San Diego, CA (US); Lillian Skidmore, San Diego, CA (US); Peter C. Canning, Noblesville, IN (US)

(73) Assignees: Elanco US Inc., Indianapolis, IN (US); Ambrx, Inc., La Jolla, CA (US)

(*) Notice: Subject to any disclaimer, the term of this patent is extended or adjusted under 35 U.S.C. 154(b) by 14 days.

(21) Appl. No.: 18/087,045

(22) Filed: Dec. 22, 2022

(65) Prior Publication Data

US 2023/0348547 A1 Nov. 2, 2023

Related U.S. Application Data

(62) Division of application No. 16/165,813, filed on Oct. 19, 2018, now Pat. No. 11,542,310, which is a division of application No. 12/507,237, filed on Jul. 22, 2009, now Pat. No. 10,138,283.

(60) Provisional application No. 61/083,132, filed on Jul. 23, 2008.

(51) Int. Cl.
*C07K 14/535* (2006.01)
*A61K 38/19* (2006.01)

(52) U.S. Cl.
CPC .......... *C07K 14/535* (2013.01); *A61K 38/193* (2013.01)

(58) Field of Classification Search
None
See application file for complete search history.

(56) References Cited

U.S. PATENT DOCUMENTS

| | | | | | |
|---|---|---|---|---|---|
| 5,849,883 | A * | 12/1998 | Boone | A61K 38/202 530/416 |
| 7,557,195 | B2 | 7/2009 | Park | |
| 2004/0096945 | A1 | 5/2004 | Dahiyat et al. | |
| 2005/0232898 | A1 | 10/2005 | Canning et al. | |
| 2008/0146781 | A1 | 6/2008 | Cho et al. | |
| 2008/0200657 | A1 | 8/2008 | Kang et al. | |

FOREIGN PATENT DOCUMENTS

WO WO 2005/074650 * 8/2005

OTHER PUBLICATIONS

Heidari et al., Veterinary Immunology and Immunopathology, 73:183-191, 2000.*

* cited by examiner

*Primary Examiner* — Marianne P Allen
(74) *Attorney, Agent, or Firm* — Barnes & Thornburg LLP

(57) ABSTRACT

Modified bovine G-CSF polypeptides and uses thereof are provided.

10 Claims, 23 Drawing Sheets

Specification includes a Sequence Listing.

Figure 2

Strain: *E. coli* derivative of the *E. coli* K12-W3110 strain
Genotype: F- l- *rph*-1 INV(*rrn*D - *rrn*E) *ara*B::*g1 tet*A

| Genotype | Explanation |
|---|---|
| $F^-$ | host lacks the F' episome |
| λ- | nonlysogenic - phage doesn't integrate into chromosome |
| *rph*-1 | frameshift in *rph* (ribonuclease PH) affecting the expression levels of *pyre* (orotate phosphoribosyltransferase) |
| INV(*rrn*E-*rrn*D) | the chromosome portion (785 kb) between the genes *rrn*E and *rrn*D is inverted |
| *ara*B::*g1 tet*A | bacteriophage T7 RNA Polymerase gene *g1* under the *ara*B promoter control. The insertion marker is *tet*A (tetracyclibe resistance) |

MODIFIED BOVINE G-CSF POLYPEPTIDES AND THEIR USES

CROSS-REFERENCE TO RELATED APPLICATIONS

This application claims the benefit of priority to and is a divisional application of U.S. patent application Ser. No. 16/165,813, filed Oct. 19, 2018, which is a divisional application of U.S. patent application Ser. No. 12/507,237, filed Jul. 22, 2009, which claims the benefit of priority to U.S. Provisional Patent Application Ser. No. 61/083,132, filed Jul. 23, 2008. The entire text of the aforementioned applications is incorporated herein by reference in its entirety.

Incorporated by reference in its entirety is a computer-readable nucleotide/amino acid sequence listing submitted concurrently herewith and identified as follows: 37,056 bytes XML file named "ST26_78045-374506," created on Dec. 22, 2022.

FIELD OF THE INVENTION

This invention relates to bovine granulocyte-colony stimulating factor (bG-CSF) polypeptides optionally modified with at least one non-naturally-encoded amino acid.

BACKGROUND OF THE INVENTION

The economic impact of infectious diseases in food animal production is well documented. Infectious diseases reduce profits, increase production costs, and endanger food products, as well as affect the performance, health, and welfare of the animal. Diseases can reduce the yield and quality of milk resulting in great economic loss to dairy farmers and beef producers, particularly when in some cases infectious microbial diseases cause morbidity and mortality of newborn, young (e.g., replacement stock) or adult animals. Two such diseases, mastitis and bovine respiratory disease (BRD), can have devastating effects on food animal production.

Mastitis is defined as an inflammation of the mammary gland. It may affect any mammal, for example cows, ewes, and goats. Bovine mastitis is an infection of the udder of ruminants such as cows, mainly caused by gram positive and gram negative bacteria and especially in cows in intensive milk producing units. The bacterial infection results in the inflammation of the mammary gland (i.e. teats and udder). Animals may become more susceptible to mastitis due to impaired neutrophil microbicidal function during the periparturient period. The disease is particularly troublesome and of considerable economic importance because the pathogen is readily transferred from one animal to another during the milking process. It often develops in the first few weeks around parturition and can recur with each lactation. Some of the main pathogenic microorganisms causing bovine mastitis are *Staphylococcus aureus, Streptococcus agalactiae, Streptococcus uberis, Streptococcus dysgalactiae, Eschelichia coli, Acrobacter acrogenes, Klebsiella pneumoniae*, and *Pseudomonas aeruginosa*. See also Bovine Mastitis, edited by Glenys Bloomfield, V&O Publications 1987, hereby incorporated by reference. These microorganisms invade the udder through the teat canal and produce inflammation of the milk-producing tissue causing the formation of scar tissue which, once formed, may cause a permanent reduction in the cow's milk production. An infection can also alter the composition, quantity, appearance and quality of the milk. Mastitis-causing pathogens fall into two categories, namely, contagious and environmental. Contagious bacteria, such as *Streptococcus agalactiae* and *Staphylococcus aureus*, primarily colonize host tissue sites such as mammary glands, teat canals, and teat skin lesions; and are spread from one infected cow to another during the milking process. Environmental bacteria, often streptococci, enterococci, and coliform organisms, are commonly present within the cow's surroundings from sources such as cow feces, soil, plant material, bedding, or water; and infect by casual opportunistic contact with an animal. The distinction between contagious and environmental pathogens, although not exclusive, is of practical importance because different dairy herd maintenance measures are needed for the different groups of microorganisms. In all bovine mastitis cases, whatever the causal microorganism, the route of transmission of the invading pathogen into the inner gland of the udder is through the teat orifice and teat canal. The common sources of harmful microorganisms include unsanitary milking equipment, the milker, other mastitic animals, fill unsanitary stable environment, and the animals own elimination (defecation/urination) processes.

There are a variety of forms or types of bovine mastitis, with varying severity and symptomatology, including the following: (1) Udder infection: The invasion of the udder cavity by microorganisms that multiply within the gland and cause inflammation; (2) Nonclinical or subclinical mastitis; A form of mastitis in which there is no swelling of the gland or observable abnormality of the milk, although there are changes in the milk that can be detected by specific tests. This type of mastitis is by far the most prevalent and causes the greatest overall loss in most herds. It often is referred to as "hidden" mastitis: (3) Clinical mastitis; A form of mastitis in which the abnormal conditions of the udder and secretion are observable. Mild clinical mastitis involves changes in the milk such as flakes, clots, and a watery or unusual appearance. Heat and sensitiveness of the udder are slight or absent, but there may be signs of swelling. Severe clinical mastitis involves a sudden onset with swelling of the infected quarter which is hot, hard and sensitive. The milk appears abnormal and milk production drops. Sometimes, in addition to the local effects in the udder, the cow herself becomes sick. There are signs of fever, rapid pulse, depression, weakness and loss of appetite. The combination of these conditions often is referred to as acute systemic mastitis, because not only the udder, but the whole animal is affected; and (4) Chronic mastitis; A form of mastitis caused by a persistent udder infection that exists most of the time in the nonclinical form but occasionally can develop into an active clinical form. After these "flare-ups" the nonclinical form usually returns temporarily. (See generally Current Concepts of Bovine Mastitis, published by The National Mastitis Council, Inc., 2nd Ed. 1978 at p.5.)

Mastitis continues to cause large economic losses to the dairy industry. Mastitis affects the profitability of a herd in a number of ways, both directly and indirectly, including: (1) loss of milk production; (2) higher culling rates of infected cows; (3) decreased value of milk; (4) discarded milk following antibiotic treatment; (5) veterinary costs (antibiotics and veterinary visits); and (6) deaths. (Bovine Mastitis, Glenys Bloomfield, supra, at p. 33.)

Another common disease affecting the cattle industry is shipping fever (bovine respiratory disease or BRD). BRD has been referred to by some as a "disease complex" for two reasons: it usually is caused by a variety of pathogens, both viral and bacterial, that interact with one another to produce full-blown disease, and because the behavior of the pathogens can follow a sequential process that, step by step, results in sick animals. Bacterial pathogens are one of the best known causes of the acute syndrome. The bacterial pathogens may invade the bovine respiratory tract after it has been compromised by a viral infection and other factors, such as the stress of weaning, shipping, change of feed and variation in ambient temperature and humidity, may precede and contribute to infection. In many instances this is added to the cattle's exposure to pathogens during shipping when they are commingling with cattle of other origin in trucks, stockyards and auction barns, resulting in the high incidence of the disease in cattle delivered to the feedlot.

Several species of bacteria have been isolated and associated with BRD, and some of the most common are *Mannhemia haemolytica, Pasteurella multocida* and (or) *Histophilus somni. Haemophilus somnus* is a virulent pathogen that causes septicemia in cattle and sometimes the resulting manifestations have been referred to as "*Haemophilus somnus* complex," of which one form is respiratory disease, viruses such as infectious bovine rhinotracheitis (IBR), bovine viral diarrhea (BVD) and bovine respiratory syncytial virus (BRSV) may also be involved m initiating a BRD complex, often opening the door to secondary bacterial infections.

Because it is virtually impossible to eliminate these orgasms from the environment, the BRD complex must be approached from the standpoint of preventing these disease-causing agents from taking hold, and detecting and treating clinical cases as quickly and effectively as possible. Respiratory diseases are a major cause of disease loss in beef cattle. It is generally recognized that the ultimate cause of death in most cases of shipping fever is a bacterial (usually *pasteurella*) pneumonia. *Pasteurella haemolytica*, particularly type 1A, is the most common bacterium isolated from cases of respiratory disease in North America. Vaccination against some of the infectious agents involved in shipping fever is sometimes helpful, but vaccines are available and efficacious for only a few of the agents known to be involved in the disease complex.

Antibiotic therapy has been a major component of mastitis and BRD control strategy. U.S. Pat. No. 7,182,948, which is incorporated by reference herein in its entirety, indicates that antimicrobial teat dips containing iodine have been shown to be effective against mammary infections and mastitis-causing bacteria (Pankey, J. W. et al., (1983) J. Dairy Sci. 66 (1), 161 167). These compositions are usually administered to the teat by clipping or spraying the teat prior to milking as well as after removal of the milking cup. To reduce mastitis, commercial teat dips have been developed containing a variety of antimicrobial agents including iodophors, quaternary aminonium compounds, chlorine release compounds (e.g. alkali hypochlorites), oxidizing compounds (e.g. hydrogen peroxide, peracids), protonated carboxylic acids (e.g. heptanoic, octanoic, nonanoic, decanoic, undecanoic acids), acid anionics (e.g. alkylaryl sulfonic acids), chlorine dioxide (from chlorite), and bisbiguanides such as chlorhexidine. These agents, which have varying degrees of effectiveness, limit the transmission of mastitis by reducing pathogen populations on the teat. However, there are problems associated with the use of antimicrobials. The most prevalent are irritation to the teat and teat cracking. To alleviate these problems, emollient additives such as glycerin and lanolin have been included in such compositions. However, even with the use of these emollients skin irritation can still occur.

U.S. Pat. No. 6,790,867, which is incorporated by reference herein in its entirety, indicates that subcutaneous injections of formulations combining a non-steroidal anti-inflammatory drug (NSAID) such as flunixin, with a fluorinated chloramphenicol or thiamphenicol derivative antibiotic such as florfenicol, may be used to treat BRD. U.S. Patent Application Publication No. 20070155799, which is incorporated by reference herein in its entirety, discloses new fenicol compounds that may be used as antibiotic prodrugs and in combination with NSAIDs or other antibiotics.

The NMC (formerly the National Mastitis Council), a not-for-profit organization devoted to reducing mastitis and enhancing milk quality, stresses the importance of proper teat sanitation, but also proper teat care for the prevention of mastitis. The economic harm caused by mastitis has led to much research in its control. Physical stresses as well as environmental conditions have been reported to be large contributors to mastitis infection. See U.S. Patent Publication No: 20020051789, which is incorporated by reference. Since it was documented that sub-clinical mastitis was directly related to poor teat condition (Neijenhuis, P. et al., (2001) J. Dairy Sci. (84) 2664 2672), a number of commercial teat dip solutions incorporating conditioning agents have evolved (National Mastitis Council, Summary of Peer-Reviewed Publications on Efficacy of Premilking and Postmilking Teat Disinfectants Published Since 1980; January 2002). Teat end callosity and roughness have been shown to have a direct relationship with clinical mastitis (Neijenhuis, F. et al., (2001) J. Dairy Sci. (84) 2664 2672). The reduction of chapping and irritation of teats as well as keeping the teat flexible is very important in controlling mammary infections. Glycerin has also been used as a teat conditioner in teat dip solutions. However, studies indicate no significant decrease in mastitis-causing bacteria such as *Staphylococcus aureus, Streptococcus agalactiae*, or coliforms when the glycerin content is increased from 2% to 10% in a 1% iodine teat dip solution (National Mastitis Council, Summary of Peer-Reviewed Publications on Efficacy of Premilking and Postmilking Teat Disinfectants Published Since 1980; January 2002). Thus, although products such as teat dip solutions are available, there is still an unmet need to modulate the incidence, recurrence, and/or severity of mastitis.

U.S. Pat. No. 5,849,883, which is incorporated by reference herein in its entirety, discloses a number of the antibiotics used in the treatment of mastitis including but not limited to, beta-lactam antibiotics such as penicillins (ampicillin, cloxacillin, hetacillin, nafcillin, penicillin G, (benzyl penicillin), procaine penicillin) and cephalosporins (cefoperazone, cefuroxime, Cefalonium, cefapirin, cefoxazole, cefracetrile); aminoglycoside antibiotics (framycetin, neomycin, novobiocin, streptomycin); macrolide antibiotics (erythromycin); tetracyclines (chlortetracycline, oxytetracycline); and polypeptide antibiotics (Polymyxin B). Antibiotic treatment for mastitis is usually given by means of intramammary infusions, either in lactating cows when clinical rnastitis is detected, or at drying off (dry cow therapy). (Bovine Mastitis, supra, at p.69.) In cases where severe clinical disease is present, antibiotics must be given parenterally since intramammary infusions are ineffective because of blockage of the ducts).

The early hopes that antibiotics would allow complete control of the disease have not been realized. None of the above mentioned antibiotics utilized thus far has been entirely satisfactory. Additionally, it has been found to be very desirable to replace antibiotic treatment with treatment by non-antibiotic chemo-therapeutic drug compounds, for the following reasons:

(1) Antibiotics effective in human medicine should not be utilized in veterinary medicine, in order not to build up strain resistance of bacteria appearing in human diseases; (2) Antibiotics should be reserved for such diseases for which no chemo-therapeutic drug compound would be available, as it has been proved that bacterial strains build up resistance to an antibiotic after extended use of such antibiotic; and (3) *Staphylococcus aureus*, one of the above-noted pathogens, has already built up a resistance against most of the antibiotics utilized in the treatment of bovine mastitis.

One such method for treatment by a non-antibiotic chemo-therapeutic chug compound is described in U.S. Pat. No. 4,610,993, which is incorporated by reference herein, which claims a method for treating animals for bovine mastitis with an effective amount of at least one pyridine-N-oxide disulfide compound. Another method by the same inventors is described in U.S. Pat. No. 4,401,666, which is incorporated by reference herein, which claims a method for treating animals for bovine mastitis with an effective amount of at least one metallic salt of pyridine 2-thione-N-oxide. Despite these several published methods, it remains very important to find cost-effective methods utilizing non-antibiotic compounds which would substantially overcome the drawbacks of antibiotics used thus far and yet would be effective in treating and preventing mastitis.

Another common disease affecting the cattle industry is shipping fever (bovine respiratory disease). Respiratory diseases are a major cause of disease loss in beef cattle. The term "shipping fever" is used to describe the respiratory disease complex observed in cattle 6 months of age or older after shipment either into feedlots or onto pasture. The stresses of weaning, castration, dehorning, fasting, overcrowding, exposure to infectious agents, dietary changes, transportation, environmental temperature extremes, and other stressors combined with viral, bacterial, mycoplasmal, and/or chlamydial infections contribute to the shipping fever complex. Mixing calves from different farms and/or sale barns greatly facilitates exposure to infectious agents. U.S. Pat. No. 6,497,869, which is incorporated by reference herein, describes some of initial infectious agents that may affect cattle. Population mixing may be a more important predisposing factor to shipping fever than stressors, although disease can occur without mixing and stressors usually dramatically worsen respiratory disease. Attempts to reduce stress by weaning, castrating, dehorning, etc. and acclimating cattle to new diets days or weeks prior to shipment are sometimes successful (but may not be cost-effective) in reducing the incidence of shipping fever. Vaccination against some of the infectious agents involved in shipping fever is sometimes helpful, but vaccines are available and efficacious for only a few of the agents known to be involved in the disease complex.

It is generally recognized that the ultimate cause of death in most cases of shipping fever is a bacterial (usually *Pasteurella*) pneumonia. *Pasteurella haemolytica*, particularly type IA, is the most common bacterium isolated from cases of respiratory disease in North America. Attempts to experimentally reproduce bacterial pneumonia in cattle are usually unsuccessful without severe stress and predisposing damage to the respiratory tract. It is generally believed that during times of stress, viruses, *mycoplasma*, and/or *chlamydia* most often provide the initial damage to the respiratory tract which predisposes to severe bacterial infection and disease.

A typical clinical respiratory disease outbreak usually begins within hours or days of the cattle's arrival at the feedlot. Recently shipped cattle in the 400 to 500 pound weight range commonly have 10 to 80% morbidity and 1 to 10% mortality, or more, to respiratory tract disease. When the serum of cattle is analyzed for a four-fold antibody rise (seroconversion) and the respiratory tract and its secretions subjected to microbiologic isolations, a myriad of etiologic agents can be identified. Many animals, those sick and those apparently healthy, can be shown to have undergone infection by one or more agents (respiratory tract disease is probably seldom due to only one infectious agent). Although bovine respiratory disease complex is recognized clinically in the feedlot after arrival, the infections giving rise to clinical disease probably start at the sale barns, where cattle are first assembled from different farms. See also Bovine Respiratory Disease, Loan, R. W. Texas A & M University Press, 1984, hereby incorporated by reference.

Administration of a compound that treats or modulates the incidence, recurrence, duration, and/or severity of mastitis or respiratory disease in cattle or other infections m non-human animals, including but not limited to, cattle, poultry, swine, horses, dogs, and cats would be useful in veterinary medicine. Examples of such infections include but are not limited to, neonatal septicemia in horses, pleuropneumaonia in pigs, and pneumonia in non-human animals. Such compounds may restore or modulate neutrophil function in the animal.

The growth hormone (GH) supergene family (Bazan, F. Immunology Today 11:350-354 (1991); Mott, H. R. and Campbell, L D. Current Opinion in Structural Biology 5:114-121 (1995); Silvennoinen, O. and Ihle, J. N. (1996) SIGNALING BY THE HEMATOPOIETIC CYTOKINE RECEPTORS) represents a set of proteins with similar structural characteristics. Each member of this family of proteins comprises a four helical bundle. While there are still more members of the family yet to be identified, some members of the family include the following: growth hormone, prolactin, placental lactogen, erythropoietin (EPO), thrombopoietin (TPO), interleukin-2 (IL-2), IL-3, IL-4, IL-5, IL-6, IL-7, IL-9, IL-10, IL-11, IL-12 (p35 subunit), IL-13, IL-15, oncostatin M, ciliary neurotrophic factor, leukemia inhibitory factor, alpha interferon, beta interferon, gamma interferon, omega interferon, tau interferon, epsilon interferon, granulocyte-colony stimulating factor (G-CSF), granulocyte-macrophage colony stimulating factor (GM-CSF), macrophage colony stimulating factor (M-CSF) and cardiotrophin-1 (CT-1) ("the GH supergene family"). Members of the GH supergene family have similar secondary and tertiary structures, despite the fact that they generally have limited amino acid or DNA sequence identity. The shared structural features allow new members of the gene family to be readily identified. Four helical bundle polypeptides are described in WO 2005/074650 entitled "Modified Human Four Helical Bundle Polypeptides and Their Uses," which is incorporated by reference in its entirety.

A member of the GH supergene family is Granulocyte Colony Stimulating Factor (G-CSF). Granulocyte colony stimulating factor (G-CSF) is one of several glycoprotein growth factors known as colony stimulating factors (CSFs) because they support the proliferation of haemopoietic progenitor cells. G-CSF stimulates the proliferation of specific bone marrow precursor cells and their differentiation into granulocytes. It is distinguished from other CSFs by its ability to both stimulate neutrophilic granulocyte colony formation in semi-solid agar and to induce terminal differentiation of murine myelomonocytic leukemic cells ill vitro. Granulocyte Colony-Stimulating Factor is a potent stimulus for neutrophil proliferation and maturation in vivo (Cohen et al., Proc. Natl. Acad. Sci. 1987; 84:2484-2488 see also Heidari et al., Vet. Immunol. Immunopathol. 2001; 81:45-57, herein incorporated by reference). G-CSF is also capable of inducing functional activation or "priming" or mature neutrophils in vitro (Weisbart, R. H., Gasson, C. G., and D. W. Golde. Annals of Internal Medicine 1989; 110:297-303). G-CSF has been shown to prime human granulocytes, and enhance superoxide release stimulated by the chemotactic peptide, N-formyl-methionyl-leucyl-phenalalanine (S. Kitagawa, et al., Biochem. Biophys. Res. Commun. 1987; 144:1143-1146, and C. F. Nathan, Blood 1989; 74:301-306), and activate human neutrophil IgA mediated phagocytosis (Weisbart, R. H., et al., Nature 1988; 332:647-649).

Neutrophils are a critical component of host defense mechanisms against bacterial and fungal infections. G-CSF is capable of inducing an increase in the absolute number of circulating neutrophils and enhances neutrophil function.

The cDNA cloning and expression of recombinant human G-CSF (hG-CSF) has been described, and it has been confirmed that the recombinant hG-CSF exhibits most, if not all, of the biological properties of the native molecule (Souza, L. et al. Science 232, 61-65 (1986)). Sequence analysis of the cDNA and genomic DNA clones has allowed the deduction of the amino acid sequence and reveals that the protein is 204 amino acids long with a signal sequence of 30 amino acids. The mature protein is 174 amino acids long and possesses no potential N-linked glycosylation sites but several possible sites for O-linked glycosylation.

The cloning and expression of cDNA encoding human G-CSF has been described by two groups (Nagata, S. et. al., Nature 319, 415-418 (1986); Souza, L. M. et al., Science 232, 61-65 (1986)). The first report of a G-CSF cDNA clone suggested that the mature protein was 177 amino acids in length. The authors reported that they had also identified a cDNA clone for G-CSF that coded for a protein that lacked a stretch of three amino acids. This shorter from of G-CSF cDNA expresses the expected G-CSF activity. The second report describes a cDNA sequence identical to this short form and makes no mention of other variants. Since these authors confirmed that the short cDNA expresses G-CSF with the expected profile of biological activity, it is probable that this is the important form of G-CSF and that the longer form is either a minor splicing variant or the result of a cloning artifact.

Matsumoto et al., in Infection and Immunity, Vol. 55, No. 11, p. 2715 (1987) discuss the protective effect of human G-CSF on microbial infection in neutropenic mice.

The following patent publications relate to G-CSF: WO 8703689, which is incorporated by reference herein, describes hybridomas producing monoclonal antibodies specific for human G-CSF and their use in the purification of G-CSF; WO 8702060, which is incorporated by reference herein, discloses human G-CSF like polypeptides and methods of producing them; U.S. Pat. No. 4,810,643, which is incorporated by reference herein, discloses human G-CSF like polypeptides, sequences encoding them and methods of their production; and WO 8604605 and WO 8604506, which are incorporated by reference herein, disclose a gene encoding human G-CSF and infection inhibitors containing human G-CSF. Isolation of h-GCSF and production of G-CSF in host cells such as *E. coli* are described in, e.g., U.S. Pat. Nos. 4,810,643; 4,999,291; 5,580,755; and 6,716,606, which are incorporated by reference herein.

G-CSF is a pharmaceutically active protein which regulates proliferation, differentiation, and functional activation of neutrophilic granulocytes (Metcalf, Blood 67:257 (1986); Yan, et al. Blood 84 (3): 795-799 (1994); Bensinger, et al. Blood 81 (11): 3158-3163 (1993); Roberts, et al., Expt'l Hematology 22:1156-1163 (1994); Neben, et al. Blood 81 (7): 1960-1967 (1993); Welte et al. PNAS-USA 82:1526-1530 (1985); Souza et al. Science 232:61-65 (1986) and Gabrilove, J. Seminars in Hematology 26:21-14 (1989)). G-CSF was purified to homogeneity from cell culture supernatants of the human bladder carcinoma cell line 5637 (Welte et al., Proc. Natl. Acad. Sci (1985) 82:1526-30). The sequence of the cDNA coding for native hG-CSF is known from Souza et al., Science (1986) 232:61-65. As a consequence of alternative splicing in the second intron two naturally occurring forms of hG-CSF exist with 204 or 207 amino acids of which the first 30 represent a signal peptide (Lymphokines, IRL Press, Oxford, Washington D.C., Editors D. Male and C. Rickwood). The mature protein was shown to have a molecular weight of about 19 kDa and has 5 cysteine residues which can form intermolecular or intramolecular disulfide bridges. Binding studies have shown that hG-CSF binds to neutrophilic granulocytes. Little to no binding is observed with erythroid, lymphoid eosinophilic cell lines as well as with macrophages.

In humans, endogenous G-CSF is detectable in blood plasma (Jones et al. Bailliere's Clinical Hematology 2:1 83-111 (1989)). hG-CSF is produced by fibroblasts, macrophages, T cells, trophoblasts, endothelial cells and epithelial cells and is the expression product of a single copy gene comprised of four exons and five introns located on chromosome seventeen. Transcription of this locus produces a mRNA species which is differentially processed, resulting in two forms of hG-CSF mRNA, one version coding for a protein of 177 amino acids, the other coding for a protein of 174 amino acids (Nagata et al. EMBO J 5:575-581 (1986)), and the form comprised of 174 amino acids has been found to have the greatest specific in vivo biological activity. hG-CSF is species cross-reactive, such that when human G-CSF is administered to another mammal such as a mouse, canine or monkey, sustained neutrophil leukocytosis is elicited (Moore et al. PNAS USA 84:7134-7138 (1987)).

G-CSF can be obtained and purified from a number of sources. Natural human G-CSF (nhG-CSF) can be isolated from the supernatants of cultured human tumor cell lines. The development of recombinant DNA technology, see, for instance, U.S. Pat. No. 4,810,643 (Souza) incorporated herein by reference, has enabled the production of commercial scale quantities of G-CSF in glycosylated form as a product of eukaryotic host cell expression, and of G-CSF in non-glycosylated form as a product of prokaryotic host cell expression.

G-CSF has been found to be useful in the treatment of indications where an increase in neutrophils will provide benefits. G-CSF can mobilize stem and precursor cells from bone marrow and is used to treat patients whose granulocytes have been depleted by chemotherapy, or as a prelude to bone marrow transplants. For example, for cancer patients, G-CSF is beneficial as a means of selectively stimulating neutrophil production to compensate for hematopoietic deficits resulting from chemotherapy or radiation therapy. Other indications include treatment of various infectious diseases and related conditions, such as sepsis, which is typically caused by a metabolite of bacteria. G-CSF is also useful alone, or in combination with other compounds, such as other cytokines, for growth or expansion of cells in culture, for example, for bone marrow transplants.

The G-CSF receptor (G-CSFR) is a member of the hematopoietic/cytokine/growth factor receptor family, which includes several other growth factor receptors, such as the interleukin (IL)-3, -4 and -6 receptors, the granulocyte macrophage colony-stimulating factor (GM-CSF) receptor, the erythropoietin (EPO) receptor, as well as the prolactin and growth hormone receptors. Sec, Bazan, Proc. Natl.

Acad. Sci USA 87:6934-6938 (1990). Members of the cytokine receptor family contain four conserved cysteine residues and a tryptophan-serine-X-tryptophan-serine motif positioned just outside the transmembrane region. The conserved sequences are thought to be involved in protein-protein interactions. Sec, e.g., Chiba et al., Biochim. Biophys. Res. Comm. 184:485-490 (1992). The G-CSF receptor consists of a single peptide chain with a molecular weight of about 150 kD (Nicola, Immunol. Today 8 (1987), 134).

Glycosylated hG-CSF has been compared with de-glycosylated hG-CSF, prepared by in vitro enzymatic digestion with neuraminidase and endo-a-N-acetylgalactosaminidase, with respect to its stability as a function of pH and temperature (Oh-eda et al., 1990, J. Biol. Chem. 265 (20): 11432-35). The de-glycosylated hG-CSF, dissolved at a concentration of 1 μg/mL in 20 mM phosphate buffer containing 0.2 M NaCl and 0.01% Tween 20 was rapidly inactivated within the pH range of from about pH 7 to about pH 8 after a two-day incubation at 37° C. In contrast, glycosylated hG-CSF retained over 80% of its activity under the same conditions. Furthermore, evaluation of the thermal stability of both forms of hG-CSF, measured by biological assay and calorimetric analysis, indicated that de-glycosylated hG-CSF was less thermally stable than the native form of hG-CSF.

A number of approaches have been taken in order to provide stable, pharmaceutically acceptable G-CSF compositions. One approach to improving the composition stability of G-CSF involves the synthesis of derivatives of the protein. U.S. Pat. No. 5,665,863 discloses the formation of recombinant chimeric proteins comprising G-CSF coupled with albumin, which have new pharmacokinetic properties. U.S. Pat. Nos. 5,824,784 and 5,320,840, disclose the chemical attachment of water-soluble polymers to proteins to improve stability and provide protection against proteolytic degradation, and more specifically, N-terminally modified G-CSF molecules carrying chemically attached polymers, including polyethylene glycol.

Structures of a number of cytokines, including G-CSF (Zink et al., FEBS Lett. 314:435 (1992); Zink et al., Biochemistry 33:8453 (1994); Hill et al., Proc. Natl. Acad. Sci. USA 90:5167 (1993)), GM-CSF (Diederichs, K., et al. Science 154:1779-1782 (1991); Walter et al., J. Mol. Biol. 224:1075-1085 (1992)), IL-2 (Bazan, J. F. Science 257:410-411 (1992); Mckay, D. B. Science 257:412 (1992)), IL-4 (Redfield et al., Biochemistry 30:11029-11035 (1991); Powers et al., Science 256:1673-1677 (1992)), and IL-5 (Milburn et al., Nature 363:172-176 (1993)) have been determined by X-ray diffraction and NMR studies and show striking conservation with the GH structure, despite a lack of significant primary sequence homology.

An alternative approach to increasing stability of G-CSF in composition involves alteration of the amino acid sequence of the protein. U.S. Pat. No. 5,416,195 discloses genetically engineered analogues of G-CSF having improved composition stability, wherein the cysteine residue normally found at position 17 of the mature polypeptide chain, the aspartic acid residue found at position 27, and at least one of the tandem praline residues found at positions 65 and 66, are all replaced with a serine residue. U.S. Pat. No. 5,773,581 discloses the genetically engineered G-CSF analogues of G-CSF that have been covalently conjugated to a water soluble polymer.

The various forms of human G-CSF, including their preparation and purification, useful in a method for treating or preventing mastitis are described in detail in U.S. Pat. No. 4,810,643, which is hereby incorporated by reference. U.S. Pat. No. 4,810,643 describes and claims novel gene segments, biologically functional recombinant plasmids and viral DNA vectors and prokaryotic and eukaryotic host cells, which contain a G-CSF gene or a genetically engineered variant of a G-CSF gene. The host cells express biologically active G-CSF or a genetically engineered variant of G-CSF. U.S. Pat. No. 5,849,883 and WO 89/10932 describe various studies with human G-CSF in cattle. The studies were performed evaluated respiratory diseases (*Pasteurella thermolytic*), responses to bacterial challenges (*Klebsiella pneumonia*), or coliform mastitis (*E. coli*) in cattle.

U.S. Pat. No. 5,849,883, which is incorporated by reference herein in its entirety, presents the polynucleotide and polypeptide sequence of mature bovine G-CSF (bG-CSF), and describes methods to clone, isolate, and purify the polypeptide and analogs thereof. Mature b-GCSF is 174 amino acids in length (SEQ ID NO: 1) that has 82% homology to hG-CSF. A bG-CSF polypeptide with an initial methionine amino acid residue is shown as SEQ ID NO: 2. The polynucleotide sequence that encodes SEQ ID NO: 1 is shown as SEQ ID NO: 3. The polynucleotide sequence that encodes SEQ ID NO: 2 is shown as SEQ ID NO: 4. Heidari et al. describe the expression, purification, and biological activities of bG-CSF in Veterinary Immunology and Immunopathology (2001) 81:45-57.

Covalent attachment of the hydrophilic polymer poly (ethylene glycol), abbreviated PEG, is a method of increasing water solubility, bioavailability, increasing serum half-life, increasing therapeutic half-life, modulating immunogenicity, modulating biological activity, or extending the circulation time of many biologically active molecules, including proteins, peptides, and particularly hydrophobic molecules. PEG has been used extensively in pharmaceuticals, on artificial implants, and in other applications where biocompatibility, lack of toxicity, and lack of immunogenicity are of importance. In order to maximize the desired properties of PEG, the total molecular weight and hydration state of the PEG polymer or polymers attached to the biologically active molecule must be sufficiently high to impart the advantageous characteristics typically associated with PEG polymer attachment, such as increased water solubility and circulating half life, while not adversely impacting the bioactivity of the parent molecule.

PEG derivatives are frequently linked to biologically active molecules through reactive chemical functionalities, such as lysine, cysteine and histidine residues, the N-terminus and carbohydrate moieties. Proteins and other molecules often have a limited number of reactive sites available for polymer attachment. Often, the sites most suitable for modification via polymer attachment play a significant role in receptor binding, and are necessary for retention of the biological activity of the molecule. As a result, indiscriminate attachment of polymer chains to such reactive sites on a biologically active molecule often leads to a significant reduction or even total loss of biological activity of the polymer-modified molecule. R. Clark et al., (1996), *J. Biol. Chem.,* 271:21969-21977. To form conjugates having sufficient polymer molecular weight for imparting the desired advantages to a target molecule, prior art approaches have typically involved random attachment of numerous polymer arms to the molecule, thereby increasing the risk of a reduction or even total loss in bioactivity of the parent molecule.

Reactive sites that form the loci for attachment of PEG derivatives to proteins are dictated by the protein's structure. Proteins, including enzymes, are composed of various sequences of alpha-amino acids, which have the general structure $H_2N$—CHR—COOH. The alpha amino moiety ($H_2N$—) of one amino acid joins to the carboxyl moiety (—COOH) of an adjacent amino acid to form amide linkages, which can be represented as $—(NH—CHR—CO)_n—$, where the subscript "n" can equal hundreds or thousands. The fragment represented by R can contain reactive sites for protein biological activity and for attachment of PEG derivatives.

For example, in the case of the amino acid lysine, there exists an $—NH_2$ moiety in the epsilon position as well as in the alpha position. The epsilon $—NH_2$ is free for reaction under conditions of basic pH. Much of the art in the field of protein derivatization with PEG has been directed to developing PEG derivatives for attachment to the epsilon $—NH_2$ moiety of lysine residues present in proteins. "Polyethylene Glycol and Derivatives for Advanced PEGylation", Nektar Molecular Engineering Catalog, 2003, pp. 1-17. These PEG derivatives all have the common limitation, however, that they cannot be installed selectively among the often numerous lysine residues present on the surfaces of proteins. This can be a significant limitation in instances where a lysine residue is important to protein activity, existing in an enzyme active site for example, or in cases where a lysine residue plays a role in mediating the interaction of the protein with other biological molecules, as in the case of receptor binding sites.

A second and equally important complication of existing methods for protein PEGylation is that the PEG derivatives can undergo undesired side reactions with residues other than those desired. Histidine contains a reactive imino moiety, represented structurally as —N(H)—, but many chemically reactive species that react with epsilon $—NH_2$ can also react with —N(H)—. Similarly, the side chain of the amino acid cysteine bears a free sulfhydryl group, represented structurally as —SH. In some instances, the PEG derivatives directed at the epsilon $—NH_2$ group of lysine also react with cysteine, histidine or other residues. This can create complex, heterogeneous mixtures of PEG-derivatized bioactive molecules and risks destroying the activity of the bioactive molecule being targeted. It would be desirable to develop PEG derivatives that permit a chemical functional group to be introduced at a single site within the protein that would then enable the selective coupling of one or more PEG polymers to the bioactive molecule at specific sites on the protein surface that are both well-defined and predictable.

In addition to lysine residues, considerable effort in the art has been directed toward the development of activated PEG reagents that target other amino acid side chains, including cysteine, histidine and the N-terminus. See, e.g., U.S. Pat. No. 6,610,281 which is incorporated by reference herein, and "Polyethylene Glycol and Derivatives for Advanced PEGylation", Nektar Molecular Engineering Catalog, 2003, pp. 1-17. A cysteine residue can be introduced site-selectively into the structure of proteins using site-directed mutagenesis and other techniques known in the art, and the resulting free sulfhydryl moiety can be reacted with PEG derivatives that bear thiol-reactive functional groups. This approach is complicated, however, in that the introduction of a free sulfhydryl group can complicate the expression, folding and stability of the resulting protein. Thus, it would be desirable to have a means to introduce a chemical functional group into bioactive molecules that enables the selective coupling of one or more PEG polymers to the protein while simultaneously being compatible with (i.e., not engaging in undesired side reactions with) sulfhydryls and other chemical functional groups typically found in proteins.

As can be seen from a sampling of the art, many of these derivatives that have been developed for attachment to the side chains of proteins, in particular, the $—NH_2$ moiety on the lysine amino acid side chain and the —SH moiety on the cysteine side chain, have proven problematic in their synthesis and use. Some form unstable linkages with the protein that are subject to hydrolysis and therefore decompose, degrade, or are otherwise unstable in aqueous environments, such as in the bloodstream. Some form more stable linkages, but are subject to hydrolysis before the linkage is formed, which means that the reactive group on the PEG derivative may be inactivated before the protein can be attached. Some are somewhat toxic and are therefore less suitable for use in vivo. Some are too slow to react to be practically useful. Some result in a loss of protein activity by attaching to sites responsible for the protein's activity. Some are not specific in the sites to which they will attach, which can also result in a loss of desirable activity and in a lack of reproducibility of results. In order to overcome the challenges associated with modifying proteins with poly(ethylene glycol) moieties, PEG derivatives have been developed that are more stable (e.g., U.S. Pat. No. 6,602,498, which is incorporated by reference herein) or that react selectively with thiol moieties on molecules and surfaces (e.g., U.S. Pat. No. 6,610,281, which is incorporated by reference herein). There is clearly a need in the art for PEG derivatives that are chemically inert in physiological environments until called upon to react selectively to form stable chemical bonds.

The use of conjugates of hydroxyalkylstarch, and in particular the use of hydroxyethylstarch (HES), covalently linked to a polypeptide have been disclosed in order to potentially alter the polypeptide's immunogenicity and/or allergenicity. HESylation is an alternative teclmology that has been disclosed in a series of patent applications assigned to Fresenius Kabi AB including U.S. Patent Publication Numbers 20050063943, 20060121073, 20010100163, 20050234230, 20050238723, 20060019877, 20070134197, 20070087961, as well as U.S. Pat. No. 7,285,661, all of which are incorporated herein by reference. HES is a modified natural polymer that has been clinically used as a plasma volume expander and HESylation represents the technology of coupling drug substances with HES derivatives in order to modify drug characteristics, such as pharmacokinetics or water solubility. This also includes the prolongation of protein plasma circulation via an increased stability of the molecule and a reduced renal clearance, resulting in an increased biological activity. In addition, the immunogenicity or allergenicity might be reduced. By varying different parameters, such as the molecular weight of HES, a wide range of HES conjugates can be customized. Nevertheless, hydroxyethyl starch shares a common disadvantage with all other presently available polymers: its polydispersity. The polymer conjugates are a mixture of molecules having molecular weights distributed around an average value. This lack of homogeneity results in a low level of chemical and biochemical characterization and could prevent the pharmaceutically active component to reach its site of action (receptor, enzyme, etc.). In these cases the drug to be active requires its delivery in the original unconjugated form, and thus cleavage of the polymer by metabolic reactions is required for its pharmaceutical efficacy.

Recently, an entirely new technology in the protein sciences has been reported, which promises to overcome many of the limitations associated with site-specific modifications of proteins. Specifically, new components have been added to the protein biosynthetic machinery of the prokaryote *Escherichia coli* (*E. coli*) (e.g., L. Wang, et al., (2001), *Science* 292:498-500) and the eukaryote *Saccharomyces cerevisiae* (*S. cerevisiae*) (e.g., J. Chin et al., *Science* 301: 964-7 (2003)), which has enabled the incorporation of non-genetically encoded amino acids to proteins in vivo. A number of new amino acids with novel chemical, physical or biological properties, including photoaffinity labels and photoisomerizable amino acids, photocrosslinking amino acids (see, e.g., Chin, J. W., et al. (2002) *Proc. Natl. Acad. Sci. U.S.A* 99:11020-11024; and, Chin, J. W., et al., (2002) *J. Am. Chem. Soc.* 124:9026-9027), keto amino acids, heavy atom containing amino acids, and glycosylated amino acids have been incorporated efficiently and with high fidelity into proteins in *E. coli* and in yeast in response to the amber codon, TAG, using this methodology. See, e.g., J. W. Chin et al., (2002), *Journal of the American Chemical Society* 124:9026-9027; J. W. Chin, & P. G. Schultz, (2002), *ChemBioChem* 3 (11): 1135-1137; J. W. Chin, et al., (2002), *PNAS United States of America* 99:11020-11024; and, L. Wang, & P. G. Schultz, (2002), *Chem. Comm.,* 1:1-11. All references are incorporated by reference in their entirety. These studies have demonstrated that it is possible to selectively and routinely introduce chemical functional groups, such as ketone groups, alkyne groups and azide moieties, that are not found in proteins, that are chemically inert to all of the functional groups found in the 20 common, genetically-encoded amino acids and that may be used to react efficiently and selectively to form stable covalent linkages.

The ability to incorporate non-genetically encoded amino acids into proteins permits the introduction of chemical functional groups that could provide valuable alternatives to the naturally-occurring functional groups, such as the epsilon —$NH_2$ of lysine, the sulfhydryl-SH of cysteine, the imino group of histidine, etc. Certain chemical functional groups are known to be inert to the functional groups found in the 20 common, genetically-encoded amino acids but react cleanly and efficiently to form stable linkages. Azide and acetylene groups, for example, are known in the art to undergo a Huisgen [3+2] cycloaddition reaction in aqueous conditions in the presence of a catalytic amount of copper. See, e.g., Tomoe, et al., (2002) *J. Org. Chem.* 67:3057-3064; and, Rostovtsev, et al., (2002) *Angew. Chem. Int. Ed.* 41:2596-2599. By introducing an azide moiety into a protein structure, for example, one is able to incorporate a functional group that is chemically inert to amines, sulfhydryls, carboxylic acids, hydroxyl groups found in proteins, but that also reacts smoothly and efficiently with an acetylene moiety to form a cycloaddition product. Importantly, in the absence of the acetylene moiety, the azide remains chemically inert and unreactive in the presence of other protein side chains and under physiological conditions.

The present invention addresses, among other things, problems associated with the activity and production of bG-CSF polypeptides, and also addresses the production of a bG-CSF polypeptide with improved biological or pharmacological properties and/or improved therapeutic half-life.

SUMMARY OF THE INVENTION

This invention provides bG-CSF polypeptides comprising one or more non-naturally encoded amino acids.

In some embodiments, the bG-CSF polypeptide comprises one or more post-translational modifications. In some embodiments, the bG-CSF polypeptide is linked to a linker, polymer, or biologically active molecule. In some embodiments, the bG-CSF polypeptide is linked to a bifunctional polymer, bifunctional linker, or at least one additional bG-CSF polypeptide.

In some embodiments, the non-naturally encoded amino acid is linked to a water soluble polymer. In some embodiments, the water soluble polymer comprises a poly(ethylene glycol) moiety. In some embodiments, the non-naturally encoded amino acid is linked to the water soluble polymer with a linker or is bonded to the water soluble polymer. In some embodiments, the poly(ethylene glycol) molecule is a bifunctional polymer. In some embodiments, the bifunctional polymer is linked to a second polypeptide. In some embodiments, the second polypeptide is a bG-CSF polypeptide.

In some embodiments, the bG-CSF polypeptide comprises at least two amino acids linked to a water soluble polymer comprising a poly(ethylene glycol) moiety. In some embodiments, at least one amino acid is a non-naturally encoded amino acid.

In some embodiments, one or more non-naturally encoded amino acids are incorporated in one or more of the following positions in bG-CSF: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175 (i.e., at the carboxyl terminus of the protein), and any combination thereof (SEQ ID NO: 1 or the corresponding amino acids in SEQ ID NO: 2 or the corresponding amino acids in another bG-CSF polypeptide).

In some embodiments, one or more non-naturally encoded amino acids are incorporated at one or more of the following positions of bG-CSF: 3, 7, 11, 33, 43, 58, 62, 67, 69, 98, 99, 123, 124, 125, 133, 134, 136, 141, 159, 166, 169, 170, 173, and any combination thereof of SEQ ID NO: 1 or the corresponding amino acids in SEQ ID NO: 2. In some embodiments, one or more non-naturally encoded amino acids are incorporated at one or more of the following positions of bG-CSF: 3, 7, 33, 43, 58, 62, 67, 69, 99, 123, 124, 133, 134, 141, 166, and any combination thereof (SEQ ID NO: 1 or the corresponding amino acids in SEQ ID NO: 2). In some embodiments, one or more non-naturally encoded amino acids are incorporated at one or more of the following positions of bG-CSF: 3, 7, 62, 133, 166, and any combination thereof of SEQ ID NO: 1 or the corresponding amino acids in SEQ ID NO: 2. In some embodiments, one or more non-naturally encoded amino acids are incorporated at one or more of the following positions of bG-CSF: 62, 133, and a combination thereof (SEQ ID NO: 1 or the corresponding amino acids in SEQ ID NO: 2). In some embodiments, one or more non-naturally encoded amino acids are incorporated at position 62 of bG-CSF (SEQ ID NO: 1 or the corresponding amino acid in SEQ ID NO: 2). In some embodiments, one or more non-naturally encoded amino acids are incorporated at position 133 of bG-CSF (SEQ ID NO: 1 or the corresponding amino acid in SEQ ID NO: 2). In some embodiments, the polypeptide of the invention comprises one or more natural amino acid substitution, addition, or deletion. In some embodiments, one or more non-natural amino acids are incorporated in a leader or signal sequence that is N or C terminal to SEQ ID NO: 1, 2, or other bG-CSF sequence.

In some embodiments, the non-naturally occurring amino acid at one or more of these positions is linked to a water soluble polymer, including but not limited to, positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175 (i.e., at the carboxyl terminus of the protein), and any combination thereof (SEQ ID NO: 1 or the corresponding amino acids in SEQ ID NO: 2 or the corresponding amino acids in another bG-CSF polypeptide).

In some embodiments, the non-naturally occurring amino acid at one or more of these positions is linked to a water soluble polymer, including but not limited to, positions: 3, 7, 11, 33, 43, 58, 62, 67, 69, 98, 99, 123, 124, 125, 133, 134, 136, 141, 159, 166, 169, 170, 173, and any combination thereof (SEQ ID NO: 1 or the corresponding amino acids in SEQ ID NO: 2). In some embodiments, the non-naturally occurring amino acid at one or more of these positions is linked to a water soluble polymer, including but not limited to, positions: 3, 7, 33, 43, 58, 62, 67, 69, 99, 123, 124, 133, 134, 141, 166, and any combination thereof (SEQ ID NO: 1 or the corresponding amino acids in SEQ ID NO: 2). In some embodiments, the non-naturally occurring amino acid at one or more of these positions is linked to a water soluble polymer, including but not limited to, positions: 3, 7, 62, 133, 166, and any combination thereof (SEQ ID NO: 1 or the corresponding amino acids in SEQ ID NO: 2). In some embodiments, the non-naturally encoded amino acid at one or more of these positions is linked to a water soluble polymer, including but not limited to, 62, 133, and a combination thereof (SEQ ID NO: 1 or the corresponding amino acids in SEQ ID NO: 2). In some embodiments, the non-naturally encoded amino acid at position 62 is linked to a water soluble polymer (SEQ ID NO: 1 or the corresponding amino acid in SEQ ID NO: 2). In some embodiments, the non-naturally encoded amino acid at position 133 is linked to a water soluble polymer (SEQ ID NO: 1 or the corresponding amino acid in SEQ ID NO: 2). In some embodiments, the non-naturally occurring amino acid in the signal or leader sequence N or C terminal to SEQ ID NO: 1, 2, or other bG-CSF sequence is linked to a water soluble polymer.

In some embodiments, the bG-CSF polypeptide comprises a substitution, addition or deletion that modulates affinity of the bG-CSF polypeptide for a receptor or binding partner, including but not limited to, a protein, polypeptide, small molecule, or nucleic acid. In some embodiments, the bG-CSF polypeptide comprises a substitution, addition, or deletion that increases the stability of the bG-CSF polypeptide when compared with the stability of the corresponding bG-CSF without the substitution, addition, or deletion. Stability and/or solubility may be measured using a number of different assays known to those of ordinary skill in the art. Such assays include but are not limited to SE-HPLC and RP-HPLC. In some embodiments, the bG-CSF polypeptide comprises a substitution, addition, or deletion that modulates the immunogenicity of the bG-CSF polypeptide when compared with the immunogenicity of the corresponding bG-CSF without the substitution, addition, or deletion. In some embodiments, the bG-CSF polypeptide comprises a substitution, addition, or deletion that modulates serum half-life or circulation time of the bG-CSF polypeptide when compared with the serum half-life or circulation time of the corresponding bG-CSF without the substitution, addition, or deletion.

In some embodiments, the bG-CSF polypeptide comprises a substitution, addition, or deletion that increases the aqueous solubility of the bG-CSF polypeptide when compared to aqueous solubility of the corresponding bG-CSF without the substitution, addition, or deletion. In some embodiments, the bG-CSF polypeptide comprises a substitution, addition, or deletion that increases the solubility of the bG-CSF polypeptide produced in a host cell when compared to the solubility of the corresponding bG-CSF without the substitution, addition, or deletion. In some embodiments, the bG-CSF polypeptide comprises a substitution, addition, or deletion that increases the expression of the bG-CSF polypeptide in a host cell or increases synthesis in vitro when compared to the expression or synthesis of the corresponding bG-CSF without the substitution, addition, or deletion. The bG-CSF polypeptide comprising this substitution retains agonist activity and retains or improves expression levels in a host cell. In some embodiments, the bG-CSF polypeptide comprises a substitution, addition, or deletion that increases protease resistance of the bG-CSF polypeptide when compared to the protease resistance of the corresponding bG-CSF without the substitution, addition, or deletion. In some embodiments, the bG-CSF polypeptide comprises a substitution, addition, or deletion that modulates signal transduction activity of the receptor when compared with the activity of the receptor upon interaction with the corresponding bG-CSF polypeptide without the substitution, addition, or deletion. In some embodiments, the bG-CSF polypeptide comprises a substitution, addition, or deletion that modulates its binding to another molecule such as a receptor when compared to the binding of the corresponding bG-CSF polypeptide without the substitution, addition, or deletion. In some embodiments, the bG-CSF polypeptide comprises a substitution, addition, or deletion that modulates haematopoiesis compared to the haematopoiesis of the corresponding bG-CSF polypeptide without the substitution, addition, or deletion. In some embodiments, the bG-CSF polypeptide comprises a substitution, addition, or deletion that modulates proliferation of neutrophils compared to the proliferation of neutrophils of the corresponding bG-CSF polypeptide without the substitution, addition, or deletion. In some embodiments, the bG-CSF polypeptide comprises a substitution, addition, or deletion that modulates maturation of neutrophils compared to the maturation of neutrophils of the corresponding bG-CSF polypeptide without the substitution, addition, or deletion.

In some embodiments, the bG-CSF polypeptide comprises a substitution, addition, or deletion that increases compatibility of the bG-CSF polypeptide with pharmaceutical preservatives (e.g., m-cresol, phenol, benzyl alcohol) when compared to compatibility of the corresponding bG-CSF without the substitution, addition, or deletion. This increased compatibility would enable the preparation of a preserved pharmaceutical formulation that maintains the physiochemical properties and biological activity of the protein during storage.

In some embodiments, one or more engineered bonds are created with one or more non-natural amino acids. The intramolecular bond may be created in many ways, including but not limited to, a reaction between two amino acids in the protein under suitable conditions (one or both amino acids may be a non-natural amino acid); a reaction with two amino acids, each of which may be naturally encoded or non-naturally encoded, with a linker, polymer, or other molecule under suitable conditions; etc.

In some embodiments, one or more amino acid substitutions in the bG-CSF polypeptide may be with one or more naturally occurring or non-naturally occurring amino acids. In some embodiments the amino acid substitutions in the bG-CSF polypeptide may be with naturally occurring or non-naturally occurring amino acids, provided that at least one substitution is with a non-naturally encoded amino acid. In some embodiments, one or more amino acid substitutions in the bG-CSF polypeptide may be with one or more naturally occurring amino acids, and additionally at least one substitution is with a non-naturally encoded amino acid.

In some embodiments, the non-naturally encoded amino acid comprises a carbonyl group, an acetyl group, an aminooxy group, a hydrazine group, a hydrazide group, a semicarbazide group, an azide group, or an alkyne group.

In some embodiments, the non-naturally encoded amino acid comprises a carbonyl group. In some embodiments, the non-naturally encoded amino acid has the structure:

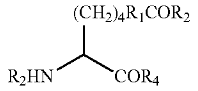

wherein n is 0-10; $R_1$ is an alkyl, aryl, substituted alkyl, or substituted aryl; $R_2$ is H, an alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group.

In some embodiments, the non-naturally encoded amino acid comprises an aminooxy group. In some embodiments, the non-naturally encoded amino acid comprises a hydrazide group. In some embodiments, the non-naturally encoded amino acid comprises a hydrazine group. In some embodiments, the non-naturally encoded amino acid residue comprises a semicarbazide group.

In some embodiments, the non-naturally encoded amino acid residue comprises an azide group. In some embodiments, the non-naturally encoded amino acid has the structure:

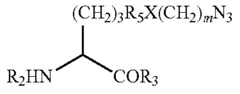

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group.

In some embodiments, the non-naturally encoded amino acid comprises an alkyne group. In some embodiments, the non-naturally encoded amino acid has the structure:

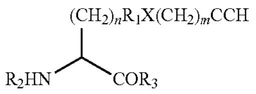

wherein n is 0-10; $R_1$ is an alkyl, aryl, substituted alkyl, or substituted aryl; X is O, N, S or not present; m is 0-10, $R_2$ is H, an amino acid, a polypeptide, or an amino terminus modification group, and $R_3$ is H, an amino acid, a polypeptide, or a carboxy terminus modification group.

In some embodiments, the polypeptide is a bG-CSF polypeptide agonist, partial agonist, antagonist, partial antagonist, or inverse agonist. In some embodiments, the bG-CSF polypeptide agonist, partial agonist, antagonist, partial antagonist, or inverse agonist comprises a non-naturally encoded amino acid linked to a water soluble polymer. In some embodiments, the water soluble polymer comprises a poly(ethylene glycol) moiety. In some embodiments, the bG-CSF polypeptide agonist, partial agonist, antagonist, partial antagonist, or inverse agonist comprises a non-naturally encoded amino acid and one or more post-translational modification, linker, polymer, or biologically active molecule.

The present invention also provides isolated nucleic acids comprising a polynucleotide that hybridizes under stringent conditions to SEQ ID NOs: 3, 4 or nucleic acids that encode polypeptides of SEQ ID NOs: 1, 2. The present invention also provides isolated nucleic acids comprising a polynucleotide that hybridizes under stringent conditions to SEQ ID NO: 3, 4 or polynucleotides that hybridize under stringent conditions to polynucleotides that encode polypeptides shown as SEQ ID NOs: 1, 2 wherein the polynucleotide comprises at least one selector codon. The present invention also provides isolated nucleic acids comprising a polynucleotide that encodes the polypeptides shown as SEQ ID NOs.: 1, 2. The present invention also provides isolated nucleic acids comprising a polynucleotide that encodes the polypeptides shown as SEQ ID NOs.: 1, 2 with one or more non-naturally encoded amino acids. It is readily apparent to those of ordinary skill in the art that a number of different polynucleotides can encode any polypeptide of the present invention.

In some embodiments, the selector codon is selected from the group consisting of an amber codon, ochre codon, opal codon, a unique codon, a rare codon, a five-base codon, and a four-base codon.

The present invention also provides methods of making a bG-CSF polypeptide linked to a water soluble polymer. In some embodiments, the method comprises contacting an isolated bG-CSF polypeptide comprising a non-naturally encoded amino acid with a water soluble polymer comprising a moiety that reacts with the non-naturally encoded amino acid. In some embodiments, the non-naturally encoded amino acid incorporated into the bG-CSF polypeptide is reactive toward a water soluble polymer that is otherwise unreactive toward any of the 20 common amino acids. In some embodiments, the non-naturally encoded amino acid incorporated into the bG-CSF polypeptide is reactive toward a linker, polymer, or biologically active molecule that is otherwise unreactive toward any of the 20 common amino acids.

In some embodiments, the bG-CSF polypeptide linked to the water soluble polymer is made by reacting a bG-CSF polypeptide comprising a carbonyl-containing amino acid with a poly(ethylene glycol) molecule comprising an aminooxy, hydrazine, hydrazide or semicarbazide group. In some embodiments, the aminooxy, hydrazine, hydrazide or semicarbazide group is linked to the poly(ethylene glycol) molecule through an amide linkage. In some embodiments, the aminooxy, hydrazine, hydrazide or semicarbazide group is linked to the poly(ethylene glycol) molecule through a carbamate linkage.

In some embodiments, the bG-CSF polypeptide linked to the water soluble polymer is made by reacting a poly (ethylene glycol) molecule comprising a carbonyl group with a polypeptide comprising a non-naturally encoded amino acid that comprises an aminooxy, hydrazine, hydrazide or semicarbazide group.

In some embodiments, the bG-CSF polypeptide linked to the water soluble polymer is made by reacting a bG-CSF polypeptide comprising an alkyne-containing amino acid with a poly(ethylene glycol) molecule comprising an azide moiety. In some embodiments, the azide or alkyne group is linked to the poly(ethylene glycol) molecule through an amide linkage.

In some embodiments, the bG-CSF polypeptide linked to the water soluble polymer is made by reacting a bG-CSF polypeptide comprising an azide-containing amino acid with a poly(ethylene glycol) molecule comprising an alkyne moiety. In some embodiments, the azide or alkyne group is linked to the poly(ethylene glycol) molecule through an amide linkage.

In some embodiments, the poly(ethylene glycol) molecule has a molecular weight of between about 0.1 kDa and about 100 kDa. In some embodiments, the poly(ethylene glycol) molecule has a molecular weight of between 0.1 kDa and 50 kDa.

In some embodiments, the poly(ethylene glycol) molecule is a branched polymer. In some embodiments, each branch of the poly(ethylene glycol) branched polymer has a molecular weight of between 1 kDa and 100 kDa, or between 1 kDa and 50 kDa.

In some embodiments, the water soluble polymer linked to the bG-CSF polypeptide comprises a polyalkylene glycol moiety. In some embodiments, the non-naturally encoded amino acid residue incorporated into the bG-CSF polypeptide comprises a carbonyl group, an aminooxy group, a hydrazide group, a hydrazine, a semicarbazide group, an azide group, or an alkyne group. In some embodiments, the non-naturally encoded amino acid residue incorporated into the bG-CSF polypeptide comprises a carbonyl moiety and the water soluble polymer comprises an aminooxy, hydrazide, hydrazine, or semicarbazide moiety. In some embodiments, the non-naturally encoded amino acid residue incorporated into the bG-CSF polypeptide comprises an alkyne moiety and the water soluble polymer comprises an azide moiety. In some embodiments, the non-naturally encoded amino acid residue incorporated into the bG-CSF polypeptide comprises an azide moiety and the water soluble polymer comprises an alkyne moiety.

The present invention also provides compositions comprising a bG-CSF polypeptide comprising a non-naturally encoded amino acid and a pharmaceutically acceptable carrier. In some embodiments, the non-naturally encoded amino acid is linked to a water soluble polymer.

The present invention also provides cells comprising a polynucleotide encoding the bG-CSF polypeptide comprising a selector codon. In some embodiments, the cells comprise an orthogonal RNA synthetase and/or an orthogonal tRNA for substituting a non-naturally encoded amino acid into the bG-CSF polypeptide.

The present invention also provides methods of making a bG-CSF polypeptide comprising a non-naturally encoded amino acid. In some embodiments, the methods comprise culturing cells comprising a polynucleotide or polynucleotides encoding a bG-CSF polypeptide, an orthogonal RNA synthetase and/or an orthogonal tRNA under conditions to permit expression of the bG-CSF polypeptide; and purifying the bG-CSF polypeptide from the cells and/or culture medium.

The present invention also provides methods of increasing therapeutic half-life, serum half-life or circulation time of bG-CSF polypeptides. The present invention also provides methods of modulating immunogenicity of bG-CSF polypeptides. In some embodiments, the methods comprise substituting a non-naturally encoded amino acid for any one or more amino acids in naturally occurring bG-CSF polypeptides and/or linking the bG-CSF polypeptide to a linker, a polymer, a water soluble polymer, or a biologically active molecule.

The present invention also provides methods of treating a patient in need of such treatment with an effective amount of a bG-CSF molecule of the present invention. In some embodiments, the methods comprise administering to the patient a therapeutically-effective amount of a pharmaceutical composition comprising a bG-CSF polypeptide comprising a non-naturally-encoded amino acid and a pharmaceutically acceptable carrier. In some embodiments, the non-naturally encoded amino acid is linked to a water soluble polymer. In some embodiments, the bG-CSF polypeptide is glycosylated. In some embodiments, the bG-CSF polypeptide is not glycosylated.

The present invention also provides bG-CSF polypeptides comprising a sequence shown in SEQ ID NO: 1, 2, or any other bG-CSF polypeptide sequence, except that at least one amino acid is substituted by a non-naturally encoded amino acid. The present invention also provides bG-CSF polypeptides comprising a sequence shown as SEQ ID NO: 1, 2. In some embodiments, the non-naturally encoded amino acid is linked to a water soluble polymer. In some embodiments, the water soluble polymer comprises a poly(ethylene glycol) moiety. In some embodiments, the non-naturally encoded amino acid comprises a carbonyl group, an aminooxy group, a hydrazide group, a hydrazine group, a semicarbazide group, an azide group, or an alkyne group.

The present invention also provides pharmaceutical compositions comprising a pharmaceutically acceptable carrier and a bG-CSF polypeptide comprising the sequence shown in SEQ ID NO: 1, 2, or any other bG-CSF polypeptide sequence, wherein at least one amino acid is substituted by a non-naturally encoded amino acid. The present invention also provides pharmaceutical compositions comprising a pharmaceutically acceptable carrier and a bG-CSF polypeptide comprising the sequence shown in SEQ ID NO: 1, 2. In some embodiments, the non-naturally encoded amino acid comprises a saccharide moiety. In some embodiments, the water soluble polymer is linked to the polypeptide via a saccharide moiety. In some embodiments, a linker, polymer, or biologically active molecule is linked to the bG-CSF polypeptide via a saccharide moiety.

The present invention also provides a bG-CSF polypeptide comprising a water soluble polymer linked by a covalent bond to the bG-CSF polypeptide at a single amino acid. In some embodiments, the water soluble polymer comprises a poly(ethylene glycol) moiety. In some embodiments, the amino acid covalently linked to the water soluble polymer is a non-naturally encoded amino acid present in the polypeptide.

In some embodiments of the present invention, a bG-CSF polypeptide comprising a HES linked by a covalent bond to the bG-CSF polypeptide is linked at a single amino acid. In some embodiments, the single amino acid covalently linked to the HES is a non-naturally encoded amino acid present in the polypeptide. In some embodiments of the present invention, a bG-CSF polypeptide comprises multiple non-naturally encoded amino acids which may be linked to multiple HES and/or PEG molecules.

The present invention provides a bG-CSF polypeptide comprising at least one linker, polymer, or biologically active molecule, wherein said linker, polymer, or biologically active molecule is attached to the polypeptide through a functional group of a non-naturally encoded amino acid ribosomally incorporated into the polypeptide. In some embodiments, the polypeptide is monoPEGylated. The present invention also provides a bG-CSF polypeptide comprising a linker, polymer, or biologically active molecule that is attached to one or more non-naturally encoded amino acid wherein said non-naturally encoded amino acid is ribosomally incorporated into the polypeptide at pre-selected sites.

Included within the scope of this invention is the bG-CSF leader or signal sequence joined to an bG-CSF coding region, as well as a heterologous signal sequence joined to an bG-CSF coding region. The heterologous leader or signal sequence selected should be one that is recognized and processed, e.g. by host cell secretion system to secrete and possibly cleaved by a signal peptidase, by the host cell. A method of treating a condition or disorder with the bG-CSF of the present invention is meant to imply treating with bG-CSF with or without a signal or leader peptide.

The present invention provides a method of treating and preventing infections in animals. The present invention also provides a method of treating and preventing mastitis and shipping fever in bovine animals. The present invention also provides a method of treating infections in animals without build up of strain resistance of bacteria. Also, the present invention provides a purified and isolated polypeptide having part or all of the primary structural confirmation and one or more of the biological properties of naturally occurring bovine G-CSF, and DNA sequences encoding such bovine G-CSF.

In another embodiment of the invention, one or more additional colony stimulating factors are administered to the infected animal with G-CSF, including but not limited to, GM-CSF, M-CSF and multi-CSP (IL-3). The CSFs are administered together or separately. In a further embodiment, animal infections are treated by administering G-CSF with one or more of: the interferons including but not limited to, a-interferon, IL2, and TNF or, with traditional antibiotics including but not limited to, penicillins, cephalosporins, and amino-glycosides.

In another embodiment, bG-CSF treatment is used in a prophylactic manner. bG-CSF may be used as a prophylactic therapy to augment the host defense of animals who are at risk for acquiring a bacterial, yeast, or fungal infection. For example, bG-CSF can be used as a prophylactic therapy in normal animals at risk of acquiring an infection, including but not limited to, pneumonia. The term "normal" as used herein means an animal which has normal immune function and normal white blood cell count and differential. Cattle are treated prophylactically prior to shipping or other occurrences which may debilitate the cattle, in order to boost and prime their capacity to fight off infections. Administration of the bG-CSF can be made at the time the cattle are processed, i.e. vaccinated, branded, etc. Treatment with bG-CSF can also be made during dry cow therapy and/or just before a cow gives birth in order to reduce the likelihood of post partum intrauterine infections, and of mastitis during the early stages of lactation. See Kehrli et al., Am. J. Vet. Res., 50, No. 2, 207 (1989); Oliver et al., J. Dairy Sci. 71:2584-2606 (1988); and Kehrli et al., J Dairy Sci. 74:4399-4412 (1991) for a description of bovine neutrophil function during the periparturient period. Conventionally, there is no treatment with antibiotics just before birth because of residues which would appear in the cows milk making it unfit for use.

In another embodiment, conjugation of the bG-CSF polypeptide comprising one or more non-naturally occurring amino acids to another molecule, including but not limited to PEG, provides substantially purified bG-CSF due to the unique chemical reaction utilized for conjugation to the non-natural amino acid. Conjugation of bG-CSF comprising one or more non-naturally encoded amino acids to another molecule, such as PEG, may be performed with other purification techniques performed prior to or following the conjugation step to provide substantially pure bG-CSF.

BRIEF DESCRIPTION OF THE DRAWINGS

FIG. 2—Details regarding a host cell line used to express bG-CSF are shown.

DEFINITIONS

Figure 1:
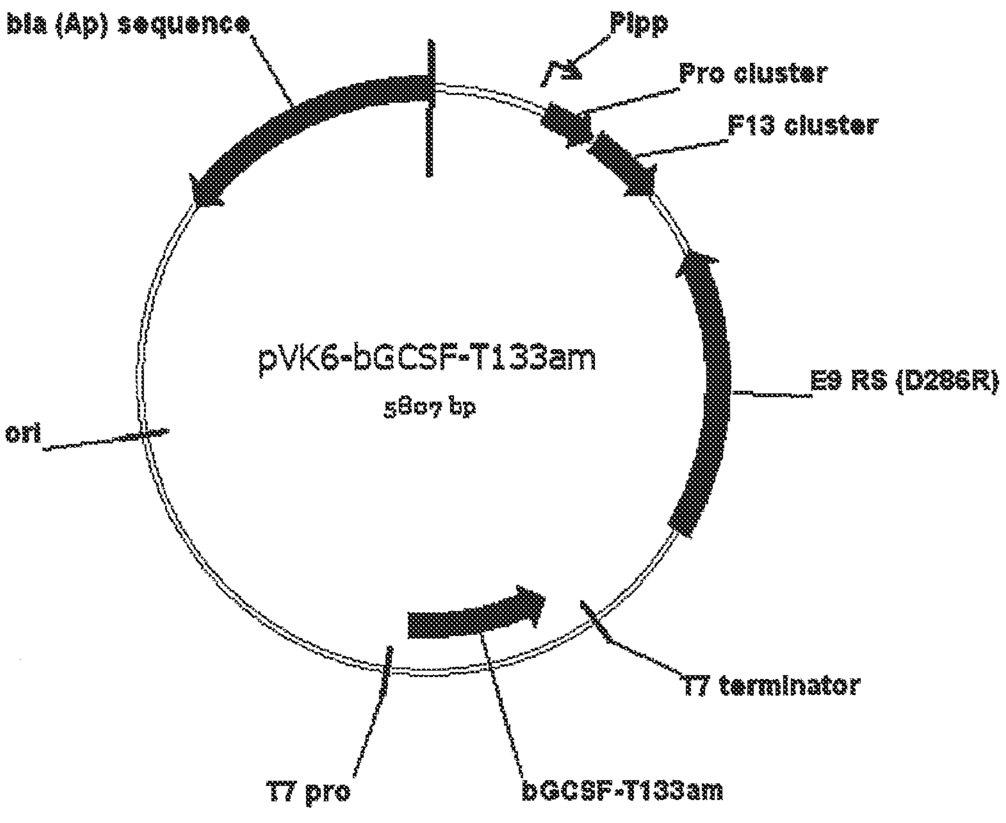
FIG. 1—A plasmid used for expression of bG-CSF is shown.

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention, which will be limited only by the appended claims.

As used herein and in the appended claims, the singular forms "a," "an," and "the" include plural reference unless the context clearly indicates otherwise. Thus, for example, reference to a "bGCSF" "bovine G-CSF," "bG-CSF," "bG-CSF," "bovine G-CSF polypeptide" or "bG-CSF polypeptide" and various hyphenated and unhyphenated forms is a reference to one or more such proteins and includes equivalents thereof known to those of ordinary skill in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

The term "substantially purified" refers to a bG-CSF polypeptide that may be substantially or essentially free of components that normally accompany or interact with the protein as found in its naturally occurring environment, i.e. a native cell, or host cell in the case of recombinantly produced bG-CSF polypeptides. bG-CSF polypeptide that may be substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the bG-CSF polypeptide or variant thereof is recombinantly produced by the host cells, the protein may be present at about 30%, about 25%, about 20%, about 15%, about 10%, about 5%, about 4%, about 3%, about 2%, or about 1% or less of the dry weight of the cells. When the bG-CSF polypeptide or variant thereof is recombinantly produced by the host cells, the protein may be present in the culture medium at about 5 g/L, about 4 g/L, about 3 g/L, about 2 g/L, about Ig/L, about 750 mg/L, about 500 mg/L, about 250 mg/L, about 100 mg/L, about 50 mg/L, about 10 mg/L, or about 1 mg/L or less of the dry weight of the cells. Thus, "substantially purified" bG-CSF polypeptide as produced by the methods of the present invention may have a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

A "recombinant host cell" or "host cell" refers to a cell that includes an exogenous polynucleotide, regardless of the method used for insertion, for example, direct uptake, transduction, £-mating, or other methods known in the art to create recombinant host cells. The exogenous polynucleotide may be maintained as a nonintegrated vector, for example, a plasmid, or alternatively, may be integrated into the host genome.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells, prokaryotic host cells, *E. coli*, or *Pseudomonas* host cells, and cell contents. Thus, the term may encompass medium in which the host cell has been grown, e.g., medium into which the bG-CSF polypeptide has been secreted, including medium either before or after a proliferation step. The term also may encompass buffers or reagents that contain host cell lysates, such as in the case where the bG-CSF polypeptide is produced intracellularly and the host cells are lysed or disrupted to release the bG-CSF polypeptide.

"Reducing agent," as used herein with respect to protein refolding, is defined as any compound or material which maintains sulfhydryl groups in the reduced state and reduces intra- or intermolecular disulfide bonds. Suitable reducing agents include, but are not limited to, dithiothreitol (DTT), 2-mercaptocthanol, dithioerythritol, cysteine, cysteamine (2-aminoethanethiol), and reduced glutathione. It is readily apparent to those of ordinary skill in the art that a wide variety of reducing agents are suitable for use in the methods and compositions of the present invention.

"Oxidizing agent," as used herein with respect to protein refolding, is defined as any compound or material which is capable of removing an electron from a compound being oxidized. Suitable oxidizing agents include, but are not limited to, oxidized glutathione, cystine, cystamine, oxidized dithiothreitol, oxidized erythreitol, and oxygen. It is readily apparent to those of ordinary skill in the art that a wide variety of oxidizing agents are suitable for use in the methods of the present invention.

"Denaturing agent" or "denaturant," as used herein, is defined as any compound or material which will cause a reversible unfolding of a protein. The strength of a denaturing agent or denaturant will be determined both by the properties and the concentration of the particular denaturing agent or denaturant. Suitable denaturing agents or denaturants may be chaotropes, detergents, organic solvents, water miscible solvents, phospholipids, or a combination of two or more such agents. Suitable chaotropes include, but are not limited to, urea, guanidine, and sodium thiocyanate. Useful detergents may include, but are not limited to, strong detergents such as sodium dodecyl sulfate, or polyoxyethylene ethers (e.g. Tween or Triton detergents), Sarkosyl, mild non-ionic detergents (e.g., digitonin), mild cationic detergents such as N→2,3-(Dioleyoxy)-propyl-N,N,N-trimethylammonium, mild ionic detergents (e.g. sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl)dimethylammonio-2-hydroxy-1-propane sulfonate (CHAPSO). Organic, water miscible solvents such as acetonitrile, lower alkanols (especially $C_2$-$C_4$ alkanols such as ethanol or isopropanol), or lower alkandiols (especially $C_2$-$C_4$ alkandiols such as ethylene-glycol) may be used as denaturants. Phospholipids useful in the present invention may be naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

"Refolding," as used herein describes any process, reaction or method which transforms disulfide bond containing polypeptides from an improperly folded or unfolded state to a native or properly folded conformation with respect to disulfide bonds.

"Cofolding," as used herein, refers specifically to refolding processes, reactions, or methods which employ at least two polypeptides which interact with each other and result in the transformation of unfolded or improperly folded polypeptides to native, properly folded polypeptides.

As used herein, "granulocyte colony stimulating factor" or "G-CSF" shall include those polypeptides and proteins that have at least one biological activity of G-CSF (such as those described in U.S. Pat. Nos. 6,716,606; 6,689,351; 6,565,841; 6,162,426; 5,811,301; 5,776,895; 5,718,893; 5,580,755; 5,536,495; 5,202,117; 5,043,156; 4,999,291; 4,810,643; and 4,968,618 for hG-CSF which are incorporated by reference herein), as well as G-CSF analogs, G-CSF isoforms, G-CSF mimetics, G-CSF fragments, hybrid G-CSF proteins, fusion proteins oligomers and multimers, homologues, glycosylation pattern variants, and muteins, regardless of the biological activity of same, and further regardless of the method of synthesis or manufacture thereof including, but not limited to, recombinant (whether produced from cDNA, genomic DNA, synthetic DNA or other form of nucleic acid), synthetic, transgenic, and gene activated methods. Specific examples of G-CSF include, but are not limited to, pegfilgrastim (NEULASTA®), filgrastim (NEUPOGEN®), G-CSF analog, G-CSF mutants, altered glycosylated G-CSF, and PEG conjugated G-CSF analogs. Specific examples of cell lines modified for expression of endogenous human G-CSF are described in Devlin et al., J. Leukoc. Biol. 41:306 (1987); U.S. Pat. Nos. 6,716,606; 6,379,661; 6,004,548; 5,830,705; 5,582,823; 4,810,643; and 6,242,218, which are incorporated by reference herein.

As used herein, "bovine granulocyte colony stimulating factor," "bovine G-CSF," or "bG-CSF" shall include those polypeptides and proteins that have at least one biological activity of bG-CSF, as well as bG-CSF analogs, bG-CSF isoforms, bG-CSF mimetics, bG-CSF fragments, hybrid bG-CSF proteins, fusion proteins oligomers and multimers, homologues, glycosylation pattern variants, and muteins, regardless of the biological activity of same, and further regardless of the method of synthesis or manufacture thereof including, but not limited to, recombinant (whether produced from cDNA, genomic DNA, synthetic DNA or other form of nucleic acid), synthetic, transgenic, and gene activated methods. Specific examples of G-CSF include, but are not limited to, bG-CSF mutants, altered glycosylated G-CSF, and PEG conjugated G-CSF analogs.

The term "bovine G-CSF (bG-CSF)" or "bG-CSF polypeptide" refers to bovine granulocyte colony stimulating factor or G-CSF as described above, as well as a polypeptide that retains at least one biological activity of naturally-occurring bG-CSF. bG-CSF polypeptides include the pharmaceutically acceptable salts and prodrugs, and prodrugs of the salts, polymorphs, hydrates, solvates, biologically-active fragments, biologically-active variants and stereoisomers of the naturally-occurring bovine G-CSF as well as agonist, mimetic, and antagonist variants of the naturally-occurring bovine G-CSF and polypeptide fusions thereof. Examples of bG-CSF polypeptides and mimetics include those described in WO 89/10932, U.S. Pat. Nos. 5,849,883 and 6,497,869, which are incorporated by reference herein in their entirety. Fusions comprising additional amino acids at the amino terminus, carboxyl terminus, or both, are encompassed by the term "bG-CSF polypeptide." Exemplary fusions include, but are not limited to, e.g., methionyl bG-CSF in which a methionine is linked to the N-terminus of bG-CSF (such as the polypeptide in SEQ ID NO: 2) resulting from the recombinant expression of the mature form of bG-CSF, fusions for the purpose of purification (including but not limited to, to poly-histidine or affinity epitopes), fusions with serum albumin binding peptides and fusions with serum proteins such as serum albumin. The naturally-occurring bG-CSF nucleic acid and amino acid sequences for full-length and mature forms are known, as are variants such as single amino acid variants and splice variants. For the mature bG-CSF amino acid sequence as well as a methionyl bG-CSF amino acid sequence, see SEQ ID NO: 1 and SEQ ID NO: 2, respectively, herein. Nucleic acid molecules encoding hG-CSF mutants and mutant hG-CSF polypeptides are known as well.

Bovine granulocyte colony stimulating factor or bG-CSF has a variety of biological activities including but not limited to binding to its receptor, causing dimerization of its receptor, stimulation of neutrophil production, and stimulating cell proliferation and differentiation. Examples of some of the biological activities of granulocyte colony stimulating factor and hG-CSF are described above and in U.S. Pat. Nos. 6,676,947; 6,579,525; 6,531,121; 6,521,245; 6,489,293; 6,368,854; 6,316,254; 6,268,336; 6,239,109; 6,165,283; 5,986,047; 5,830,851; 5,043,156; and 5,773,569, which are incorporated by reference herein.

As used herein, "bovine G-CSF polypeptide," "bG-CSF polypeptide," "bovine G-CSF" or "bG-CSF" and hyphenated and unhyphenated forms thereof shall include those polypeptides and proteins that have at least one biological activity of a CSF, bG-CSF analogs, bG-CSF mutants, altered glycosylated bG-CSF, PEG conjugated bG-CSF, bG-CSF isoforms, bG-CSF mimetics, bG-CSF fragments, hybrid bG-CSF proteins, fusion proteins, oligomers and multimers, homologues, glycosylation pattern variants, variants, splice variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), in vitro, in vivo, by microinjection of nucleic acid molecules, synthetic, transgenic, and gene activated methods. The term "bovine G-CSF polypeptide," "bG-CSF polypeptide," "bovine G-CSF" or "bG-CSF" encompass bG-CSF polypeptides comprising one or more amino acid substitutions, additions or deletions. See U.S. Pat. No. 5,849,883, which is incorporated by reference herein, for analogs of bovine G-CSF.

Substitutions in a wide variety of amino acid positions in bG-CSF have been described. Substitutions including but not limited to, those that modulate pharmaceutical stability, increase agonist activity, increase protease resistance, convert the polypeptide into an antagonist, etc. and are encompassed by the term 11bG-CSF polypeptide," "bovine G-CSF polypeptide," "bovine G-CSF," or "bG-CSF."

In a further aspect, the invention provides recombinant nucleic acids encoding the variant proteins, expression vectors containing the variant nucleic acids, host cells comprising the variant nucleic acids and/or expression vectors, and methods for producing the variant proteins. In an additional aspect, the invention provides treating an infection by administering to an animal a variant protein, usually with a pharmaceutical carrier, in a therapeutically effective amount.

bG-CSF mutants discussed in U.S. Pat. No. 5,849,883, which is incorporated by reference in its entirety, include polypeptides designed with codon optimization for *E. coli* and hybrid proteins generated with bovine and human G-CSF sequence. U.S. Pat. No. 5,416,195, which is included herein by reference, in its entirety, describes hG-CSF mutants in which at least one of the following amino acid substitutions have been made (amino acid numbering is in reference to the mature protein; therefore where an N-terminal methionine is present, it is assigned position −1 or 0): Cys17 of the native sequence replaced by a Ser17 residue, Asp27 of the native sequence replaced by a Ser27 residue, Leu15 of the native sequence replaced by a Glu15 residue, Lys23 of the native sequence replaced by an Arg23 residue, Gly28 of the native sequence replaced by an Ala28 residue, Lys40 of the native sequence replaced by an Arg40 residue, Pro44 of the native sequence replaced by an Ala44 residue, Leu49 of the native sequence replaced by a Lys49 residue, Gly55 of the native sequence replaced by an Ala55 residue, Cys60 of the native sequence replaced by a Ser.60 residue, Pro111 of the native sequence replaced by a Glu111 residue, Thr115 of the native sequence replaced by a Ser115 residue, and Tyr165 of the native sequence replaced by an Arg165 residue. Many of these residues are present in the bG-CSF sequence and one or more of these substitutions may be found in a bG-CSF polypeptide of the invention. Carter et al. Biologicals (2004) 32:37 describe mutated hG-CSF lacking glycosylation sites. Similar mutations may be found in bG-CSF polypeptides of the invention.

In some embodiments, bG-CSF polypeptides of the invention are substantially identical to SEQ ID NOs: 1, 2, or any other sequence of a bG-CSF polypeptide. Nucleic acid molecules encoding bG-CSF polypeptides including mutants and methods to express and purify bG-CSF polypeptides are well known.

The term "bG-CSF polypeptide" also includes the pharmaceutically acceptable salts and prodrugs, and prodrugs of the salts, polymorphs, hydrates, solvates, biologically-active fragments, biologically active variants and stereoisomers of the naturally-occurring bG-CSF as well as agonist, mimetic, and antagonist variants of the naturally-occurring bG-CSF and polypeptide fusions thereof. Fusions comprising additional amino acids at the amino terminus, carboxyl terminus, or both, are encompassed by the term "bG-CSF polypeptide." Exemplary fusions include, but are not limited to, e.g., methionyl bG-CSF in which a methionine is linked to the N-terminus of bG-CSF resulting from the recombinant expression of the mature form of bG-CSF lacking the leader or signal peptide or portion thereof (a methionine is linked to the N-terminus of bG-CSF resulting from the recombinant expression), fusions for the purpose of purification (including, but not limited to, to poly-histidine or affinity epitopes), fusions with serum albumin binding peptides and fusions with serum proteins such as serum albumin. U.S. Pat. No. 5,750,373, which is incorporated by reference herein, describes a method for selecting novel proteins such as growth hormone and antibody fragment variants having altered binding properties for their respective receptor molecules. The method comprises fusing a gene encoding a protein of interest to the carboxy terminal domain of the gene III coat protein of the filamentous phage M13. Chimeric molecules comprising bG-CSF and one or more other molecules. The chimeric molecule can contain specific regions or fragments of one or both of the bG-CSF and the other molecule(s). Any such fragments can be prepared from the proteins by standard biochemical methods, or by expressing a polynucleotide encoding the fragment. bG-CSF, or a fragment thereof, can be produced as a fusion protein comprising human serum albumin (HSA), Fe, or a portion thereof. Such fusion constructs are suitable for enhancing expression of the bG-CSF, or fragment thereof, in an eukaryotic host cell. Exemplary HSA portions include the N-terminal polypeptide (amino acids 1-369, 1-419, and intermediate lengths starting with amino acid 1), as disclosed in U.S. Pat. No. 5,766,883, and publication WO 97/24445, which are incorporated by reference herein. Other chimeric polypeptides can include a HSA protein with bG-CSF, or fragments thereof, attached to each of the C-terminal and N-terminal ends of the HSA. Other fusions may be created by fusion of bG-CSF with a) the Fe portion of an immunoglobulin; b) an analog of the Fe portion of an immunoglobulin; and c) fragments of the Fe portion of an immunoglobulin.

Various references disclose modification of polypeptides by polymer conjugation or glycosylation. The term "bG-CSF polypeptide" includes polypeptides conjugated to a polymer such as PEG and may be comprised of one or more additional derivitizations of cysteine, lysine, or other residues. In addition, the bG-CSF polypeptide may comprise a linker or polymer, wherein the amino acid to which the linker or polymer is conjugated may be a non-natural amino acid according to the present invention, or may be conjugated to a naturally encoded amino acid utilizing techniques known in the art such as coupling to lysine or cysteine.

Polymer modification of polypeptides has been reported. IFNβ is mentioned as one example of a polypeptide belonging to the growth hormone superfamily. WO 00/23114 discloses glycosylated and pegylated IFNβ. WO 00/23472 discloses IFNβ fusion proteins. U.S. Pat. No. 4,904,584 discloses PEGylated lysine depleted polypeptides, wherein at least one lysine residue has been deleted or replaced with any other amino acid residue. WO 99/67291 discloses a process for conjugating a protein with PEG, wherein at least one amino acid residue on the protein is deleted and the protein is contacted with PEG under conditions sufficient to achieve conjugation to the protein. WO 99/03887 discloses PEGylated variants of polypeptides belonging to the growth hormone superfamily, wherein a cysteine residue has been substituted with a non-essential amino acid residue located in a specified region of the polypeptide. WO 00/26354 discloses a method of producing a glycosylated polypeptide variant with reduced allergenicity, which as compared to a corresponding parent polypeptide comprises at least one additional glycosylation site. U.S. Pat. No. 5,218,092, which is incorporated by reference herein, discloses modification of granulocyte colony stimulating factor (G-CSF) and other polypeptides so as to introduce at least one additional carbohydrate chain as compared to the native polypeptide.

The term "bG-CSF polypeptide" also includes glycosylated bG-CSF, such as but not limited to, polypeptides glycosylated at any amino acid position, N-linked or O-linked glycosylated forms of the polypeptide. Variants containing single nucleotide changes are also considered as biologically active variants of bG-CSF polypeptide. Variants containing single nucleotide changes are also considered as biologically active variants of bG-CSF. In addition, splice variants are also included. The term "bG-CSF polypeptide" also includes bG-CSF heterodimers, homodimers, heteromultimers, or homomultimers of any one or more bG-CSF or any other polypeptide, protein, carbohydrate, polymer, small molecule, linker, ligand, or other active molecule of any type, linked by chemical means or expressed as a fusion protein (see U.S. Pat. Nos. 6,261,550; 6,166,183; 6,204,247; 6,261,550; 6,017,876, which are incorporated by reference herein), as well as polypeptide analogues containing, for example, specific deletions or other modifications yet maintain biological activity (U.S. Pat. Nos. 6,261,550; 6,004,548; 6,632,426, which are incorporated by reference herein).

All references to amino acid positions in bG-CSF described herein are based on the position in SEQ ID NO: 1, unless otherwise specified (i.e., when it is stated that the comparison is based on SEQ ID NO: 2, or other bG-CSF sequence). For example, the amino acid at position 1 of SEQ ID NO: 1, is a threonine and the corresponding threonine is located in SEQ ID NO: 2 at position 2. Those of skill in the art will appreciate that amino acid positions corresponding to positions in SEQ ID NO: 1 can be readily identified in any other bG-CSF molecule such as SEQ ID NO: 2. Those of skill in the art will appreciate that amino acid positions corresponding to positions in SEQ ID NO: 1, 2, or any other bG-CSF sequence can be readily identified in any other bG-CSF molecule such as bG-CSF fusions, variants, fragments, etc. For example, sequence alignment programs such as BLAST can be used to align and identify a particular position in a protein that corresponds with a position in SEQ ID NO: 1, 2, or other bG-CSF sequence. Substitutions, deletions or additions of amino acids described herein in reference to SEQ ID NO: 1, 2, or other bG-CSF sequence are intended to also refer to substitutions, deletions or additions in corresponding positions in bG-CSF fusions, variants, fragments, etc. descn'bed herein or known in the art and are expressly encompassed by the present invention.

The term "bG-CSF polypeptide" or "bG-CSF" encompasses bG-CSF polypeptides comprising one or more amino acid substitutions, additions or deletions. bG-CSF polypeptides of the present invention may be comprised of modifications with one or more natural amino acids in conjunction with one or more non-natural amino acid modification. Exemplary substitutions in a wide variety of amino acid positions in naturally-occurring bG-CSF polypeptides have been described, including but not limited to substitutions that modulate pharmaceutical stability, that modulate one or more of the biological activities of the bG-CSF polypeptide, such as but not limited to, increase agonist activity, increase solubility of the polypeptide, decrease protease susceptibility, convert the polypeptide into an antagonist, etc. and are encompassed by the term "bG-CSF polypeptide." In some embodiments, the bG-CSF antagonist comprises a non-naturally encoded amino acid linked to a water soluble polymer that is present in a receptor binding region of the bG-CSF molecule.

In some embodiments, the bG-CSF polypeptides further comprise an addition, substitution or deletion that modulates biological activity of the bG-CSF polypeptide. In some embodiments, the bG-CSF polypeptides further comprise an addition, substitution or deletion that modulates neutrophil proliferation, function, and/or differentiation of the bG-CSF polypeptide. For example, the additions, substitutions or deletions may modulate one or more properties or activities of bG-CSF. For example, the additions, substitutions or deletions may modulate affinity for a receptor, modulate circulating half-life, modulate therapeutic half-life, modulate stability of the polypeptide, modulate cleavage by proteases, modulate dose, modulate release or bio-availability, facilitate purification, or improve or alter a particular route of administration. Similarly, bG-CSF polypeptides may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

The term "bG-CSF polypeptide" also encompasses homodimers, heterodimers, homomultimers, and heteromultimers that are linked, including but not limited to those linked directly via non-naturally encoded amino acid side chains, cither to the same or different non-naturally encoded amino acid side chains, to naturally-encoded amino acid side chains, or indirectly via a linker. Exemplary linkers including but are not limited to, small organic compounds, water soluble polymers of a variety of lengths such as poly (ethylene glycol) or polydextran, or polypeptides of various lengths.

A "non-naturally encoded amino acid" refers to an amino acid that is not one of the 20 common amino acids or pyrrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water soluble polymers, peptides or proteins such as serum albumin, or other moieties that increase serum half-life of peptides.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "linkage" or "linker" is used herein to refer to groups or bonds that normally are formed as the result of a chemical reaction and typically are covalent linkages.

Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a fonnate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include, but are not limited to, any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, vaccines, immunogens, hard drugs, soft drugs, carbohydrates, inorganic atoms or molecules, dyes, lipids, nucleosides, radionuclides, oligonucleotides, toxoids, toxins, prokaryotic and eukaryotic cells, viruses, polysaccharides, nucleic acids and portions thereof obtained or derived from viruses, bacteria, insects, animals or any other cell or cell type, liposomes, microparticles and micelles. The bG-CSF polypeptides may be added in a micellular formulation. Classes of biologically active agents that are suitable for use with the invention include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

A "bifunctional polymer" refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Application No. 188,256; U.S. Pat. Nos. 4,671,958, 4,659,839, 4,414,148, 4,699,784; 4,680,338; and 4,569,789 which are incorporated by reference herein. A "multi-functional polymer" refers to a polymer comprising two or more discrete functional groups that are capable of reacting specifically with other moieties (including but not limited to, amino acid side groups) to form covalent or non-covalent linkages. A bi-functional polymer or multi-functional polymer may be any desired length or molecular weight, and may be selected to provide a particular desired spacing or conformation between one or more molecules linked to the bG-CSF and its receptor or bG-CSF.

Where substituent groups are specified by their conventional chemical formulas, written from left to right, they equally encompass the chemically identical substituents that would result from writing the structure from right to left, for example, the structure $—CH_2O—$ is equivalent to the structure $—OCH_2—$.

The term "substituents" includes but is not limited to "non-interfering substituents". "Non-interfering substituents" are those groups that yield stable compounds. Suitable non-interfering substituents or radicals include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_1$-$C_{12}$ aralkyl, $C_1$-$C_{12}$ alkaryl, $C_1$-$C_{12}$ cycloalkyl, $C_3$-$C_{12}$ cycloalkenyl, phenyl, substituted phenyl, toluoyl, xylenyl, biphenyl, $C_2$-$C_{12}$ alkoxyalkyl, $C_2$-$C_{12}$ alkoxyaryl, $C_7$-$C_{12}$ aryloxyalkyl, $C_7$-$C_{12}$ oxyaryl, $C_1$-$C_6$ alkylsulfinyl, $C_1$-$C_{10}$ alkylsulfonyl, $—(CH_2)_m—O—(C_1$-$C_{10}$ alkyl) wherein m is from 1 to 8, aryl, substituted aryl, substituted alkoxy, fluoroalkyl, heterocyclic radical, substituted heterocyclic radical, nitroalkyl, $—NO_2$, —CN, —NRC(O)—($C_1$-$C_{10}$ alkyl), —C(O)—($C_1$-$C_{10}$ alkyl), $C_2$-$C_{10}$ alkyl thioalkyl, —C(O)O—($C_1$-$C_{10}$ alkyl), —OH, $—SO_2$, |S, —COOH, $—NR_2$, carbonyl, —C(O)—($C_1$-$C_{10}$ alkyl)-$CF_3$, —C(O)—$CF_3$, —C(O)$NR_2$, —($C_1$-$C_{10}$ aryl)—S—($C_6$-$C_{10}$ aryl), —C(O)—($C_1$-$C_{10}$ aryl), $—(CH_2)_m—O—+—(CH_2)_m—O—(C_1$-$C_{10}$ alkyl) wherein each m is from 1 to 8, —C(O)$NR_2$, —C(S)$NR_2$, $—SO_2NR_2$, —NRC(O)$NR_2$, —NRC(S)$NR_2$, salts thereof, and the like. Each R as used herein is H, alkyl or substituted alkyl, aryl or substituted aryl, aralkyl, or alkaryl.

The term "halogen" includes fluorine, chlorine, iodine, and bromine.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by the structures —$CH_2CH_2$ and —$C_2C_2C_2C_2C_2$, and further includes those groups described below as "heteroalkylene." Typically, an alkyl (or alkylene) group will have from 1 to 24 carbon atoms, with those groups having 10 or fewer carbon atoms being a particular embodiment of the methods and compositions described herein. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$C_2$—$C_2$—O—$CH_3$, —$C_2$—$C_2$—NH—$CH_3$, —$C_2$—$C_2$—N($CH_3$)—$CH_3$, —$C_2$—S—$C_2$—$CH_3$, —$C_2$—$C_2$, —S(O)—$CH_3$, —$C_2$—$C_2$—S$(O)_2$—$CH_3$, —CH—CH—O—$CH_3$, —Si$(CH_3)_3$, —$CH_2$—CH═N—$OCH_3$, and —CH═CH—N($CH_3$)—$CH_3$. Up to two heteroatoms may be consecutive, such as, for example, —$CH_2$—NH—$OCH_3$ and —$CH_2$—O—Si$(CH_3)_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$—and —$CH_2$—S—$CH_2$—$CH_2$—NH—$CH_2$—. For heteroalkylene groups, the same or different heteroatoms can also occupy either or both of the chain termini (including but not limited to, alkyleneoxy, alkylenedioxy, alkyleneamino, alkylenediamino, aminooxyalkylene, and the like). Still further, for alkylene and heteroalkylene linking groups, no orientation of the linking group is implied by the direction in which the formula of the linking group is written. For example, the formula —C$(O)_2$R'— represents both —C$(O)_2$R'— and —R'C$(O)_2$—.

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated, partially unsaturated and fully unsaturated ring linkages. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Additionally, the term encompasses bicyclic and tricyclic ring structures. Similarly, the term "heterocycloalkylene" by itself or as part of another substituent means a divalent radical derived from heterocycloalkyl, and the term "cycloalkylene" by itself or as part of another substituent means a divalent radical derived from cycloalkyl.

As used herein, the term "water soluble polymer" refers to any polymer that is soluble in aqueous solvents. Linkage of water soluble polymers to bG-CSF polypeptides can result in changes including, but not limited to, increased or modulated serum half-life, or increased or modulated therapeutic half-life relative to the unmodified form, modulated immunogenicity, modulated physical association characteristics such as aggregation and multimer formation, altered receptor binding, altered binding to one or more binding partners, and altered receptor dimerization or multimerization. The water soluble polymer may or may not have its own biological activity, and may be utilized as a linker for attaching bG-CSF to other substances, including but not limited to one or more bG-CSF polypeptides, or one or more biologically active molecules. Suitable polymers include, but are not limited to, polyethylene glycol, polyethylene glycol propionaldehyde, mono C1-C10 alkoxy or aryloxy derivatives thereof (described in U.S. U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. Examples of such water soluble polymers include, but are not limited to, polyethylene glycol and serum albumin. WO 03/074087 and WO 03/074088 describe the conjugation of proteins or small molecules to hydroxyalkyl starch (HAS). Examples of hydroxylalkyl starches, include but are not limited to, hydroxyethyl starch. Conjugates of hydroxyalkyl starch and another molecule, for example, may comprise a covalent linkage between terminal aldehyde groups of the HAS and reactive groups of the other molecule.

As used herein, the term "polyalkylene glycol" or "poly(alkene glycol)" refers to polyethylene glycol (poly(ethylene glycol)), polypropylene glycol, polybutylene glycol, and derivatives thereof. The term "polyalkylene glycol" encompasses both linear and branched polymers and average molecular weights of between 0.1 kDa and 100 kDa. Other exemplary embodiments are listed, for example, in commercial supplier catalogs, such as Shearwater Corporation's catalog "Polyethylene Glycol and Derivatives for Biomedical Applications" (2001).

The term "aryl" means, unless otherwise stated, a polyunsaturated, aromatic, hydrocarbon substituent which can be a single ring or multiple rings (including but not limited to, from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (including but not limited to, aryloxy, arylthioxy, arylalkyl) includes both aryl and heteroaryl rings as defined above. Thus, the term "arylalkyl" is meant to include those radicals in which an aryl group is attached to an alkyl group (including but not limited to, benzyl, phenethyl, pyridylmethyl and the like) including those alkyl groups in which a carbon atom (including but not limited to, a methylene group) has been replaced by, for example, an oxygen atom (including but not limited to, phenoxymethyl, 2-pyridyloxymethyl, 3-(1-naphthyloxy) propyl, and the like).

Each of the above terms (including but not limited to, "alkyl," "heteroalkyl," "aryl" and "heteroaryl") are meant to include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —$CO_2$R', CONR'R", —OC(O)NR'R", —NR"C(O)R', —NR'—C(O)NR"R'", —NR"$C(O)_2$R', —NR—C(NR'R"R'")=NR"", —NR—C(NR'R")—NR'", —S(O)R', —$S(O)_2$R', —$S(O)_2$NR'R", —$NRSO_2$R', —CN and —$NO_2$ in a number ranging from zero to (2m'+1), where m' is the total number of carbon atoms in such a radical. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —$CF_3$ and —$CH_2CF_3$) and acyl (including but not limited to, —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, but are not limited to: halogen, —OR', =O, =NR'=N—OR', —NR'R", —SR', -halogen, —SiR'R"R'"—OC(O)R', —C(O)R', —$CO_2$R', —CONR'R", —OC(O)NR'R", —NR"C(O)R', —NR'—C(O)NR"R'", —NR"$C(O)_2$R', —NR—C(NR'R"R'")=NR"", —NR—C(NR'R")=NR'", —S(O)R', —$S(O)_2$R', —$S(O)_2$NR'R", —$NRSO_2$R', —CN and $NO_2$, —R', —$N_3$, —$CH(Ph)_2$, fluoro ($C_1$-$C_4$)alkoxy, and fluoro ($C_1$-$C_4$)alkyl, in a number ranging from zero to the total number of open valences on the aromatic ring system; and where R', R", R'" and R"" are independently selected from hydrogen, alkyl, heteroalkyl, aryl and heteroaryl. When a compound of the invention includes more than one R group, for example, each of the R groups is independently selected as are each R', R", R'" and R"" groups when more than one of these groups is present.

As used herein, the term "modulated serum half-life" means the positive or negative change in circulating half-life of a modified bG-CSF relative to its non-modified form. Serum half-life is measured by taking blood samples at various time points after administration of bG-CSF, and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of the therapeutically effective amount of bG-CSF, relative to its non-modified form. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, increased or decreased breakdown of the molecule by enzymes such as proteases, or an increase or decrease in another parameter or mechanism of action of the non-modified molecule or an increase or decrease in receptor-mediated clearance of the molecule.

The term "isolated," when applied to a nucleic acid or protein, denotes that the nucleic acid or protein is free of at least some of the cellular components with which it is associated in the natural state, or that the nucleic acid or protein has been concentrated to a level greater than the concentration of its in vivo or in vitro production. It can be in a homogeneous state. Isolated substances can be in either a dry or semi-dry state, or in solution, including but not limited to, an aqueous solution. It can be a component of a pharmaceutical composition that comprises additional pharmaceutically acceptable carriers and/or excipients. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it may mean that the nucleic acid or protein is at least 85% pure, at least 90% pure, at least 95% pure, at least 99% or greater pure.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorotbioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J Biol. Chem.* 260:2605-2608 (1985); Rossolini et al., *Mol. Cell. Probes* 8:91-98 (1994)).

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, praline, serine, tlueonine, tryptophan, tyrosine, and valine) and pyirolysine and selenocysteine. Amino acid analogs refers to compounds that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amina acids; D-amino acids, chemically modified amino acids such as amino acid variants and derivatives; naturally occurring non-proteogenic amino acids such as β-alanine, ornithine, etc.; and chemically synthesized compounds having properties known in the art to be characteristic of amino acids. Examples of non-naturally occurring amino acids include, but are not limited to, α-methyl amino acids (e.g., α-methyl alanine), D-amino acids, histidine-like amino acids (e.g., 2-amino-histidine, β-hydroxy-histidine, homohistidine, α-fluoromethyl-histidine and α-methyl-histidine), amino acids having an extra methylene in the side chain ("homo" amino acids), and amino acids in which a carboxylic acid functional group in the side chain is replaced with a sulfonic acid group (e.g., cysteic acid). The incorporation of non-natural amino acids, including synthetic non-native amino acids, substituted amino acids, or one or more D-amino acids into the proteins of the present invention may be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class II-restricted presentation to T helper cells, and are therefore, less likely to induce humoral immune responses in the whole organism.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TOG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles of the invention.

Conservative substitution tables providing functionally similar amino acids are known to those of ordinary skill in the art. The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);

7) Serine(S), Threonine (T); and

8) Cysteine (C), Methionine (M)

(see, e.g., Creighton, *Proteins: Structures and Molecular Properties* (W H Freeman & Co.; 2nd edition (December 1993)

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the present invention, including homologs from species other than human, may be obtained by a process comprising the steps of screening a library under stringent hybridization conditions with a labeled probe having a polynucleotide sequence of the invention or a fragment thereof, and isolating full-length cDNA and genomic clones containing said polynucleotide sequence. Such hybridization techniques are well known to the skilled artisan.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are known to those of ordinary skill in the art. Optimal alignment of sequences for comparison can be conducted, including but not limited to, by the local homology algorithm of Smith and Waterman (1970) *Adv. Appl. Math.* 2: 482c, by the homology alignment algorithm of Needleman and Wunsch (1970) *J Mal. Biol.* 48:443, by the search for similarity method of Pearson and Lipman (1988) *Proc. Nat'l. Acad. Sci. USA* 85:2444; by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

One example of an algorithm that is suitable for determining percent sequence identity and sequence similarity are the BLAST and BLAST 2.0 algorithm, which are described in Altschul et al. (1997) *Nuc. Acids Res.* 25:3389 3402, and Altschul et al. (1990) *J Mol. Biol.* 215:403-410, respectively. Software for performing BLAST analyses is publicly available through the National Center for Biotechnology Information available at the World Wide Web at ncbi.nlm.nih.gov. The BLAST algorithm parameters W, T, and X determine the sensitivity and speed of the alignment. The BLASTN program (for nucleotide sequences) uses as defaults a wordlength (W) of 11, an expectation (E) or 10, M=S, N=-4 and a comparison of both strands. For amino acid sequences, the BLASTP program uses as defaults a wordlength of 3, and expectation (E) of 10, and the BLOSUM62 scoring matrix (see Henikoff and Henikoff (1992) *Proc. Natl. Acad. Sci. USA* 89:10915) alignments (B) of 50, expectation (E) of 10, M=5, N=-4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or less than about 0.01, or less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not Limited to, total cellular or library DNA or RNA).

The phrase "stringent hybridization conditions" refers to hybridization of sequences of DNA, RNA, PNA, or other nucleic acid mimics, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, *Laboratory Techniques in Biochemistry and Atfolecular Biology—Hybridization with Nucleic Probes*, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, typically about 0.01 to 1.0 M sodium ion concentration (or other salts) at pH 7.0 to 8.3 and the temperature is at least about 30° C. for short probes (including but not limited to, 10 to 50 nucleotides) and at least about 60° C. for long probes (including but not limited to, greater than 50 nucleotides). Stringent conditions may also be achieved with the addition of destabilizing agents such as formamide. For selective or specific hybridization, a positive signal may be at least two times background, optionally 10 times background hybridization. Exemplary stringent hybridization conditions can be as following: 50% formamide, S×SSC, and 1% SDS, incubating at 42° C., or S×SSC, 1% SDS, incubating at 65° C., with wash in 0.2×SSC, and 0.1% SDS at 65° C. Such washes can be performed for 5, 15, 30, 60, 120, or more minutes.

As used herein, the term "eukaryote" refers to orgasms belonging to the phylogenetic domain Eucarya such as animals (including but not limited to, mammals, insects, reptiles, birds, etc.), ciliates, plants (including but not limited to, monocots, dicots, algae, etc.), fungi, yeasts, *flagellates*, microsporidia, protists, etc.

As used herein, the term "non-eukaryote" refers to non-eukaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fidgidus, Pyrococcus furiosus, Pyrococcus horikoshii, Aeuropyrum pernix*, etc.) phylogenetic domain.

The term "subject" as used herein, refers to an animal, in some embodiments a mammal, and in other embodiments a human, who is the object of treatment, observation or experiment. An animal may be a companion animal (e.g., dogs, cats, and the like), farm animal (e.g., cows, sheep, pigs, horses, and the like) or a laboratory animal (e.g., rats, mice, guinea pigs, and the like).

The term "effective amount" as used herein refers to that amount of the modified non-natural amino acid polypeptide being administered which will relieve to some extent one or more of the symptoms of the disease, condition or disorder being treated. Compositions containing the modified non-natural amino acid polypeptide described herein can be administered for prophylactic, enhancing, and/or therapeutic treatments.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in an animal, amounts effective for this use will depend on the severity and course of the disease, disorder or condition, previous therapy, the animal's health status and response to the drugs, and the judgment of the treating veterinarian.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

The term "post-translationally modified" refers to any modification of a natural or non-natural amino acid that occurs to such an amino acid after it has been incorporated into a polypeptide chain. The term encompasses, by way of example only, co-translational in vivo modifications, co-translational in vitro modifications (such as in a cell-free translation system), post-translational in vivo modifications, and post-translational in vitro modifications.

In prophylactic applications, compositions containing the bG-CSF polypeptide are administered to an animal susceptible to or otherwise at risk of a particular disease, disorder or condition. Such an amount is defined to be a "prophylactically effective amount." In this use, the precise amounts also depend on the animal's state of health, weight, and the like. It is considered well within the skill of the art for one to determine such prophylactically effective amounts by routine experimentation (e.g., a dose escalation clinical trial).

The term "protected" refers to the presence of a "protecting group" or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in or with the methods and compositions described herein, including photolabile groups such as Nvoc and MeNvoc. Other protecting groups known in the art may also be used in or with the methods and compositions described herein.

By way of example only, blocking/protecting groups may be selected from:

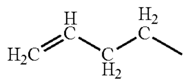

allyl

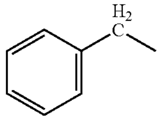

Bn

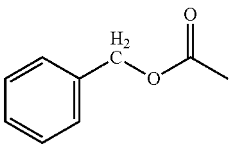

Cbz

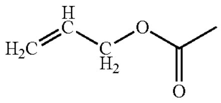

alloc

Me

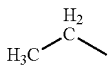

Et

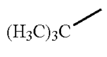

t-butyl

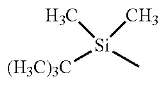

TBDMS

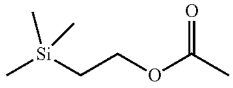

Teoc

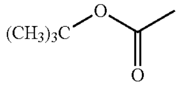

Boc

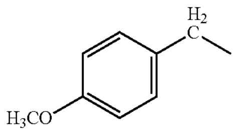

pMBn

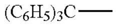

trityl

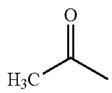

acetyl

-continued

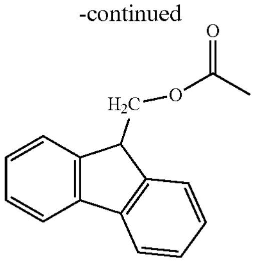

Fmoc

Other protecting groups are described in Greene and Wuts, Protective Groups in Organic Synthesis, 3rd Ed., John Wiley & Sons, New York, NY, 1999, which is incorporated herein by reference in its entirety.

In therapeutic applications, compositions containing the modified non-natural amino acid polypeptide are administered to an animal already suffering from a disease, condition or disorder, in an amount sufficient to cure or at least partially arrest the symptoms of the disease, disorder or condition. Such an amount is defined to be a "therapeutically effective amount," and will depend on the severity and course of the disease, disorder or condition, previous therapy, the animal's health status and response to the drugs, and the judgment of the treating veterinarian. It is considered well within the skill of the art for one to determine such therapeutically effective amounts by routine experimentation (e.g., a dose escalation clinical trial).

The term "treating" is used to refer to either prophylactic and/or therapeutic treatments.

Non-naturally encoded amino acid polypeptides presented herein may include isotopically-labelled compounds with one or more atoms replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^{2}H$, $^{3}H$, $^{13}C$, $^{14}C$, $^{15}N$, $^{18}O$, $^{17}O$, $^{35}S$, $^{18}F$, $^{36}Cl$, respectively. Certain isotopically-labelled compounds described herein, for example those into which radioactive isotopes such as $^{3}H$ and $^{14}C$ are incorporated, may be useful in drug and/or substrate tissue distribution assays. Further, substitution with isotopes such as deuterium, i.e., $^{2}H$, can afford certain therapeutic advantages resulting from greater metabolic stability, for example increased in vivo half-life or reduced dosage requirements.

All isomers including but not limited to diastereorners, enantiomers, and mixtures thereof are considered as pait of the compositions described herein. In additional or further embodiments, the non-naturally encoded amino acid polypeptides are metabolized upon administration to an organism in need to produce a metabolite that is then used to produce a desired effect, including a desired therapeutic effect. In further or additional embodiments are active metabolites of non-naturally encoded amino acid polypeptides.

In some situations, non-naturally encoded amino acid polypeptides may exist as tautomers. In addition, the non-naturally encoded amino acid polypeptides described herein can exist in unsolvated as well as solvated forms with pharmaceutically acceptable solvents such as water, ethanol, and the like. The solvated forms are also considered to be disclosed herein. Those of ordinary skill in the art will recognize that some of the compounds herein can exist in several tautomeric forms. All such tautomeric forms are considered as part of the compositions described herein.

Unless otherwise indicated, conventional methods of mass spectroscopy, NMR, HPLC, protein chemistry, biochemistry, recombinant DNA techniques and pharmacology, within the skill of the art are employed.

DETAILED DESCRIPTION

I. Introduction b-GCSF molecules comprising at least one unnatural amino acid are provided in the invention. In certain embodiments of the invention, the b-GCSF polypeptide with at least one unnatural amino acid includes at least one post-translational modification. In one embodiment, the at least one post-translational modification comprises attachment of a molecule including but not limited to, hydroxyalkyl starch (HAS), hydroxyethyl starch (HES), a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent a detectable label, a small molecule, a quantum dot, a nanotransmitter, a radionucleotide, a radiotransmitter, a neutron-capture agent, or any combination of the above or any other desirable compound or substance, comprising a second reactive group to at least one unnatural amino acid comprising a first reactive group utilizing chemistry methodology that is known to one of ordinary skill in the art to be suitable for the particular reactive groups. For example, the first reactive group is an alkynyl moiety (including but not limited to, in the unnatural amino acid p-propargyloxyphenylalanine, where the propargyl group is also sometimes referred to as an acetylene moiety) and the second reactive group is an azido moiety, and [3+2] cycloaddition chemistry methodologies are utilized. In another example, the first reactive group is the azido moiety (including but not limited to, in the unnatural amino acid p-azido-L-phenylalanine) and the second reactive group is the alkynyl moiety. In certain embodiments of the modified b-GCSF polypeptide of the present invention, at least one unnatural amino acid (including but not limited to, unnatural amino acid containing a keto functional group) comprising at least one post-translational modification, is used where the at least one post-translational modification comprises a saccharide moiety. In certain embodiments, the post-translational modification is made in vivo in a eukaryotic cell or in a non-eukaryotic cell. A linker, polymer, water soluble polymer, or other molecule may attach the molecule to the polypeptide. The molecule may be linked directly to the polypeptide.

In certain embodiments, the protein includes at least one post-translational modification that is made in vivo by one host cell, where the post-translational modification is not normally made by another host cell type. In certain embodiments, the protein includes at least one post-translational modification that is made in vivo by a eukaryotic cell, where the post-translational modification is not normally made by a non-eukaryotic cell. Examples of post-translational modifications include, but are not limited to, glycosylation, acetylation, acylation, lipid-modification, pahnitoylation, palmitate addition, phosphorylation, glycolipid-linkage modification, and the like.

In some embodiments, the b-GCSF polypeptide comprises one or more non-naturally encoded amino acids for glycosylation, acetylation, acylation, lipid-modification, palmitoylation, palmitate addition, phosphorylation, or glycolipid-linkage modification of the polypeptide. In some embodiments, the b-GCSF polypeptide comprises one or more non-naturally encoded amino acids for glycosylation of the polypeptide. In some embodiments, the b-GCSF polypeptide comprises one or more naturally encoded amino acids for glycosylation, acetylation, acylation, lipid-modification, palmitoylation, palmitate addition, phosphorylation, or glycolipid-linkage modification of the polypeptide. In some embodiments, the b-GCSF polypeptide comprises one or more naturally encoded amino acids for glycosylation of the polypeptide.

In some embodiments, the b-GCSF polypeptide comprises one or more non-naturally encoded amino acid additions and/or substitutions that enhance glycosylation of the polypeptide. In some embodiments, the b-GCSF polypeptide comprises one or more deletions that enhance glycosylation of the polypeptide. In some embodiments, the b-GCSF polypeptide comprises one or more non-naturally encoded amino acid additions and/or substitutions that enhance glycosylation at a different amino acid in the polypeptide. In some embodiments, the b-GCSF polypeptide comprises one or more deletions that enhance glycosylation at a different amino acid in the polypeptide. In some embodiments, the b-GCSF polypeptide comprises one or more non-naturally encoded amino acid additions and/or substitutions that enhance glycosylation at a non-naturally encoded amino acid in the polypeptide. In some embodiments, the b-GCSF polypeptide comprises one or more non-naturally encoded amino acid additions and/or substitutions that enhance glycosylation at a naturally encoded amino acid in the polypeptide. In some embodiments, the b-GCSF polypeptide comprises one or more naturally encoded amino acid additions and/or substitutions that enhance glycosylation at a different amino acid in the polypeptide. In some embodiments, the b-GCSF polypeptide comprises one or more non-naturally encoded amino acid additions and/or substitutions that enhance glycosylation at a naturally encoded amino acid in the polypeptide. In some embodiments, the b-GCSF polypeptide comprises one or more non-naturally encoded amino acid additions and/or substitutions that enhance glycosylation at a non-naturally encoded amino acid in the polypeptide.

In one embodiment, the post-translational modification comprises attachment of an oligosaccharide to an asparagine by a GlcNAc-asparagine linkage (including but not limited to, where the oligosaccharide comprises (GlcNAc-Man) 2-Man-GlcNAc-GlcNAc, and the like). In another embodiment, the post-translational modification comprises attachment of an oligosaccharide (including but not limited to, Gal-GalNAc, Gal-GlcNAc, etc.) to a serine or threonine by a GalNAc-serine, a GalNAc-threonine, a GlcNAc-serine, or a GlcNAc-threonine linkage. In certain embodiments, a protein or polypeptide of the invention can comprise a secretion or localization sequence, an epitope tag, a FLAG tag, a polyhistidine tag, a GST fusion, and/or the like. Examples of secretion signal sequences include, but are not limited to, a prokaryotic secretion signal sequence, a eukaryotic secretion signal sequence, a eukaryotic secretion signal sequence 5'-optimized for bacterial expression, a novel secretion signal sequence, pectate lyase secretion signal sequence, Omp A secretion signal sequence, and a phage secretion signal sequence. Examples of secretion signal sequences, include, but are not limited to, STII (prokaryotic), Fd GIII and M13 (phage), Bgl2 (yeast), and the signal sequence bla derived from a transposon. Any such sequence may be modified to provide a desired result with the polypeptide, including but not limited to, substituting one signal sequence with a different signal sequence, substituting a leader sequence with a different leader sequence, etc.

The protein or polypeptide of interest can contain at least one, at least two, at least three, at least four, at least five, at least six, at least seven, at least eight, at least nine, or ten or more unnatural amino acids. The unnatural amino acids can be the same or different, for example, there can be 1, 2, 3, 4, 5, 6, 7, 8, 9, 10 or more different sites in the protein that comprise 1, 2, 3, 4, 5, 6, 7, 8, 9, 10 or more different unnatural amino acids. In certain embodiments, at least one, but fewer than all, of a particular amino acid present in a naturally occurring version of the protein is substituted with an unnatural amino acid.

The present invention provides methods and compositions based on b-GCSF comprising at least one non-naturally encoded amino acid. Introduction of at least one non-naturally encoded amino acid into b-GCSF can allow for the application of conjugation chemistries that involve specific chemical reactions, including, but not limited to, with one or more non-naturally encoded amino acids while not reacting with the commonly occurring 20 amino acids. In some embodiments, b-GCSF comprising the non-nah1rally encoded amino acid is linked to a water soluble polymer, such as polyethylene glycol (PEG), via the side chain of the non-naturally encoded amino acid. This invention provides a highly efficient method for the selective modification of proteins with PEG derivatives, which involves the selective incorporation of non-genetically encoded amino acids, including but not limited to, those amino acids containing functional groups or substituents not found in the 20 naturally incorporated amino acids, including but not limited to a ketone, an azide or acetylene moiety, into proteins in response to a selector codon and the subsequent modification of those amino acids with a suitably reactive PEG derivative. Once incorporated, the amino acid side chains can then be modified by utilizing chemistry methodologies known to those of ordinary skill in the art to be suitable for the particular functional groups or substituents present in the non-naturally encoded amino acid. Known chemistry methodologies of a wide variety are suitable for use in the present invention to incorporate a water soluble polymer into the protein. Such methodologies include but are not limited to a Huisgen [3+2] cycloaddition reaction (see, e.g., Padwa, A. in *Comprehensive Organic Synthesis*, Vol. 4, (1991) Ed. Trost, B. M., Pergamon, Oxford, p. 1069-1109 and, Huisgen, R. in 1,3-*Dipolar Cycloaddition Chemistry*, (1984) Ed. Padwa, A., Wiley, New York, p. 1-176) with, including but not limited to, acetylene or azide derivatives, respectively.

Because the Huisgen [3+2] cycloaddition method involves a cycloaddition rather than a nucleophilic substitution reaction, proteins can be modified with extremely high selectivity. The reaction can be carried out at room temperature in aqueous conditions with excellent regioselectivity (1,4>1,5) by the addition of catalytic amounts of Cu(I) salts to the reaction mixture. See, e.g., Tomoe, et al., (2002) *J. Org. Chem.* 67:3057-3064; and, Rostovtsev, et al., (2002) *Angew. Chem. Int. Ed.* 41:2596-2599; and WO 03/101972. A molecule that can be added to a protein of the invention through a [3+2] cycloaddition includes virtually any molecule with a suitable functional group or substituent including but not limited to an azido or acetylene derivative. These molecules can be added to fill unnatural amino acid with an acetylene group, including but not limited to, p-propargyloxyphenylalanine, or azido group, including but not limited to p-azido-phenylalanine, respectively.

The five-membered ring that results from the Huisgen [3+2] cycloaddition is not generally reversible in reducing environments and is stable against hydrolysis for extended periods in aqueous environments. Consequently, the physical and chemical characteristics of a wide variety of substances can be modified under demanding aqueous conditions with the active PEG derivatives of the present invention. Even more importantly, because the azide and acetylene moieties are specific for one another (and do not, for example, react with any of the 20 common, genetically-encoded amino acids), proteins can be modified in one or more specific sites with extremely high selectivity.

The invention also provides water soluble and hydrolytically stable derivatives of PEG derivatives and related hydrophilic polymers having one or more acetylene or azide moieties. The PEG polymer derivatives that contain acetylene moieties are highly selective for coupling with azide moieties that have been introduced selectively into proteins in response to a selector codon. Similarly, PEG polymer derivatives that contain azide moieties are highly selective for coupling with acetylene moieties that have been introduced selectively into proteins in response to a selector codon.

More specifically, the azide moieties comprise, but are not limited to, alkyl azides, aryl azides and derivatives of these azides. The derivatives of the alkyl and aryl azides can include other substituents so long as the acetylene-specific reactivity is maintained. The acetylene moieties comprise alkyl and aryl acetylenes and derivatives of each. The derivatives of the alkyl and aryl acetylenes can include other substituents so long as the azide-specific reactivity is maintained.

The present invention provides conjugates of substances having a wide variety of functional groups, substituents or moieties, with other substances including but not limited to hydroxyalkyl starch (HAS); hydroxyethyl starch (HES); a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance. The present invention also includes conjugates of substances having azide or acetylene moieties with PEG polymer derivatives having the corresponding acetylene or azide moieties. For example, a PEG polymer containing an azide moiety can be coupled to a biologically active molecule at a position in the protein that contains a non-genetically encoded amino acid beating an acetylene functionality. The linkage by which the PEG and the biologically active molecule are coupled includes but is not limited to the Huisgen [3+2] cycloaddition product.

It is well established in the art that PEG can be used to modify the surfaces of biomaterials (see, e.g., U.S. Pat. No. 6,610,281; Mehvar, R., J. Phann Pharm Sci., 3 (1): 125-136 (2000) which are incorporated by reference herein). The invention also includes biomaterials comprising a surface having one or more reactive azide or acetylene sites and one or more of the azide- or acetylene-containing polymers of the invention coupled to the surface via the Huisgen [3+2] cycloaddition linkage. Biomaterials and other substances can also be coupled to the azide- or acetylene-activated polymer derivatives through a linkage other than the azide or acetylene linkage, such as through a linkage comprising a carboxylic acid, amine, alcohol or thiol moiety, to leave the azide or acetylene moiety available for subsequent reactions.

The invention includes a method of synthesizing the azide- and acetylene-containing polymers of the invention. In the case of the azide-containing PEG derivative, the azide can be bonded directly to a carbon atom of the polymer. Alternatively, the azide-containing PEG derivative can be prepared by attaching a linking agent that has the azide moiety at one terminus to a conventional activated polymer so that the resulting polymer has the azide moiety at its terminus. In the case of the acetylene-containing PEG derivative, the acetylene can be bonded directly to a carbon atom of the polymer. Alternatively, the acetylene-containing PEG derivative can be prepared by attaching a linking agent that has the acetylene moiety at one terminus to a conventional activated polymer so that the resulting polymer has the acetylene moiety at its terminus.

More specifically, in the case of the azide-containing PEG derivative, a water soluble polymer having at least one active hydroxyl moiety undergoes a reaction to produce a substituted polymer having a more reactive moiety, such as a mesylate, h•esylate, tosylate or halogen leaving group, thereon. The preparation and use of PEG derivatives containing sulfonyl acid halides, halogen atoms and other leaving groups are known to those of ordinary skill in the art. The resulting substituted polymer then undergoes a reaction to substitute for the more reactive moiety an azide moiety at the terminus of the polymer. Alternatively, a water soluble polymer having at least one active nucleophilic or electrophilic moiety undergoes a reaction with a linking agent that has an azide at one terminus so that a covalent bond is formed between the PEG polymer and the linking agent and the azide moiety is positioned at the terminus of the polymer.

Nucleophilic and electrophilic moieties, including amines, thiols, hydrazides, hydrazines, alcohols, carboxylates, aldehydes, ketones, thioesters and the like, are known to those of ordinary skill in the art.

More specifically, in the case of the acetylene-containing PEG derivative, a water soluble polymer having at least one active hydroxyl moiety undergoes a reaction to displace a halogen or other activated leaving group from a precursor that contains an acetylene moiety. Alternatively, a water soluble polymer having at least one active nucleophilic or electrophilic moiety undergoes a reaction with a linking agent that has an acetylene at one terminus so that a covalent bond is formed between the PEG polymer and the linking agent and the acetylene moiety is positioned at the terminus of the polymer. The use of halogen moieties, activated leaving group, nucleophilic and electrophilic moieties in the context of organic synthesis and the preparation and use of PEG derivatives is well established to practitioners in the art.

The invention also provides a method for the selective modification of proteins to add other substances to the modified protein, including but not limited to water soluble polymers such as PEG and PEG derivatives containing an azide or acetylene moiety. The azide- and acetylene containing PEG derivatives can be used to modify the properties of surfaces and molecules where biocompatibility, stability, solubility and lack of immunogenicity are important, while at the same time providing a more selective means of attaching the PEG derivatives to proteins than was previously known in the art.

II. Bovine GCSF bG-CSF polypeptides of the invention may be used to ameliorate or prevent infections in animals. The biological activities as well as the assays to characterize the biological activities of bovine and human G-CSF are known to one of ordinary skill in the art. Assays that involve an assessment of neutrophil number and neutrophil function are known to one of ordinary skill in the art.

III. General Recombinant Nucleic Acid Methods for Use with the Invention

In numerous embodiments of the present invention, nucleic acids encoding a bG-CSF polypeptide of interest will be isolated, cloned and often altered using recombinant methods. Such embodiments are used, including but not limited to, for protein expression or during the generation of variants, derivatives, expression cassettes, or other sequences derived from a bG-CSF polypeptide. In some embodiments, the sequences encoding the polypeptides of the invention are operably linked to a heterologous promoter. Isolation of hG-CSF and production of G-CSF in host cells are described in, e.g., U.S. Pat. Nos. 4,810,643; 4,999,291; 5,580,755; and 6,716,606, which are incorporated by reference herein.

A nucleotide sequence encoding a bG-CSF polypeptide comprising a non-naturally encoded amino acid may be synthesized on the basis of the amino acid sequence of the parent polypeptide, including but not limited to, having the amino acid sequence shown in SEQ ID NO: 1, 2 and then changing the nucleotide sequence so as to effect introduction (i.e., incorporation or substitution) or removal (i.e., deletion or substitution) of the relevant amino acid residue(s). The nucleotide sequence may be conveniently modified by site-directed mutagenesis in accordance with conventional methods. Alternatively, the nucleotide sequence may be prepared by chemical synthesis, including but not limited to, by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction. See, e.g., Barany, et al., *Proc. Natl. Acad. Sci.* 88:189-193 (1991); U.S. Pat. No. 6,521,427 which are incorporated by reference herein.

This invention utilizes routine techniques in the field of recombinant genetics. Basic texts disclosing the general methods of use in this invention include Sambrook et al., *Molecular Cloning, A Laboratory Manual* (3rd ed. 2001); Kriegler, Gene *Transfer and Expression: A Laboratory Manual* (1990); and *Current Protocols in Molecular Biology* (Ausubel et al., eds., 1994)).

General texts which describe molecular biological techniques include Berger and Kimmel, *Guide to Molecular Cloning Techniques, Methods in Enzymology* volume 152 Academic Press, Inc., San Diego, CA (Berger); Sambrook et al., *Molecular Cloning—A Laboratory Manual* (2nd Ed.), Vol. 1-3, Cold Spring Harbor Laboratory, Cold Spring Harbor, New York, 1989 ("Sambrook") and *Current Protocols in Molecular Biology*, F. M. Ausubel et al., eds., *Current Protocols, a joint venture between* Greene Publishing Associates, Inc. and John Wiley & Sons, Inc., (supplemented through 1999) ("Ausubel")). These texts describe mutagenesis, the use of vectors, promoters and many other relevant topics related to, including but not limited to, the generation of genes or polynucleotides that include selector codons for production of proteins that include unnatural amino acids, orthogonal tRNAs, orthogonal synthetases, and pairs thereof.

Various types of mutagenesis are used in the invention for a variety of purposes, including but not limited to, to produce novel synthetases or tRNAs, to mutate tRNA molecules, to mutate polynucleotides encoding synthetases, to produce libraries of tRNAs, to produce libraries of synthetases, to produce selector codons, to insert selector codons that encode unnatural amino acids in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, PCT-mediated mutagenesis, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, including but not limited to, involving chimeric constructs, are also included in the present invention. In one embodiment, mutagenesis can be guided by known information of the naturally occurring molecule or altered or mutated naturally occurring molecule, including but not limited to, sequence, sequence comparisons, physical properties, secondary, tertiary, or quaternary structure, crystal structure or the like.

The texts and examples found herein describe these procedures. Additional information is found in the following publications and references cited within: Ling et al., *Approaches to DNA mutagenesis: an overview, Anal Biochem.* 254 (2): 157-178 (1997); Dale et al., *Oligonucleotide-directed random mutagenesis using the phosphorothioate method, Methods Mol. Biol.* 57:369-374 (1996); Smith, *In vitro mutagenesis, Ann. Rev. Genet.* 19:423-462 (1985); *Botstein & Shortle, Strategies and applications of in*

*vitro mutagenesis, Science* 229:1193-1201 (1985); Carter, *Site-directed mutagenesis, Biochem. J.* 237:1-7 (1986); Kunkel, *The efficiency of oligonucleotide directed mutagenesis, in Nucleic Acids & Molecular Biology* (Eckstein, F. and Lilley, D. M. J. eds., Springer Verlag, Berlin) (1987); Kunkel, *Rapid and efficient site-specific mutagenesis without phenotypic selection, Proc. Natl. Acad. Sci. USA* 82:488-492 (1985); Kunkel et al., *Rapid and efficient site-specific mutagenesis without phenotypic selection, Methods in Enzymol.* 154, 367-382 (1987); Bass et al., *Mutant Trp repressors with new DNA-binding specificities, Science* 242:240-245 (1988); Zoller & Smith, *Oligonucleotide-directed mutagenesis using Ml 3-derived vectors: an efficient and general procedure for the production of point mutations in any DNA fragment, Nucleic Acids Res.* 10:6487-6500 (1982); Zoller & Smith, *Oligonucleotide-directed mutagenesis of DNA fragments cloned into MJ3 vectors, Methods in Enzymol.* 100: 468-500 (1983); Zoller & Smith, *Oligonucleotide-directed mutagenesis: a simple method using two oligonucleotide primers and a single-stranded DNA template, Methods in Enzymol.* 154:329-350 (1987); Taylor et al., *The use of phosphorothioate-modified DNA in restriction enzyme reactions to prepare nicked DNA, Nucl. Acids Res.* 13:8749-8764 (1985); Taylor et al., The rapid generation of oligonucleotide-directed mutations at high frequency using phosphorothioate-modified DNA, *Nucl. Acids Res.* 13:8765-8785 (1985); Nakamaye & Eckstein, *Inhibition of restriction endonuclease Nci I cleavage by phosphorothioate groups and its application to oligonucleotide-directed mutagenesis, Nucl. Acids Res.* 14:9679-9698 (1986); Sayers et al., 5'-3' Exonucleases in phosphorothioate-based oligonucleotide-directed mutagenesis, *Nucl. Acids Res.* 16:791-802 (1988); Sayers et al., *Strand specific cleavage of phosphorothioate-containing DNA by reaction with restriction endonucleases in the presence of ethidium bromide*, (1988) *Nucl. Acids Res.* 16:803-814; Kramer et al., *The gapped duplex DNA approach to oligonucleotide-directed mutation construction, Nucl. Acids Res.* 12:9441-9456 (1984); Kramer & Fritz *Oligonucleotide-directed construction of mutations via gapped duplex DNA, Methods in Enzymol.* 154:350-367 (1987); Kramer et al., *Improved enzymatic in vitro reactions in the gapped duplex DNA approach to oligonucleotide-directed construction of mutations, Nucl. Acids Res.* 16:7207 (1988); Fritz et al., *Oligonucleotide-directed construction of mutations: a gapped duplex DNA procedure without enzymatic reactions in vitro, Nucl. Acids Res.* 16:6987-6999 (1988); Kramer et al., *Different base/base mismatches are corrected with different efficiencies by the methyl-directed DNA mismatch-repair system of E. coli, Cell* 38:879-887 (1984); Carter et al., *Improved oligonucleotide site-directed mutagenesis using M13 vectors, Nucl. Acids Res.* 13:4431-4443 (1985); Caiter, *Improved oligonucleotide-directed mutagenesis using MJ3 vectors, Methods in Enzyrnol.* 154: 382-403 (1987); Eghtedarzadch & Henikoff, *Use of oligonucleotides to generate large deletions, Nucl. Acids Res.* 14:5115 (1986); Wells et al., *Importance of hydrogen-bond formation in stabilizing the transition state of subtilisin, Phil. Trans. R. Soc. Lond. A* 317:415-423 (1986); Nambiar et al., *Total synthesis and cloning of a gene coding for the ribonuclease S protein, Science* 223:1299-1301 (1984); Sakrnar and Khorana, *Total synthesis and expression of a gene for the alpha-subunit of bovine rod outer segment guanine nucleotide-binding protein (transducin), Nucl. Acids Res.* 14:6361-6372 (1988); Wells et al., *Cassette mutagenesis: an efficient method for generation of multiple mutations at defined sites, Gene* 34:315-323 (1985); Grundstrom et al., *Oligonucleotide-directed mutagenesis by microscale 'shot-gun' gene synthesis, Nucl. Acids Res.* 13:3305-3316 (1985); Mandecki, *Oligonucleotide-directed double-strand break repair in plasmids of Escherichia coli: a method for site-specific mutagenesis, Proc. Natl. Acad. Sci. USA,* 83:7177-7181 (1986); Arnold, *Protein engineering for unusual environments, Current Opinion in Biotechnology* 4:450-455 (1993); Sieber, et al., *Nature Biotechnology,* 19:456-460 (2001); W. P. C. Stemmer, *Nature* 370, 389-91 (1994); and, I. A. Lorimer, I. Pastan, *Nucleic Acids Res.* 23, 3067-8 (1995). *Additional details on many of the above methods can be found in Methods in Enzymology* Volume 154, which also describes useful controls for trouble-shooting problems with various mutagenesis methods.

Oligonucleotides, e.g., for use in mutagenesis of the present invention, e.g., mutating libraries of synthetases, or altering tRNAs, are typically synthesized chemically according to the solid phase phosphoramidite triester method described by Beaucage and Caruthers, Tetrahedron Letts. 22 (20): 1859-1862, (1981) e.g., using an automated synthesizer, as described in Needham-VanDevanter et al., Nucleic Acids Res., 12:6159-6168 (1984).

The invention also relates to eukaryotic host cells, non-eukaryotic host cells, and organisms for the in vivo incorporation of an unnatural amino acid via orthogonal tRNA/RS parrs. Host cells are genetically engineered (including but not limited to, transformed, transduced or transfected) with the polynucleotides of the invention or constructs which include a polynucleotide of the invention, including but not limited to, a vector of the invention, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. The vector can be, for example, in the form of a plasmid, a cosmid, a phage, a bacterium, a virus, a naked polynucleotide, or a conjugated polynucleotide. The vectors are introduced into cells and/or microorganisms by standard methods including electroporation (Fromm et al., *Proc. Natl. Acad. Sci. USA* 82, 5824 (1985)), infection by viral vectors, high velocity ballistic penetration by small particles with the nucleic acid either within the matrix of small beads or particles, or on the surface (Klein et al., *Nature* 327, 70-73 (1987)), and/or the like. Techniques suitable for the transfer of nucleic acid into cells in vitro include the use of liposomes, microinjection, cell fusion, DEAE-dextran, the calcium phosphate precipitation method, etc. In vivo gene transfer techniques include, but are not limited to, transfection with viral (typically retroviral) vectors and viral coat protein-liposome mediated transfection [Dzau et al., Trends in Biotechnology 11:205-210 (1993)]. In some situations it may be desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life.

The engineered host cells can be cultured in conventional nutrient media modified as appropriate for such activities as, for example, screening steps, activating promoters or selecting transformants. These cells can optionally be cultured into transgenic organisms. Other useful references, including but not limited to for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, NY; Gamborg and Phillips (eds.) (1995) *Plant Cell, Tissue and Organ Culture*; Fundamental Methods Springer Lab Manual, Springer-Verlag (Berlin Heidelberg New York) and Atlas and Parks (eds.) *The Handbook of Microbiological Media* (1993) CRC Press, Boca Raton, FL.

Several well-known methods of introducing target nucleic acids into cells are available, any of which can be used in the invention. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, kits are commercially available for the purification of plasmids from bacteria, (see, e.g., EasyPrep™, FlexiPrep™, both from Pharmacia Biotech; StrataClean™ from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (including but not limited to, shuttle vectors) and selection markers for both prokaryotic and eukaryotic systems. Vectors are suitable for replication and integration in prokaryotes, eukaryotes, or both. See, Gillam & Smith, *Gene* 8:81 (1979); Roberts, et al., *Nature,* 328:731 (1987); Schneider, E., et al., *Protein Expr. Purif.* 6 (1): 10-14 (1995); Ausubel, Sambrook, Berger (all supra). A catalogue of bacteria and bacteriophages useful for cloning is provided, e.g., by the ATCC, e.g., *The ATCC Catalogue of Bacteria and Bacteriophage* (1992) Ghema et al. (eds) published by the ATCC. Additional basic procedures for sequencing, cloning and other aspects of molecular biology and underlying theoretical considerations are also found in Watson et al. (1992) *Recombinant DNA Second Edition* Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, TX available on the World Wide Web at mere.com), The Great American Gene Company (Ramona, CA available on the World Wide Web at genco.com), ExpressGen Inc. (Chicago, IL available on the World Wide Web at expressgen.com), Operon Technologies Inc. (Alameda, CA) and many others.

Selector Codons

Selector codons of the invention expand the genetic codon framework of protein biosynthetic machinery. For example, a selector codon includes, but is not limited to, a unique three base codon, a nonsense codon, such as a stop codon, including but not limited to, an amber codon (UAG), ml ochre codon, or an opal codon (UGA), an unnatural codon, a four or more base codon, a rare codon, or the like. It is readily apparent to those of ordinary skill in the art that there is a wide range in the number of selector codons that can be introduced into a desired gene or polynucleotide, including but not limited to, one or more, two or more, three or more, 4, 5, 6, 7, 8, 9, 10 or more in a single polynucleotide encoding at least a portion of the bG-CSF polypeptide.

In one embodiment, the methods involve the use of a selector codon that is a stop codon for the incorporation of one or more unnatural amino acids in vivo. For example, an O-tRNA is produced that recognizes the stop codon, including but not limited to, UAG, and is aminoacylated by an O—RS with a desired unnatural amino acid. This O-tRNA is not recognized by the naturally occurring host's aminoacyl-tRNA synthetases. Conventional site-directed mutagenesis can be used to introduce the stop codon, including but not limited to, TAG, at the site of interest in a polypeptide of interest. See, e.g., Sayers, J. R., et al. (1988), 5'-3′ *Exonucleases in phosphorothioate-based oligonucleotide-directed mutagenesis. Nucleic Acids Res,* 16:791-802. When the O-RS, O-tRNA and the nucleic acid that encodes the polypeptide of interest are combined in vivo, the unnatural amino acid is incorporated in response to the UAG codon to give a polypeptide containing the unnatural amino acid at the specified position.

The incorporation of unnatural amino acids in vivo can be done without significant perturbation of the eukaryotic host cell. For example, because the suppression efficiency for the UAG codon depends upon the competition between the O-tRNA, including but not limited to, the amber suppressor tRNA, and a eukaryotic release factor (including but not limited to, eRF) (which binds to a stop codon and initiates release of the growing peptide from the ribosome), the suppression efficiency can be modulated by, including but not limited to, increasing the expression level of O-tRNA, and/or the suppressor tRNA.

Unnatural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., *Biochemistry,* 32:7939 (1993). In this case, the synthetic tRNA competes with the naturally occurring RNAArg, which exists as a minor species in *Escherichia coli*. Some organisms do not use all triplet codons. An unassigned codon AGA in *Micrococcus luteus* has been utilized for insertion of amino acids in an in vitro transcription/translation extract. See, e.g., Kowal and Oliver, *Nucl. Acid. Res.,* 25:4685 (1997). Components of the present invention can be generated to use these rare codons in vivo.

Selector codons also comprise extended codons, including but not limited to, four or more base codons, such as, four, five, six or more base codons. Examples of four base codons include, but are not limited to, AGGA, CUAG, UAGA, CCCU and the like. Examples of five base codons include, but are not limited to, AGGAC, CCCCU, CCCUC, CUAGA, CUACU, UAGGC and the like. A feature of the invention includes using extended codons based on frameshift suppression. Four or more base codons can insert, including but not limited to, one or multiple unnatural amino acids into the same protein. For example, in the presence of mutated O-tRNAs, including but not limited to, a special frameshift suppressor tRNAs, with anticodon loops, for example, with at least 8-10 nt anticodon loops, the four or more base codon is read as single amino acid. In other embodiments, the anticodon loops can decode, including but not limited to, at least a four-base codon, at least a five-base codon, or at least a six-base codon or more. Since there are 256 possible four-base codons, multiple unnatural amino acids can be encoded in the same cell using a four or more base codon. See, Anderson et al., (2002) *Exploring the Limits of Codon and Anticodon Size, Chemistry and Biology,* 9:237-244; Magliery, (2001) *Expanding the Genetic Code: Selection of Efficient Suppressors of Four-base Codons and Identification of "Shifty" Four-base Codons with a Library Approach in Escherichia coli, J. Mol. Biol.* 307:755-769.

For example, four-base codons have been used to incorporate unnatural amino acids into proteins using in vitro biosynthetic methods. See, e.g., Ma et al., (1993) *Biochemistry.* 32:7939; and Hohsaka et al., (1999) *J. Am. Chem. Soc.,* 121:34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.,* 121:12194. In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with an efficiency of 13 to 26% with little decoding in the 0 or −1 frame. See, Moore et al., (2000) *J. Mol. Biol.,* 298:195. In one embodiment, extended codons based on rare codons or nonsense codons can be used in the present invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for inc01porating amino acid analogues into protein, Nature Biotechnology,* 20:177-182. Sec, also, Wu, Y., et al., (2002) *J. Am. Chem. Soc.* 124:14626-14630. Other relevant publications are listed below.

For in vivo usage, the unnatural nucleoside is membrane permeable and is phosphorylated to form the corresponding tdphosphate. In addition, the increased genetic information is stable and not destroyed by cellular enzymes. Previous efforts by Benner and others took advantage of hydrogen bonding patterns that are different from those in canonical Watson-Ctick pairs, the most noteworthy example of which is the iso-C: iso-G pair. See, e.g., Switzer et al., (1989) *J. Am. Chem. Soc.,* 111:8322; and Piccirilli et al., (1990) Nature, 343:33; Kool, (2000) *Curr. Opin. Chem. Biol.,* 4:602. These bases in general mispair to some degree with natural bases and cannot be enzymatically replicated. Kool and co-workers demonstrated that hydrophobic packing interactions between bases can replace hydrogen bonding to drive the formation of base pair. See, Kool, (2000) *Curr. Opin. Chem. Biol.,* 4:602; and Guckian and Kool, (1998) *Angew. Chem. Int. Ed. Engl.,* 36, 2825. In an effort to develop an unnatural base pair satisfying all the above requirements, Schultz, Romesberg and co-workers have systematically synthesized and studied a series of unnatural hydrophobic bases. A PICS: PICS self-pair is found to be more stable than natural base pairs, and can be efficiently incorporated into DNA by Klenow fragment of *Eschelichia coli* DNA polymerase I (KF). See, e.g., McMinn et al., (1999) *J. Am. Chem. Soc.,* 121:11585-6; and Ogawa et al., (2000) *J. Am. Chem. Soc.,* 122:3274. A 3 MN:3 MN self-pair can be synthesized by KF with efficiency and selectivity sufficient for biological function. See, e.g., Ogawa et al., (2000) *J. Am. Chem. Soc.,* 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.,* 123:7439. A novel metallobase pair, Dipic:Py, has also been developed, which forms a stable pair upon binding Cu(II). See, Meggers et al., (2000) *J. Am. Chem. Soc.,* 122:10714. Because extended codons and unnatural codons are intrinsically orthogonal to natural codons, the methods of the invention can take advantage of this property to generate orthogonal tRNAs for them.

A translational bypassing system can also be used to incorporate an unnatural amino acid in a desired polypeptide. In a translational bypassing system, a large sequence is incorporated into a gene but is not translated into protein. The sequence contains a structure that serves as a cue to induce the ribosome to hop over the sequence and resume translation downstream of the insertion.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods known to one of ordinary skill in the ait and described herein to include, for example, one or more selector codon for the incorporation of an unnatural amino acid. For example, a nucleic acid for a protein of interest is mutagenized to include one or more selector codon, providing for the incorporation of one or more unnatural amino acids. The invention includes any such variant, including but not limited to, mutant, versions of any protein, for example, including at least one unnatural amino acid. Similarly, the invention also includes corresponding nucleic acids, i.e., any nucleic acid with one or more selector codon that encodes one or more unnatural amino acid.

Nucleic acid molecules encoding a protein of interest such as a bG-CSF polypeptide may be readily mutated to introduce a cysteine at any desired position of the polypeptide. Cysteine is widely used to introduce reactive molecules, water soluble polymers, proteins, or a wide variety of other molecules, onto a protein of interest. Methods suitable for the incorporation of cysteine into a desired position of a polypeptide are known to those of ordinary skill in the art, such as those described in U.S. Pat. No. 6,608,183, which is incorporated by reference herein, and standard mutagenesis techniques.

IV. Non-Naturally Encoded Amino Acids

A very wide variety of non-naturally encoded amino acids are suitable for use in the present invention. Any number of non-naturally encoded amino acids can be introduced into a bG-CSF polypeptide. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, a bG-CSF polypeptide that includes a non-naturally encoded amino acid containing an azido functional group can be reacted with a polymer (including but not limited to, poly(ethylene glycol) or, alternatively, a second polypeptide containing an alkyne moiety to form a stable conjugate resulting for the selective reaction of the azide and the alkyne functional groups to form a Huisgen [3+2] cycloaddition product.

The generic structure of an alpha-amino acid is illustrated as follows (Formula I):

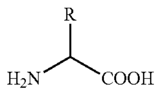

I

A non-naturally encoded amino acid is typically any structure having the above-listed formula wherein the R group is any substituent other than one used in the twenty natural amino acids, and may be suitable for use in the present invention. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxyalanine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to nah1ral amino acids, including but not limited to, polyethers or long chain hydrocarbons, including but not limited to, greater than about 5 or greater than about 10 carbons, carbon-linked sugar-containing amino acids, redox active amino acids, amino thioacid containing amino acids, and amino acids comprising one or more toxic moiety.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature-including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, MO, USA), Novabiochem (a division of EMD Biosciences, Darmstadt, Germany), or Peptech (Burlington, MA, USA). Those that are not commercially available are optionally synthesized as provided herein or using standard methods known to those of ordinary skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (*Third Edition,* 1985, *Wiley and Sons*, New York); and *Advanced Organic Chemistry* by Carey and Sundberg (Tirird Edition, *Parts A and B,* 1990, Plenum Press, New York). See, also, U.S. Pat. Nos. 7,045,337 and 7,083,970, which are incorporated by reference herein. In addition to unnatural amino acids that contain novel side chains, unnatural amino acids that may be suitable for use in the present invention also optionally comprise modified backbone structures, including but not limited to, as illustrated by the structures of Formula II and III:

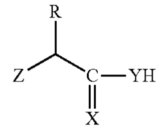

II

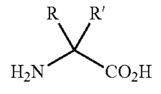

III wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as praline analogues as well as 3, 4, 6, 7, 8, and 9 membered ring praline analogues, β and γ amino acids such as substituted β-alamine and γ-amino butyric acid.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenyalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl) alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a $_p$-acyl-L-phenylalanine, a $_p$-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002) *Incorporation of azides into recombinant proteins for chemoselective modification by the Staudinger ligation, PNAS* 99:19-24, which is incorporated by reference herein, for additional methionine analogs. International Application No. PCT/US06/47822 entitled "Compositions Containing, Methods Involving, and Uses of Non-natural Amino Acids and Polypeptides," which is incorporated by reference herein, describes reductive alkylation of an aromatic amine moieties, including but not limited to, p-amino-phenylalanine and reductive amination.

In one embodiment, compositions of a bG-CSF polypeptide that include an unnatural amino acid (such as p-(propargyloxy)-phenyalanine) are provided. Various compositions comprising p-(propargyloxy)-phenyalanine and, including but not limited to, proteins and/or cells, are also provided. In one aspect, a composition that includes the p-(propargyloxy)-phenyalanine unnatural amino acid, further includes an orthogonal tRNA. The unnatural amino acid can be bonded (including but not limited to, covalently) to the orthogonal tRNA, including but not limited to, covalently bonded to the orthogonal tRNA though an aminoacyl bond, covalently bonded to a 3'OH or a 2'OH of a terminal ribose sugar of the othogonal tRNA, etc.

The chemical moieties via unnatural amino acids that can be incorporated into proteins offer a variety of advantages and manipulations of the protein. For example, the unique reactivity of a keto functional group allows selective modification of proteins with any of a number of hydrazine- or hydroxylamine-containing reagents in vitro and in vivo. A heavy atom unnatural amino acid, for example, can be useful for phasing X-ray structure data. The site-specific introduction of heavy atoms using unnatural amino acids also provides selectivity and flexibility in choosing positions for heavy atoms. Photoreactive unnatural amino acids (including but not limited to, amino acids with benzophenone and arylazides (including but not limited to, phenylazide) side chains), for example, allow for efficient in vivo and in vitro photocrosslinking of protein. Examples of photoreactive unnatural amino acids include, but are not limited to, p-azido-phenylalanine and p-benzoyl-phenylalanine. The protein with the photoreactive unnatural amino acids can then be crosslinked at will by excitation of the photoreactive group-providing temporal control. In one example, the methyl group of an unnatural amino can be substituted with an isotopically labeled, including but not limited to, methyl group, as a probe of local structure and dynamics, including but not limited to, with the use of nuclear magnetic resonance and vibrational spectroscopy. Alkynyl or azido functional groups, for example, allow the selective modification of proteins with molecules through a [3+2] cycloaddition reaction.

A non-natural amino acid incorporated into a polypeptide at the amino terminus can be composed of an R group that is any substituent other than one used in the twenty natural amino acids and a $2^{nd}$ reactive group different from the $NH_2$ group normally present in a-amino•acids (see Formula I). A similar non-natural amino acid can be incorporated at the carboxyl terminus with a $2^{nd}$ reactive group different from the COOH group normally present in a-amino acids (see Formula 1).

The unnatural amino acids of the invention may be selected or designed to provide additional characteristics unavailable in the twenty natural amino acids. For example, unnatural amino acid may be optionally designed or selected to modify the biological properties of a protein, e.g., into which they are incorporated. For example, the following properties may be optionally modified by inclusion of an unnatural amino acid into a protein: toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, redox potential, half-life, ability to react with other molecules, e.g., covalently or noncovalently, and the like.

Structure and Synthesis of Non-Natural Amino Acids: Carbonyl, Carbonyl-Like, Masked Carbonyl, Protected Carbonyl Groups, and Hydroxylamine Groups In some embodiments the present invention provides bG-CSF linked to a water soluble polymer, e.g., a PEG, by an oxime bond, Many types of non-naturally encoded amino acids are suitable for formation of oxime bonds. These include, but are not limited to, non-naturally encoded amino acids containing a carbonyl, dicarbonyl, or hydroxylamine group. Such amino acids are described in U.S. Patent Publication Nos. 2006/0194256, 2006/0217532, and 2006/0217289 and WO 2006/069246 entitled "Compositions containing, methods involving, and uses of non-natural amino acids and polypeptides," which are incorporated herein by reference in their entirety. Non-naturally encoded amino acids are also described in U.S. Pat. Nos. 7,083,970 and 7,045,337, which are incorporated by reference herein in their entirety.

Some embodiments of the invention utilize bG-CSF polypeptides that are substituted at one or more positions with a para-acetylphenylalanine amino acid. The synthesis of p-acetyl-(+/−)-phenylalanine and m-acetyl-(+/−)-phenylalanine are described in Zhang, Z., et al., Biochemistry 42:6735-6746 (2003), incorporated by reference. Other carbonyl- or dicarbonyl-containing amino acids can be similarly prepared by one of ordinary skill in the art. Further, non-limiting exemplary syntheses of non-natural amino acid that are included herein are presented in FIGS. 4, 24-34 and 36-39 of U.S. Pat. No. 7,083,970, which is incorporated by reference herein in its entirety.

Amino acids with an electrophilic reactive group allow for a variety of reactions to link molecules via nucleophilic addition reactions among others. Such electrophilic reactive groups include a carbonyl group (including a keto group and a dicarbonyl group), a carbonyl-like group (which has reactivity similar to a carbonyl group (including a keto group and a dicarbonyl group) and is structurally similar to a carbonyl group), a masked carbonyl group (which can be readily converted into a carbonyl group (including a keto group and a dicarbonyl group)), or a protected carbonyl group (which has reactivity similar to a carbonyl group (including a keto group and a dicarbonyl group) upon deprotection). Such amino acids include amino acids having the structure of Formula (IV):

(IV)

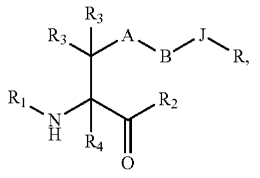

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)k (alkylene or substituted alkylene)-, —C(O)—, —C(O)-

(alkylene or substituted alkylene)-, —C(S)—, —C(S)— (alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO— (alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

J is

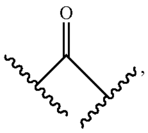, 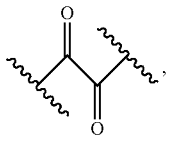, 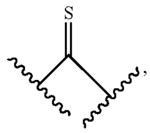,

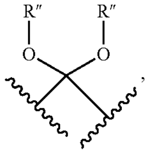, 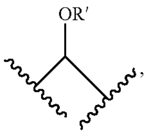, 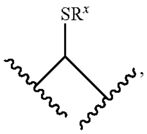,

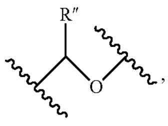, or 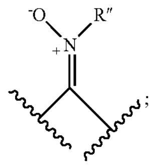;

R is H, alkyl, substituted alkyl, cycloalkyl, or substituted cycloalkyl;

each R" is independently H, alkyl, substituted alkyl, or a protecting group, or when more than one R" group is present, two R" optionally from a heterocycloalkyl;

$R_1$ is optional, and when present, is H, an amino protecting group, resm, amino acid, polypeptide, or polynucleotide; and $R_2$ is optional, and when present, is OH, an ester protecting group, resm, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

or the -A-B-J-R groups together form a bicyclic or tricyclic cycloalkyl or heterocycloalkyl comprising at least one carbonyl group, including a dicarbonyl group, protected carbonyl group, including a protected dicarbonyl group, or masked carbonyl group, including a masked dicarbonyl group;

or the -J-R group together forms a monocyclic or bicyclic cycloalkyl or heterocycloalkyl comprising at least one carbonyl group, including a dicarbonyl group, protected carbonyl group, including a protected dicarbonyl group, or masked carbonyl group, including a masked dicarbonyl group;

with a proviso that when A is phenylene and each $R_3$ is H, B is present; and that when A is —$(CH_2)_4$— and each $R_3$ is H, B is not —$NHC(O)(CH_2CH_2)$—; and that when A and Bare absent and each $R_3$ is H, R is not methyl.

In addition, having the structure of Formula (V) are included:

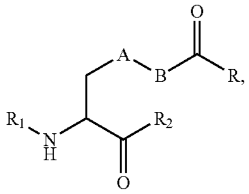

(V)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —$S(O)_k$— where k is 1, 2, or 3, —$S(O)_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —$S(O)_k$N(R')—, —N(R')C(O)N(R')—, —N(R')C(S)N(R')—, —N(R')$S(O)_k$N(R')—, —N(R')—N═, —C(R')═N—, —C(R')═N—N(R')—, —C(R')═N—N═, —$C(R')_2$—N═N—, and —$C(R')_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resm, amino acid, polypeptide, or polynucleotide; and $R_2$ is optional, and when present, is OH, an ester protecting group, resm, amino acid, polypeptide, or polynucleotide;

with a proviso that when A is phenylene, B is present; and that when A is —$(CH_2)_4$—, B is not —NHC(O)($CH_2CH_2$)—; and that when A and Bare absent, R is not methyl.

In addition, amino acids having the structure of Formula (VI) are included:

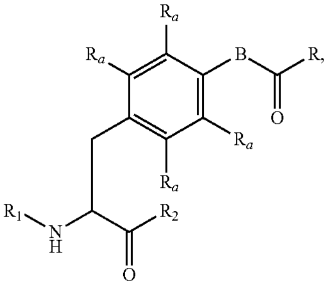

(VI)

wherein:

B is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —$S(O)_k$— where k is 1, 2, or 3, —S(O)k(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —$S(O)_k$N(R')—, —N(R')C(O)N(R')—, —N(R')C(S) N(R')—, —N(R')S$(O)_k$N(R')—, —N(R')—N═, —C(R')═N—, —C(R')═N—N(R')—, —C(R')═N—N═, —$C(R')_2$—N═N—, and —$C(R')_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resm, amino acid, polypeptide, or polynucleotide;

each $R_a$ is independently selected from the group consisting of H, halogen, alkyl, substituted alkyl, —$N(R')_2$, —$C(O)_k$R' where k is 1, 2, or 3, —$C(O)N(R')_2$, —OR', and —$S(O)_k$R', where each R' is independently H, alkyl, or substituted alkyl.

In addition, the following amino acids are included:

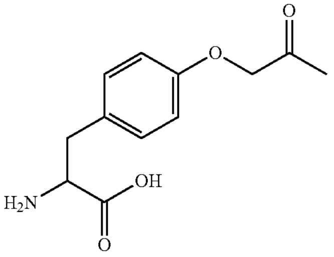

,

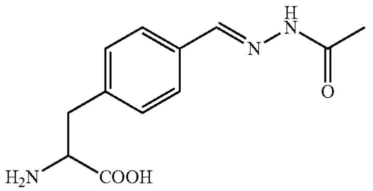

,

-continued

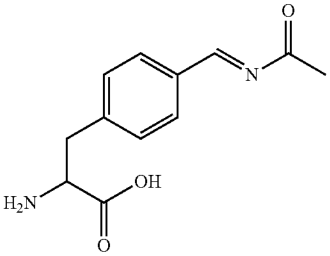

,

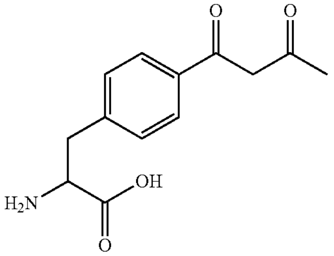

,

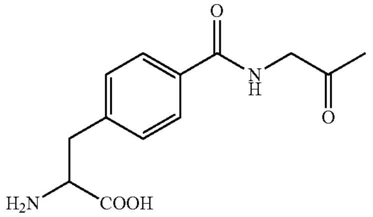

,

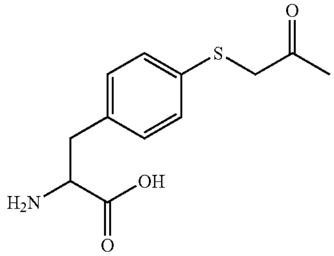

,

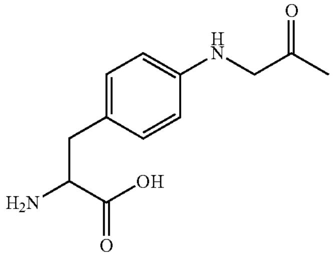

, and

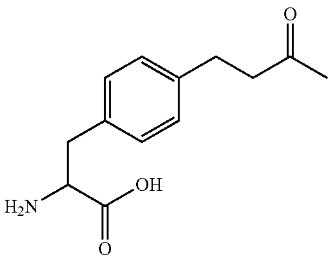

, wherein such compounds are optionally amino protected group, carboxyl protected or a salt thereof. In addition, any of the following non-natural amino acids may be incorporated into a non-natural amino acid polypeptide.

In addition, the following amino acids having the structure of Formula (VII) are included:

(VII)

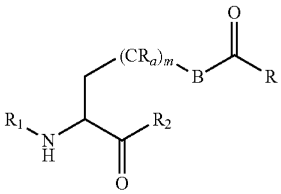

wherein

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, $—S(O)_k—$ where k is 1, 2, or 3, —S(O)k (alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN (R')—, —CSN(R')-(alkylene or substituted alkylene)-, —N(R')CO-(alkylene or substituted alkylene)-, —N(R')C(O)O—, $—S(O)_kN(R')—$, —N(R')C(O)N (R')—, —N(R')C(S)N(R')—, $—N(R')S(O)_kN(R')—$, —N(R')—N═, —C(R')═N—, —C(R')═N—N (R')—, —C(R')═N—N═, $—C(R')_2—N═N—$, and $—C(R')_2—N(R')—N(R')—$, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

each Ra is independently selected from the group consisting of H, halogen, alkyl, substituted alkyl, $—N(R')_2$, $—C(O)_kR'$ where k is 1, 2, or 3, $—C(O)N(R')_2$, —OR', and $—S(O)_kR'$, where each R' is independently H, alkyl, or substituted alkyl; and n is 0 to 8;

with a proviso that when A is $—(CH_2)_4—$, B is not $—NHC(O)(CH_2CH_2)—$.

In addition, the following amino acids are included:

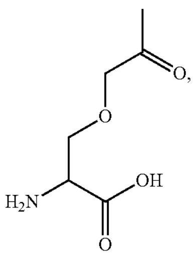

,

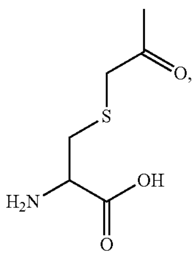

,

-continued

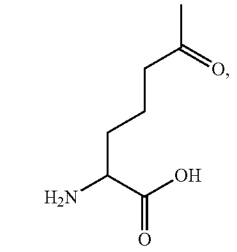

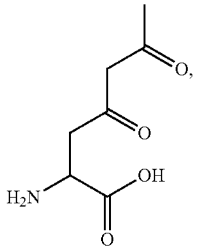

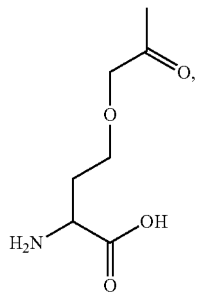

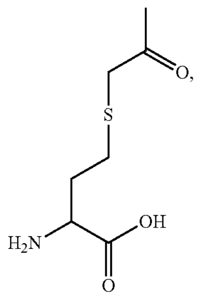

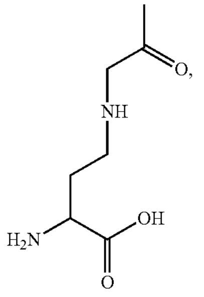

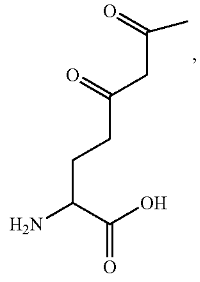

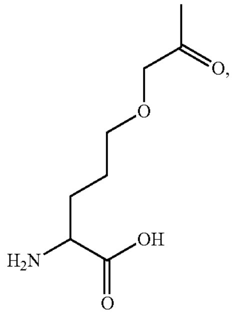

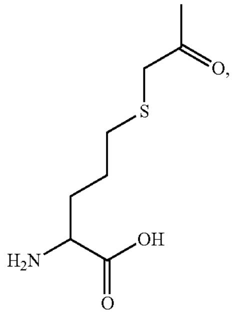

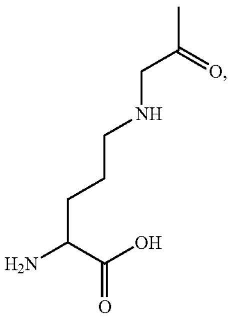

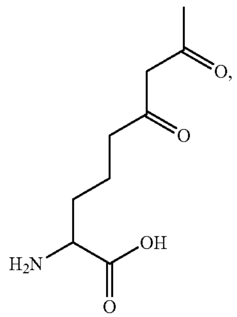

-continued

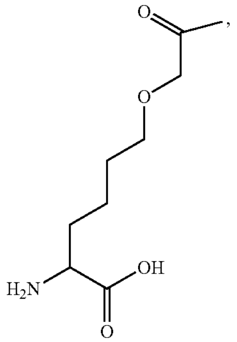

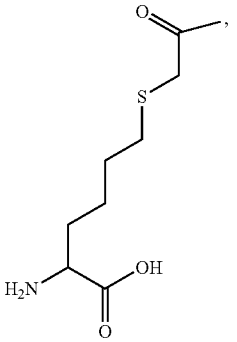

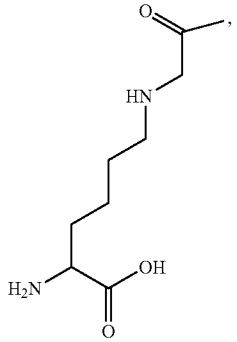

and

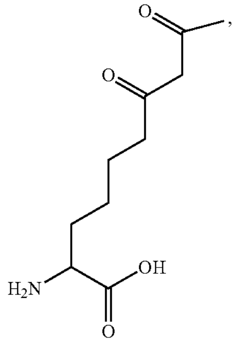

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (VIII) are included:

(VIII)

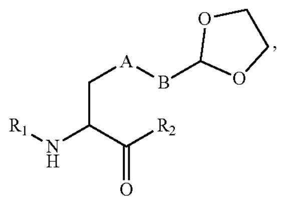

wherein A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —$S(O)_k$— where k is 1, 2, or 3, —$S(O)_k$(alkylene or substituted alkylene)-, —C(O)—, —C(O)-(alkylene or substituted alkylene —C(S)—, —C(S)-(alkylene or substituted alkylene)-, —N(R')—, —NR'-

(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide.

In addition, the following amino acids having the structure of Formula (IX) are included:

(IX)

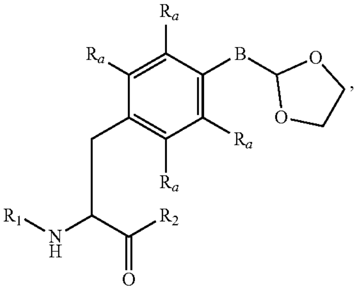

B is optional, and when present is a linker selected from the group consisting of lower alkylene, substih1ted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resm, amino acid, polypeptide, or polynucleotide; and $R_2$ is optional, and when present, is OH, an ester protecting group, resm, amino acid, polypeptide, or polynucleotide;

wherein each Ra is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

In addition, the following amino acids are included:

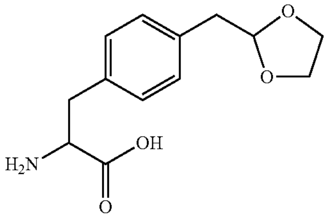

,

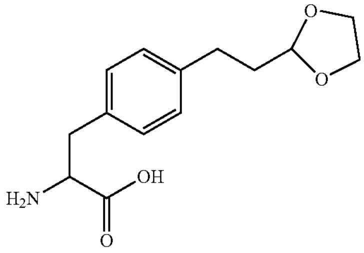

,

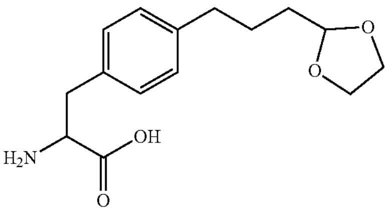

,

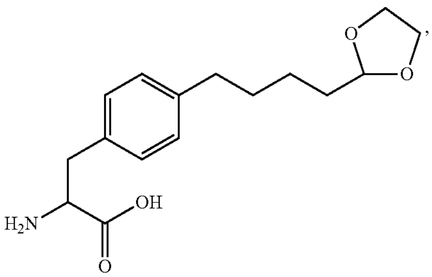

,

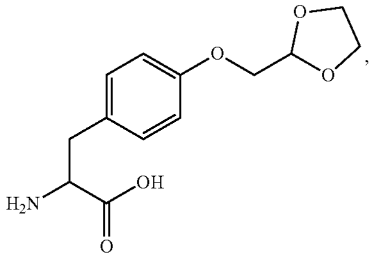

,

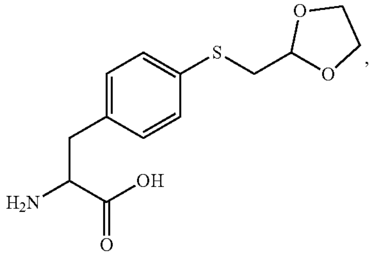

,

-continued

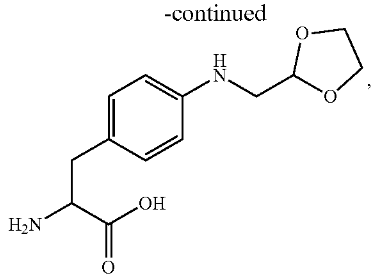

, and

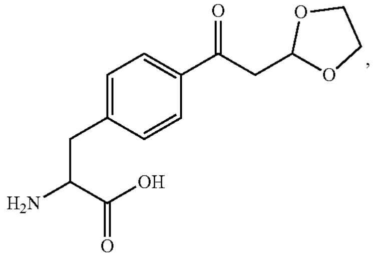

, wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (X) are included:

(X)

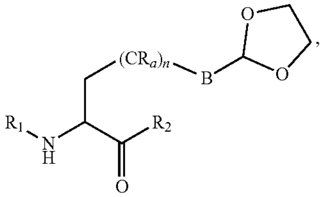

, wherein B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —$S(O)_k$— where k is 1, 2, or 3, —$S(O)_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkyleneh —N(R')C(O)O—, —$S(O)_k$N(R')—, —N(R')C(O)N(R')—, N(R')C(S)N(R')—, —N(R')$S(O)_k$N(R')—, —N(R')—N═, —C(R')═N—, —C(R')═N—N(R')—, —C(R')═N—N═, —$C(R')_2$—N—N—, and —$C(R')_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resm, amino acid, polypeptide, or polynucleotide; and $R_2$ is optional, and when present, is OH, an ester protecting group, resm, amino acid, polypeptide, or polynucleotide;

each $R_a$ is independently selected from the group consisting of H, halogen, alkyl, substituted alkyl, —$N(R')_2$, —$C(O)_k$R' where k is 1, 2, or 3, —C(O)$N(R')_2$, —OR', and —$S(O)_k$R', where each R' is independently H, alkyl, or substituted alkyl; and n is 0 to 8.

In addition, the following amino acids are included:

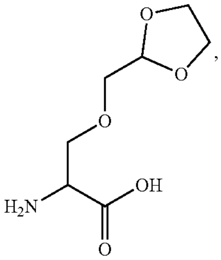

,

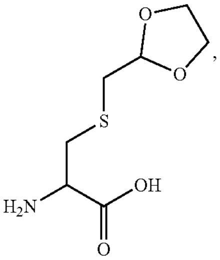

,

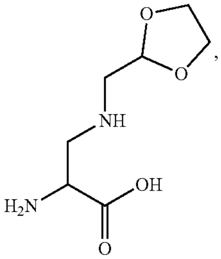

,

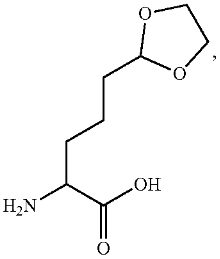

,

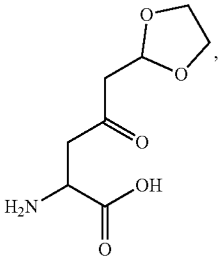

,

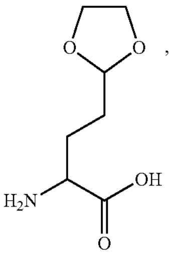

,

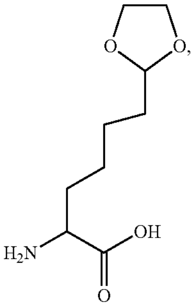

, and

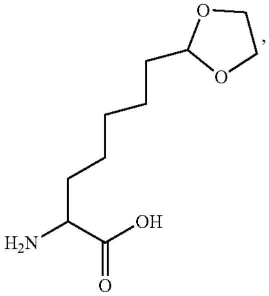

, wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition to monocarbonyl structures, the non-natural amino acids described herein may include groups such as dicarbonyl, dicarbonyl like, masked dicarbonyl and protected dicarbonyl groups.

For example, the following amino acids having the structure of Formula (XI) are included:

(XI)

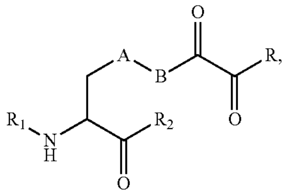

wherein A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —$S(O)_k$— where k is 1, 2, or 3, —$S(O)_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —$S(O)_k$N(R')—, —N(R') C(O)N(R')—, —N(R')C(S)N(R')—, —N(R')$S(O)_k$N(R')—, —N(R')—N═, —C(R')═N—, —C(R')═N—N(R')—, —C(R')═N—N═, —$C(R')_2$—N═N—, and —$C(R')_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resm, amino acid, polypeptide, or polynucleotide; and $R^2$ is optional, and when present, is OH, an ester protecting group, resm, amino acid, polypeptide, or polynucleotide.

In addition, the following amino acids having the structure of Formula (XII) are included:

(XII)

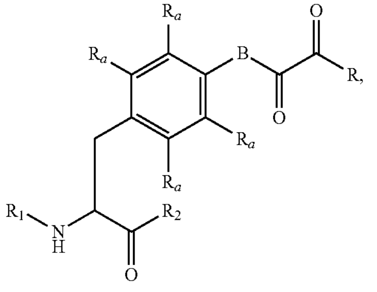

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —$S(O)_k$— where k is 1, 2, or 3, —$S(O)_k$(alkylene or substituted alkylene)-, —C(O)—, —C(O)-(alkylene or substituted alkylene)-, —C(S)—, —C(S)-(alkylene or substituted alkyleneh —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —$S(O)_k$N(R')—, —N(R')C(O)N(R')—, —N(R')C(S) N(R')—, —N(R')$S(O)_k$N(R')—, —N(R')—N═, —C(R')═N—, —C(R')═N—N(R')—, —C(R')═N—N═, —$C(R')_2$—N═N—, and —$C(R')_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resm, amino acid, polypeptide, or polynucleotide; and $R_2$ is optional, and when present, is OH, an ester protecting group, resm, amino acid, polypeptide, or polynucleotide;

wherein each Ra is independently selected from the group consisting of H, halogen, alkyl, substituted alkyl, —$N(R')_2$, —$C(O)_k$R' where k is 1, 2, or 3, —C(O)N$(R')_2$, —OR', and —$S(O)_k$R', where each R' is independently H, alkyl, or substituted alkyl.

In addition, the following amino acids are included:

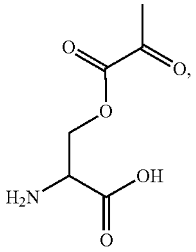
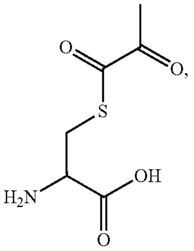
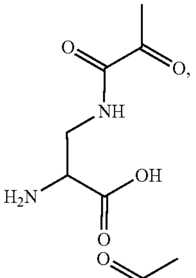
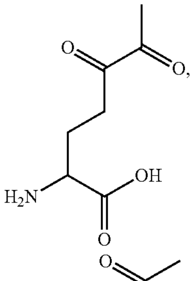
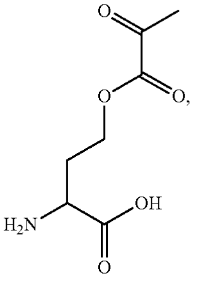
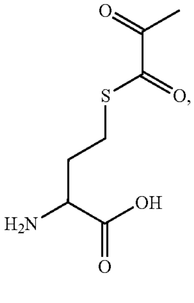

-continued

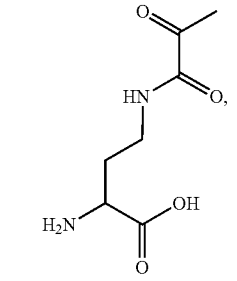
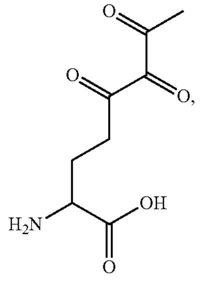
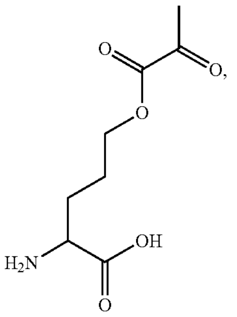
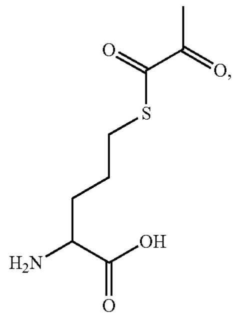
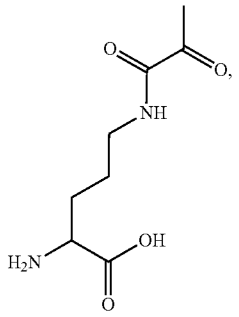
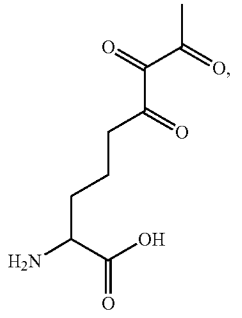
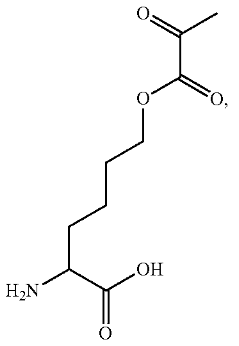
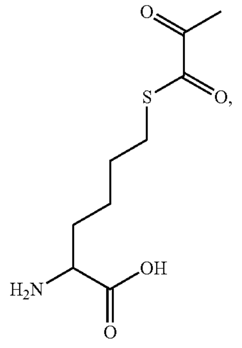
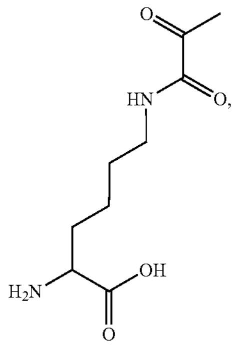
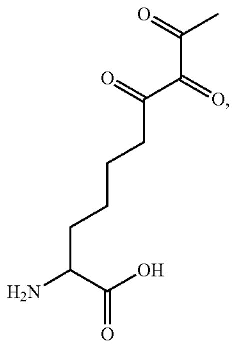

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (XIII) are included:

(XIV)

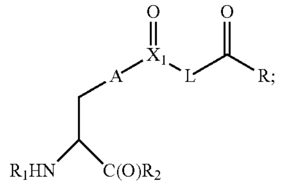

wherein B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —$S(O)_k$— where k is 1, 2, or 3, —$S(O)_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R') C(O)O—, —$S(O)_k$N(R')—, —N(R')C(O)N(R')—, —N(R')C(S)N(R')—, —N(R')$S(O)_k$N(R')—, —N(R')—N=, —C(R')=N—, —C(R')=N—N(R')—, —C(R')—N—N=, —$C(R')_2$—N—N—, and —$C(R')_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resm, amino acid, polypeptide, or polynucleotide; and $R_2$ is optional, and when present, is OH, an ester protecting group, resin, amino acid, polypeptide, or polynucleotide;

each $R_a$ is independently selected from the group consisting of H, halogen, alkyl, substituted alkyl, —$N(R')_2$, —$C(O)_k$R' where k is 1, 2, or 3, —$C(O)N(R')_2$, —OR', and —$S(O)_k$R', where each R' is independently H, alkyl, or substituted alkyl; and n is 0 to 8.

In addition, the following amino acids are included:

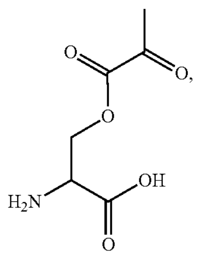
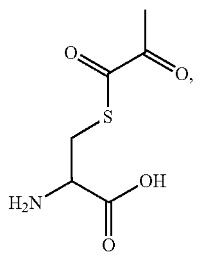

-continued

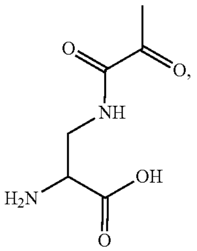
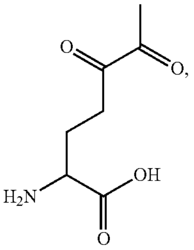
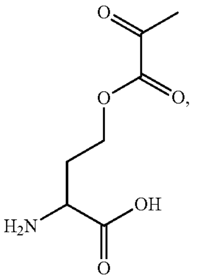
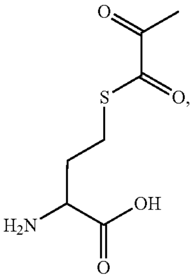
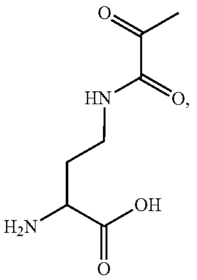
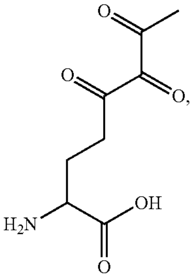
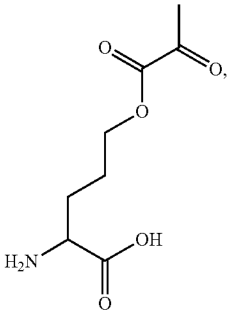
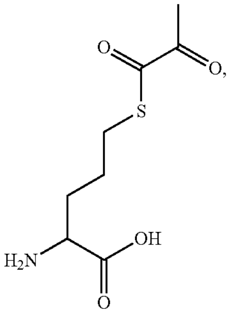
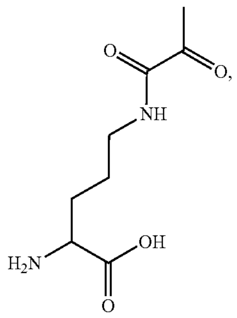
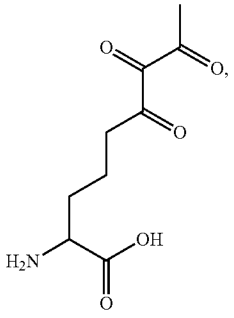

-continued

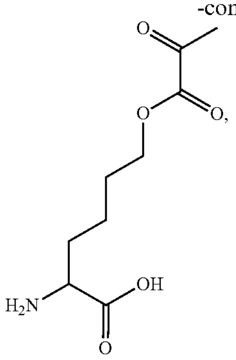
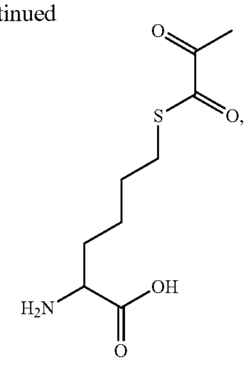
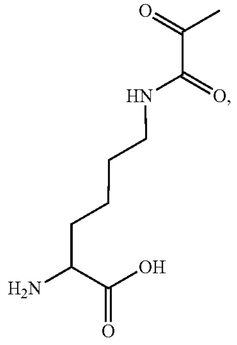
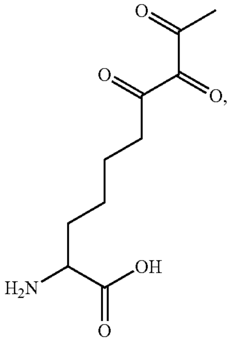

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (XIV) are included:

(XIV)

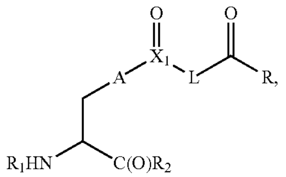

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resm, amino acid, polypeptide, or polynucleotide; and $R_2$ is optional, and when present, is OH, an ester protecting group, resm, amino acid, polypeptide, or polynucleotide;

$X_1$ is C, S, or S(O); and L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XIV-A) are included:

(XIV-A)

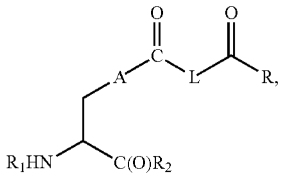

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resm, amino acid, polypeptide, or polynucleotide;

L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XIV-B) are included:

(XIV-B)

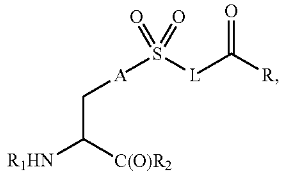

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resm, amino acid, polypeptide, or polynucleotide; and $R_2$ is optional, and when present, is OH, an ester protecting group, resin, amino acid, polypeptide, or polynucleotide;

L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XV) are included:

(XV)

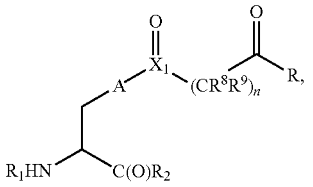

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resm, amino acid, polypeptide, or polynucleotide; and $R_2$ is optional, and when present, is OH, an ester protecting group, resin, amino acid, polypeptide, or polynucleotide;

$X_1$ is C, S, or S(O); and n is 0, 1, 2, 3, 4, or 5; and each $R^8$ and $R^9$ on each $CR^8R^9$ group is independently selected from the group consisting of H, alkoxy, alkylamine, halogen, alkyl, aryl, or any $R^8$ and $R^9$ can together form =O or a cycloalkyl, or any to adjacent $R^8$ groups can together form a cycloalkyl.

In addition, the following amino acids having the structure of Formula (XV-A) are included:

(XV-A)

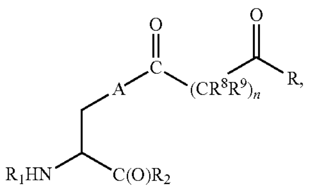

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resm, amino acid, polypeptide, or polynucleotide; and $R_2$ is optional, and when present, is OH, an ester protecting group, resm, amino acid, polypeptide, or polynucleotide;

n is 0, 1, 2, 3, 4, or 5; and each $R^8$ and $R^9$ on each $CR^8R^9$ group is independently selected from the group consisting of H, alkoxy, alkylamine, halogen, alkyl, aryl, or any $R^8$ and $R^9$ can together form =O or a cycloalkyl, or any to adjacent $R^8$ groups can together form a cycloalkyl.

In addition, the following amino acids having the structure of Formula (XV-B) are included:

(XV-B)

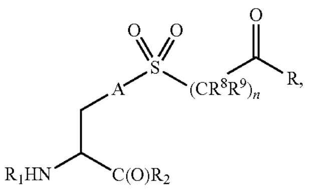

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resm, amino acid, polypeptide, or polynucleotide; and $R_2$ is optional, and when present, is OH, an ester protecting group, resm, amino acid, polypeptide, or polynucleotide;

n is 0, 1, 2, 3, 4, or 5; and each $R^8$ and $R^9$ on each $CR^8R^9$ group is independently selected from the group consisting of H, alkoxy, alkylamine, halogen, alkyl, aryl, or any $R^8$ and $R^9$ can together form =O or a cycloalkyl, or any to adjacent $R^8$ groups can together form a cycloalkyl.

In addition, the following amino acids having the structure of Formula (XVI) are included:

(XVI)

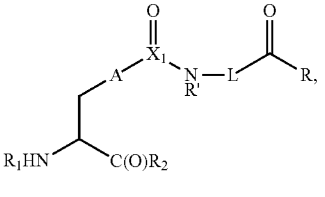

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

$X_1$ is C, S, or S(O); and L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XVI-A) are included:

(XVI-A)

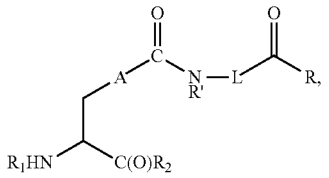

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XVI-B) are included:

(XVI-B)

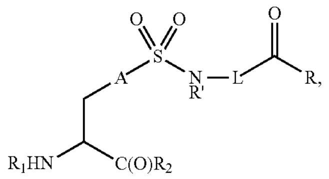

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

L is alkylene, substituted alkylene, N(R')(alkylene) or N(R')(substituted alkylene), where R' is H, alkyl, substituted alkyl, cycloalkyl, or substituted cycloalkyl.

In addition, amino acids having the structure of Formula (XVII) are included:

(XVII)

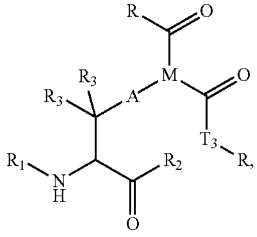

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

M is —C($R_3$)—,

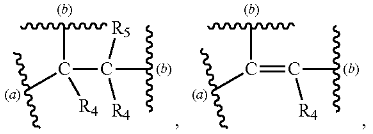

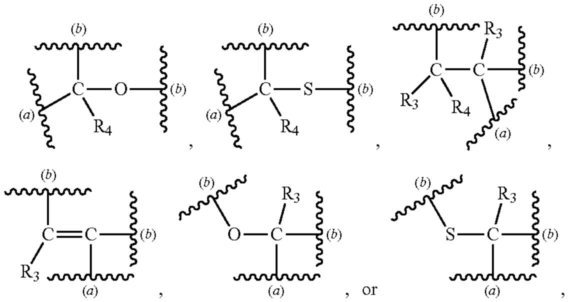

, or , where (a) indicates bonding to the A group and (b) indicates bonding to respective carbonyl groups, $R_3$ and are independently chosen from H, halogen, alkyl, substituted alkyl, cycloalkyl, or substituted cycloalkyl, or $R_3$ and $R_4$ or two $R_3$ groups or two groups optionally form a cycloalkyl or a heterocycloalkyl;

R is H, halogen, alkyl, substituted alkyl, cycloalkyl, or substituted cycloalkyl;

$T_3$ is a bond, C(R)(R), O, or S, and R is H, halogen, alkyl, substituted alkyl, cycloalkyl, or substituted cycloalkyl;

$R_1$ is optional, and when present, is H, an amino protecting group, resm, amino acid, polypeptide, or polynucleotide; and $R_2$ is optional, and when present, is OH, an ester protecting group, resm, amino acid, polypeptide, or polynucleotide.

In addition, amino acids having the structure of Formula (XVIII) are included:

(XVIII)

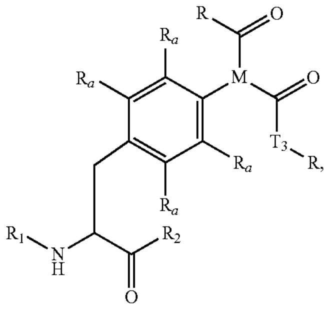

wherein:

M is —C(R3)—,

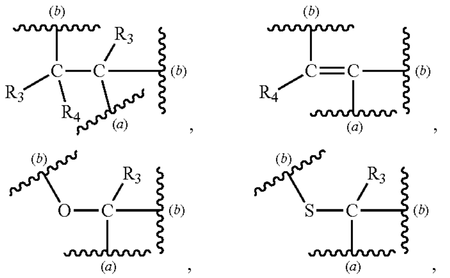

where (a) indicates bonding to the A group and (b) indicates bonding to respective carbonyl groups, $R_3$ and $R_4$ are independently chosen from H, halogen, alkyl, substituted alkyl, cycloalkyl, or substituted cycloalkyl, or $R_3$ and $R_4$ or two $R_3$ groups or two R4 groups optionally form a cycloalkyl or a heterocycloalkyl;

R is H, halogen, alkyl, substituted alkyl, cycloalkyl, or substituted cycloalkyl;

$T_3$ is a bond, C(R)(R), O, or S, and R is H, halogen, alkyl, substituted alkyl, cycloalkyl, or substituted cycloalkyl;

$R_1$ is optional, and when present, is H, an amino protecting group, resm, amino acid, polypeptide, or polynucleotide; and $R_2$ is optional, and when present, is OH, an ester protecting group, resm, amino acid, polypeptide, or polynucleotide;

each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

In addition, amino acids having the structure of Formula (XIX) are included:

(XIX)

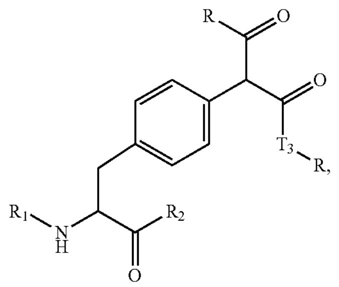

wherein:

R is H, halogen, alkyl, substituted alkyl, cycloalkyl, or substituted cycloalkyl; and $T_3$ is O, or S.

In addition, amino acids having the structure of Formula (XX) are included:

(XX)

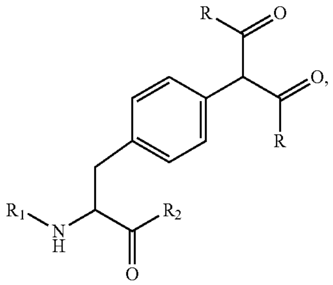

wherein:

R is H, halogen, alkyl, substituted alkyl, cycloalkyl, or substituted cycloalkyl.

In addition, the following amino acids having structures of Formula (XXI) are included:

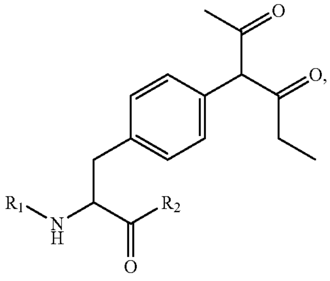

and

-continued

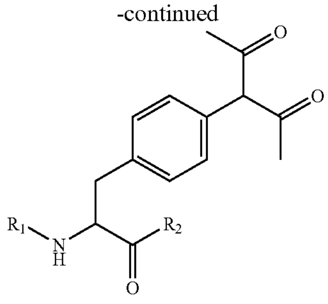

In some embodiments, a polypeptide comprising a non-natural amino acid is chemically modified to generate a reactive carbonyl or dicarbonyl functional group. For instance, an aldehyde functionality useful for conjugation reactions can be generated from a functionality having adjacent amino and hydroxyl groups. Where the biologically active molecule is a polypeptide, for example, an N-terminal serine or threonine (which may be normally present or may be exposed via chemical or enzymatic digestion) can be used to generate an aldehyde functionality under mild oxidative cleavage conditions using periodate. See, e.g., Gaertner, et. al., Bioconjug. Chem. 3:262-268 (1992); Geoghegan, K. & Stroh, J., Bioconjug. Chem. 3:138-146 (1992); Gaertner et al., J. Biol. Chem. 269:7224-7230 (1994). However, methods known in the art are restricted to the amino acid at the N-terminus of the peptide or protein.

In the present invention, a non-natural amino acid beaiing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685.

The carbonyl or dicarbonyl functionality can be reacted selectively with a hydroxylamine-containing reagent under mild conditions in aqueous solution to form the corresponding oxime linkage that is stable under physiological conditions. See, e.g., Jencks, W. P., J. Am. Chem. Soc. 81, 475-481 (1959); Shao, J. and Tam, J. P., J. Am. Chem. Soc. 117:3893-3899 (1995). Moreover, the unique reactivity of the carbonyl or dicarbonyl group allows for selective modification in the presence of the other amino acid side chains. Sec, e.g., Comish, V. W., et al., J. Am. Chem. Soc. 118: 8150-8151 (1996); Geoghegan, K. F. & Stroh, J. G., Bioconjug. Chem. 3:138-146 (1992); Mahal, L. K., et al., Science 276:1125-1128 (1997).

Structure and Synthesis of Non-Natural Amino Acids: Hydroxy/Amine-Containing Amino Acids U.S. Provisional Patent Application No. 60/638,418 is incorporated by reference in its entirety. Thus, the disclosures provided in Section V (entitled "Non-natural Amino Acids"), Part B (entitled "Structure and Synthesis of Non-Natural Amino Acids: Hydroxylamine-Containing Amino Acids"), in U.S. Provisional Patent Application No. 60/638, 418 apply fully to the methods, compositions (including Formulas I-XXXV), techniques and strategies for making, purifying, characterizing, and using non-natural amino acids, non-natural amino acid polypeptides and modified non-natural amino acid polypeptides described herein to the same extent as if such disclosures were fully presented herein. U.S. Patent Publication Nos. 2006/0194256, 2006/0217532, and 2006/0217289 and WO 2006/069246 entitled "Compositions containing, methods involving, and uses of non-natural amino acids and polypeptides," are also incorporated herein by reference in their entirety.

Chemical Synthesis of Unnatural Amino Acids

Many of the natural amino acids suitable for use in the present invention are commercially available, e.g., from Sigma (USA) or Aldrich (Milwaukee, WI, USA). Those that are not commercially available are optionally synthesized as provided herein or as provided in various publications or using standard methods known to those of ordinary skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) *J. Med. Chem.*, 38, 4660-4669; King, F. E. & Kidd, D. A. A. (1949) *A New Synthesis of Glutamine and of γ-Dipeptides of Glutamic Acid from Phthylated Intermediates. J. Chem. Soc.*, 3315-3319; Friedman, O. M. & Chatterrji, R. (1959) *Synthesis of Derivatives of Glutamine as Model Substrates for Anti-Tumor Agents. J. Am. Chem. Soc.* 81, 3750-3752; Craig, J. C. et al. (1988) *Absolute Configuration of the Enantiomers of 7-Chloro-4[[4-(diethylamino)-1-methylbutyl]amino]quinoline (Chloroquine). J. Org. Chem.* 53, 1167-1170; Azoulay, M., Vilmont, M. & Frappier, F. (1991) *Glutamine analogues as Potential Antimalarials, Eur. J. Med. Chem.* 26, 201-5; Koskinen, A. M. P. & Rapoport, H. (1989) *Synthesis of 4-Substituted Pralines as Conformationally Constrained Amino Acid Analogues. J. Org. Chem.* 54, 1859-1866; Christie, B. D. & Rapoport, H. (1985) *Synthesis of Optically Pure Pipecolates from L-Asparagine. Application to the Total Synthesis of (+)-Apovincamine through Amino Acid Decarbonylation and Iminium Jon Cyclization. J. Org. Chem.* 50:1239-1246; Barton et al., (1987) *Synthesis of Novel alpha-Amino-Acids and Derivatives Using Radical Chemistry: Synthesis of L-and D-alpha-Amino-Adipic Acids, L-alpha-aminopimelic Acid and Appropriate Unsaturated Derivatives. Tetrahedron* 43:4297-4308; and, Subasinghe et al., (1992) *Quisqualic acid analogues: synthesis of beta-heterocyclic 2-aminopropanoic acid derivatives and their activity at a novel quisqualate-sensitized site. J. Med. Chem.* 35:4602-7. See also, U.S. Patent Publication No. US 2004/0198637 entitled "Protein Arrays," which is incorporated by reference herein.

A. Carbonyl Reactive Groups

Amino acids with a carbonyl reactive group allow for a variety of reactions to link molecules (including but not limited to, PEG or other water soluble molecules) via nucleophilic addition or aldol condensation reactions among others.

Exemplary carbonyl-containing amino acids can be represented as follows:

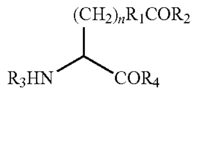

wherein n is 0-10; $R_1$ is an alkyl, aryl, substituted alkyl, or substituted aryl; $R_2$ is H, alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group. In some embodiments, n is 1, $R_1$ is phenyl and $R_2$ is a simple alkyl (i.e., methyl, ethyl, or propyl) and the ketone moiety is positioned in the para position relative to the alkyl side chain. In some embodiments, n is 1, $R_1$ is phenyl and $R_2$ is a simple alkyl (i.e., methyl, ethyl, or propyl) and the ketone moiety is positioned in the meta position relative to the alkyl side chain.

The synthesis of p-acetyl-(+/−)-phenylalanine and m-acetyl-(+/−)-phenylalanine is described in Zhang, Z., et al., Biochemistry 42:6735-6746 (2003), which is incorporated by reference herein. Other carbonyl-containing amino acids can be similarly prepared by one of ordinary skill in the art.

In some embodiments, a polypeptide comprising a non-naturally encoded amino acid is chemically modified to generate a reactive carbonyl functional group. For instance, an aldehyde functionality useful for conjugation reactions can be generated from a functionality having adjacent amino and hydroxyl groups. Where the biologically active molecule is a polypeptide, for example, an N-terminal serine or threonine (which may be n01mally present or may be exposed via chemical or enzymatic digestion) can be used to generate an aldehyde functionality under mild oxidative cleavage conditions using periodate. See, e.g., Gaertner, et al., *Bioconjug. Chem.* 3:262-268 (1992); Geoghegan, K. & Stroh, J., *Bioconjug. Chem.* 3:138-146 (1992); Gaertner et al., *J Biol. Chem.* 269:7224-7230 (1994). However, methods known in the art are restricted to the amino acid at the N-terminus of the peptide or protein.

In the present invention, a non-naturally encoded amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685, which is incorporated by reference herein.

The carbonyl functionality can be reacted selectively with a hydrazine-, hydrazide-, hydroxylamine-, or semicarbazide-containing reagent under mild conditions in aqueous solution to form the corresponding hydrazone, oxime, or sernicarbazone linkages, respectively, that are stable under physiological conditions. See, e.g., Jencks, W. P., *J. Am. Chem. Soc.* 81, 475-481 (1959); Shao, *J. and Tam, J. P., J. Am. Chem. Soc.* 117:3893-3899 (1995). Moreover, the unique reactivity of the carbonyl group allows for selective modification in the presence of the other amino acid side chains. See, e.g., Cornish, V. W., et al., *J. Arn. Chem. Soc.* 118:8150-8151 (1996); Geoghegan, K. F. & Stroh, J. G., *Bioconjug. Chem.* 3:138-146 (1992); Mahal, L. K., et al., *Science* 276:1125-1128 (1997).

B. Hydrazine, Hydrazide or Semicarbazide Reactive Groups

Non-naturally encoded amino acids containing a nucleophilic group, such as a hydrazine, hydrazide or semicarbazide, allow for reaction with a variety of electrophilic groups to form conjugates (including but not limited to, with PEG or other water soluble polymers).

Exemplary hydrazine, hydrazide or sernicarbazide-containing amino acids can be represented as follows:

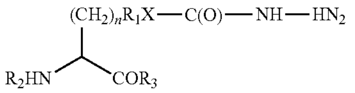

wherein n is 0-10; $R_1$ is an alkyl, aryl, substituted alkyl, or substituted aryl or not present; X, is O, N, or S or not present; $R_2$ is H, an amino acid, a polypeptide, or an amino terminus modification group, and $R_3$ is H, an amino acid, a polypeptide, or a carboxy terminus modification group.

In some embodiments, n is 4, $R_1$ is not present, and X is N. In some embodiments, n is 2, $R._1$ is not present, and X is not present. In some embodiments, n is 1, $R_1$ is phenyl, X is O, and the oxygen atom is positioned para to the aliphatic group on the aryl ring.

Hydrazide-, hydrazine-, and semicarbazide-containing amino acids are available from commercial somces. For instance, L-glutamate-γ-hydrazide is available from Sigma Chemical (St. Louis, MO). Other amino acids not available commercially can be prepared by one of ordinary skill in the art. See, e.g., U.S. Pat. No. 6,281,211, which is incorporated by reference herein.

Polypeptides containing non-naturally encoded amino acids that bear hydrazide, hydrazine or semicarbazide functionalities can be reacted efficiently and selectively with a variety of molecules that contain aldehydes or other functional groups with similar chemical reactivity. See, e.g., Shao, J. and Tam, J., *J. Am. Chem. Soc.* 117:3893-3899 (1995). The unique reactivity of hydrazide, hydrazine and semicarbazide functional groups makes them significantly more reactive toward aldehydes, ketones and other electrophilic groups as compared to the nucleophilic groups present on the 20 common amino acids (including but not limited to, the hydroxyl group of serine or threonine or the amino groups of lysine and the N-terminus).

C. Aminooxy-Containing Amino Acids

Non-naturally encoded amino acids containing an aminooxy (also called a hydroxylamine) group allow for reaction with a variety of electrophic groups to form conjugates (including but not limited to, with PEG or other water soluble polymers). Like hydrazines, hydrazides and semicarbazides, the enhanced nucleophilicity of the aminooxy group permits it to react efficiently and selectively with a variety of molecules that contain aldehydes or other functional groups with similar chemical reactivity. See, e.g., Shao, J. and Tarn, J., *J. Am. Chem. Soc.* 117:3893-3899 (1995); H. Hang and C. Bertozzi, *Acc. Chem. Res.* 34:727-736 (2001). Whereas the result of reaction with a hydrazine group is the corresponding hydrazone, however, an oxime results generally from the reaction of an aminooxy group with a carbonyl-containing group such as a ketone.

Exemplary amino acids containing aminooxy groups can be represented as follows:

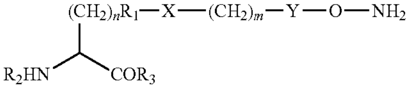

wherein n is 0-10; $R_1$ is an alkyl, aryl, substituted alkyl, or substituted aryl or not present; X is O, N, S or not present; m is 0-10; Y=C(O) or not present; $R_2$ is H, an amino acid, a polypeptide, or an amino terminus modification group, and $R_3$ is H, an amino acid, a polypeptide, or a carboxy te1minus modification group. In some embodiments, n is 1, $R_1$ is phenyl, X is O, m is 1, and Y is present. In some embodiments, n is 2, $R_1$ and X are not present, m is 0, and Y is not present.

Aminooxy-containing amino acids can be prepared from readily available amino acid precursors (homoserine, serine and threonine). See, e.g., M. Carrasco and R. Brown, *J. Org. Chem.* 68:8853-8858 (2003). Certain aminooxy-containing amino acids, such as L-2-amino-4-(aminooxy)butyric acid), have been isolated from natural sources (Rosenthal, G., Life Sci. 60:1635-1641 (1997). Other aminooxy-containing amino acids can be prepared by one of ordinary skill in the art.

D. Azide and Alkyne Reactive Groups

The unique reactivity of azide and alkyne functional groups makes them extremely useful for the selective modification of polypeptides and other biological molecules. Organic azides, particularly aliphatic azides, and alkynes are generally stable toward common reactive chemical conditions. In particular, both the azide and the alkyne functional groups are inert toward the side chains (i.e., R groups) of the 20 common amino acids found in naturally-occurring polypeptides. When brought into close proximity, however, the "spring-loaded" nature of the azide and alkyne groups is revealed and they react selectively and efficiently via Huisgen [3+2] cycloaddition reaction to generate the corresponding triazole. See, e.g., Chin J., et al., *Science* 301:964-7 (2003); Wang, Q., et al., *J Am. Chem. Soc.* 125, 3192-3193 (2003); Chin, J. W., et al., *J Am. Chem. Soc.* 124:9026-9027 (2002).

Because the Huisgen cycloaddition reaction involves a selective cycloaddition reaction (see, e.g., Padwa, A., in Comprehensive Organic Synthesis, Vol. 4, (ed. Trost, B. M., 1991), p. 1069-1109; Huisgen, R. in 1,3-Dipolar Cycloaddition Chemistry, (ed. Padwa, A., 1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing bG-CSF polypeptide can be earned out at room temperature under aqueous conditions by the addition of Cu(II) (including but not limited to, in the form of a catalytic amount of CuSO4) in the presence of a reducing agent for reducing Cu(II) to Cu (1), in situ, in catalytic amount. See, e.g., Wang, Q., et al., *J. Am. Chem. Soc.* 125, 3192-3193 (2003); Tornoe, C. W., et al., *J. Org. Chem.* 67:3057-3064 (2002); Rostovtsev, et al., *Angew. Chem. Int. Ed.* 41:2596-2599 (2002). Exemplary reducing agents include, including but not limited to, ascorbate, metallic copper, quinine, hydroquinone, vitamin K, glutathione, cysteine, $Fe^{2+}$, $Co^{2+}$, and an applied electric potential.

In some cases, where a Huisgen [3+2] cycloaddition reaction between an azide and an alkyne is desired, the bG-CSF polypeptide comprises a non-naturally encoded amino acid comprising an alkyne moiety and the water soluble polymer to be attached to the amino acid comprises an azide moiety. Alternatively, the converse reaction (i.e., with the azide moiety on the amino acid and the alkyne moiety present on the water soluble polymer) can also be performed.

The azide functional group can also be reacted selectively with a water soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, *Science* 287, 2007-2010 (2000). The azide-containing amino acid can be either an alkyl azide (including but not limited to, 2-amino-6-azido-1-hexanoic acid) or an aryl azide (p-azido-phenylalanine).

Exemplary water soluble polymers containing an aryl ester and a phosphine moiety can be represented as follows:

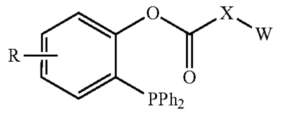

wherein X can be O, N, Sor not present, Ph is phenyl, W is a water soluble polymer and R can be H, alkyl, aryl, substituted alkyl and substituted aryl groups. Exemplary R groups include but are not limited to —$CH_2$, —$C(CH_3)_3$, —OR', —NR'R", —SR', -halogen, —C(O)R', —CONR'R", —$S(O)_2R'$, —$S(O)_2NR'R"$, —CN and —$NO_2$, R', R", R"' and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyffolidinyl and 4-morpbolinyl. From the above discussion of substituents, one of skill in the art will understand that the term "alkyl" is meant to include groups including carbon atoms bound to groups other than hydrogen groups, such as baloalkyl (including but not limited to, —$CF_3$ and —$CH_2CF_3$) and acyl (including but not limited to, —$C(O)CH_3$, —$C(O)CF_3$, —$C(O)CH_2OCH_3$, and the like).

The azide functional group can also be reacted selectively with a water soluble polymer containing a thioester and appropriately functionalized with an aryl phosphine moiety to generate an amide linkage. The aryl phosphine group reduces the azide in situ and the resulting amine then reacts efficiently with the thioester linkage to generate the corresponding amide. Exemplary water soluble polymers containing a thioester and a phosphine moiety can be represented as follows:

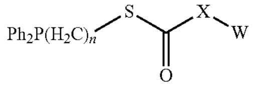

wherein n is 1-10; X can be O, N, S or not present, Ph is phenyl, and W is a water soluble polymer.

Exemplary alkyne-containing amino acids can be represented as follows:

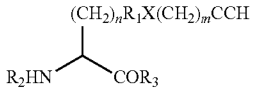

wherein n is 0-10; $R_1$ is an alkyl, aryl, substituted alkyl, or substituted aryl or not present; X is O, N, Sor not present; m is 0-10, $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is not present, m is O and the acetylene moiety is positioned in the para position relative to the alkyl side chain. In some embodiments, n is 1, $R_1$ is phenyl, X is O, m is 1 and the propargyloxy group is positioned in the para position relative to the alkyl side chain (i.e., O-propargyl-tyrosine). In some embodiments, n is 1, $R_1$ and X are not present and m is 0 (i.e., propargylglycine).

Alkyne-containing amino acids are commercially available. For example, propargylglycine is commercially available from Peptech (Burlington, MA). Alternatively, alkyne-containing amino acids can be prepared according to standard methods. For instance, p-propargyloxyphenylalanine can be synthesized, for example, as described in Deiters, A., et al., *J. Am. Chem. Soc.* 125:11782-11783 (2003), and 4-alkynyl-L-phenylalanine can be synthesized as described in Kayser, B., et al., *Tetrahedron* 53 (7): 2475-2484 (1997). Other alkyne-containing amino acids can be prepared by one of ordinary skill in the art.

Exemplary azide-containing amino acids can be represented as follows:

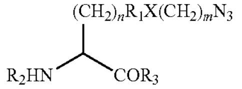

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R^3$ is H, an amino acid, a polypeptide, or a carboxy terminus modification group. In some embodiments, n is 1, $R_1$ is phenyl, X is not present, m is 0 and the azide moiety is positioned para to the alkyl side chain. In some embodiments, n is 0-4 and $R_1$ and X are not present, and m=0. In some embodiments, n is 1, $R_1$ is phenyl, X is 0, m is 2 and the ß-azidoethoxy moiety is positioned in the para position relative to the alkyl side chain.

Azide-containing amino acids are available from commercial sources. For instance, 4-azidophenylalanine can be obtained from Chem-Impex International, Inc. (Wood Dale, IL). For those azide-containing amino acids that are not commercially available, the azide group can be prepared relatively readily using standard methods known to those of ordinary skill in the art, including but not limited to, via displacement of a suitable leaving group (including but not limited to, halide, mesylate, tosylate) or via opening of a suitably protected lactone. See, e.g., *Advanced Organic Chemistry* by March (Third Edition, 1985, Wiley and Sons, New York).

E. Aminothiol Reactive Groups

The unique reactivity of beta-substituted aminothiol functional groups makes them extremely useful for the selective modification of polypeptides and other biological molecules that contain aldehyde groups via formation of the thiazolidine. See, e.g., J. Shao and J. Tam, *J. Am. Chem. Soc.* 1995, 117 (14) 3893-3899. In some embodiments, beta-substituted aminothiol amino acids can be incorporated into bG-CSF polypeptides and then reacted with water soluble polymers comprising an aldehyde functionality. In some embodiments, a water soluble polymer, drug conjugate or other payload can be coupled to a bG-CSF polypeptide comprising a beta-substituted aminothiol amino acid via formation of the thiazolidine.

F. Additional Reactive Groups

Additional reactive groups and non-naturally encoded amino acids, including but not limited to para-amino-phenylalanine, that can be incorporated into bG-CSF polypeptides of the invention are described in the following patent applications which are all incorporated by reference in their entirety herein: U.S. Patent Publication No. 2006/0194256, U.S. Patent Publication No. 2006/0217532, U.S. Patent Publication No. 2006/0217289, U.S. Provisional Patent No. 60/755,338; U.S. Provisional Patent No. 60/755,711; U.S. Provisional Patent No. 60/755,018; International Patent Application No. PCT/US06/49397; WO 2006/069246; U.S. Provisional Patent No. 60/743,041; U.S. Provisional Patent No. 60/743,040; International Patent Application No. PCT/US06/47822; U.S. Provisional Patent No. 60/882,819; U.S. Provisional Patent No. 60/882,500; and U.S. Provisional Patent No. 60/870,594. These applications also discuss reactive groups that may be present on PEG or other polymers, including but not limited to, hydroxylamine (aminooxy) groups for conjugation.

Cellular Uptake of Unnatural Amino Acids

Unnatural amino acid uptake by a cell is one issue that is typically considered when designing and selecting unnatural amino acids, including but not limited to, for incorporation into a protein. For example, the high charge density of a-amino acids suggests that these compounds are unlikely to be cell permeable. Natural amino acids are taken up into the eukaryotic cell via a collection of protein-based transport systems. A rapid screen can be done which assesses which unnatural amino acids, if any, are taken up by cells. See, e.g., the toxicity assays in, e.g., U.S. Patent Publication No. US 2004/0198637 entitled "Protein Arrays" which is incorporated by reference herein; and Liu, D. R. & Schultz, P. G. (1999) *Progress toward the evolution of an organism with an expanded genetic code. PNAS United States* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, including but not limited to, in a cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923 entitled "In vivo incorporation of unnatural amino acids") relies on the addition of a combination of known enzymes from other organisms. The genes for these enzymes can be introduced into a eukaryotic cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, for example, in Genbank. Artificially evolved enzymes are also optionally added into a cell in the same manner. In this manner, the cellular machine1y and resources of a cell are manipulated to produce unnatural amino acids.

A variety of methods are available for producing novel enzymes for use in biosynthetic pathways or for evolution of existing pathways. For example, recursive recombination, including but not limited to, as developed by Maxygen, Inc. (available on the World Wide Web at maxygen.com), is optionally used to develop novel enzymes and pathways. See, e.g., Stemmer (1994), Rapid evolution of a protein in vitro by DNA shuffling, *Nature* 370 (4): 389-391; and, Stemmer, (1994), *DNA shuffling by random fragmentation and reassembly: In vitro recombination for molecular evolution, Proc. Natl. Acad. Sci. USA.,* 91:10747-10751. Similarly DesignPath™, developed by Genencor (available on the World Wide Web at genencor.com) is optionally used for metabolic pathway engineering, including but not limited to, to engineer a pathway to create O-methyl-L-tyrosine in a cell. This technology reconstructs existing pathways in host organisms using a combination of new genes, including but not limited to, those identified through functional genomics, and molecular evolution and design. *Diversa* Corporation (available on the World Wide Web at *diversa*.com) also provides technology for rapidly screening libraries of genes and gene pathways, including but not limited to, to create new pathways.

Typically, the unnatural amino acid produced with an engineered biosynthetic pathway of the invention is produced in a concentration sufficient for efficient protein biosynthesis, including but not limited to, a natural cellular amount, but not to such a degree as to affect the concentration of the other amino acids or exhaust cellular resources. Typical concentrations produced in vivo in this manner are about 10 mM to about 0.05 mM. Once a cell is transformed with a plasmid comprising the genes used to produce enzymes desired for a specific pathway and an unnatural amino acid is generated, in vivo selections are optionally used to further optimize the production of the unnatural amino acid for both ribosomal protein synthesis and cell growth.

Polypeptides with Unnatural Amino Acids

The incorporation of an unnatural amino acid can be done for a variety of purposes, including but not limited to, tailoring changes in protein structure and/or function, changing size, acidity, nucleophilicity, hydrogen bonding, hydrophobicity, accessibility of protease target sites, targeting to a moiety (including but not limited to, for a protein array), adding a biologically active molecule, attaching a polymer, attaching a radionuclide, modulating serum half-life, modulating tissue penetration (e.g. tumors), modulating active transport, modulating tissue, cell or organ specificity or distribution, modulating immunogenicity, modulating protease resistance, etc. Proteins that include an unnatural amino acid can have enhanced or even entirely new catalytic or biophysical properties. For example, the following properties are optionally modified by inclusion of an unnatural amino acid into a protein: toxicity, biodistribution, structural properties, spectroscopic properties, chemical and/or photochemical properties, catalytic ability, half-life (including but not limited to, serum half-life), ability to react with other molecules, including but not limited to, covalently or non-covalently, and the like. The compositions including proteins that include at least one unnatural amino acid are useful for, including but not limited to, novel therapeutics, diagnostics, catalytic enzymes, industrial enzymes, binding proteins (including but not limited to, antibodies), and including but not limited to, the study of protein structure and function. See, e.g., Dougherty, (2000) *Unnatural Amino Acids as Probes of Protein Structure and Function, Current Opinion in Chemical Biology,* 4:645-652.

In one aspect of the invention, a composition includes at least one protein with at least one, including but not limited to, at least two, at least three, at least four, at least five, at least six, at least seven, at least eight, at least nine, or at least ten or more unnatural amino acids. The unnatural amino acids can be the same or different, including but not limited to, there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is substituted with the natural amino acid. For a given protein with more than one unnahrral amino acids, the unnatural amino acids can be identical or different (including but not limited to, the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Proteins or polypeptides of interest with at least one unnatural amino acid are a feature of the invention. The invention also includes polypeptides or proteins with at least one unnatural amino acid produced using the compositions and methods of the invention. An excipient (including but not limited to, a pharmaceutically acceptable excipient) can also be present with the protein.

By producing proteins or polypeptides of interest with at least one unnatural amino acid in eukaryotic cells, proteins or polypeptides will typically include eukaryotic post-translational modifications. In certain embodiments, a protein includes at least one unnatural amino acid and at least one post-translational modification that is made in vivo by a eukaryotic cell, where the post-translational modification is not made by a prokaryotic cell. For example, the post-translation modification includes, including but not limited to, acetylation, acylation, lipid-modification, palmitoylation, palmitate addition, phosphorylation, glycolipid-linkage modification, glycosylation, and the like. In one aspect, the post-translational modification includes attachment of an oligosaccharide (including but not limited to, (GlcNAc-Man) 2-Man-GlcNAc-GlcNAc)) to an asparagine by a GlcNAc-asparagine linkage. See Table 1 which lists some examples of N-linked oligosaccharides of eukaryotic proteins (additional residues can also be present, which are not shown). In another aspect, the post-translational modification includes attachment of an oligosaccharide (including but not limited to, Gal-GalNAc, Gal-GlcNAc, etc.) to a serine or threonine by a GalNAc-serine or GalNAc-threonine linkage, or a GlcNAc-serine or a GlcNAc-threonine linkage.

TABLE 1

EXAMPLES OF OLIGOSACCHARIDES THROUGH GlcNAc-LINKAGE

| Type | Base Structure |
|---|---|
| High-mannose | Manα1-6 / Manα1-3 > Manα1-6 / Manα1-3 > Manβ1-4GlcNAcβ1-4GlcNAcβ1-Asn |
| Hybrid | Manα1-6 / GlcNAcβ1-2— Manα1-3 > Manβ1-4GlcNAcβ1-4GlcNAcβ1-Asn |
| Complex | GlcNAcβ1-2— Manα1-6 / GlcNAcβ1-2— Manα1-3 > Manβ1-4GlcNAcβ1-4GlcNAcβ1-Asn |
| Xylose | Manα1-6 / Xylβ1-2 > Manβ1-4GlcNAcβ1-4GlcNAcβ1-Asn |

In yet another aspect, the post-translation modification includes proteolytic processing of precursors (including but not limited to, calcitonin precursor, calcitonin gene-related peptide precursor, preproparathyroid hormone, preproinsulin, proinsulin, prepro-opiomelanocortin, pro-opiomelanocortin and the like), assembly into a multisubunit protein or macromolecular assembly, translation to another site in the cell (including but not limited to, to organelles, such as the endoplasmic reticulum, the Golgi apparatus, the nucleus, lysosomes, peroxisomes, mitochondria, chloroplasts, vacuoles, etc., or through the secretoly pathway). In certain embodiments, the protein comprises a secretion or localization sequence, an epitope tag, a FLAG tag, a polyhistidine tag, a GST fusion, or the like.

One advantage of an unnatural amino acid is that it presents additional chemical moieties that can be used to add additional molecules. These modifications can be made in vivo in a eukaryotic or non-eukaryotic cell, or in vitro. Thus, in certain embodiments, the post-translational modification is through the umlatural amino acid. For example, the post-translational modification can be through a nucleophilic-electrophilic reaction. Most reactions currently used for the selective modification of proteins involve covalent bond formation between nucleophilic and electrophilic reaction partners, including but not limited to the reaction of a.-haloketones with histidine or cysteine side chains. Selectivity in these cases is determined by the number and accessibility of the nucleophilic residues in the protein. In proteins of the invention, other more selective reactions can be used such as the reaction of an unnatural keto-amino acid with hydrazides or aminooxy compounds, in vitro and in vivo. See, e.g., Cornish, et al., (1996) *J. Am. Chem. Soc.,* 118:8150-8151 Mahal, et al., (1997) *Science,* 276:1125-1128; Wang, et al., (2001) Science 292:498-500; Chin, et al., (2002) *J. Am. Chem. Soc.* 124:9026-9027; Chin, et al., (2002) *Proc. Natl. Acad. Sci.,* 99:11020-11024; Wang, et al., (2003) Proc. Natl. Acad. Sci., 100:56-61; Zhang, et al., (2003) *Biochemistry,* 42:6735-6746; and, Chin, et al., (2003) *Science,* 301:964-7, all of which are incorporated by reference herein. This allows the selective labeling of virtually any protein with a host of reagents including fluorophores, crosslinking agents, saccharide derivatives and cytotoxic molecules. See also, U.S. Pat. No. 6,927,042 entitled "Glycoprotein synthesis," which is: incorporated by reference herein. Post-translational modifications, including but not limited to, through an azido amino acid, can also made through the Staudinger ligation (including but not limited to, with triarylphosphine reagents). See, e.g., Kiick et al., (2002) *Incorporation of azides into recombinant proteins for chemoselective modification by the Staudinger ligation, PNAS* 99:19-24.

This invention provides another highly efficient method for the selective modification of proteins, which involves the genetic incorporation of unnatural amino acids, including but not limited to, containing an azide or alkynyl moiety into proteins in response to a selector codon. These amino acid side chains can then be modified by, including but not limited to, a Huisgen [3+2] cycloaddition reaction (see, e.g., Padwa, A. in Comprehensive Organic Synthesis, Vol. 4, (1991) Ed. Trost, B. M., Pergamon, Oxford, p. 1069-1109; and, Huisgen, R. in 1,3-*Dipolar Cycloaddition Chemistry*, (1984) Ed. Padwa, A., Wiley, New York, p. 1-176) with, including but not limited to, alkynyl or azide derivatives, respectively. Because this method involves a cycloaddition rather than a nucleophilic substitution, proteins can be modified with extremely high selectivity. This reaction can be carried out at room temperature in aqueous conditions with excellent regioselectivity (1,4>1,5) by the addition of catalytic amounts of Cu(I) salts to the reaction mixture. See, e.g., Tomoe, et al., (2002) *J. Org. Chem.* 67:3057-3064; and, Rostovtsev, et al., (2002) *Angew. Chem. Int. Ed.* 41:2596-2599. Another method that can be used is the ligand exchange on a bisarsenic compound with a tetracysteine motif, see, e.g., Griffin, et al., (1998) *Science* 281:269-272.

A molecule that can be added to a protein of the invention through a [3+2] cycloaddition includes virtually any molecule with an azide or alkynyl derivative. Molecules include, but are not limited to, dyes, fluorophores, crosslinking agents, saccharide derivatives, polymers (including but not limited to, derivatives of polyethylene glycol), photocrosslinkers, cytotoxic compounds, affinity labels, derivatives of biotin, resins, beads, a second protein or polypeptide (or more), polynucleotide(s) (including but not limited to, DNA, RNA, etc.), metal chelators, cofactors, fatty acids, carbohydrates, and the like. These molecules can be added to an unnatural amino acid with an alkynyl group, including but not limited to, p-propargyloxyphenylalanine, or azido group, including but not limited to, p-azido-phenylalanine, respectively.

V. In Vivo Generation of bG-CSF Polypeptides Comprising Non-Naturally-Encoded Amino Acids The bG-CSF polypeptides of the invention can be generated in vivo using modified tRNA and tRNA synthetases to add to or substitute amino acids that are not encoded in naturally-occurring systems.

Methods for generating tRNAs and tRNA synthetases which use amino acids that are not encoded in naturally-occurring systems are described in, e.g., U.S. Pat. Nos. 7,045,337 and 7,083,970 which are incorporated by reference herein. These methods involve generating a translational machinery that functions independently of the synthetases and tRNAs endogenous to the translation system (and are therefore sometimes referred to as "orthogonal"). Typically, the translation system comprises an orthogonal tRNA (O-tRNA) and an orthogonal aminoacyl tRNA synthetase (O-RS). Typically, the O-RS preferentially aminoacylates the O-tRNA with at least one non-naturally occurring amino acid in the translation system and the O-tRNA recognizes at least one selector codon that is not recognized by other tRNAs in the system. The translation system thus inserts the non-naturally-encoded amino acid into a protein produced in the system, in response to an encoded selector codon, thereby "substituting" an amino acid into a position in the encoded polypeptide.

A wide variety of orthogonal tRNAs and aminoacyl tRNA synthetases have been described in the art for inserting particular synthetic amino acids into polypeptides, and are generally suitable for use in the present invention. For example, keto-specific O-tRNNaminoacyl-tRNA synthetases are described in Wang, L., et al., *Proc. Natl. Acad. Sci. USA* 100:56-61 (2003) and Zhang, Z. et al., *Biochem.* 42 (22): 6735-6746 (2003). Exemplary O-RS, or portions thereof, are encoded by polynucleotide sequences and include amino acid sequences disclosed in U.S. Pat. Nos. 7,045,337 and 7,083,970, each incorporated herein by reference. Corresponding O-tRNA molecules for use with the O-RSs are also described in U.S. Pat. Nos. 7,045,337 and 7,083,970 which are incorporated by reference herein. Additional examples of O-tRNA/aminoacyl-tRNA synthetase pairs are described in WO 2005/007870, WO 2005/007624; and WO 2005/019415.

An example of an azide-specific O-tRNA/aminoacyl-tRNA synthetase system is described in Chin, J. W., et al., *J. Am. Chem. Soc.* 124:9026-9027 (2002). Exemplary O-RS sequences for p-azido-L-Phe include, but are not limited to, nucleotide sequences SEQ ID NOS: 14-16 and 29-32 and amino acid sequences SEQ ID NOs: 46-48 and 61-64 as disclosed in U.S. Pat. No. 7,083,970 which is incorporated by reference herein. Exemplary O-tRNA sequences suitable for use in the present invention include, but are not limited to, nucleotide sequences SEQ ID NOs: 1-3 as disclosed in U.S. Pat. No. 7,083,970, which is incorporated by reference herein. Other examples of O-tRNA/aminoacyl-tRNA synthetase pairs specific to particular non-naturally encoded amino acids are described in U.S. Pat. No. 7,045,337 which is incorporated by reference herein. O-RS and O-tRNA that incorporate both keto- and azide-containing amino acids in *S. cerevisiae* are described in Chin, J. W., et al., *Science* 301:964-967 (2003).

Several other orthogonal pairs have been rep01ted. Glutaminyl (see, e.g., Liu, D. R., and Schultz, P. G. (1999) *Proc. Natl. Acad. Sci. U.S.A* 96:4780-4785), aspartyl (see, e.g., Pastrnak, M., et al., (2000) *Helv. Chim. Acta* 83:2277-2286), and tyrosyl (see, e.g., Ohno, S., et al., (1998) *J. Biochem.* (Tokyo, Jpn.) 124:1065-1068; and, Kowal, A. K., et al., (2001) *Proc. Natl. Acad. Sci. U.S.A* 98:2268-2273) systems derived from *S. cerevisiae* RNA's and synthetases have been described for the potential incorporation of unnatural amino acids in £. *coli*. Systems derived from the *E. coli* glutaminyl (see, e.g., Kowal, A. K., et al., (2001) *Proc. Natl. Acad. Sci. U.S.A* 98:2268-2273) and tyrosyl (see, e.g., Edwards, H., and Schimmel, P. (1990) *Mal. Cell. Biol.* 10:1633-1641) synthetases have been described for use in *S. cerevisiae*. The *E. coli* tyrosyl system has been used for the incorporation of 3-iodo-L-tyrosine in vivo, in mammalian cells. See, Sakamoto, K., et al., (2002) *Nucleic Acids Res.* 30:4692-4699.

Use of O-tRNA/arninoacyl-tRNA synthetases involves selection of a specific codon which encodes the non-naturally encoded amino acid. While any codon can be used, it is generally desirable to select a codon that is rarely or never used in the cell in which the O-tRNAfarninoacyl-tRNA synthetase is expressed. For example, exemplary codons include nonsense codon such as stop codons (amber, ochre, and opal), four or more base codons and other natural three-base codons that are rarely or unused.

Specific selector codon(s) can be introduced into appropriate positions in the bG-CSF polynucleotide coding sequence using mutagenesis methods known in the art (including but not limited to, site-specific mutagenesis, cassette mutagenesis, restriction selection mutagenesis, etc.).

Methods for generating components of the protein biosynthetic machinery, such as O-RSs, O-tRNAs, and orthogonal O-tRNA/O-RS pairs that can be used to incorporate a non-naturally encoded amino acid are described in Wang, L., et al., *Science* 292:498-500 (2001); Chin, J. W., et al., *J. Am. Chem. Soc.* 124:9026-9027 (2002); Zhang, Z. et al., *Biochemistry* 42:6735-6746 (2003). Methods and compositions for the in vivo incorporation of non-naturally encoded amino acids are described in U.S. Pat. No. 7,045,337, which is incorporated by reference herein. Methods for selecting an orthogonal tRNA-tRNA synthetase pair for use in in vivo translation system of an organism are also described in U.S. Pat. Nos. 7,045,337 and 7,083,970 which are incorporated by reference herein. PCT Publication No. WO 04/035743 entitled "Site Specific Incorporation of Keto Amino Acids into Proteins," which is incorporated by reference herein in its entirety, describes orthogonal RS and tRNA pairs for the incorporation of keto amino acids. PCT Publication No. WO 04/094593 entitled "Expanding the Eukaryotic Genetic Code," which is incorporated by reference herein in its entirety, describes orthogonal RS and tRNA pairs for the incorporation of non-naturally encoded amino acids in eukaryotic host cells.

Methods for producing at least one recombinant orthogonal aminoacyl-tRNA synthetase (O-RS) comprise: (a) generating a library of (optionally mutant) RSs derived from at least one aminoacyl-tRNA synthetase (RS) from a first organism, including but not limited to, a prokaryotic organism, such as *Methanococcus jannaschii, Methanobacterium thermoautotrophicum, Halobacterium, Escherichia coli, A. fulgidus, P. furiosus, P. horikoshii, A. pernix, T. thermophilus*, or the like, or a eukaryotic organism; (b) selecting (and/or screening) the library of RSs (optionally mutant RSs) for members that aminoacylate an orthogonal tRNA (O-tRNA) in the presence of a non-naturally encoded amino acid and a natural amino acid, thereby providing a pool of active (optionally mutant) RSs; and/or, (c) selecting (optionally through negative selection) the pool for active RSs (including but not limited to, mutant RSs) that preferentially aminoacylate the O-tRNA in the absence of the non-naturally encoded amino acid, thereby providing the at least one recombinant O-RS; wherein the at least one recombinant O-RS preferentially aminoacylates the O-tRNA with the non-naturally encoded amino acid.

In one embodiment, the RS is an inactive RS. The inactive RS can be generated by mutating an active RS. For example, the inactive RS can be generated by mutating at least about 1, at least about 2, at least about 3, at least about 4, at least about 5, at least about 6, or at least about 10 or more amino acids to different amino acids, including but not limited to, alanine.

Libraries of mutant RSs can be generated using various techniques known in the art, including but not limited to rational design based on protein three dimensional RS structure, or mutagenesis of RS nucleotides in a random or rational design technique. For example, the mutant RSs can be generated by site-specific mutations, random mutations, diversity generating recombination mutations, chimeric constructs, rational design and by other methods described herein or known in the art.

In one embodiment, selecting (and/or screening) the library of RSs (optionally mutant RSs) for members that are active, including but not limited to, that aminoacylate an orthogonal tRNA (O-tRNA) in the presence of a non-naturally encoded amino acid and a natural amino acid, includes: introducing a positive selection or screening marker, including but not limited to, an antibiotic resistance gene, or the like, and the library of (optionally mutant) RSs into a plurality of cells, wherein the positive selection and/or screening marker comprises at least one selector codon, including but not limited to, an amber, ochre, or opal codon; growing the plurality of cells in the presence of a selection agent; identifying cells that survive (or show a specific response) in the presence of the selection and/or screening agent by suppressing the at least one selector codon in the positive selection or screening marker, thereby providing a subset of positively selected cells that contains the pool of active (optionally mutant) RSs. Optionally, the selection and/or screening agent concentration can be varied.

In one aspect, the positive selection marker is a chloramphenicol acetyltransferase (CAT) gene and the selector codon is an amber stop codon in the CAT gene. Optionally, the positive selection marker is β-lactamase gene and the selector codon is an amber stop codon in the β-lactamase gene. In another aspect the positive screening marker comprises a fluorescent or luminescent screening marker or an affinity based screening marker (including but not limited to, a cell surface marker).

In one embodiment, negatively selecting or screening the pool for active RSs (optionally mutants) that preferentially aminoacylate the O-tR1'JA in the absence of the non-naturally encoded amino acid includes: introducing a negative selection or screening marker with the pool of active (optionally mutant) RSs from the positive selection or screening into a plurality of cells of a second organism, wherein the negative selection or screening marker comprises at least one selector codon (including but not limited to, an antibiotic resistance gene, including but not limited to, a chloramphenicol acetyltransferase (CAT) gene); and, identifying cells that survive or show a specific screening response in a first medium supplemented with the non-naturally encoded amino acid and a screening or selection agent, but fail to survive or to show the specific response in a second medium not supplemented with the non-naturally encoded amino acid and the selection or screening agent, thereby providing surviving cells or screened cells with the at least one recombinant O-RS. For example, a CAT identification protocol optionally acts as a positive selection and/or a negative screening in determination of appropriate O-RS recombinants. For instance, a pool of clones is optionally replicated on growth plates containing CAT (which comprises at least one selector codon) either with or without one or more non-naturally encoded amino acid. Colonies growing exclusively on the plates containing non-naturally encoded amino acids are thus regarded as containing recombinant 0-RS. In one aspect, the concentration of the selection (and/or screening) agent is varied. In some aspects the first and second organisms are different. Thus, the first and/or second organism optionally comprises: a prokaryote, a eukaryote, a mammal, an *Escherichia coli*, a fungi, a yeast, an archaebacterium, a cubacterium, a plant, an insect, a protist, etc. In other embodiments, the screening marker comprises a fluorescent or luminescent screening marker or an affinity based screening marker.

In another embodiment, screening or selecting (including but not limited to, negatively selecting) the pool for active (optionally mutant) RSs includes: isolating the pool of active mutant RSs from the positive selection step (b); introducing a negative selection or screening marker, wherein the negative selection or screening marker comprises at least one selector codon (including but not limited to, a toxic marker gene, including but not limited to, a ribonuclease barnase gene, comprising at least one selector codon), and the pool of active (optionally mutant) RSs into a plurality of cells of a second organism; and identifying cells that survive or show a specific screening response in a first medium not supplemented with the non-naturally encoded amino acid, but fail to survive or show a specific screening response in a second medium supplemented with the non-naturally encoded amino acid, thereby providing surviving or screened cells with the at least one recombinant O-RS, wherein the at least one recombinant O-RS is specific for the non-naturally encoded amino acid. In one aspect, the at least one selector codon comprises about two or more selector codons. Such embodiments optionally can include wherein the at least one selector codon comprises two or more selector codons, and wherein the first and second organism are different (including but not limited to, each organism is optionally, including but not limited to, a prokaryote, a eukaryote, a mammal, an *Escherichia coli*, a fungi, a yeast, an archaebacteria, a cubacteria, a plant, an insect, a protist, etc.). Also, some aspects include wherein the negative selection marker comprises a ribonuclease bamase gene (which comprises at least one selector codon). Other aspects include wherein the screening marker optionally comprises a fluorescent or luminescent screening marker or an affinity based screening marker. In the embodiments herein, the screenings and/or selections optionally include variation of the screening and/or selection stringency.

In one embodiment, the methods for producing at least one recombinant orthogonal aminoacyl-tRNA synthetase (O-RS) can further comprise: (d) isolating the at least one recombinant O-RS; (e) generating a second set of O-RS (optionally mutated) derived from the at least one recombinant O-RS; and, (f) repeating steps (b) and (c) until a mutated O-RS is obtained that comprises an ability to preferentially aminoacylate the O-tRNA. Optionally, steps (d)-(f) are repeated, including but not limited to, at least about two times. In one aspect, the second set of mutated O-RS derived from at least one recombinant O-RS can be generated by mutagenesis, including but not limited to, random mutagenesis, site-specific mutagenesis, recombination or a combination thereof.

The stringency of the selection/screening steps, including but not limited to, the positive selection/screening step (b), the negative selection/screening step (c) or both the positive and negative selection/screening steps (b) and (c), in the above-described methods, optionally includes varying the selection/screening stringency. In another embodiment, the positive selection/screening step (b), the negative selection/screening step (c) or both the positive and negative selection/screening steps (b) and (c) comprise using a reporter, wherein the reporter is detected by fluorescence-activated cell sorting (FACS) or wherein the repmter is detected by luminescence. Optionally, the reporter is displayed on a cell surface, on a phage display or the like and selected based upon affinity or catalytic activity involving the non-naturally encoded amino acid or an analogue. In one embodiment, the mutated synthetase is displayed on a cell surface, on a phage display or the like.

Methods for producing a recombinant orthogonal tRNA (O-tRNA) include: (a) generating a library of mutant tRNAs derived from at least one tRNA, including but not limited to, a suppressor tRNA, from a first organism; (b) selecting (including but not limited to, negatively selecting) or screening the library for (optionally mutant) tRNAs that are aminoacylated by an aminoacyl-tRNA synthetase (RS) from a second organism in the absence of a RS from the first organism, thereby providing a pool of tRNAs (optionally mutant); and, (c) selecting or screening the pool of tRNAs (optionally mutant) for members that are aminoacylated by an introduced orthogonal RS (O-RS), thereby providing at least one recombinant O-tRNA; wherein the at least one recombinant O-tRNA recognizes a selector codon and is not efficiency recognized by the RS from the second organism and is preferentially aminoacylated by the O-RS. In some embodiments the at least one tRNA is a suppressor tRNA and/or comprises a unique three base codon of natural and/or unnatural bases, or is a nonsense codon, a rare codon, an unnatural codon, a codon comprising at least 4 bases, an amber codon, an ochre codon, or an opal stop codon. In one embodiment, the recombinant O-tRNA possesses an improvement of orthogonality. It will be appreciated that in some embodiments, O-tRNA is optionally imported into a first organism from a second organism without the need for modification. In various embodiments, the first and second organisms are either the same or different and are optionally chosen from, including but not limited to, prokaryotes (including but not limited to, *Methanococcus jannaschii, Methanobacterium thermoautotrophicum, Escherichia coli, Halobacterium*, etc.), eukaryotes, mammals, fungi, yeasts, archaebacteria, cubacteria, plants, insects, protists, etc. Additionally, the recombinant tRNA is optionally aminoacylated by a non-naturally encoded amino acid, wherein the non-naturally encoded amino acid is biosynthesized in vivo either naturally or through genetic manipulation. The non-naturally encoded amino acid is optionally added to a growth medium for at least the first or second organism.

In one aspect, selecting (including but not limited to, negatively selecting) or screening the library for (optionally mutant) tRNAs that are aminoacylated by an arninoacyl-tRNA synthetase (step (b)) includes: introducing a toxic marker gene, wherein the toxic marker gene comprises at least one of the selector codons (or a gene that leads to the production of a toxic or static agent or a gene essential to the organism wherein such marker gene comprises at least one selector codon) and the library of (optionally mutant) tRNAs into a plurality of cells from the second organism; and, selecting surviving cells, wherein the surviving cells contain the pool of (optionally mutant) tRNAs comprising at least one orthogonal tRNA or nonfunctional tRNA. For example, surviving cells can be selected by using a comparison ratio cell density assay.

In another aspect, the toxic marker gene can include two or more selector codons. In another embodiment of the methods, the toxic marker gene is a ribonuclease bamase gene, where the ribonuclease barnase gene comprises at least one amber codon. Optionally, the ribonuclease bamase gene can include two or more amber codons.

In one embodiment, selecting or screening the pool of (optionally mutant) tRNAs for members that are aminoacylated by an introduced orthogonal RS (O-RS) can include: introducing a positive selection or screening marker gene, wherein the positive marker gene comprises a dmg resistance gene (including but not limited to, B-lactamase gene, comprising at least one of the selector codons, such as at least one amber stop codon) or a gene essential to the organism, or a gene that leads to detoxification of a toxic agent, along with the O-RS, and the pool of (optionally mutant) tRNAs into a plurality of cells from the second organism; and, identifying surviving or screened cells grown in the presence of a selection or screening agent, including but not limited to, an antibiotic, thereby providing a pool of cells possessing the at least one recombinant tRNA, where the at least one recombinant tRNA is aminoacylated by the O-RS and inserts an amino acid into a translation product encoded by the positive marker gene, in response to the at least one selector codons. In another embodiment, the concentration of the selection and/or screening agent is varied.

Methods for generating specific O-tRNA/O-RS pairs are provided. Methods include: (a) generating a library of mutant tRNAs derived from at least one tRNA from a first organism; (b) negatively selecting or screening the library for (optionally mutant) tRNAs that are aminoacylated by an aminoacyl-tRNA synthetase (RS) from a second organism in the absence of a RS from the first organism, thereby providing a pool of (optionally mutant) tRNAs; (c) selecting or screening the pool of (optionally mutant) tRNAs for members that are aminoacylated by an introduced orthogonal RS (O-RS), thereby providing at least one recombinant O-tRNA. The at least one recombinant O-tRNA recognizes a selector codon and is not efficiency recognized by the RS from the second organism and is preferentially aminoacylated by the O-RS. The method also includes (d) generating a library of (optionally mutant) RSs derived from at least one aminoacyl-tRNA synthetase (RS) from a third organism; (e) selecting or screening the library of mutant RSs for members that preferentially aminoacylate the at least one recombinant O-tRNA in the presence of a non-naturally encoded amino acid and a natural amino acid, thereby providing a pool of active (optionally mutant) RSs; and, (f) negatively selecting or screening the pool for active (optionally mutant) RSs that preferentially aminoacylate the at least one recombinant O-tRNA in the absence of the non-naturally encoded amino acid, thereby providing the at least one specific O-tRNA/O-RS pair, wherein the at least one specific O-tRNA/O-RS pair comprises at least one recombinant O-RS that is specific for the non-naturally encoded amino acid and the at least one recombinant O-tRNA. Specific O-tRNA/O-RS pairs produced by the methods are included. For example, the specific O-tRNA/O-RS pair can include, including but not limited to, a mutRNATyr-mutTyrRS pair, such as a mutRNATyr-SS12TyrRS pair, a mutRNALeu-mutLeuRS pair, a mutRNAThr-mutThrRS pair, a mutRNAGlu-mutGluRS pair, or the like. Additionally, such methods include wherein the first and third organism are the same (including but not limited to, Methanococcus jannaschii).

Methods for selecting an orthogonal tRNA-tRNA synthetase pair for use in an in vivo translation system of a second organism are also included in the present invention. The methods include: introducing a marker gene, a tRNA and an aminoacyl-tRNA synthetase (RS) isolated or derived from a first organism into a first set of cells from the second organism; introducing the marker gene and the tRNA into a duplicate cell set from a second organism; and, selecting for surviving cells in the first set that fail to survive in the duplicate cell set or screening for cells showing a specific screening response that fail to give such response in the duplicate cell set, wherein the first set and the duplicate cell set are grown in the presence of a selection or screening agent, wherein the surviving or screened cells comprise the orthogonal tRNA-tRNA synthetase pair for use in the in the in vivo translation system of the second organism. In one embodiment, comparing and selecting or screening includes an in vivo complementation assay. The concentration of the selection or screening agent can be varied.

The organisms of the present invention comprise a variety of organism and a variety of combinations. For example, the first and the second organisms of the methods of the present invention can be the same or different. In one embodiment, the organisms are optionally a prokaryotic organism, including but not limited to, *Methanococcus jannaschii, Methanobacterium thermoautotrophicum, Halobacterium, Escherichia coli, A. fulgidus, P. furiosus, P. horikoshii, A. pernix, T. thermophilus*, or the like. Alternatively, the organisms optionally comprise a eukaryotic organism, including but not limited to, plants (including but not limited to, complex plants such as monocots, or dicots), algae, protists, fungi (including but not limited to, yeast, etc), animals (including but not limited to, mammals, insects, arthropods, etc.), or the like. In another embodiment, the second organism is a prokaryotic organism, including but not limited to, *Methanococcus jannaschii, Methanobacterium thermoautotrophicum, Halobacterium, Escherichia coli, A. fitlgidus, Halobacterium, P. furiosus, P. horikoshii, A. pernix, T. thermophilus*, or the like. Alternatively, the second organism can be a eukaryotic organism, including but not limited to, a yeast, a animal cell, a plant cell, a fungus, a mammalian cell, or the like. In various embodiments the first and second organisms are different.

VI. Location of Non-Naturally-Occurring Amino Acids in bG-CSF Polypeptides

The present invention contemplates incorporation of one or more non-naturally-occurring amino acids into bG-CSF polypeptides. One or more non-naturally-occurring amino acids may be incorporated at a particular position which does not disrupt activity of the polypeptide. This can be achieved by making conservative" substitutions, including but not limited to, substituting hydrophobic amino acids with hydrophobic amino acids, bulky amino acids for bulky amino acids, hydrophilic amino acids for hydrophilic amino acids and/or inserting the non-naturally-occurring amino acid in a location that is not required for activity.

A variety of biochemical and structural approaches can be employed to select the desired sites for substitution with a non-naturally encoded amino acid within the bG-CSF polypeptide. It is readily apparent to those of ordinary skill in the art that any position of the polypeptide chain is suitable for selection to incorporate a non-naturally encoded amino acid, and selection may be based on rational design or by random selection for any or no particular desired purpose. Selection of desired sites may be for producing a bG-CSF molecule having any desired property or activity, including but not limited to, agonists, super-agonists, inverse agonists, antagonists, receptor binding modulators, receptor activity modulators, dimer or multimer formation, no change to activity or property compared to the native molecule, or manipulating any physical or chemical property of the polypeptide such as solubility, aggregation, or stability. For example, locations in the polypeptide required for biological activity of bG-CSF polypeptides can be identified using point mutation analysis, alanine scanning, saturation mutagenesis and screening for biological activity, or homolog scanning methods known in the art. Other methods can be used to identify residues for modification of bG-CSF polypeptides include, but are not limited to, sequence profiling, rotamer library selections, residue pair potentials, and rational design using Protein Design Automation® technology. (See U.S. Pat. Nos. 6,188,965; 6,269,312; 6,403,312; WO98/47089, which are incorporated by reference). Residues that are critical for bG-CSF bioactivity, residues that are involved with pharmaceutical stability, antibody epitopes, or receptor binding residues may be mutated. U.S. Pat. Nos. 5,580,723; 5,834,250; 6,013,478; 6,428,954; and 6,451,561, which are incorporated by reference herein, describe methods for the systematic analysis of the structure and function of polypeptides such as bG-CSF by identifying active domains which influence the activity of the polypeptide with a target substance. G-CSF alanine scanning mutagenesis studies are described in Reidhaar-Olson J F et al., Biochemistry (1996) July 16; 35 (28): 9034-41, Young D C et al. Protein Sci. (1997) June; 6 (6): 1228-36, and Layton et al. (1997) JBC 272 (47): 29735-29741. Residues other than those identified as critical to biological activity by alanine or homolog scanning mutagenesis may be good candidates for substitution with a non-naturally encoded amino acid depending on the desired activity sought for the polypeptide. Alternatively, the sites identified as critical to biological activity may also be good candidates for substitution with a non-naturally encoded amino acid, again depending on the desired activity sought for the polypeptide. Another alternative would be to simply make serial substitutions in each position on the polypeptide chain with a non-naturally encoded amino acid and observe the effect on the activities of the polypeptide. It is readily apparent to those of ordinary skill in the art that any means, technique, or method for selecting a position for substitution with a non-natural amino acid into any polypeptide is suitable for use in the present invention.

The structure and activity of mutants of bG-CSF polypeptides that contain deletions can also be examined to determine regions of the protein that are likely to be tolerant of substitution with a non-naturally encoded amino acid. In a similar manner, protease digestion and monoclonal antibodies can be used to identify regions of bG-CSF that are responsible for binding its receptor. Layton et al. (2001) JBC 276 (39) 36779-36787 describes antibody studies with bG-CSF and its receptor. Once residues that are likely to be intolerant to substitution with non-naturally encoded amino acids have been eliminated, the impact of proposed substitutions at each of the remaining positions can be examined. Models may be generated from the three-dimensional crystal structures of other CSP family members and CSF receptors. Protein Data Bank (PDB, available on the World Wide Web at resb.org) is a centralized database containing three-dimensional structural data of large molecules of proteins and nucleic acids. Models may be made investigating the secondary and tertiary structure of polypeptides, if three-dimensional structural data is not available. X-ray crystallographic and NMR structures of hG-CSF are available in the Protein Data Bank with PDB ID's: 1CD9, IPGR, IRHG, IGNC, as well as in U.S. Pat. Nos. 5,581,476; and 5,790,421, which are incorporated by reference herein. Thus, those of ordinary skill in the art can readily identify amino acid positions that can be substituted with non-naturally encoded amino acids.

In some embodiments, the bG-CSF polypeptides of the invention comprise one or more non-naturally occurring amino acids positioned in a region of the protein that does not disrupt the structure of the polypeptide.

Exemplary residues of incorporation of a non-naturally encoded amino acid may be those that are excluded from potential receptor binding regions, may be fully or partially solvent exposed, have minimal or no hydrogen-bonding interactions with nearby residues, may be minimally exposed to nearby reactive residues, may be on one or more of the exposed faces, may be a site or sites that are juxtaposed to a second bG-CSF, or other molecule or fragment thereof, may be in regions that are highly flexible, or structurally rigid, as predicted by the three-dimensional, secondary, tertiary, or quaternary structure of bG-CSF, bound or unbound to its receptor, or coupled or not coupled to another biologically active molecule, or may modulate the conformation of the bG-CSF itself or a dimer or multimer comprising one or more bG-CSF, by altering the flexibility or rigidity of the complete structure as desired.

One of ordinary skill in the art recognizes that such analysis of bG-CSF enables the determination of which amino acid residues are surface exposed compared to amino acid residues that are buried within the tertiary structure of the protein. Therefore, it is an embodiment of the present invention to substitute a non-naturally encoded amino acid for an amino acid that is a surface exposed residue.

In some embodiments, one or more non-naturally encoded amino acids are incorporated in one or more of the following positions in bG-CSF: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175 (i.e., at the carboxyl terminus of the protein), and any combination thereof (SEQ ID NO: 1 or the corresponding amino acids in SEQ ID NO: 2 or the corresponding amino acids in another bG-CSF polypeptide).

In some embodiments, one or more non-naturally encoded amino acids are incorporated at one or more of the following positions of bG-CSF: 3, 7, 11, 33, 43, 58, 62, 67, 69, 98, 99, 123, 124, 125, 133, 134, 136, 141, 159, 166, 169, 170, 173, and any combination thereof of SEQ ID NO: 1 or the corresponding amino acids in SEQ ID NO: 2. In some embodiments, one or more non-naturally encoded amino acids are incorporated at one or more of the following positions of bG-CSF: 3, 7, 33, 43, 58, 62, 67, 69, 99, 123, 124, 133, 134, 141, 166, and any combination thereof (SEQ ID NO: 1 or the corresponding amino acids in SEQ ID NO: 2). In some embodiments, one or more non-naturally encoded amino acids are incorporated at one or more of the following positions of bG-CSF: 3, 7, 62, 133, 166, and any combination thereof of SEQ ID NO: 1 or the corresponding amino acids in SEQ ID NO: 2. In some embodiments, one or more non-naturally encoded amino acids are incorporated at one or more of the following positions of bG-CSF: 62, 133, and a combination thereof (SEQ ID NO: 1 or the corresponding amino acids in SEQ ID NO: 2). In some embodiments, one or more non-naturally encoded amino acids are incorporated at position 62 of bG-CSF (SEQ ID NO: 1 or the corresponding amino acid in SEQ ID NO: 2). In some embodiments, one or more non-naturally encoded amino acids are incorporated at position 133 of bG-CSF (SEQ ID NO: 1 or the corresponding amino acid in SEQ ID NO: 2). In some embodiments, the polypeptide of the invention comprises one or more natural amino acid substitution, addition, or deletion. In some embodiments, one or more non-natural amino acids are incorporated in a leader or signal sequence that is N or C terminal to SEQ ID NO: 1, 2, or other bG-CSF sequence. In some embodiments, one or more non-naturally encoded amino acids are incorporated at one or more positions of the bG-CSF (SEQ ID NO: 1) and the one or more non-naturally encoded amino acid or acids do not include histidine, arginine, lysine, isoleucine, phenylalanine, leucine, tryptophan, alanine, cysteine, asparagines, valine, glycine, serine, glutamine, tyrosine, aspartic acid, glutamic acid, threonine, or naturally occurring non-proteogenic amino acids such as—alanine, omithine, etc. In some embodiments, one or more non-naturally encoded amino acids are incorporated at one or more positions of the bG-CSF (SEQ ID NO: 2) and the one or more non-naturally encoded amino acid or acids do not include histidine, arginine, lysine, isoleucine, phenylalanine, leucine, tryptophan, alanine, cysteine, asparagines, valine, glycine, serine, glutamine, tyrosine, aspartic acid, glutamic acid, threonine, or naturally occurring non-proteogenic amino acids such as β-alanine, ornithine, etc. In some embodiments, the amino acid incorporated at position 133 of SEQ ID NO: 1, or the corresponding position in SEQ ID NO: 2, is an amino acid other than histidine, arginine, lysine, isoleucine, phenylalanine, leucine, tryptophan, alanine, cysteine, asparagines, valine, glycine, serine, glutamine, tyrosine, aspartic acid, glutamic acid, threonine, or naturally occurring non-proteogenic amino acids such as β-alanine, ornithine, etc.

In some embodiments, one or more non-naturally encoded amino acids are ribosomally incorporated at one or more positions of the bG-CSF (SEQ ID NO: 1) and the one or more non-naturally encoded amino acid or acids do not include histidine, arginine, lysine, isoleucine, phenylalanine, leucine, tryptophan, alanine, cysteine, asparagines, valine, glycine, serine, glutamine, tyrosine, aspartic acid, glutamic acid, threonine, or naturally occurring non-proteogenic amino acids such as β-alanine, ornithine, etc. In some embodiments, one or more non-naturally encoded amino acids are ribosomally incorporated at one or more positions of the bG-CSF (SEQ ID NO: 2) and the one or more non-naturally encoded amino acid or acids do not include histidine, arginine, lysine, isoleucine, phenylalanine, leucine, tryptophan, alanine, cysteine, asparagines, valine, glycine, serine, glutamine, tyrosine, aspartic acid, glutamic acid, threonine, or naturally occurring non-proteogenic amino acids such as β-alanine, ornithine, etc. In some embodiments, the amino acid ribosomally incorporated at position 133 of SEQ ID NO: 1, or the corresponding position in SEQ ID NO: 2, is an amino acid other than histidine, arginine, lysine, isoleucine, phenylalanine, leucine, tryptophan, alanine, cysteine, asparagines, valine, glycine, serine, glutamine, tyrosine, aspartic acid, glutamic acid, threonine, or naturally occurring non-proteogenic amino acids such as β-alanine, ornithine, etc. In some embodiments, one or more non-naturally encoded amino acids are incorporated at one or more positions of the bG-CSF (SEQ ID NO: 1) wherein the one or more non-naturally encoded amino acid or acids has or have a functional group or groups not recognized by an endogenous RS. In some embodiments, one or more non-naturally encoded amino acids are incorporated at one or more positions of the bG-CSF (SEQ ID NO: 2) wherein the one or more non-naturally encoded amino acid or acids has or have a functional group or groups not recognized by an endogenous RS. In some embodiments 1 the bG-CSF polypeptide of the present invention has an amino acid incorporated at position 133 of SEQ ID NO: 1, or the corresponding position in SEQ ID NO: 2, wherein the amino acid has a functional group or groups not recognized by an endogenous RS. In some embodiments, the bG-CSF polypeptide of the present invention has a para-acetylphenylalanine incorporated at position 133 of SEQ ID NO: 1, or the corresponding position in SEQ ID NO: 2. In some embodiments, the bG-CSF polypeptide of the present invention has a para-aminophenylalanine incorporated at position 133 of SEQ ID NO: 1, or the corresponding position in SEQ ID NO: 2.

In some embodiments, the non-naturally occurring amino acid at one or more of these positions is linked to a water soluble polymer, including but not limited to, positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 7 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 1601 161, 162, 163, 164, 165, 166, 167, 168, 169, 170, 171, 172, 173, 174, 175 (i.e., at the carboxyl terminus of the protein), and any combination thereof (SEQ ID NO: 1 or the corresponding amino acids in SEQ ID NO: 2 or the corresponding amino acids in another bG-CSF polypeptide).

In some embodiments, the non-naturally occurring amino acid at one or more of these positions is linked to a water soluble polymer, including but not limited to, positions: 3, 7, 11, 33, 43, 58, 62, 67, 69, 98, 99, 123, 124, 125, 133, 134, 136, 141, 159, 166, 169, 170, 173, and any combination thereof (SEQ ID NO: 1 or the corresponding amino acids in SEQ ID NO: 2). In some embodiments, the non-naturally occurring amino acid at one or more of these positions is linked to a water soluble polymer, including but not limited to, positions: 3, 7, 33, 43, 58, 62, 67, 69, 99, 123, 124, 133, 134, 141, 166, and any combination thereof (SEQ ID NO: 1 or the corresponding amino acids in SEQ ID NO: 2). In some embodiments, the non-naturally occurring amino acid at one or more of these positions is linked to a water soluble polymer, including but not limited to, positions: 3, 7, 62, 133, 166, and any combination thereof (SEQ ID NO: 1 or the corresponding amino acids in SEQ ID NO: 2). In some embodiments, the non-naturally encoded amino acid at one or more of these positions is linked to a water soluble polymer, including but not limited to, 62, 133, and a combination thereof (SEQ ID NO: 1 or the corresponding amino acids in SEQ ID NO: 2). In some embodiments, the non-naturally encoded amino acid at position 62 is linked to a water soluble polymer (SEQ ID NO: 1 or the corresponding amino acid in SEQ ID NO: 2). In some embodiments, the non-naturally encoded amino acid at position 133 is linked to a water soluble polymer (SEQ ID NO: 1 or the corresponding amino acid in SEQ ID NO: 2). In some embodiments, the non-naturally occurring amino acid in the signal or leader sequence N or C terminal to SEQ ID NO: 1, 2, or other bG-CSF sequence is linked to a water soluble polymer.

An examination of the crystal structure of bG-CSF or bG-CSF family member(s) and its interaction with the G-CSF receptor can indicate which certain amino acid residues have side chains that are fully or partially accessible to solvent. The side chain of a non-naturally encoded amino acid at these positions may point away from the protein surface and out into the solvent.

A wide variety of non-naturally encoded amino acids can be substituted for, or incorporated into, a given position in a bG-CSF polypeptide. In general, a particular non-naturally encoded amino acid is selected for incorporation based on an examination of the three dimensional crystal structure of a bG-CSF polypeptide or other G-CSF family member with its receptor, a preference for conservative substitutions (i.e., aryl-based non-naturally encoded amino acids, such as p-acetylphenylalanine or O-propargyltyrosine substituting for Phe, Tyr or Trp), and the specific conjugation chemistry that one desires to introduce into the bG-CSF polypeptide (e.g., the introduction of 4-azidophenylalanine if one wants to effect a Huisgen [3+2] cycloaddition with a water soluble polymer bearing an alkyne moiety or a amide bond formation with a water soluble polymer that bears an aryl ester that, in turn, incorporates a phosphine moiety).

In one embodiment, the method further includes incorporating into the protein the unnatural amino acid, where the unnatural amino acid comprises a first reactive group; and contacting the protein with a molecule (including but not limited to, hydroxyalkyl starch (HAS), hydroxyethyl starch (HES), a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above, or any other desirable compound or substance) that comprises a second reactive group. The first reactive group reacts with the second reactive group to attach the molecule to the unnatural amino acid through a [3+2] cycloaddition. In one embodiment, the first reactive group is an alkynyl or azido moiety and the second reactive group is an azido or alkynyl moiety. For example, the first reactive group is the alkynyl moiety (including but not limited to, in unnatural amino acid p-propargyloxyphenylalanine) and the second reactive group is the azido moiety. In another example, the first reactive group is the azido moiety (including but not limited to, in the unnatural amino acid p-azido-L-phenylalanine) and the second reactive group is the alkynyl moiety.

In some cases, the non-naturally encoded amino acid substitution(s) will be combined with other additions, substitutions or deletions within the bG-CSF polypeptide to affect other biological traits of the bG-CSF polypeptide. In some cases, the other additions, substitutions or deletions may increase the stability (including but not limited to, resistance to proteolytic degradation) of the bG-CSF polypeptide or increase affinity of the bG-CSF polypeptide for its receptor. In some cases, the other additions, substitutions or deletions may increase the pharmaceutical stability of the bG-CSF polypeptide. In some cases, the other additions, substitutions or deletions may enhance the biological activity of the bG-CSF polypeptide. In some cases, the other additions, substitutions or deletions may increase the solubility (including but not limited to, when expressed in *E. coli* or other host cells) of the bG-CSF polypeptide. In some embodiments additions, substitutions or deletions may increase the bG-CSF polypeptide solubility following expression in *E. coli* or other recombinant host cells. In some embodiments sites are selected for substitution with a naturally encoded or non-natural amino acid in addition to another site for incorporation of a non-natural amino acid that results in increasing the polypeptide solubility following expression in *E. coli* or other recombinant host cells. In some embodiments, the bG-CSF polypeptides comprise another addition, substitution or deletion that modulates affinity for a receptor, binding proteins, or associated ligand, modulates signal transduction after binding to a receptor, modulates circulating half-life, modulates release or bioavailability, facilitates purification, or improves or alters a particular route of administration. In some embodiments, the bG-CSF polypeptides comprise an addition, substitution or deletion that increases the affinity of the bG-CSF variant for its receptor. Similarly, bG-CSF polypeptides can comprise chemical or enzyme cleavage sequences, protease cleavage sequences, reactive groups, antibody-binding domains (including but not limited to, FLAG or poly-His) or other affinity based sequences (including, but not limited to, FLAG, poly-His, GST, etc.) or linked molecules (including, but not limited to, biotin) that improve detection (including, but not limited to, GFP), purification, transport through tissues or cell membranes, prodrug release or activation, bG-CSF size reduction, or other traits of the polypeptide.

In some embodiments, the substitution of a non-naturally encoded amino acid generates an bG-CSF antagonist. In some embodiments, a non-naturally encoded amino acid is substituted or added in a region involved with receptor binding. In some embodiments, bG-CSF antagonists comprise at least one substitution that cause bG-CSF to act as an antagonist. In some embodiments, the bG-CSF antagonist comprises a non-naturally encoded amino acid linked to a water soluble polymer that is present in a receptor binding region of the bG-CSF molecule.

In some embodiments, the substitution of a non-naturally encoded amino acid generates a bG-CSF antagonist. In some embodiments, the bG-CSF antagonist comprises a non-naturally encoded amino acid linked to a water soluble polymer that is present in a receptor binding region of the bG-CSF molecule.

In some cases, 1, 2, 3, 4, 5, 6, 7, 8, 9, 10, or more amino acids are substituted with one or more non-naturally-encoded amino acids. In some cases, the bG-CSF polypeptide further includes 1, 2, 3, 4, 5, 6, 7, 8, 9, 10, or more substitutions of one or more non-naturally encoded amino acids for naturally-occurring amino acids. For example, in some embodiments, one or more residues in bG-CSF are substituted with one or more non-naturally encoded amino acids. In some cases, the one or more non-naturally encoded residues are linked to one or more lower molecular weight linear or branched PEGs, thereby enhancing binding affinity and comparable serum half-life relative to the species attached to a single, higher molecular weight PEG.

In some embodiments, up to two of the following residues of bG-CSF are substituted with one or more non-naturally-encoded amino acids.

VII. Expression in Non-Eukaryotes and Eukaryotes

To obtain high level expression of a cloned bG-CSF polynucleotide, one typically subclones polynucleotides encoding a bG-CSF polypeptide of the invention into an expression vector that contains a strong promoter to direct transcription, a transcription/translation terminator, and if for a nucleic acid encoding a protein, a ribosome binding site for translational initiation. Suitable bacterial promoters are known to those of ordinary skill in the art and described, e.g., in Sambrook et al. and Ausubel et al.

Bacterial expression systems for expressing bG-CSF polypeptides of the invention are available in, including but not limited to, *E. coli, Bacillus* sp., *Pseudomonas jluorescens, Pseudomonas aeruginosa, Pseudomonas putida*, and *Salmonella* (Palva et al., Gene 22:229-235 (1983); Mosbach et al., *Nature* 302:543-545 (1983)). Kits for such expression systems are commercially available. Eukaryotic expression systems for mammalian cells, yeast, and insect cells are known to those of ordinary skill in the art and are also commercially available. In cases where orthogonal tRNAs and aminoacyl tRNA synthetases (described above) are used to express the bG-CSF polypeptides of the invention, host cells for expression are selected based on their ability to use the orthogonal components. Exemplary host cells include Gram-positive bacteria (including but not limited to *B. brevis, B. subtilis*, or *Streptomyces*) and Gram-negative bacteria (*E. coli, Pseudomonas fluorescens, Pseudomonas aeruginosa, Pseudomonas putida*), as well as yeast and other eukaryotic cells. Cells comprising O-tRNA/O-RS pairs can be used as described herein.

A eukaryotic host cell or non-eukaryotic host cell of the present invention provides the ability to synthesize proteins that comprise unnatural amino acids in large useful quantities. In one aspect, the composition optionally includes, including but not limited to, at least 10 micrograms, at least 50 micrograms, at least 75 micrograms, at least 100 micrograms, at least 200 micrograms, at least 250 micrograms, at least 500 micrograms, at least 1 milligram, at least 10 milligrams, at least 100 milligrams, at least one gram, or more of the protein that comprises an unnatural amino acid, or an amount that can be achieved with in vivo protein production methods (details on recombinant protein production and purification are provided herein). In another aspect, the protein is optionally present in the composition at a concentration of, including but not limited to, at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, including but not limited to, a cell lysate, a buffer, a pharmaceutical buffer, or other liquid suspension (including but not limited to, in a volume of, including but not limited to, anywhere from about 1 nl to about 100 L or more). The production of large quantities (including but not limited to, greater that that typically possible with other methods, including but not limited to, in vitro translation) of a protein in a eukaryotic cell including at least one unnatural amino acid is a feature of the invention.

A eukaryotic host cell or non-eukaryotic host cell of the present invention provides the ability to biosynthesize proteins that comprise unnatural amino acids in large useful quantities. For example, proteins comprising an unnah1ral amino acid can be produced at a concentration of, including but not limited to, at least 10 μg/liter, at least 50 μg/liter, at least 75 μg/liter, at least 100 μg/liter, at least 200 μg/liter, at least 250 μg/liter, or at least 500 μg/liter, at least 1 mg/liter, at least 2 mg/liter, at least 3 mg/liter, at least 4 mg/liter, at least 5 mg/liter, at least 6 mg/liter, at least 7 mg/liter, at least 8 mg/liter, at least 9 mg/liter, at least 10 mg/liter, at least 20, 30, 40, 50, 60, 70, 80, 90, 100, 200, 300, 400, 500, 600, 700, 800, 900 mg/liter, 1 g/liter, 5 g/liter, 10 g/liter or more of protein in a cell extract, cell lysate, culture medium, a buffer, and/or the like.

A number of vectors suitable for express10n of bG-CSF are commercially available. Useful expression vectors for eukaryotic hosts, include but are not limited to, vectors comprising expression control sequences from SV40, bovine papilloma virus, adenovirus and cytomegalovirus. Such vectors include pCDNA3.1(+)\Hyg (Invitrogen, Carlsbad, Calif., USA) and pCI-neo (Stratagene, La Jolla, Calif., USA). Bacterial plasmids, such as plasmids from *E. coli*, including pBR322, pET3a and pET12a, wider host range plasmids, such as RP4, phage DNAs, e.g., the numerous derivatives of phage lambda, e.g., NM989, and other DNA phages, such as M13 and filamentous single stranded DNA phages may be used. The 2μ plasmid and derivatives thereof, the POTI vector (U.S. Pat. No. 4,931,373 which is incorporated by reference), the pJSO37 vector described in (Okkels, Ann. New York Aced. Sci. 782, 202 207, 1996) and pPICZ A, B or C (Invitrogen) may be used with yeast host cells. For insect cells, the vectors include but are not limited to, pVL941, pBG311 (Cate et al., "Isolation of the Bovine and Human Genes for Mullerian Inhibiting Substance And Expression of the Human Gene In Animal Cells", Cell, 45, pp. 685 98 (1986), pBluebac 4.5 and pMelbac (Invitrogen, Carlsbad, CA).

The nucleotide sequence encoding an bG-CSF polypeptide may or may not also include sequence that encodes a signal peptide. The signal peptide is present when the polypeptide is to be secreted from the cells in which it is expressed. Such signal peptide may be any sequence. The signal peptide may be prokaryotic or eukaryotic. Coloma, M (1992) J. Imm. Methods 152:89 104) describe a signal peptide for use in mammalian cells (murine 1 g kappa light chain signal peptide). Other signal peptides include but are not limited to, the a-factor signal peptide from *S. cerevisiae* (U.S. Pat. No. 4,870,008 which is incorporated by reference herein), the signal peptide of mouse salivary amylase (O. Hagenbuchle et al., Nature 289, 1981, pp. 643-646), a modified carboxypeptidase signal peptide (L. A. Valls et al., Cell 48, 1987, pp. 887-897), the yeast BARI signal peptide (WO 87/02670, which is incorporated by reference herein), and the yeast aspartic protease 3 (YAP3) signal peptide (cf. M. Egel-Mitani et al., Yeast 6, 1990, pp. 127-137).

Examples of suitable mammalian host cells are known to those of ordinary skill in the art. Such host cells may be Chinese hamster ovary (CHO) cells, (e.g. CHO-K1; ATCC CCL-61), Green Monkey cells (COS) (e.g. COS 1 (ATCC CRL-1650), COS 7 (ATCC CRL-1651)); mouse cells (e.g. NS/O), Baby Hamster Kidney (BHK) cell lines (e.g. ATCC CRL-1632 or ATCC CCL-10), and human cells (e.g. HEK 293 (ATCC CRL-1573)), as well as plant cells in tissue culture. These cell lines and others are available from public depositories such as the American Type Culture Collection, Rockville, Md. In order to provide improved glycosylation of the bG-CSF polypeptide, a mammalian host cell may be modified to express sialyltransferase, e.g. 1,6-sialyltransferase, e.g. as described in U.S. Pat. No. 5,047,335, which is incorporated by reference herein.

Methods for the introduction of exogenous DNA into mammalian host cells include but are not limited to, calcium phosphate-mediated transfection, electroporation, DEAE-dextran mediated transfection, liposome-mediated transfection, viral vectors and the transfection methods described by Life Technologies Ltd, Paisley, UK using Lipofectamin 2000 and Roche Diagnostics Corporation, Indianapolis, USA using FuGENE 6. These methods are well known in the art and are described by Ausbel et al. (eds.), 1996, Current Protocols in Molecular Biology, John Wiley & Sons, New York, USA. The cultivation of mammalian cells may be performed according to established methods, e.g. as disclosed in (Animal Cell Biotechnology, Methods and Protocols, Edited by Nigel Jenkins, 1999, Human Press Inc. Totowa, N.J., USA and Harrison Mass. and Rac IF, General Techniques of Cell Culture, Cambridge University Press 1997).

I. Expression Systems, Culture, and Isolation bG-CSF polypeptides may be expressed in any number of suitable expression systems including, for example, yeast, insect cells, mammalian cells, and bacteria. A description of exemplary expression systems is provided below.

Yeast As used herein, the term "yeast" includes any of the various yeasts capable of expressing a gene encoding a bG-CSF polypeptide. Such yeasts include, but are not limited to, ascosporogenous yeasts (*Endomycetales*), basidiosporogenous yeasts and yeasts belonging to the Fungi imperfecti (*Blastomycetes*) group. The ascosporogenous yeasts are divided into two families, *Spermophthoraceae* and *Saccharomycesaceae*. The latter is comprised of four subfamilies, *Schizosaccharomycoideae* (e.g., genus *Schizosaccharomyces*), *Nadsonioideae, Lipomycoideae* and *Saccharomycoideae* (e.g., genera *Pichia, Kluyveromyces* and *Saccharomyces*). The basidiosporogenous yeasts include the genera *Leucosporidium, Rhodosporidium, Sporidiobolus, Filobasidium*, and *Filobasidiella*. Yeasts belonging to the Fungi Imperfecti (*Blastomycetes*) group are divided into two families, *Sporobolomycetaceae* (e.g., genera *Sporobolomyces* and *Bullera*) and *Cryptococcaceae* (e.g., genus *Candida*).

Of particular interest for use with the present invention are species within the genera *Pichia, Kluyveromyces, Saccharomyces, Schizosaccharomyces, Hansenula, Torulopsis*, and *Candida*, including, but not limited to, *P. pastoris, P. guillerimondii, S. cerevisiae, S. carlsbergensis, S. diastaticus, S. douglasii, S. kluyveri, S, norbensis, S. oviformis, K. lactis, K. fragilis, C. albicans, C. maltosa*, and *H polymorpha*.

The selection of suitable yeast for expression of bG-CSF polypeptides is within the skill of one of ordinary skill in the art. In selecting yeast hosts for expression, suitable hosts may include those shown to have, for example, good secretion capacity, low proteolytic activity, good secretion capacity, good soluble protein production, and overall robustness. Yeast are generally available from a variety of sources including, but not limited to, the Yeast Genetic Stock Center, Department of Biophysics and Medical Physics, University of California (Berkeley, CA), and the American Type Culture Collection ("ATCC") (Manassas, VA).

The term "yeast host" or "yeast host cell" includes yeast that can be, or has been, used as a recipient for recombinant vectors or other transfer DNA. The term includes the progeny of the original yeast host cell that has received the recombinant vectors or other transfer DNA. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a bG-CSF polypeptide, are included in the progeny intended by this definition.

Expression and transformation vectors, including extrachromosomal replicons or integrating vectors, have been developed for transformation into many yeast hosts. For example, expression vectors have been developed for *S. cerevisiae* (Sikorski et al., GENETICS (1989) 122:19; Ito et al., J. Bacteriol. (1983) 153:163; Hinnen et al., Proc. Natl. Acad. Sci. USA (1978) 75:1929); *C. albicans* (Kurtz et al., Mol. Cell. Biol. (1986) 6:142); *C. maltosa* (Kunze et al., J. Basic Microbiol. (1985) 25:141); *H. polymorpha* (Gleeson et al., J. Gen. Microbiol. (1986) 132:3459; Roggenkamp et al., Mol. Genetics and Genomics (1986) 202:302); *K. fragilis* (Das et al., J. Bacteriol. (1984) 158:1165); *K. lactis* (De Louvencourt et al., J. Bacteriol. (1983) 154:737; Van den Berg et al., Biotechnology (NY) (1990) 8:135); *P. guillerimondii* (Kunze et al., J. Basic Microbiol. (1985) 25:141); *P. pastoris* (U.S. Pat. Nos. 5,324,639; 4,929,555; and 4,837,148; Cregg et al., Mol. Cell. Biol. (1985) 5:3376); *Schizosaccharomyces pombe* (Beach et al., Nature (1982) 300:706); and *Y. lipolytica; A. nidulans* (Ballance et al., Biochem. Biophys. Res. Commun. (1983) 112:284-89; Tilbum et al., Gene (1983) 26:205-221; and Yelton et. al., Proc. Natl. Acad. Sci. USA (1984) 81:1470-74); *A. niger* (Kelly and Hynes, EMBO J. (1985) 4:475-479); T reesia (EP O 244 234); and filamentous fungi such as, e.g., *Neurospora, Penicillium, Tolypocladium* (WO 91/00357), each incorporated by reference herein.

Control sequences for yeast vectors are known to those of ordinary skill in the art and include, but are not limited to, promoter regions from genes such as alcohol dehydrogenase (ADH) (EP O 284 044); enolase; glucokinase; glucose-6-phosphate isomerase; glyceraldehyde-3-phosphate-dehydrogenase (GAP or GAPDH); hexokinase; phosphofructokinase; 3-phosphoglycerate mutase; and pyruvate kinase (PyK) (EP O 329 203). The yeast PHO5 gene, encoding acid phosphatase, also may provide useful promoter sequences (Miyanohara et al., Proc. Natl. Acad. Sci. USA (1983) 80:1). Other suitable promoter sequences for use with yeast hosts may include the promoters for 3-phosphoglycerate kinase (Hitzeman et al., J. Biol. Chem. (1980) 255:12073); and other glycolytic enzymes, such as pyruvate decarboxylase, triosephosphate isomerase, and phosphoglucose isomerase (Holland et al., Biochemistry (1978) 17:4900; Hess et al., J. Adv. Enzyme Reg. (1969) 7:149). Inducible yeast promoters having the additional advantage of transcription controlled by growth conditions may include the promoter regions for alcohol dehydrogenase 2; isocytochrome C; acid phosphatase; metallothionein; glyceraldehyde-3-phosphate dehydrogenase; degradative enzymes associated with nitrogen metabolism; and enzymes responsible for maltose and galactose utilization. Suitable vectors and promoters for use in yeast expression are further described in EP 00 073 657.

Yeast enhancers also may be used with yeast promoters. In addition, synthetic promoters may also function as yeast promoters. For example, the upstream activating sequences (UAS) of a yeast promoter may be joined with the transcription activation region of another yeast promoter, creating a synthetic hybrid promoter. Examples of such hybrid promoters include the ADH regulatory sequence linked to the GAP transcription activation region. See U.S. Pat. Nos. 4,880,734 and 4,876,197, which are incorporated by reference herein. Other examples of hybrid promoters include promoters that consist of the regulatory sequences of the ADH2, GAL4, GALlO, or PHO5 genes, combined with the transcriptional activation region of a glycolytic enzyme gene such as GAP or PyK. See EP O 164 556. Furthermore, a yeast promoter may include naturally occurring promoters of non-yeast origin that have the ability to bind yeast RNA polymerase and initiate transcription.

Other control elements that may comprise part of the yeast expression vectors include terminators, for example, from GAPDH or the enolase genes (Holland et al., J. Biol. Chem. (1981) 256:1385). In addition, the origin of replication from the 2μ plasmid origin is suitable for yeast. A suitable selection gene for use in yeast is the trpl gene present in the yeast plasmid. See Tschumper et al., Gene (1980) 10:157; Kingsman et al., Gene (1979) 7:141. The trpl gene provides a selection marker for a mutant strain of yeast lacking the ability to grow in tryptophan. Similarly, Leu2-deficient yeast strains (ATCC 20,622 or 38,626) are complemented by known plasmids bearing the Leu2 gene.

Methods of introducing exogenous DNA into yeast hosts are known to those of ordinary skill in the art, and typically include, but are not limited to, either the transformation of spheroplasts or of intact yeast host cells treated with alkali cations. For example, transformation of yeast can be carried out according to the method described in Hsiao et al., Proc. Natl. Acad. Sci. USA (1979) 76:3829 and Van Solingen et al., J. Bact. (1977) 130:946. However, other methods for introducing DNA into cells such as by nuclear injection, electroporation, or protoplast fusion may also be used as described generally in Sambrook Et Al., Molecular Cloning: A Lab. Manual (2001). Yeast host cells may then be cultured using standard techniques known to those of ordinary skill in the art.

Other methods for expressing heterologous proteins in yeast host cells are known to those of ordinary skill in the art. See generally U.S. Patent Publication No. 20020055169, U.S. Pat. Nos. 6,361,969; 6,312,923; 6,183,985; 6,083,723; 6,017,731; 5,674,706; 5,629,203; 5,602,034; and 5,089,398; U.S. Reexamined Pat. Nos. RE37,343 and RE35,749; PCT Published Patent Applications WO 99/07862; WO 98/37208; and WO 98/26080; European Patent Applications EP O 946 736; EP O 732 403; EP O 480 480; WO 90/10277; EP O 340 986; EP O 329 203; EP O 324 274; and EP O 164 556. See also Gellissen et al., Antonie Van Leeuwenhoek (1992) 62 (1-2): 79-93; Romanos et al., Yeast (1992) 8 (6): 423-488; Goeddel, Methods in Enzymology (1990) 185:3-7, each incorporated by reference herein.

The yeast host strains may be grown in fermentors during the amplification stage using standard feed batch fermentation methods known to those of ordinary skill in the art. The fermentation methods may be adapted to account for differences in a particular-yeast host's carbon utilization pathway or mode of expression control. For example, fermentation of a *Saccharomyces* yeast host may require a single glucose feed, complex nitrogen source (e.g., casein hydrolysates), and multiple vitamin supplementation. In contrast, the methylotrophic yeast *P. pastoris* may require glycerol, methanol, and trace mineral feeds, but only simple aminonium (nitrogen) salts for optimal growth and expression. See, e.g., U.S. Pat. No. 5,324,639; Elliott et al., J. Protein Chem. (1990) 9:95; and Fieschko et al., Biotech. Bioeng. (1987) 29:1113, incorporated by reference herein.

Such fermentation methods, however, may have certain common features independent of the yeast host strain employed. For example, a growth limiting nutrient, typically carbon, may be added to the fermentor during the amplification phase to allow maximal growth. In addition, fermentation methods generally employ a fermentation medium designed to contain adequate amounts of carbon, nitrogen, basal salts, phosphorus, and other minor nutrients (vitamins, trace minerals and salts, etc.). Examples of fermentation media suitable for use with *Pichia* are described in U.S. Pat. Nos. 5,324,639 and 5,231,178, which are incorporated by reference herein.

Baculovirus-Infected Insect Cells The te1m "insect host" or "insect host cell" refers to a insect that can be, or has been, used as a recipient for recombinant vectors or other transfer DNA. The term includes the progeny of the original insect host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a bG-CSF polypeptide, are included in the progeny intended by this definition.

The selection of suitable insect cells for expression of bG-CSF polypeptides is known to those of ordinary skill in the art. Several insect species are well described in the art and are commercially available including *Aedes aegypti, Bombyx mori, Drosophila melanogaster, Spodoptera frugiperda*, and *Trichoplusia ni*. In selecting insect hosts for expression, suitable hosts may include those shown to have, inter alia, good secretion capacity, low proteolytic activity, and overall robustness. Insect are generally available from a variety of sources including, but not limited to, the Insect Genetic Stock Center, Department of Biophysics and Medical Physics, University of California (Berkeley, CA); and the American Type Culture Collection ("ATCC") (Manassas, VA).

Generally, the components of a baculovirus-infected insect expression system include a transfer vector, usually a bacterial plasmid, which contains both a fragment of the baculovirus genome, and a convenient restriction site for insertion of the heterologous gene to be expressed; a wild type baculovirus with sequences homologous to the baculovirus-specific fragment in the transfer vector (this allows for the homologous recombination of the heterologous gene in to the baculovirus genome); and appropriate insect host cells and growth media. The materials, methods and techniques used in constructing vectors, transfecting cells, picking plaques, growing cells in culture, and the like are known in the art and manuals are available describing these techniques.

After inserting the heterologous gene into the transfer vector, the vector and the wild type viral genome are transfected into an insect host cell where the vector and viral genome recombine. The packaged recombinant virus is expressed and recombinant plaques are identified and purified. Materials and methods for baculovirus/insect cell expression systems are commercially available in kit form from, for example, Invitrogen Corp. (Carlsbad, CA). These techniques are generally known to those of ordinary skill in the art and fully described in Summers and Smith, Texas Agricultural Experiment Station Bulletin No. 1555 (1987), herein incorporated by reference. See also, Richardson, 39 Methods In Molecular Biology: Baculovir.Us Expression Protocols (1995); Ausubel Et Al., Current Protocols In Molecular Biology 16.9-16.11 (1994); King and Possee, The Baculovirus System: A Laboratory Guide (1992); and O'Reilly et al., Baculovirus Expression Vectors: A Laboratory Manual (1992).

Indeed, the production of various heterologous proteins using baculovirus/insect cell expression systems is known to those of ordinary skill in the art. See, e.g., U.S. Pat. Nos. 6,368,825; 6,342,216; 6,338,846; 6,261,805; 6,245,528, 6,225,060; 6,183,987; 6,168,932; 6,126,944; 6,096,304; 6,013,433; 5,965,393; 5,939,285; 5,891,676; 5,871,986; 5,861,279; 5,858,368; 5,843,733; 5,762,939; 5,753,220; 5,605,827; 5,583,023; 5,571,709; 5,516,657; 5,290,686; WO 02/06305; WO 01/90390; WO 01/27301; WO 01/05956; WO 00/55345; WO 00/20032; WO 99/51721; WO 99/45130; WO 99/31257; WO 99/10515; WO 99/09193; WO 97/26332; WO 96/29400; WO 96/25496; WO 96/06161; WO 95/20672; WO 93/03173; WO 92/16619; WO 92/02628; WO 92/01801; WO 90/14428; WO 90/10078; WO 90/02566; WO 90/02186; WO 90/01556; WO 89/01038; WO 89/01037; WO 88/07082, which are incorporated by reference herein.

Vectors that are useful in baculovirus/insect cell expression systems are known in the ait and include, for example, insect expression and transfer vectors derived from the baculovirus *Autographa californica* nuclear polyhedrosis virus (AcNPV), which is a helper-independent, viral expression vector. Viral expression vectors derived from this system usually use the strong viral polyhedrin gene promoter to drive expression of heterologous genes. See generally, O'Reilly et al., Baculovirus Expression Vectors: A Laboratory Manual (1992).

Prior to inserting the foreign gene into the baculovirus genome, the above-described components, comprising a promoter, leader (if desired), coding sequence of interest, and transcription termination sequence, are typically assembled into an intermediate transplacement construct (transfer vector). Intermediate transplacement constructs are often maintained in a replicon, such as an extra chromosomal element (e.g., plasmids) capable of stable maintenance in a host, such as bacteria The replicon will have a replication system, thus allowing it to be maintained in a suitable host for cloning and amplification. More specifically, the plasmid may contain the polyhedrin polyadenylation signal (Miller, Ann. Rev. Microbiol. (1988) 42:177) and a prokaryotic ampicillin-resistance (amp) gene and origin of replication for selection and propagation in *E. coli.*

One commonly used transfer vector for introducing foreign genes into AcNPV is pAc373. Many other vectors, known to those of skill in the art, have also been designed including, for example, pVL985, which alters the polyhedrin start codon from ATG to ATI, and which introduces a BamHI cloning site 32 base pairs downstream from the ATT. See Luckow and Summers, VIROLOGY 170:31 (1989). Other commercially available vectors include, for example, PBlucBac4.5N5-His; pBlueBacHis2; pMelBac; pBlueBac4.5 (Invitrogen Corp., Carlsbad, CA).

After insertion of the heterologous gene, the transfer vector and wild type baculoviral genome are co-transfected into an insect cell host. Methods for introducing heterologous DNA into the desired site in the baculovirus virus are known in the art. See Summers and Smith, Texas Agricultural Experiment Station Bulletin No. 1555 (1987); Smith et al., Mol. Cell. Biol. (1983) 3:2156; Luckow and Summers, Virology (1989) 170:31. For example, the insertion can be into a gene such as the polyhedrin gene, by homologous double crossover recombination; insertion can also be into a restriction enzyme site engineered into the desired baculovirus gene. See Miller et al., Bioessays (1989) 11 (4): 91.

Transfection may be accomplished by electroporation. See Trotter and Wood, 39 Methods in Molecular Biology (1995); Mann and King, J. Gen. Virol. (1989) 70:3501. Alternatively, liposomes may be used to transfect the insect cells with the recombinant expression vector and the baculovirus. See, e.g., Liebman et al., Biotechniques (1999) 26 (1): 36; Graves et al., Biochemistry (1998) 37:6050; Nomura et al., J. Biol. Chem. (1998) 273 (22): 13570; Schmidt et al., Protein Expression and Purification (1998) 12:323; Siffert et al., Nature Genetics (1998) 18:45; Tilkins et al., Cell Biology: A Laboratory Handbook 145-154 (1998); Cai et al., Protein Expression and Purification (1997) 10:263; Dolphin et al., Nature Genetics (1997) 17:491; Kost et al., Gene (1997) 190:139; Jakobsson et al., J. Biol. Chem. (1996) 271:22203; Rowles et al., J. Biol. Chem. (1996) 271 (37): 22376; Reverey et al., J. Biol. Chem. (1996) 271 (39): 23607-10; Stanley et al., J. Biol. Chem. (1995) 270:4121; Sisk et al., J. Virol. (1994) 68 (2): 766; and Peng et al., Biotechniques (1993) 14 (2): 274. Commercially available liposomes include, for example, Cellfectin® and Lipofectin® (Invitrogen, Corp., Carlsbad, CA). In addition, calcium phosphate transfection may be used. See Trotter and Wood, 39 Methods in Molecular Biology (1995); Kitts, NAR (1990) 18 (19): 5667; and Mann and King, J. Gen. Virol. (1989) 70:3501.

Baculovirus expression vectors usually contain a baculovirus promoter. A baculovirus promoter is any DNA sequence capable of binding a baculovirus RNA polymerase and initiating the downstream (3') transcription of a coding sequence (e.g., structural gene) into mRNA. A promoter will have a transcription initiation region which is usually placed proximal to the 5' end of the coding sequence. This transcription initiation region typically includes an RNA polymerase binding site and a transcription initiation site. A baculovirus promoter may also have a second domain called an enhancer, which, if present, is usually distal to the structural gene. Moreover, expression may be either regulated or constitutive.

Structural genes, abundantly transcribed at late times in the infection cycle, provide particularly useful promoter sequences. Examples include sequences derived from the gene encoding the viral polyhedron protein (Friesen et al., The Regulation of Baculovirus Gene Expression in The Molecular Biology of Baculoviruses (1986); EP 0 127 839 and 0 155 476) and the gene encoding the p10 protein (Vlak et al., J. Gen. Virol. (1988) 69:765).

The newly formed baculovirus expression vector is packaged into an infectious recombinant baculovirus and subsequently grown plaques may be purified by techniques known to those of ordinary skill in the art. See Miller et al., Bioessays (1989) 11 (4): 91; Summers and Smith, Texas Agricultural Experiment Station Bulletin No. 1555 (1987).

Recombinant baculovirus expression vectors have been developed for infection into several insect cells. For example, recombinant baculoviruses have been developed for, inter alia, *Aedes aegypti* (ATCC No. CCL-125), *Bombyx mori* (ATCC No. CRL 8910), *Drosophila melanogaster* (ATCC No. 1963), *Spodoptera frugiperda*, and *Trichoplusia ni*. See Wright, Nature (1986) 321:718; Carbonell et al., J. Virol. (1985) 56:153 Smith et al., Mol. Cell. Biol. (1983) 3:2156. See generally, Fraser et al., In Vitro Cell. Dev. Biol.

(1989) 25:225. More specifically, the cell lines used for baculovirus expression vector systems commonly include, but are not limited to, Sf9 (*Spodoptera frugiperda*) (ATCC No. CRL-1711), Sf21 (*Spodoptera frugiperda*) (Invitrogen Corp., Cat. No. 11497-013 (Carlsbad, CA)), Tri-368 (*Trichopulsia ni*), and High-Five™ BTI-IN-5B1-4 (*Trichopulsia ni*).

Cells and culture media are commercially available for both direct and fusion expression of heterologous polypeptides in a baculovirus/expression, and cell culture technology is generally known to those of ordinary skill in the art.

*E. Coli. Pseudomonas* species. and other Prokaryotes Bacterial expression techniques are known to those of ordinary skill in the all. A wide variety of vectors are available for use in bacterial hosts. The vectors may be single copy or low or high multicopy vectors. Vectors may serve for cloning and/or expression. In view of the ample literature concerning vectors, commercial availability of many vectors, and even manuals describing vectors and their restriction maps and characteristics, no extensive discussion is required here. As is well-known, the vectors normally involve markers allowing for selection, which markers may provide for cytotoxic agent resistance, prototrophy or immunity. Frequently, a plurality of markers is present, which provide for different characteristics.

A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al., Annu. Rev. Genet. (1984) 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al., Nature (1977) 198:1056], and maltose. Additional examples include promoter sequences derived from biosynthetic enzymes such as tryptophan (trp) [Goeddel et al., Nuc. Acids Res. (1980) 8:4057; Yelverton et al., Nucl. Acids Res. (1981) 9:731; U.S. Pat. No. 4,738,921; EP Pub. Nos. 036 776 and 121 775, which are incorporated by reference herein]. The β-galactosidase (bla) promoter system [Weissmann (1981) "The cloning of interferon and other mistakes." In Interferon 3 (Ed. I. Gresser)], bacteriophage lambda PL [Shimatake et al., Nature (1981) 292:128] and T5 [U.S. Pat. No. 4,689,406, which are incorporated by reference herein] promoter systems also provide useful promoter sequences. Preferred methods of the present invention utilize strong promoters, such as the T7 promoter to induce bG-CSF polypeptides at high levels. Examples of such vectors are known to those of ordinary skill in the art and include the pET29 series from Novagen, and the pPOP vectors described in WO99/05297, which is incorporated by reference herein. Such expression systems may produce high levels of bG-CSF polypeptides in the host without compromising host cell viability or growth parameters. pET19 (Novagen) is another vector known in the art.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551, 433, which is incorporated by reference herein]. For example, the tac promoter is a hybrid trp-lac promoter comprised of both trp promoter and lac operon sequences that is regulated by the lac repressor [Amann et al., Gene (1983) 25:167; de Boer et al., Proc. Natl. Acad. Sci. (1983) 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al., J. Mol. Biol. (1986) 189:113; Tabor et al., Proc Natl. Acad. Sci. (1985) 82:1074]. In addition, a hybrid promoter can also be comprised of a bacteriophage promoter and an *E. coli* operator region (EP Pub. No. 267 851).

In addition to a functioning promoter sequence, an efficient ribosome binding site is also useful for the expression of foreign genes in prokaryotes. In *E. coli*, the ribosome binding site is called the Shine-Dalgamo (SD) sequence and includes an initiation codon (ATG) and a sequence 3-9 nucleotides in length located 3-11 nucleotides upstream of the initiation codon [Shine et al., Nature (1975) 254:34]. The SD sequence is thought to promote binding of mRNA to the ribosome by the pairing of bases between the SD sequence and the 3' and of *E. coli* 16S rRNA [Steitz et al. "Genetic signals and nucleotide sequences in messenger RNAU, In Biological Regulation and Development: Gene Expression (Ed. R. F. Goldberger, 1979)]. To express eukaryotic genes and prokaryotic genes with weak ribosome-binding site [Sambrook et al. "Expression of cloned genes in *Escherichia coli*", Molecular Cloning: A Laboratory Manual, 1989].

The term "bacterial host" or "bacterial host cell" refers to a bacterial that can be. or has been, used as a recipient for recombinant vectors or other transfer DNA. The term includes the progeny of the original bacterial host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a bG-CSF polypeptide, are included in the progeny intended by this definition.

The selection of suitable host bacteria for expression of bG-CSF polypeptides is known to those of ordinary skill in the art. In selecting bacterial hosts for expression, suitable hosts may include those shown to have, inter alia, good inclusion body formation capacity, low proteolytic activity, and overall robustness. Bacterial hosts are generally available from a variety of sources including, but not limited to, the Bacterial Genetic Stock Center, Department of Biophysics and Medical Physics, University of California (Berkeley, CA); and the American Type Culture Collection ("ATCC") (Manassas, VA). Industrial/pharmaceutical fermentation generally use bacterial derived from K strains (e.g. W3110) or from bacteria derived from B strains (e.g. BL21). These strains are particularly useful because their growth parameters are extremely well known and robust. In addition, these strains are non-pathogenic, which is commercially important for safety and environmental reasons. Other examples of suitable *E. coli* hosts include, but are not limited to, strains of BL21, DHl0B, or derivatives thereof. In another embodiment of the methods of the present invention, the *E. coli* host is a protease minus strain including, but not limited to, OMP- and LON-. The host cell strain may be a species of *Pseudomonas*, including but not limited to, *Pseudomonas fluorescens, Pseudomonas aentginosa*, and *Pseudomonas putida. Pseudomonas fluorescens* biovar 1, designated strain MB101, is known to be useful for recombinant production and is available for therapeutic protein production processes. Examples of a *Pseudomonas* expression system include the system available from The Dow Chemical Company as a host strain (Midland, MI available on the World Wide Web at dow.com).

Once a recombinant host cell strain has been established (i.e., the expression construct has been introduced into the host cell and host cells with the proper expression construct are isolated), the recombinant host cell strain is cultured under conditions appropriate for production of bG-CSF polypeptides. As will be apparent to one of skill in the art, the method of culture of the recombinant host cell strain will be dependent on the nature of the expression construct utilized and the identity of the host cell. Recombinant host strains are normally cultured using methods that are known to those of ordinary skill in the art. Recombinant host cells are typically cultured in liquid medium containing assimilable sources of carbon, nitrogen, and inorganic salts and, optionally, containing vitamins, amino acids, growth factors, and other proteinaceous culture supplements known to those of ordinary skill in the art. Liquid media for culture of host cells may optionally contain antibiotics or anti-fungals to prevent the growth of undesirable microorganisms and/or compounds including, but not limited to, antibiotics to select for host cells containing the expression vector.

Recombinant host cells may be cultured in batch or continuous formats, with either cell harvesting (in the case where the bG-CSF polypeptide accumulates intracellularly) or harvesting of culture supernatant in either batch or continuous formats. For production in prokaryotic host cells, batch culture and cell harvest are preferred.

The bG-CSF polypeptides of the present invention are normally purified after expression in recombinant systems. The bG-CSF polypeptide may be purified from host cells or culture medium by a variety of methods known to the art. U.S. Pat. No. 5,849,883 and WO 89/10932, which are incorporated by reference herein in their entirety, describe the cloning of b-GCSF and analogs thereof into host cells and methods for isolation and purification. bG-CSF polypeptides produced in bacterial host cells may be poorly soluble or insoluble (in the fo1m of inclusion bodies). In one embodiment of the present invention, amino acid substitutions may readily be made in the bG-CSF polypeptide that are selected for the purpose of increasing the solubility of the recombinantly produced protein utilizing the methods disclosed herein as well as those known in the alt. In the case of insoluble protein, the protein may be collected from host cell lysates by centrifugation and may further be followed by homogenization of the cells. In the case of poorly soluble protein, compounds including, but not limited to, polyethylene imine (PEI) may be added to induce the precipitation of partially soluble protein. The precipitated protein may then be conveniently collected by centrifugation. Recombinant host cells may be disrupted or homogenized to release the inclusion bodies from within the cells using a variety of methods known to those of ordinary skill in the art. Host cell disruption or homogenization may be performed using well known techniques including, but not limited to, enzymatic cell disruption, sonication, dounce homogenization, or high pressure release disruption. In one embodiment of the method of the present invention, the high pressure release technique is used to disrupt the *E. coli* host cells to release the inclusion bodies of the bG-CSF polypeptides. When handling inclusion bodies of bG-CSF polypeptide, it may be advantageous to minimize the homogenization time on repetitions in order to maximize the yield of inclusion bodies without loss due to factors such as solubilization, mechanical shearing or proteolysis.

Insoluble or precipitated bG-CSF polypeptide may then be solubilized using any of a number of suitable solubilization agents known to the art. The bG-CSF polypeptide may be solubilized with urea or guanidine hydrochloride. The volume of the solubilized bG-CSF polypeptide should be minimized so that large batches may be produced using conveniently manageable batch sizes. This factor may be significant in a large-scale commercial setting where the recombinant host may be grown in batches that are thousands of liters in volume. In addition, when manufacturing bG-CSF polypeptide in a large-scale commercial setting, in particular for human pharmaceutical uses, the avoidance of harsh chemicals that can damage the machinery and container, or the protein product itself, should be avoided, if possible. It has been shown in the method of the present invention that the milder denaturing agent urea can be used to solubilize the bG-CSF polypeptide inclusion bodies in place of the harsher denaturing agent guanidine hydrochloride. The use of urea significantly reduces the risk of damage to stainless steel equipment utilized in the manufacturing and purification process of bG-CSF polypeptide while efficiently solubilizing the bG-CSF polypeptide inclusion bodies.

In the case of soluble bG-CSF protein, the bG-CSF may be secreted into the periplasmic space or into the culture medium. In addition, soluble bG-CSF may be present in the cytoplasm of the host cells. It may be desired to concentrate soluble bG-CSF prior to performing purification steps. Standard techniques known to those of ordinary skill in the art may be used to concentrate soluble bG-CSF from, for example, cell lysates or culture medium. In addition, standard techniques known to those of ordinary skill in the art may be used to disrupt host cells and release soluble bG-CSF from the cytoplasm or periplasmic space of the host cells.

When bG-CSF polypeptide is produced as a fusion protein, the fusion sequence may be removed. Removal of a fusion sequence may be accomplished by enzymatic or chemical cleavage. Enzymatic removal of fusion sequences may be accomplished using methods known to those of ordinary skill in the art. The choice of enzyme for removal of the fusion sequence will be determined by the identity of the fusion, and the reaction conditions will be specified by the choice of enzyme as will be apparent to one of ordinary skill in the art. Chemical cleavage may be accomplished using reagents known to those of ordinary skill in the alt, including but not limited to, cyanogen bromide, TEV protease, and other reagents. The cleaved bG-CSF polypeptide may be purified from the cleaved fusion sequence by methods known to those of ordinary skill in the art. Such methods will be determined by the identity and properties of the fusion sequence and the bG-CSF polypeptide, as will be apparent to one of ordinary skill in the art. Methods for purification may include, but ai•e not limited to, size-exclusion chromatography, hydrophobic interaction chromatography, ion-exchange chromatography or dialysis or any combination thereof.

The bG-CSF polypeptide may also be purified to remove DNA from the protein solution. DNA may be removed by any suitable method known to the art, such as precipitation or ion exchange chromatography, but may be removed by precipitation with a nucleic acid precipitating agent, such as, but not limited to, protamine sulfate. The bG-CSF polypeptide may be separated from the precipitated DNA using standard well known methods including, but not limited to, centrifugation or filtration. Removal of host nucleic acid molecules is an important factor in a setting where the bG-CSF polypeptide is to be used to treat animals or humans and the methods of the present invention reduce host cell DNA to pharmaceutically acceptable levels.

Methods for small-scale or large-scale fermentation can also be used in protein expression, including but not limited to, fermentors, shake flasks, fluidized bed bioreactors, hollow fiber bioreactors, roller bottle culture systems, and stirred tank bioreactor systems. Each of these methods can be performed in a batch, fed-batch, or continuous mode process.

bG-CSF polypeptides of the invention can generally be recovered using methods standard in the art. For example, culture medium or cell lysate can be centrifuged or filtered to remove cellular debris. The supernatant may be concentrated or diluted to a desired volume or diafiltered into a suitable buffer to condition the preparation for further purification. Further purification of the bG-CSF polypeptide of the present invention includes separating deamidated and clipped forms of the bG-CSF polypeptide variant from the intact form.

Any of the following exemplary procedures can be employed for purification of bG-CSF polypeptides of the invention: affinity chromatography; anion- or cation-exchange chromatography (using, including but not limited to, DEAE SEPHAROSE); chromatography on silica; high performance liquid chromatography (HPLC); reverse phase HPLC; gel filtration (using, including but not limited to, SEPHADEX G-75); hydrophobic interaction chromatography; size-exclusion chromatography; metal-chelate chromatography; ultrafiltration/diafiltration; ethanol precipitation; aminonium sulfate precipitation; chromatofocusing; displacement chromatography; electrophoretic procedures (including but not limited to preparative isoelectric focusing), differential solubility (including but not limited to aminonium sulfate precipitation), SDS-PAGE, or extraction.

Proteins of the present invention, including but not limited to, proteins comprising unnatural amino acids, peptides comprising unnatural amino acids, antibodies to proteins comprising unnatural amino acids, binding partners for proteins comprising unnatural amino acids, etc., can be purified, either partially or substantially to homogeneity, according to standard procedures known to and used by those of skill in the art. Accordingly, polypeptides of the invention can be recovered and purified by any of a number of methods known to those of ordinary skill in the art, including but not limited to, aminonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against unnatural amino acids (or proteins or peptides comprising unnatural amino acids) are used as purification reagents, including but not limited to, for affinity-based purification of proteins or peptides comprising one or more unnatural amino acid(s). Once purified, partially or to homogeneity, as desired, the polypeptides are optionally used for a wide variety of utilities, including but not limited to, as assay components, therapeutics, prophylaxis, diagnostics, research reagents, and/or as: immunogens for antibody production. Antibodies generated against polypeptides of the present invention may be obtained by administering the polypeptides or epitope-bearing fragments, or cells to an animal, preferably a non-human animal, using routine protocols. One of ordinary skill in the art could generate antibodies using a variety of known techniques. Also, transgenic mice, or other organisms, including other mammals, may be used to express humanized antibodies. The above-described antibodies may be employed to isolate or to identify clones expressing the polypeptide or to purify the polypeptides. Antibodies against polypeptides of the present invention may also be employed to treat diseases.

Polypeptides and polynucleotides of the present invention may also be used as vacuums. Accordingly, in a further aspect, the present invention relates to a method for inducing an immunological response in a mammal that comprises inoculating the mammal with a polypeptide of the present invention, adequate to produce antibody and/or T cell immune response, including, for example, cytokine-producing T cells or cytotoxic T cells, to protect said animal from disease, whether that disease is already established within the individual or not. An immunological response in a minimal may also be induced by a method comprises delivering a polypeptide of the present invention via a vector directing expression of the polynucleotide and coding for the polypeptide in vivo in order to induce such an immunological response to produce antibody to protect said animal from diseases of the invention. One way of administering the vector is by accelerating it into the desired cells as a coating on particles or otherwise. Such nucleic acid vector may comprise DNA, RNA, a modified nucleic acid, or a DNA/RNA hybrid. For use as a vaccine, a polypeptide or a nucleic acid vector will be normally provided as a vaccine formulation (composition). The formulation may further comprise a suitable carrier. Since a polypeptide may be broken down in the stomach, it may be administered parenterally (for instance, subcutaneous, intramuscular, intravenous, or intradermal injection). Formulations suitable for parenteral administration include aqueous and non-aqueous sterile injection solutions that may contain antioxidants, buffers, bacteriostats and solutes that render the formulation instonic with the blood of the recipient; and aqueous and non-aqueous sterile suspensions that may include suspending agents or thickening agents. The vaccine formulation may also include adjuvant systems for enhancing the immunogenicity of the formulation which are known to those of ordinary skill in the art. The dosage will depend on the specific activity of the vaccine and can be readily determined by routine experimentation.

In addition to other references noted herein, a variety of purification/protein folding methods are known to those of ordinary skill in the art, including, but not limited to, those set forth in R. Scopes, *Protein Purification*, Springer-Verlag, N.Y. (1982); Deutscher, *Methods in Enzymology Vol.* 182*: Guide to Protein Purification*, Academic Press, Inc. N. Y. (1990); Sandana, (1997) *Bioseparation of Proteins*, Academic Press, Inc.; Bollag et al. (1996) *Protein Methods,* 2nd Edition Wiley-Liss, NY; Walker, (1996) *The Protein Protocols Handbook* Humana Press, NJ, Hanis and Angal, (1990) *Protein Purification Applications: A Practical Approach* IRL Press at Oxford, Oxford, England; Harris and Angal, *Protein Purification Methods: A Practical Approach* IRL Press at Oxford, Oxford, England; Scopes, (1993) *Protein Purification: Principles and Practice* 3rd *Edition* Springer Verlag, NY; Janson and Ryden, (1998) *Protein Purification: Principles, High Resolution Methods and Applications, Second Edition* Wiley-VCH, NY; and Walker (1998), *Protein Protocols on CD-ROM* Humana Press, NJ; and the references cited therein.

One advantage of producing a protein or polypeptide of interest with an unnatural amino acid in a eukaryotic host cell or non-eukaryotic host cell is that typically the proteins or polypeptides will be folded in their native conformations. However, in certain embodiments of the invention, those of skill in the art will recognize that, after synthesis, expression and/or purification, proteins or peptides can possess a conformation different from the desired conformations of the relevant polypeptides. In one aspect of the invention, the expressed protein or polypeptide is optionally denatured and then renatured. This is accomplished utilizing methods known in the art, including but not limited to, by adding a chaperonin to the protein or polypeptide of interest, by solubilizing the proteins in a chaotropic agent such as guanidine HCl, utilizing protein disulfide isomerase, etc.

In general, it is occasionally desirable to denature and reduce expressed polypeptides and then to cause the polypeptides to re-fold into the preferred conformation. For example, guanidine, urea, DTI, DTE, and/or a chaperonin can be added to a translation product of interest. Methods of reducing, denaturing and renaturing proteins are known to those of ordinary skill in the art (see, the references above, and Debinski, et al. (1993) *J. Biol. Chem.,* 268:14065-14070; Kreitman and Pastan (1993) *Bioconjug. Chem.,* 4:581-585; and Buchner, et al., (1992) *Anal. Biochem.,* 205:263-270). Debinski, et al., for example, describe the denaturation and reduction of inclusion body proteins in guanidine-DTE. The proteins can be refolded in a redox buffer containing, including but not limited to, oxidized glutathione and L-arginine. Refolding reagents can be flowed or otherwise moved into contact with the one or more polypeptide or other expression product, or vice-versa.

In the case of prokaryotic production of bG-CSF polypeptide, the bG-CSF polypeptide thus produced may be misfolded and thus lacks or has reduced biological activity. The bioactivity of the protein may be restored by “refolding”. In general, misfolded bG-CSF polypeptide is refolded by solubilizing (where the bG-CSF polypeptide is also insoluble), unfolding and reducing the polypeptide chain using, for example, one or more chaotropic agents (e.g. urea and/or guanidine) and a reducing agent capable of reducing disulfide bonds (e.g. dithiothreitol, DTT or 2-mercaptoethanol, 2-ME). At a moderate concentration of chaotrope, an oxidizing agent is then added (e.g., oxygen, cystine or cystamine), which allows the reformation of disulfide bonds. bG-CSF polypeptide may be refolded using standard methods known in the art, such as those described in U.S. Pat. Nos. 4,511,502, 4,511,503, and 4,512,922, which are incorporated by reference herein. The bG-CSF polypeptide may also be cofolded with other proteins to form heterodimers or heteromultimers.

After refolding, the bG-CSF may be further purified. Purification of bG-CSF may be accomplished using a variety of techniques known to those of ordinary skill in the art, including hydrophobic interaction chromatography, size exclusion chromatography, ion exchange chromatography, reverse-phase high performance liquid chromatography, affinity chromatography, and the like or any combination thereof. Additional purification may also include a step of drying or precipitation of the purified protein.

After purification, bG-CSF may be exchanged into different buffers and/or concentrated by any of a variety of methods known to the art, including, but not limited to, diafiltration and dialysis. bG-CSF that is provided as a single purified protein may be subject to aggregation and precipitation.

The purified bG-CSF may be at least 90% pure (as measured by reverse phase high performance liquid chromatography, RP-HPLC, or sodium dodecyl sulfate-polyacrylamide gel electrophoresis, SDS-PAGE) or at least 95% pure, or at least 98% pure, or at least 99% or greater pure. Regardless of the exact numerical value of the purity of the bG-CSF, the bG-CSF is sufficiently pure for use as a pharmaceutical product or for further processing, such as conjugation with a water soluble polymer such as PEG.

Certain bG-CSF molecules may be used as therapeutic agents in the absence of other active ingredients or proteins (other than excipients, carriers, and stabilizers, serum albumin and the like), or they may be complexed with another protein or a polymer.

General Purification Methods Any one of a variety of isolation steps may be performed on the cell lysate, extract, culture medium, inclusion bodies, periplasmic space of the host cells, cytoplasm of the host cells, or other material, comprising bG-CSF polypeptide or on any bG-CSF polypeptide mixtures resulting from any isolation steps including, but not limited to, affinity chromatography, ion exchange chromatography, hydrophobic interaction chromatography, gel filtration chromatography, high performance liquid chromatography (“HPLC”), reversed phase-HPLC (“RP-HPLC”), expanded bed adsorption, or any combination and/or repetition thereof and in any appropriate order.

Equipment and other necessary materials used in performing the techniques described herein are commercially available. Pumps, fraction collectors, monitors, recorders, and entire systems are available from, for example, Applied Biosystems (Foster City, CA), Bio-Rad Laboratories, Inc. (Hercules, CA), and Amersham Biosciences, Inc. (Piscataway, NJ). Chromatographic materials including, but not limited to, exchange matrix materials, media, and buffers are also available from such companies.

Equilibration, and other steps in the column chromatography processes described herein such as washing and elution, may be more rapidly accomplished using specialized equipment such as a pump. Commercially available pumps include, but are not limited to, HILOAD® Pump P-50, Peristaltic Pump P-1, Pump P-901, and Pump P-903 (Amersham Biosciences, Piscataway, NJ).

Examples of fraction collectors include RediFrac Fraction Collector, FRAC-100 and FRAC-200 Fraction Collectors, and SUPERFRAC® Fraction Collector (Amersham Biosciences, Piscataway, NJ). Mixers are also available to form pH and linear concentration gradients. Commercially available mixers include Gradient Mixer GM-1 and In-Line Mixers (Amersham Biosciences, Piscataway, NJ).

The chromatographic process may be monitored using any commercially available monitor. Such monitors may be used to gather information like UV, pH, and conductivity. Examples of detectors include Monitor UV-I, UVICORD® S II, Monitor UV-M II, Monitor UV-900, Monitor UPC-900, Monitor pH/C-900, and Conductivity Monitor (Amersham Biosciences, Piscataway, NJ). Indeed, entire systems are commercially available including the various AK.TA® systems from Amersham Biosciences (Piscataway, NJ).

In one embodiment of the present invention, for example, the bG-CSF polypeptide may be reduced and denatured by first denaturing the resultant purified bG-CSF polypeptide in mea, followed by dilution into TRIS buffer containing a reducing agent (such as DTT) at a suitable pH. In another embodiment, the bG-CSF polypeptide is denatured in urea in a concentration range of between about 2 M to about 9 M, followed by dilution in TRIS buffer at a pH in the range of about 5.0 to about 8.0. The refolding mixture of this embodiment may then be incubated. In one embodiment, the refolding mixture is incubated at room temperature for four to twenty-four hours. The reduced and denatured bG-CSF polypeptide mixture may then be further isolated or purified.

As stated herein, the pH of the first bG-CSF polypeptide mixture may be adjusted prior to performing any subsequent isolation steps. In addition, the first bG-CSF polypeptide mixture or any subsequent mixture thereof may be concentrated using techniques known in the art. Moreover, the elution buffer comprising the first bG-CSF polypeptide mixture or any subsequent mixture thereof may be exchanged for a buffer suitable for the next isolation step using techniques known to those of ordinary skill in the art.

Ion Exchange Chromatography In one embodiment, and as an optional, additional step, ion exchange chromatography may be performed on the first bG-CSF polypeptide mixture. See generally ION EXCHANGE CHROMATOGRAPHY: PRINCIPLES AND METHODS (Cat. No. 18-1114-21, Amersham Biosciences (Piscataway, NJ)). Commercially available ion exchange columns include HITRAP®, HIPREP®, and HILOADR Columns (Amersham Biosciences, Piscataway, NJ). Such columns utilize strong anion exchangers such as Q SEPHAROSE® Fast Flow, Q SEPHAROSE® High Performance, and Q SEPHAROSE® XL; strong cation exchangers such as SP SEPHAROSE® High Performance, SP SEPHAROSE® Fast Flow, and SP SEPHAROSE® XL; weak anion exchangers such as DEAE SEPHAROSE® Fast Flow; and weak cation exchangers such as CM SEPHAROSE® Fast Flow (Amersham Biosciences, Piscataway, NJ). Anion or cation exchange column chromatography may be performed on the bG-CSF polypeptide at any stage of the purification process to isolate substantially purified bG-CSF polypeptide. The cation exchange chromatography step may be performed using any suitable cation exchange matrix. Useful cation exchange matrices include, but are not limited to, fibrous, porous, non-porous, microgranular, beaded, or cross-linked cation exchange matrix materials. Such cation exchange matrix materials include, but are not limited to, cellulose, agarose, dextran, polyacrylate, polyvinyl, polystyrene, silica, polyether, or composites of any of the foregoing.

The cation exchange matrix may be any suitable cation exchanger including strong and weak cation exchangers. Strong cation exchangers may remain ionized over a wide pH range and thus, may be capable of binding bG-CSF over a wide pH range. Weak cation exchangers, however, may lose ionization as a function of pH. For example, a weak cation exchanger may lose charge when the pH drops below about pH 4 or pH 5. Suitable strong cation exchangers include, but are not limited to, charged functional groups such as sulfopropyl (SP), methyl sulfonate(S), or sulfoethyl (SE). The cation exchange matrix may be a strong cation exchanger, preferably having an bG-CSF binding pH range of about 2.5 to about 6.0. Alternatively, the strong cation exchanger may have an bG-CSF binding pH range of about pH 2.5 to about pH 5.5. The cation exchange matrix may be a strong cation exchanger having an bG-CSF binding pH of about 3.0. Alternatively, the cation exchange matrix may be a sb•ong cation exchanger, preferably having an bG-CSF binding pH range of about 6.0 to about 8.0. The cation exchange matrix may be a strong cation exchanger preferably having an bG-CSF binding pH range of about 8.0 to about 12.5. Alternatively, the strong cation exchanger may have an bG-CSF binding pH range of about pH 8.0 to about pH 12.0.

Prior to loading the bG-CSF, the cation exchange matrix may be equilibrated, for example, using several column volumes of a dilute, weak acid, e.g., four column volumes of 20 mM acetic acid, pH 3. Following equilibration, the bG-CSF may be added and the column may be washed one to several times, prior to elution of substantially purified bG-CSF, also using a weak acid solution such as a weak acetic acid or phosphoric acid solution. For example, approximately 2-4 column volumes of 20 mM acetic acid, pH 3, may be used to wash the column. Additional washes using, e.g., 2-4 column volumes of 0.05 M sodium acetate, pH 5.5, or 0.05 M sodium acetate mixed with 0.1 M sodium chloride, pH 5.5, may also be used. Alternatively, using methods known in the art, the cation exchange matrix may be equilibrated using several column volumes of a dilute, weak base.

Alternatively, substantially purified bG-CSF may be eluted by contacting the cation exchanger matrix with a buffer having a sufficiently low pH or ionic strength to displace the bG-CSF from the matrix. The pH of the elution buffer may range from about pH 2.5 to about pH 6.0. More specifically, the pH of the elution buffer may range from about pH 2.5 to about pH 5.5, about pH 2.5 to about pH 5.0. The elution buffer may have a pH of about 3.0. In addition, the quantity of elution buffer may vary widely and will generally be in the range of about 2 to about 10 column volumes.

Following adsorption of the bG-CSF polypeptide to the cation exchanger matrix, substantially purified bG-CSF polypeptide may be eluted by contacting the matrix with a buffer having a sufficiently high pH or ionic strength to displace the bG-CSF polypeptide from the matrix. Suitable buffers for use in high pH elution of substantially purified bG-CSF polypeptide may include, but not limited to, citrate, phosphate, fonnate, acetate, HEPES, and MES buffers ranging in concentration from at least about 5 mM to at least about 100 mM.

Reverse-Phase Chromatography RP-HPLC may be performed to purify proteins following suitable protocols that are known to those of ordinary skill in the art. See, e.g., Pearson et al., Anal Biochem. (1982) 124:217-230 (1982); Rivier et al., J. Chrom. (1983) 268:112-119; Kunitani et al., J. Chrom. (1986) 359:391-402. RP-HPLC may be performed on the bG-CSF polypeptide to isolate substantially purified bG-CSF polypeptide. In this regard, silica derivatized resins with alkyl functionalities with a wide variety of lengths, including, but not limited to, at least about $C_3$ to at least about $C_{30}$, at least about $C_3$ to at least about $C_{20}$, or at least about $C_3$ to at least about $C_{18}$, resins may be used. Alternatively, a polymeric resin may be used. For example, TosoHaas Amberchrome CG1000sd resin may be used, which is a styrene polymer resin. Cyano or polymeric resins with a wide variety of alkyl chain lengths may also be used. Furthermore, the RP-HPLC column may be washed with a solvent such as ethanol. The Source RP column is another example of a RP-HPLC column.

A suitable elution buffer containing an ion pairing agent and an organic modifier such as methanol, isopropanol, tetrahydrofuran, acetonitrile or ethanol, may be used to elute the bG-CSF polypeptide from the RP-HPLC column. The most commonly used ion pairing agents include, but are not limited to, acetic acid, formic acid, perchloric acid, phosphoric acid, trifluoroacetic acid, heptafluorobutyric acid, triethylamine, tetramethylammonium, tetrabutylammonium, and triethylammonium acetate. Elution may be performed using one or more gradients or isocratic conditions, with gradient conditions preferred to reduce the separation time and to decrease peak width. Another method involves the use of two gradients with different solvent concentration ranges. Examples of suitable elution buffers for use herein may include, but are not limited to, aminonium acetate and acetonitrile solutions.

Hydrophobic Interaction Chromatography Purification Techniques Hydrophobic interaction chromatography (HIC) may be performed on the bG-CSF polypeptide. See generally HYDROPHOBIC INTERACTION CHROMATOGRAPHY HANDBOOK: PRINCIPLES AND METHODS (Cat. No. 18-1020-90, Amersham Biosciences (Piscataway, NJ) which is incorporated by reference herein. Suitable HIC matrices may include, but are not limited to, alkyl- or aryl-substituted matrices, such as butyl-, hexyl-, octyl- or phenyl-substituted matrices including agarose, sepharose, cellulose, silica, dextran, polystyrene, agarose, cross-linked poly(methacrylate) matrices, and mixed mode resins, including but not limited to, a polyethyleneamine resin or a butyl- or phenyl-substituted poly(methacrylate) matrix. Commercially available sources for hydrophobic interaction column chromatography include, but are not limited to, HITRAP®, HIPREP®, and HILOAD® columns (Amersham Biosciences, Piscataway, NJ).

Briefly, prior to loading, the HIC column may be equilibrated using standard buffers known to those of ordinary skill in the art, such as an acetic acid/sodium chloride solution or HEPES containing aminonium sulfate. Aminonium sulfate may be used as the buffer for loading the HIC column. After loading the bG-CSF polypeptide, the column may then washed using standard buffers and conditions to remove unwanted materials but retaining the bG-CSF polypeptide on the HIC column. The bG-CSF polypeptide may be eluted with about 3 to about 10 column volumes of a standard buffer, such as a HEPES buffer containing EDTA and lower aminonium sulfate concentration than the equilibrating buffer, or an acetic acid/sodium chlmide buffer, among others. A decreasing linear salt gradient using, for example, a gradient of potassium phosphate, may also be used to elute the bG-CSF molecules. The eluant may then be concentrated, for example, by filtration such as diafiltration or ultra-filtration. Diafiltration may be utilized to remove the salt used to elute the bG-CSF polypeptide.

Other Purification Techniques Yet another isolation step using, for example, gel filtration (GEL FILTRATION: PRINCIPLES AND METHODS (Cat. No. 18-1022-18, Amersham Biosciences, Piscataway, NJ) which is incorporated by reference herein, hydroxyapatite chromatography (suitable matrices include, but are not limited to, HA-Ultrogel, High Resolution (Calbiochem), CHT Ceramic Hydroxyapatite (BioRad), Bio-Gel HTP Hydroxyapatite (BioRad)), HPLC, expanded bed adsorption, ultrafiltration, diafiltration, lyophilization, and the like, may be performed on the first bG-CSF polypeptide mixture or any subsequent mixture thereof, to remove any excess salts and to replace the buffer with a suitable buffer for the next isolation step or even formulation of the final drug product.

The yield of bG-CSF polypeptide, including substantially purified bG-CSF polypeptide, may be monitored at each step described herein using techniques known to those of ordinary skill in the art. Such techniques may also be used to assess the yield of substantially purified bG-CSF polypeptide following the last isolation step. For example, the yield of bG-CSF polypeptide may be monitored using any of several reverse phase high pressure liquid chromatography columns, having a variety of alkyl chain lengths such as cyano RP-HPLC, C18RP-HPLC; as well as cation exchange HPLC and gel filtration HPLC.

In specific embodiments of the present invention, the yield of bG-CSF after each purification step may be at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.9%, or at least about 99.99%, of the bG-CSF in the starting material for each purification step.

Purity may be determined using standard techniques, such as SDS-PAGE, or by measuring bG-CSF polypeptide using Western blot and ELISA assays. For example, polyclonal antibodies may be generated against proteins isolated from negative control yeast fermentation and the cation exchange recovery. The antibodies may also be used to probe for the presence of contaminating host cell proteins.

RP-HPLC material Vydac C4 (Vydac) consists of silica gel particles, the surfaces of which carry C4-alkyl chains. The separation of bG-CSF polypeptide from the proteinaceous impurities is based on differences in the strength of hydrophobic interactions. Elution is performed with an acetonitrile gradient in diluted trifluoroacetic acid. Preparative HPLC is performed using a stainless steel column (filled with 2.8 to 3.2 liter of Vydac C4 silicagel). The Hydroxyapatite Ultrogel eluate is acidified by adding trifluoroacetic acid and loaded onto the Vydac C4 column. For washing and elution an acetonitrile gradient in diluted trifluoroacetic acid is used. Fractions are collected and immediately neutralized with phosphate buffer. The bG-CSF polypeptide fractions which are within the IPC limits are pooled.

DEAE Sepharose (Pharmacia) material consists of diethylaminoethyl (DEAE)-groups which are covalently bound to the surface of Sepharose beads. The binding of bG-CSF polypeptide to the DEAE groups is mediated by ionic interactions. Acetonitrile and trifluoroacetic acid pass through the column without being retained. After these substances have been washed off, trace impurities are removed by washing the column with acetate buffer at a low pH. Then the column is washed with neutral phosphate buffer and bG-CSF polypeptide is eluted with a buffer with increased ionic strength. The column is packed with DEAE Sepharose fast flow. The column volume is adjusted to assure a bG-CSF polypeptide load in the range of 3-10 mg bG-CSF polypeptide/ml gel. The column is washed with water and equilibration buffer (sodium/potassium phosphate). The pooled fractions of the HPLC eluate are loaded and the column is washed with equilibration buffer. Then the column is washed with washing buffer (sodium acetate buffer) followed by washing with equilibration buffer. Subsequently, bG-CSF polypeptide is eluted from the column with elution buffer (sodium chloride, sodium/potassium phosphate) and collected in a single fraction in accordance with the master elution profile. The eluate of the DEAE Sepharose column is adjusted to the specified conductivity. The resulting drug substance is sterile filtered into Teflon bottles and stored at −70° C.

Additional methods that may be employed include, but are not limited to, steps to remove endotoxins. Endotoxins are lipopoly-saccharides (LPSs) which are located on the outer membrane of Gram-negative host cells, such as, for example, *Escherichia coli*. Methods for reducing endotoxin levels are known to one of ordinary skill in the art and include, but are not limited to, purification techniques using silica supports, glass powder or hydroxyapatite, reverse-phase, affinity, size-exclusion, anion-exchange chromatography, hydrophobic interaction chromatography, a combination of these methods, and the like. Modifications or additional methods may be required to remove contaminants such as co-migrating proteins from the polypeptide of interest. Methods for measuring endotoxin levels are known to one of ordinary skill in the art and include, but are not limited to, Limulus Amebocyte Lysate (LAL) assays. The Endosafe™-PTS assay is a colorimetric, single tube system that utilizes cartridges preloaded with LAL reagent, chromogenic subsh•ate, and control standard endotoxin along with a handheld spectrophotometer. Alternate methods include, but are not limited to, a Kinetic LAL method that is turbidimetric and uses a 96 well format.

A wide variety of methods and procedures can be used to assess the yield and purity of a bG-CSF protein comprising one or more non-naturally encoded amino acids, including but not limited to, the Bradford assay, SDS-PAGE, silver stained SDS-PAGE, coomassie stained SDS-PAGE, mass spectrometry (including but not limited to, MALDI-TOF) and other methods for characterizing proteins known to one of ordinary skill in the art.

Additional methods include, but are not limited to: SDS•PAGE coupled with protein staining methods, immunoblotting, matrix assisted laser desorption/ionization•mass spectrometry (MALDI•MS), liquid chromatography/mass spectrometry, isoelectric focusing, analytical anion exchange, chromatofocusing, and circular dichroism.

VIII. Expression in Alternate Systems

Several strategies have been employed to introduce unnatural amino acids into proteins in non-recombinant host cells, mutagenized host cells, or in cell-free systems. These systems are also suitable for use in making the bG-CSF polypeptides of the present invention. Derivatization of amino acids with reactive side chains such as Lys, Cys and Tyr resulted in the conversion of lysine to $N^2$-acetyl-lysine. Chemical synthesis also provides a straightforward method to incorporate unnatural amino acids. With the recent development of enzymatic ligation and native chemical ligation of peptide fragments, it is possible to make larger proteins. See, e.g., P. E. Dawson and S. B. H. Kent, *Annu. Rev. Biochem,* 69:923 (2000). Chemical peptide ligation and native chemical ligation are described in U.S. Pat. No. 6,184,344, U.S. Patent Publication No. 2004/0138412, U.S. Patent Publication No. 2003/0208046, WO 02/098902, and WO 03/042235, which are incorporated by reference herein. A general in vitro biosynthetic method in which a suppressor tRNA chemically acylated with the desired unnatural amino acid is added to an in vitro extract capable of supporting protein biosynthesis, has been used to site-specifically incorporate over 100 unnatural amino acids into a variety of proteins of virtually any size. See, e.g., V. W. Comish, D. Mendel and P. G. Schultz, *Angew. Chem. Int. Ed. Engl.,* 1995, 34:621 (1995); C. J. Noren, S. J. Anthony-Cahill, M. C. Griffith, P. G. Schultz, *A general method for site-specific incorporation of unnatural amino acids into proteins, Science* 244:182-188 (1989); and, J. D. Bain, C. G. Glabe, T. A. Dix, A. R. Chamberlin, E. S. Diala, *Biosynthetic site-specific incorporation of a non-natural amino acid into a polypeptide, J. Am. Chem. Soc.* 111:8013-8014 (1989). A broad range of functional groups has been introduced into proteins for studies of protein stability, protein folding, enzyme mechanism, and signal transduction.

An in vivo method, termed selective pressure incorporation, was developed to exploit the promiscuity of wild-type synthetases. See, e.g., N. Budisa, C. Minks, S. Alefelder, W. Wenger, F. M. Dong, L. Moroder and R. Huber, FASEB J., 13:41 (1999). An auxotrophic strain, in which the relevant metabolic pathway supplying the cell with a particular natural amino acid is switched off, is grown in minimal media containing limited concentrations of the natural amino acid, while transcription of the target gene is repressed. At the onset of a stationary growth phase, the natural amino acid is depleted and replaced with the unnatural amino acid analog. Induction of expression of the recombinant protein results in the accumulation of a protein containing the unnatural analog. For example, using this strategy, o, m and p-fluorophenylalanines have been incorporated into proteins, and exhibit two characteristic shoulders in the UV spectrum which can be easily identified, see, e.g., C. Minks, R. Huber, L. Moroder and N. Budisa, *Anal. Biochem.,* 284:29 (2000); trifluoromethionine has been used to replace methionine in bacteriophage T4 lysozyme to study its interaction with chitooligosaccharide ligands by $^{19}F$ NMR, see, e.g., H. Duewel, E. Daub, V. Robinson and J. F. Hanek, *Biochemistry,* 36:3404 (1997); and trifluoroleucine has been incorporated in place of leucine, resulting in increased thermal and chemical stability of a leucine-zipper protein. See, e.g., Y. Tang, G. Ghirlanda, W. A. Petka, T. Nakajima, W. F. DeGrado and D. A. Tirrell, *Angew. Chem. Int. Ed. Engl.,* 40:1494 (2001). Moreover, selenomethionine and telluromethionine are incorporated into various recombinant proteins to facilitate the solution of phases in X-ray crystallography. See, e.g., W. A. Hendrickson, J. R. Horton and D. M. Lemaster, *EMBO J.,* 9:1665 (1990); J. O. Boles, K. Lewinski, M. Kunkle, J. D. Odom, B. Dunlap, L. Lebioda and M. Hatada, *Nat. Struct. Biol.,* 1:283 (1994); N. Budisa, B. Steipe, P. Demange, C. Eckerskom, J. Kellermann and R. Huber, *Eur. J. Biochem.,* 230:788 (1995); and, N. Budisa, W. Kambrock, S. Steinbacher, A. Humm, L. Prade, T. Neuefeind, L. Moroder and R. Huber, *J. Mol. Biol.,* 270:616 (1997). Methionine analogs with alkene or alkyne functionalities have also been incorporated efficiently, allowing for additional modification of proteins by chemical means. See, e.g., J. C. van Rest and D. A. Tirrell, *FEBS Lett.,* 428:68 (1998); J. C. van Hest, K. L. Kiick and D. A. Tirrell, *J. Am. Chem. Soc.,* 122:1282 (2000); and, K. L. Kiick and D. A. Tirrell, Tetrahedron, 56:9487 (2000); U.S. Pat. No. 6,586, 207; U.S. Patent Publication 2002/0042097, which are incorporated by reference herein.

The success of this method depends on the recognition of the unnatural amino acid analogs by aminoacyl-tRNA synthetases, which, in general, require high selectivity to insure the fidelity of protein translation. One way to expand the scope of this method is to relax the substrate specificity of aminoacyl-tRNA synthetases, which has been achieved in a limited number of cases. For example, replacement of $Ala^{294}$ by Gly in *Escherichia coli* phenylalanyl-tRNA synthetase (PheRS) increases the size of substrate binding pocket, and results in the acylation of tRNAPhe by p-Cl-phenylalanine (p-Cl-Phe). See, M. Tuba, P. Kast and H. Hennecke, *Biochemistry,* 33:7107 (1994). An *Escherichia coli* strain harboring this mutant PheRS allows the incorporation of p-Cl-phenylalanine or p-Br-phenylalanine in place of phenylalanine. See, e.g., M. Tuba and H. Hennecke, *FEBS Lett.,* 364:272 (1995); and, N. Sharma, R. Furter, P. Kast and D. A. Tirrell, *FEBS Lett.,* 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See, F. Hamano-Takaku, T. Iwama, S. Saito-Yano, K. Takaku, Y. Monden, M. Kitabatake, D. Soll and S. Nishimura, *J. Biol. Chem.,* 275:40324 (2000).

Another strategy to incorporate unnatural amino acids into proteins in vivo is to modify synthetases that have proofreading mechanisms. These synthetases cannot discriminate and therefore activate amino acids that are structurally similar to the cognate natural amino acids.

This error is corrected at a separate site, which deacylates the mischarged amino acid from the tRNA to maintain the fidelity of protein translation. If the proofreading activity of the synthetase is disabled, structural analogs that are misactivated may escape the editing function and be incorporated. This approach has been demonstrated recently with the valyl-tRNA synthetase (ValRS). See, V. Doring, H. D. Mootz, L. A. Nangle, T. L. Hendrickson, V. de Crecy-Lagard, P. Schimmel and P. Marliere, Science, 292:501 (2001). ValRS can misaminoacylate tRNA Val with Cys, Thr, or aminobutyrate (Abu); these noncognate amino acids are subsequently hydrolyzed by the editing domain. After random mutagenesis of the *Escherichia coli* chromosome, a mutant *Escherichia coli* strain was selected that has a mutation in the editing site of ValRS. This edit-defective ValRS incorrectly charges tRNA Val with Cys. Because Abu sterically resembles Cys (—SH group of Cys is replaced with —CH3 in Abu), the mutant ValRS also incorporates Abu into proteins when this mutant *Escherichia coli* strain is grown in the presence of Abu. Mass spectrometric analysis shows that about 24% of valines are replaced by Abu at each valine position in the native protein.

Solid-phase synthesis and semisynthetic methods have also allowed for the synthesis of a number of proteins containing novel amino acids. For example, see the following publications and references cited within, which are as follows: Crick, F. H. C., Barrett, L. Brenner, S. Watts-Tobin, R. *General nature of the genetic code for proteins. Nature,* 192:1227-1232 (1961); Hofmann, K., Bohn, H. *Studies on polypeptides. XXXVI. The effect of pyrazole-imidazole replacements on the S-protein activating potency of an S-peptide fragment, J. Am Chem,* 88 (24): 5914-5919 (1966); Kaiser, E. T. *Synthetic approaches to biologically active peptides and proteins including enyzmes, Ace Chem Res,* 22:47-54 (1989); Nakatsuka, T., Sasaki, T., Kaiser, E. T. Peptide segment coupling catalyzed by the semisynthetic enzyme thiosubtilisin, *J Am Chem Soc,* 109:3808-3810 (1987); Schnolzer, M., Kent, S B H. *Constructing proteins by dovetailing unprotected synthetic peptides: backbone-engineered HIV protease, Science,* 256 (5054): 221-225 (1992); Chaiken, L M. *Semisynthetic peptides and proteins, CRC Crit Rev Biochem,* 11 (3): 255-301 (1981); Offord, R. E. *Protein engineering by chemical means? Protein Eng.,* 1 (3): 151-157 (1987); and, Jackson, D. Y., Burnier, J., Quan, C., Stanley, M., Tom, J., Wells, J. A. *A Designed Peptide Ligase for Total Synthesis of Ribonuclease A with Unnatural Catalytic Residues, Science,* 266 (5183): 243 (1994).

Chemical modification has been used to introduce a variety of unnatural side chains, including cofactors, spin labels and oligonucleotides into proteins in vitro. See, e.g., Corey, D. R., Schultz, P. G. *Generation of a hybrid sequence-specific single-stranded deoxyribonuclease, Science,* 238 (4832): 1401-1403 (1987); Kaiser, E. T., Lawrence D. S., Rokita, S. E. *The chemical modification of enzymatic specificity, Annu Rev Biochem,* 54:565-595 (1985); Kaiser, E. T., Lawrence, D. S. *Chemical mutation of enzyme active sites, Science,* 226 (4674): 505-511 (1984); Neet, K. E., Nanci A, Koshland, D. E. *Properties of thiol-subtilisin, J Biol. Chem,* 243 (24): 6392-6401 (1968); Polgar, L. et M. L. Bender. *A new enzyme containing a synthetically formed active site. Thiol-subtilisin. J. Am Chem Soc,* 88:3153-3154 (1966); and, Pollack, S. J., Nakayama, G. Schultz, P. G. *Introduction of nucleophiles and spectroscopic probes into antibody combining sites, Science,* 242 (4881): 1038-1040 (1988).

Alternatively, biosynthetic methods that employ chemically modified aminoacyl-tRNAs have been used to incorporate several biophysical probes into proteins synthesized in vitro. See the following publications and references cited within: Bnmner, J. *New Photolabeling and crosslinking methods, Annu. Rev Biochem,* 62:483-514 {1993); and, Krieg, U. C., Walter, P., Hohnson, A. E. *Photocrosslin1dng of the signal sequence of nascent preprolactin of the 54-ld-lodalton polypeptide of the signal recognition particle, Proc. Natl. Acad. Sci,* 83 (22): 8604-8608 (1986).

Previously, it has been shown that unnatural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotropic for a particular amino acid. See, e.g., Noren, C. J., Anthony-Cahill, Griffith, M. C., Schultz, P. G. *A general method for site-specific incorporation of unnatural amino acids into proteins, Science,* 244:182-188 (1989); M. W. Nowak, et al., *Science* 268:439-42 (1995); Bain, J. D., Glabe, C. G., Dix, T. A., Chamberlin, A. R., Diala, E. S. *Biosynthetic site-specific Incorporation of a non-natural amino acid into a polypeptide, J. Am Chem Soc,* 111:8013-8014 (1989); N. Budisa et al., *FASEB J.* 13:41-51 (1999); Ellman, J. A., Mendel, D., Anthony-Cahill, S., Noren, C. J., Schultz, P. G. *Biosynthetic method for introducing unnatural amino acids site-specifically into proteins, Methods in Enz.,* vol. 202, 301-336 (1992); and, Mendel, D., Cornish, V. W. & Schultz, P. G. *Site-Directed Mutagenesis with an Expanded Genetic Code, Annu Rev Biophys. Biomol Struct.* 24, 435-62 (1995).

For example, a suppressor tRNA was prepared that recognized the stop codon UAG and was chemically aminoacylated with an unnatural amino acid. Conventional site-directed mutagenesis was used to introduce the stop codon TAG, at the site of interest in the protein gene. See, e.g., Sayers, J. R., Schmidt, W. Eckstein, F. 5'-3'*Exonucleases in phosphorothioate-based oligonucleotide-directed mutagenesis, Nucleic Acids Res,* 16 (3): 791-802 (1988). When the acylated suppressor tRNA and the mutant gene were combined in an in vitro transcription/translation system, the unnatural amino acid was incorporated in response to the UAG codon which gave a protein containing that amino acid at the specified position. Experiments using [$^3$H]-Phe and experiments with α-hydroxy acids demonstrated that only the desired amino acid is incorporated at the position specified by the UAG codon and that this amino acid is not incorporated at any other site in the protein. See, e.g., Noren, et al, supra; Kobayashi et al., (2003) Nature Structural Biology 10 (6): 425-432; and, Ellman, J. A., Mendel, D., Schultz, P. G. *Site-specific incorporation of novel backbone structures into proteins, Science,* 255 (5041): 197-200 (1992).

A tRNA may be aminoacylated with a desired amino acid by any method or technique, including but not limited to, chemical or enzymatic aminoacylation.

Aminoacylation may be accomplished by aminoacyl tRNA synthetases or by other enzymatic molecules, including but not limited to, ribozymes. The term "ribozyme" is interchangeable with "catalytic RNA." Cech and coworkers (Cech, 1987, Science, 236:1532-1539; Mccorkle et al., 1987, Concepts Biochem. 64:221-226) demonstrated the presence of naturally occurring RNAs that can act as catalysts (ribozymes). However, although these natural RNA catalysts have only been shown to act on ribonucleic acid substrates for cleavage and splicing, the recent development of artificial evolution of ribozymes has expanded the repertoire of catalysis to various chemical reactions. Studies have identified RNA molecules that can catalyze aminoacyl-RNA bonds on their own (2')3'-termini (Illangakekare et al., 1995 Science 267:643-647), and an RNA molecule which can transfer an amino acid from one RNA molecule to another (Lohse et al., 1996, Nature 381:442-444).

U.S. Patent Application Publication 2003/0228593, which is incorporated by reference herein, describes methods to construct ribozymes and their use in aminoacylation of tRNAs with naturally encoded and non-naturally encoded amino acids. Substrate-immobilized forms of enzymatic molecules that can aminoacylate tRNAs, including but not limited to, ribozymes, may enable efficient affinity purification of the aminoacylated products. Examples of suitable substrates include agarose, sepharose, and magnetic beads. The production and use of a substrate-immobilized form of ribozyme for aminoacylation is described in Chemistry and Biology 2003, 10:1077-1084 and U.S. Patent Application Publication 2003/0228593, which are incorporated by reference herein.

Chemical aminoacylation methods include, but are not limited to, those introduced by Hecht and coworkers (Hecht, S. M. Acc. Chem. Res. 1992, 25, 545; Heckler, T. G.; Roesser, J. R.; Xu, C.; Chang, P.; Hecht, S. M. Biochemistry 1988, 27, 7254; Hecht, S. M.; Alford, B. L.; Kuroda, Y.; Kitano, S. J. Biol. Chem. 1978, 253, 4517) and by Schultz, Chamberlin, Dougherty and others (Cornish, V. W.; Mendel, D.; Schultz, P. G. Angew. Chem. Int. Ed. Engl. 1995, 34,621; Robertson, S. A.; Ellman, J. A.; Schultz, P. G. J. Am. Chem. Soc. 1991, 113, 2722; Noren, C. J.; Anthony-Cahill, S. J.; Griffith, M. C.; Schultz, P. G. Science 1989, 244, 182; Bain, J. D.; Glabe, C. G.; Dix, T. A.; Chamberlin, A. R. J. Am. Chem. Soc. 1989, 111, 8013; Bain, J. D. et al. Nature 1992, 356, 537; Gallivan, J. P.; Lester, H. A.; Dougherty, D. A. Chem. Biol. 1997, 4, 740; Turcatti, et al. J. Biol. Chem. 1996, 271, 19991; Nowak, M. W. et al. Science, 1995, 268, 439; Saks, M. E. et al. J. Biol. Chem. 1996, 271, 23169; Hohsaka, T. et al. J. Am. Chem. Soc. 1999, 121, 34), which are incorporated by reference herein, to avoid the use of synthetases in aminoacylation. Such methods or other chemical aminoacylation methods may be used to aminoacylate tRNA molecules.

Methods for generating catalytic RNA may involve generating separate pools of randomized ribozyme sequences, performing directed evolution on the pools, screening the pools for desirable aminoacylation activity, and selecting sequences of those ribozymes exhibiting desired aminoacylation activity.

Ribozymes can comprise motifs and/or regions that facilitate acylation activity, such as a GGU motif and a U-rich region. For example, it has been reported that U-rich regions can facilitate recognition of an amino acid substrate, and a GGU-motif can form base pairs with the 3' termini of a tRNA. In combination, the GGU and motif and U-rich region facilitate simultaneous recognition of both the amino acid and tRNA simultaneously, and thereby facilitate aminoacylation of the 3' terminus of the tRNA Ribozymes can be generated by in vitro selection using a partially randomized r24mini conjugated with $tRNA^{Asn}_{CCG3}$, followed by systematic engineering of a consensus sequence found in the active clones. An exemplary ribozyme obtained by this method is termed "Fx3 ribozyme" and is described in U.S. Pub. App. No. 2003/0228593, the contents of which is incorporated by reference herein, acts as a versatile catalyst for the synthesis of various aminoacyl-tRNAs charged with cognate non-natural amino acids.

Immobilization on a substrate may be used to enable efficient affinity purification of the aminoacylated tRNAs. Examples of suitable substrates include, but are not limited to, agarose, sepharose, and magnetic beads. Ribozymes can be immobilized on resins by taking advantage of the chemical structure of RNA, such as the 3'-cis-diol on the ribose of RNA can be oxidized with periodate to yield the corresponding dialdehyde to facilitate immobilization of the RNA on the resin. Various types of resins can be used including inexpensive hydrazide resins wherein reductive amination makes the interaction between the resin and the ribozyme an irreversible linkage. Synthesis of aminoacyl-tRNAs can be significantly facilitated by this on-column aminoacylation technique. Kourouklis et al. Methods 2005; 36:239-4 describe a column-based aminoacylation system.

Isolation of the aminoacylated tRNAs can be accomplished in a variety of ways. One suitable method is to elute the aminoacylated tRNAs from a column with a buffer such as a sodium acetate solution with 10 mM EDTA, a buffer containing 50 mM N-(2-hydroxyethyl) piperazine-N'-(3-propanesulfonic acid), 12.5 mM KCl, pH 7.0, 10 mM EDTA, or simply an EDTA buffered water (pH 7.0).

The aminoacylated tRNAs can be added to translation reactions in order to incorporate the amino acid with which the tRNA was aminoacylated in a position of choice in a polypeptide made by the translation reaction. Examples of translation systems in which the aminoacylated tRNAs of the present invention may be used include, but are not limited to cell lysates. Cell lysates provide reaction components necessary for in vitro translation of a polypeptide from an input mRNA. Examples of such reaction components include but are not limited to ribosomal proteins, rRNA, amino acids, tRNAs, GTP, ATP, translation initiation and elongation factors and additional factors associated with translation. Additionally, translation systems may be batch translations or compartmentalized translation. Batch translation systems combine reaction components in a single compartment while compartmentalized translation systems separate the translation reaction components from reaction products that can inhibit the translation efficiency. Such translation systems are available commercially.

Further, a coupled transcription/translation system may be used. Coupled transcription/translation systems allow for both transcription of an input DNA into a corresponding mRNA, which is in turn translated by the reaction components. An example of a commercially available coupled transcription/translation is the Rapid Translation System (RTS, Roche Inc.). The system includes a mixture containing *E. coli* lysate for providing translational components such as ribosomes and translation factors. Additionally, an RNA polymerase is included for the transcription of the input DNA into an mRNA template for use in translation. RTS can use compartmentalization of the reaction components by way of a membrane interposed between reaction compartments, including a supply/waste compartment and a transcription/translation compartment.

Aminoacylation of tRNA may be performed by other agents, including but not limited to, transferases, polymerases, catalytic antibodies, multi-functional proteins, and the like.

Stephan in Scientist 2005 Oct. 10; pages 30-33 describes additional methods to incorporate non-naturally encoded amino acids into proteins. Lu et al. in Mol Cell. 2001 October; 8 (4): 759-69 describe a method in which a protein is chemically ligated to a synthetic peptide containing unnatural amino acids (expressed protein ligation).

Microinjection techniques have also been use incorporate unnatural amino acids into proteins. See, e.g., M. W. Nowak, P. C. Kearney, J. R. Sampson, M. E. Saks, C. G. Labarca, S. K. Silverman, W. G. Zhong, J. Thorson, J. N. Abelson, N. Davidson, P. G. Schultz, D. A. Dougherty and H. A. Lester, *Science,* 268:439 (1995); and, D. A. Dougherty, *Curr. Opin. Chem. Biol.,* 4:645 (2000). A *Xenopus* oocyte was coinjected with two RNA species made in vitro: an mRNA encoding the target protein with a UAG stop codon at the amino acid position of interest and an amber suppressor tRNA aminoacylated with the desired unnatural amino acid. The translational machinery of the oocyte then inserts the unnatural amino acid at the position specified by UAG. This method has allowed in vivo structure-function studies of integral membrane proteins, which are generally not amenable to in vitro expression systems. Examples include the incorporation of a fluorescent amino acid into tachykinin neurokinin-2 receptor to measure distances by fluorescence resonance energy transfer, see, e.g., G. Turcatti, K. Nemeth, M. D. Edgerton, U. Meseth, F. Talabot, M. Peitsch, J. Knowles, H. Vogel and A. Chollet, *J. Biol. Chem.,* 271:19991 (1996); the incorporation of biotinylated amino acids to identify surface-exposed residues in ion channels, see, e.g., J. P. Gallivan, H. A. Lester and D. A. Dougherty, *Chem. Biol.,* 4:739 (1997); the use of caged tyrosine analogs to monitor conformational changes in an ion channel in real time, see, e.g., J. C. Miller, S. K. Silverman, P. M. England, D. A. Dougherty and H. A. Lester, Neuron, 20:619 (1998); and, the use of alpha hydroxy amino acids to change ion channel backbones for probing their gating mechanisms. See, e.g., P. M. England, Y. Zhang, D. A. Dougherty and H. A. Lester, *Cell,* 96:89 (1999); and, T. Lu, A. Y. Ting, J. Mainland, L. Y. Jan, P. G. Schultz and J. Yang, *Nat. Neurosci.,* 4:239 (2001).

The ability to incorporate unnatural amino acids directly into proteins in vivo offers a wide variety of advantages including but not limited to, high yields of mutant proteins, technical case, the potential to study the mutant proteins in cells or possibly in living organisms and the use of these mutant proteins in therapeutic treatments and diagnostic uses. The ability to include unnatural amino acids with various sizes, acidities, nucleophilicities, hydrophobicities, and other properties into proteins can greatly expand our ability to rationally and systematically manipulate the structures of proteins, both to probe protein function and create new proteins or organisms with novel properties.

In one attempt to site-specifically incorporate para-F-Phe, a yeast amber suppressor tRNAPheCUA/phenylalanyl-tRNA synthetase pair was used in a p-F-Phe resistant, Phe auxotrophic *Escherichia coli* strain. See, e.g., R. Purter, *Protein Sci.,* 7:419 (1998).

It may also be possible to obtain expression of a bG-CSF polynucleotide of the present invention using a cell-free (in-vitro) translational system. Translation systems may be cellular or cell-free, and may be prokaryotic or eukaryotic. Cellular translation systems include, but are not limited to, whole cell preparations such as permeabilized cells or cell cultures wherein a desired nucleic acid sequence can be transcribed to mRNA and the mRNA translated. Cell-free translation systems are commercially available and many different types and systems are well-known. Examples of cell-free systems include, but are not limited to, prokaryotic lysates such as *Escherichia coli* lysates, and eukaryotic lysates such as wheat germ extracts, insect cell lysates, rabbit reticulocyte lysates, rabbit oocyte lysates and human cell lysates. Eukaryotic extracts or lysates may be preferred when the resulting protein is glycosylated, phosphorylated or otherwise modified because many such modifications are only possible in eukaryotic systems. Some of these extracts and lysates are available commercially (Promega; Madison, Wis.; Stratagene; La Jolla, Calif.; Amersham; Arlington Heights, Ill.; GIBCO/BRL; Grand Island, N.Y.). Membranous extracts, such as the canine pancreatic extracts containing microsomal membranes, are also available which are useful for translating secretory proteins. In these systems, which can include either mRNA as a template (in-vitro translation) or DNA as a template (combined in-vitro transcription and translation), the in vitro synthesis is directed by the ribosomes. Considerable effort has been applied to the development of cell-free protein expression systems. Sec, e.g., Kim, D. M. and J. R. Swartz, *Biotechnology and Bioengineering,* 74:309-316 (2001); Kim, D. M. and J. R. Swartz, *Biotechnology Letters,* 22, 1537-1542, (2000); Kim, D. M., and J. R. Swartz, *Biotechnology Progress,* 16, 385-390, (2000); Kim, D. M., and J. R. Swartz, *Biotechnology and Bioengineering,* 66, 180-188, (1999); and Patnaik, R. and J. R. Swartz, *Biotechniques* 24, 862-868, (1998); U.S. Pat. No. 6,337,191; U.S. Patent Publication No. 2002/0081660; WO 00/55353; WO 90/05785, which are incorporated by reference herein. Another approach that may be applied to the expression of bG-CSF polypeptides comprising a non-naturally encoded amino acid includes the mRNA-peptide fusion technique. See, e.g., R. Roberts and J. Szostak, Proc. Natl Acad. Sci. (USA) 94:12297-12302 (1997); A. Frankel, et al., *Chemistry & Biology* 10:1043-1050 (2003). In this approach, an mRNA template linked to puromycin is translated into peptide on the ribosome. If one or more tRNA molecules has been modified, non-natural amino acids can be incorporated into the peptide as well. After the last mRNA codon has been read, puromycin captures the C-terminus of the peptide. If the resulting mRNA-peptide conjugate is found to have interesting properties in an in vitro assay, its identity can be easily revealed from the mRNA sequence. In this way, one may screen libraries of bG-CSF polypeptides comprising one or more non-naturally encoded amino acids to identify polypeptides having desired properties. More recently, in vitro ribosome translations with purified components have been reported that permit the synthesis of peptides substituted with non-naturally encoded amino acids. See, e.g., A. Forster et al., *Proc. Natl Acad. Sci.* (USA) 100:6353 (2003).

Reconstituted translation systems may also be used. Mixtures of purified translation factors have also been used successfully to translate mRNA into protein as well as combinations of lysates or lysates supplemented with purified translation factors such as initiation factor-1 (IF-1), IF-2, IF-3 (α or ß), elongation factor T (EF-Tu), or termination factors. Cell-free systems may also be coupled transcription/translation systems wherein DNA is introduced to the system, transcribed into mRNA and the mRNA translated as described in *Current Protocols in Molecular Biology* (F. M. Ausubel et al. editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

IX. Macromolecular Polymers Coupled to bG-CSF Polypeptides

Various modifications to the non-natural amino acid polypeptides described herein can be effected using the compositions, methods, techniques and strategies described herein. These modifications include the incorporation of further functionality onto the non-natural amino acid component of the polypeptide, including but not limited to, hydroxyalkyl starch (HAS), hydroxyethyl starch (HES); a label; a dye; a polymer; a water-soluble polymer; a derivative of polyethylene glycol; a photocrosslinker; a radionuclide; a cytotoxic compound; a drug; an affinity label a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance. As an illustrative, non-limiting example of the compositions, methods, techniques and strategies described herein, the following description will focus on adding macromolecular polymers to the non-natural amino acid polypeptide with the understanding that the compositions, methods, techniques and strategies described thereto are also applicable (with appropriate modifications, if necessary and for which one of skill in the art could make with the disclosures herein) to adding other functionalities, including but not limited to those listed above.

A wide variety of macromolecular polymers and other molecules can be linked to bG-CSF polypeptides of the present invention to modulate biological properties of the bG-CSF polypeptide, and/or provide new biological properties to the bG-CSF molecule. These macromolecular polymers can be linked to the bG-CSF polypeptide via a naturally encoded amino acid, via a non-naturally encoded amino acid, or any functional substituent of a natural or non-natural amino acid, or any substituent or functional group added to a natural or non-natural amino acid. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

The present invention provides substantially homogenous preparations of polymer:protein conjugates. "Substantially homogenous" as used herein means that polymer:protein conjugate molecules are observed to be greater than half of the total protein. The polymer:protein conjugate has biological activity and the present "substantially homogenous" PEGylated bG-CSF polypeptide preparations provided herein are those which are homogenous enough to display the advantages of a homogenous preparation, e.g., case m clinical application in predictability of lot to lot pharmacokinetics.

One may also choose to prepare a mixture of polymer:protein conjugate molecules, and the advantage provided herein is that one may select the proportion of mono-polymer:protein conjugate to include in the mixture. Thus, if desired, one may prepare a mixture of various proteins with various numbers of polymer moieties attached (i.e., di-, tri-, tetra-, etc.) and combine said conjugates with the mono-polymer:protein conjugate prepared using the methods of the present invention, and have a mixture with a predetermined proportion of mono-polymer:protein conjugates.

The polymer selected may be water soluble so that the protein to which it is attached does not precipitate in an aqueous environment, such as a physiological environment. The polymer may be branched or unbranched. For therapeutic use of the end-product preparation, the polymer will be pharmaceutically acceptable.

Examples of polymers include but are not limited to polyalkyl ethers and alkoxy-capped analogs thereof (e.g., polyoxyethylene glycol, polyoxyethylene/propylene glycol, and methoxy or ethoxy-capped analogs thereof, especially polyoxyethylene glycol, the latter is also known as polyethyleneglycol or PEG); polyvinylpyffolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof; hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof; terpolymers thereof; mixtures thereof; hydroxyalkyl starch (HAS), including but not limited to, hydroxyethyl starch (HES); and derivatives of the foregoing.

The proportion of polyethylene glycol molecules to protein molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer: protein ratio.

As used herein, and when contemplating PEG:bG-CSF polypeptide conjugates, the term "therapeutically effective amount 11 refers to an amount which gives the desired benefit to an annual. The amount will vary from one individual to another and will depend upon a number of factors, including the overall physical condition of the patient and the underlying cause of the condition to be treated. The amount of bG-CSF polypeptide used for therapy gives an acceptable rate of change and maintains desired response at a beneficial level. A therapeutically effective amount of the present compositions may be readily ascertained by one of ordinary skill in the art using publicly available materials and procedures.

The water soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments of this invention.

PEG is a well-known, water soluble polymer that is commercially available or can be prepared by ring-opening polymerization of ethylene glycol according to methods known to those of ordinary skill in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to the bG-CSF polypeptide by the formula:

$$XO—(CH_2CH_2O)_n—CH_2CH_2—Y$$

where n is 2 to 10,000 and X is H or a terminal modification, including but not limited to, a $C_{1-4}$ alkyl, a protecting group, or a terminal functional group.

In some cases, a PEG used in the invention terminates on one end with hydroxy or methoxy, i.e., X is H or $CH_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to a bG-CSF polypeptide via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the bG-CSF polypeptide to form a Huisgen [3+2] cycloaddition product. Alternatively, an alkyne group on the PEG can be reacted with an azide group present in a non-naturally encoded amino acid to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the bG-CSF polypeptide via a non-naturally encoded amino acid and used to react preferentially with a ketone or aldehyde group present in the water soluble polymer.

Any molecular mass for a PEG can be used as practically desired, including but not limited to, from about 100 Daltons (Da) to 100,000 Da or more as desired (including but not limited to, sometimes 0.1-50 kDa or 10-40 kDa). The molecular weight of PEG may be of a wide range, including but not limited to, between about 100 Da and about 100,000 Da or more. PEG may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, PEG is between about 100 Da and about 50,000 Da. In some embodiments, PEG is between about 100 Da and about 40,000 Da. In some embodiments, PEG is between about 1,000 Da and about 40,000 Da. In some embodiments, PEG is between about 5,000 Da and about 40,000 Da. In some embodiments, PEG is between about 10,000 Da and about 40,000 Da. Branched chain PEGs, including but not limited to, PEG molecules with each chain having a MW ranging from 1-100 kDa (including but not limited to, 1-50 kDa or 5-20 kDa) can also be used. The molecular weight of each chain of the branched chain PEG may be, including but not limited to, between about 1,000 Da and about 100,000 Da or more. The molecular weight of each chain of the branched chain PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of each chain of the branched chain PEG is between about 1,000 Da and about 50,000 Da. In some embodiments, the molecular weight of each chain of the branched chain PEG is between about 1,000 Da and about 40,000 Da. In some embodiments, the molecular weight of each chain of the branched chain PEG is between about 5,000 Da and about 40,000 Da. In some embodiments, the molecular weight of each chain of the branched chain PEG is between about 5,000 Da and about 20,000 Da. A wide range of PEG molecules are described in, including but not limited to, the Shearwater Polymers, Inc. catalog, Nektar Therapeutics catalog, incorporated herein by reference.

Generally, at least one terminus of the PEG molecule is available for reaction with the non-naturally-encoded amino acid. For example, PEG derivatives bearing alkyne and azide moieties for reaction with amino acid side chains can be used to attach PEG to non-naturally encoded amino acids as described herein. If the non-naturally encoded amino acid comprises an azide, then the PEG will typically contain either an alkyne moiety to effect formation of the [3+2] cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive groups described above can be used, i.e., an azide moiety in the non-naturally encoded amino acid can be reacted with a PEG derivative containing an alkyne.

In some embodiments, the bG-CSF polypeptide variant with a PEG derivative contains a chemical functionality that is reactive with the chemical functionality present on the side chain of the non-naturally encoded amino acid.

The invention provides in some embodiments azide- and acetylene-containing polymer derivatives comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not Limited to poly(ethylene)glycol and other related polymers, including poly(dextran) and poly(propylene glycol), are also suitable for use in the practice of this invention and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

PEG is typically clear, colorless, odorless, soluble in water, stable to heat, inert to many chemical agents, does not hydrolyze or deteriorate, and is generally non-toxic. Poly (ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects. PEG having the formula $—CH_2CH_2O—(CH_2CH_2O)_n—CH_2CH_2—$, where n is from about 3 to about 4000, typically from about 20 to about 2000, is suitable for use in the present invention. PEG having a molecular weight of from about 800 Da to about 100,000 Da are in some embodiments of the present invention particularly useful as the polymer backbone. The molecular weight of PEG may be of a wide range, including but not limited to, between about 100 Da and about 100,000 Da or more. The molecular weight of PEG may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of PEG is between about 100 Da and about 50,000 Da. In some embodiments, the molecular weight of PEG is between about 100 Da and about 40,000 Da. In some embodiments, the molecular weight of PEG is between about 1,000 Da and about 40,000 Da. In some embodiments, the molecular weight of PEG is between about 5,000 Da and about 40,000 Da. In some embodiments, the molecular weight of PEG is between about 10,000 Da and about 40,000 Da.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as R(-PEG-OH)m in which R is derived from a core moiety, such as glycerol, glycerol oligomers, or pentaerythritol, and m represents the number of anns. Multi-armed PEG molecules, such as those described in U.S. Pat. Nos. 5,932,462; 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by PEG(--YCHZ2)n, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown below, this hydrolysis results in cleavage of the polymer into fragments of lower molecular weight:

$$\text{-PEG-}CO_2\text{-PEG-}+H_2O \rightarrow \text{PEG-}CO_2H+\text{HO-PEG-}$$

It is understood by those of ordinary skill in the art that the term poly(ethylene glycol) or PEG represents or includes all the forms known in the art including but not limited to those disclosed herein.

Many other polymers are also suitable for use in the present invention. In some embodiments, polymer backbones that are water-soluble, with from 2 to about 300 termini, are particularly useful in the invention. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Dato about 100,000 Da, often from about 6,000 Dato about 80,000 Da. The molecular weight of each chain of the polymer backbone may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of each chain of the polymer backbone is between about 100 Da and about 50,000 Da. In some embodiments, the molecular weight of each chain of the polymer backbone is between about 100 Da and about 40,000 Da. In some embodiments, the molecular weight of each chain of the polymer backbone is between about 1,000 Da and about 40,000 Da. In some embodiments, the molecular weight of each chain of the polymer backbone is between about 5,000 Da and about 40,000 Da. In some embodiments, the molecular weight of each chain of the polymer backbone is between about 10,000 Da and about 40,000 Da.

Those of ordinary skill in the art will recognize that the foregoing list for substantially water soluble backbones is by no means exhaustive and is merely illustrative, and that all polymeric materials having the qualities described above are contemplated as being suitable for use in the present invention.

In some embodiments of the present invention the polymer derivatives are "multi-functional", meaning that the polymer backbone has at least two termini, and possibly as many as about 300 termini, functionalized or activated with a functional group. Multifunctional polymer derivatives include, but are not limited to, linear polymers having two termini, each terminus being bonded to a functional group which may be the same or different.

In one embodiment, the polymer derivative has the structure:

X-A-POLY-B—N═N═N wherein:

N═N═N is an azide moiety;

B is a linking moiety, which may be present or absent;

POLY is a water-soluble non-antigenic polymer;

A is a linking moiety, which may be present or absent and which may be the same as B or different; and X is a second functional group.

Examples of a linking moiety for A and B include, but are not limited to, a multiply-functionalized alkyl group containing up to 18, and may contain between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and may contain 5-6 carbon atoms. The aryl group may be substituted with one more carbon atoms, nitrogen, oxygen or sulfur atoms. Other examples of suitable linking groups include those linking groups described in U.S. Pat. Nos. 5,932,462; 5,643,575; and U.S. Pat. Appl. Publication 2003/0143596, each of which is incorporated by reference herein. Those of ordinary skill in the art will recognize that the foregoing list for linking moieties is by no means exhaustive and is merely illustrative, and that all linking moieties having the qualities described above are contemplated to be suitable for use in the present invention.

Examples of suitable functional groups for use as X include, but are not limited to, hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, tresylate, alkene, ketone, and azide. As is understood by those of ordinary skill in the art, the selected X moiety should be compatible with the azide group so that reaction with the azide group does not occur. The azide-containing polymer derivatives may be homobifunctional, meaning that the second functional group (i.e., X) is also an azide moiety, or heterobifunctional, meaning that the second functional group is a different functional group.

The term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the present invention.

Specific examples of terminal functional groups in the literature include, but are not limited to, N-succinimidyl carbonate (see e.g., U.S. Pat. Nos. 5,281,698, 5,468,478), amine (see, e.g., Buckmann et al. Makromol. Chem. 182: 1379 (1981), Zalipsky et al. Eur. Polym. J. 19:1177 (1983)), hydrazide (Sec, e.g., Andresz et al. Makromol. Chem. 179: 301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al. Makromol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11:141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. Nos. 5,824,784, 5,252,714), maleimide (see, e.g., Goodson et al. Biotechnology (NY) 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4: 314 (1993)), acrylol (see, e.g., Sawhney et al., Macromolecules, 26:581 (1993)), vinylsulfone (see, e.g., U.S. Pat. No. 5,900,461). All of the above references and patents are incorporated herein by reference.

In certain embodiments of the present invention, the polymer derivatives of the invention comprise a polymer backbone having the structure:

$$X—CH_2CH_2O—(CH_2CH_2O)_n—CH_2CH_2—N{=}N{=}N$$

wherein:

X is a functional group as described above; and n is about 20 to about 4000.

In another embodiment, the polymer derivatives of the invention comprise a polymer backbone having the structure:

$$X—CH_2CH_2O—(CH_2CH_2O)_n—CH_2CH_2—O—(CH_2)_m—W—N{=}N{=}N$$

wherein:

W is an aliphatic or aromatic linker moiety comprising between 1-10 carbon atoms; n is about 20 to about 4000; and X is a functional group as described above. M is between 1 and 10.

The azide-containing PEG derivatives of the invention can be prepared by a variety of methods known in the art and/or disclosed herein. In one method, shown below, a water soluble polymer backbone having an average molecular weight from about 800 Da to about 100,000 Da, the polymer backbone having a first terminus bonded to a first functional group and a second terminus bonded to a suitable leaving group, is reacted with an azide anion (which may be paired with any of a number of suitable counter-ions, including sodium, potassium, tert-butylammonium and so forth). The leaving group undergoes a nucleophilic displacement and is replaced by the azide moiety, affording the desired azide-containing PEG polymer.

$$X\text{-PEG-L}+N_3^- \rightarrow X\text{-PEG-}N_3$$

As shown, a suitable polymer backbone for use in the present invention has the formula X-PEG-L, wherein PEG is poly(ethylene glycol) and X is a functional group which does not react with azide groups and L is a suitable leaving group. Examples of suitable functional groups include, but are not limited to, hydroxyl, protected hydroxyl, acetal, alkenyl, amine, aminooxy, protected amine, protected hydrazide, protected thiol, carboxylic acid, protected carboxylic acid, maleimide, dithiopyridine, and vinylpyridine, and ketone. Examples of suitable leaving groups include, but are not limited to, chloride, bromide, iodide, mesylate, tresylate, and tosylate.

In another method for preparation of the azide-containing polymer derivatives of the present invention, a linking agent bearing an azide functionality is contacted with a water soluble polymer backbone having an average molecular weight from about 800 Da to about 100,000 Da, wherein the linking agent bears a chemical functionality that will react selectively with a chemical functionality on the PEG polymer, to form an azide-containing polymer derivative product wherein the azide is separated from the polymer backbone by a linking group.

An exemplary reaction scheme is shown below:

$$X\text{-PEG-M+N-linker-}N{=}N{=}N \rightarrow \text{PG-X-PEG-linker-}N{=}N{=}N$$

wherein:

PEG is poly(ethylene glycol) and X is a capping group such as alkoxy or a functional group as described above; and M is a functional group that is not reactive with the azide functionality but that will react efficiently and selectively with the N functional group.

Examples of suitable functional groups include, but are not limited to, M being a carboxylic acid, carbonate or active ester if N is an amine; M being a ketone if N is a hydrazide or aminooxy moiety; M being a leaving group if N is a nucleophile.

Purification of the crude product may be accomplished by known methods including, but are not limited to, precipitation of the product followed by chromatography, if necessary.

A more specific example is shown below in the case of PEG diamine, in which one of the amines is protected by a protecting group moiety such as tert-butyl-Boc and the resulting mono-protected PEG diamine is reacted with a linking moiety that bears the azide functionality:

$$\text{BocHN-PEG-NH}_2\text{+HO}_2\text{C—(CH}_2)_3\text{—N}{=}\text{N}{=}\text{N}$$

In this instance, the amine group can be coupled to the carboxylic acid group using a variety of activating agents such as thionyl chloride or carbodiimide reagents and N-hydroxysuccinimide or N-hydroxybenzotriazole to create an amide bond between the monoamine PEG derivative and the azide-bearing linker moiety. After successful formation of the amide bond, the resulting N-tert-butyl-Boc-protected azide-containing derivative can be used directly to modify bioactive molecules or it can be further elaborated to install other useful functional groups. For instance, the N-t-Boc group can be hydrolyzed by treatment with strong acid to generate an omega-amino-PEG-azide. The resulting amine can be used as a synthetic handle to install other useful functionality such as maleimide groups, activated disulfides, activated esters and so forth for the creation of valuable heterobifunctional reagents.

Heterobifunctional derivatives are particularly useful when it is desired to attach different molecules to each terminus of the polymer. For example, the omega-N-amino-N-azido PEG would allow the attachment of a molecule having an activated electrophilic group, such as an aldehyde, ketone, activated ester, activated carbonate and so forth, to one terminus of the PEG and a molecule having an acetylene group to the other terminus of the PEG.

In another embodiment of the invention, the polymer derivative has the structure:

X-A-POLY—B—C≡C—R wherein:

R can be either H or an alkyl, alkene, alkyoxy, or aryl or substituted aryl group; B is a linking moiety, which may be present or absent;

POLY is a water-soluble non-antigenic polymer;

A is a linking moiety, which may be present or absent and which may be the same as B or different; and X is a second functional group.

Examples of a linking moiety for A and B include, but are not limited to, a multiply-functionalized alkyl group containing up to 18, and may contain between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and may contain 5-6 carbon atoms. The aryl group may be substituted with one more carbon atoms, nitrogen, oxygen, or sulfur atoms. Other examples of suitable linking groups include those linking groups described in U.S. Pat. Nos. 5,932,462 and 5,643,575 and U.S. Pat. Appl. Publication 2003/0143596, each of which is incorporated by reference herein. Those of ordinary skill in the art will recognize that the foregoing list for linking moieties is by no means exhaustive and is intended to be merely illustrative, and that a wide variety of linking moieties having the qualities described above are contemplated to be useful in the present invention.

Examples of suitable functional groups for use as X include hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, ketone, and acetylene. As would be understood, the selected X moiety should be compatible with the acetylene group so that reaction with the acetylene group does not occur. The acetylene-containing polymer derivatives may be homobifunctional, meaning that the second functional group (i.e., X) is also an acetylene moiety, or heterobifunctional, meaning that the second functional group is a different functional group.

In another embodiment of the present invention, the polymer derivatives comprise a polymer backbone having the structure:

$X—CH_2CH_2O—(CH_2CH_2O)_n—CH_2CH_2—O—(CH_2)_m—C≡CH$ wherein:

X is a functional group as described above; n is about 20 to about 4000; and m is between 1 and 10.

Specific examples of each of the heterobifunctional PEG polymers are shown below.

The acetylene-containing PEG derivatives of the invention can be prepared using methods known to those of ordinary skill in the art and/or disclosed herein. In one method, a water soluble polymer backbone having an average molecular weight from about 800 Da to about 100,000 Da, the polymer backbone having a first terminus bonded to a first functional group and a second terminus bonded to a suitable nucleophilic group, is reacted with a compound that bears both an acetylene functionality and a leaving group that is suitable for reaction with the nucleophilic group on the PEG. When the PEG polymer bearing the nucleophilic moiety and the molecule bearing the leaving group are combined, the leaving group undergoes a nucleophilic displacement and is replaced by the nucleophilic moiety, affording the desired acetylene-containing polymer.

X-PEG-Nu+L-A-C→X-PEG-Nu-A-C≡CR'

As shown, a preferred polymer backbone for use in the reaction has the formula X-PEG-Nu, wherein PEG is poly(ethylene glycol), Nu is a nucleophilic moiety and X is a functional group that does not react with Nu, L or the acetylene functionality.

Examples of Nu include, but are not limited to, amine, alkoxy, aryloxy, sulfhydryl, imino, carboxylate, hydrazide, aminoxy groups that would react primarily via a SN2-type mechanism. Additional examples of Nu groups include those functional groups that would react primarily via an nucleophilic addition reaction. Examples of L groups include chloride, bromide, iodide, mesylate, tresylate, and tosylate and other groups expected to undergo nucleophilic displacement as well as ketones, aldehydes, thioesters, olefins, alpha-beta unsaturated carbonyl groups, carbonates and other electrophilic groups expected to undergo addition by nucleophiles.

In another embodiment of the present invention, A is an aliphatic linker of between 1-10 carbon atoms or a substituted aryl ring of between 6-14 carbon atoms. X is a functional group which does not react with azide groups and L is a suitable leaving group In another method for preparation of the acetylene-containing polymer derivatives of the invention, a PEG polymer having an average molecular weight from about 800 Da to about 100,000 Da, bearing either a protected functional group or a capping agent at one terminus and a suitable leaving group at the other terminus is contacted by an acetylene aruon.

An exemplary reaction scheme is shown below:

X-PEG-L+—C≡CR'→X-PEG-C≡CR' wherein:

PEG is poly(ethylene glycol) and X is a capping group such as alkoxy or a functional group as described above; and R' is either H, an alkyl, alkoxy, aryl or aryloxy group or a substituted alkyl, alkoxyl, aryl or aryloxy group.

In the example above, the leaving group L should be sufficiently reactive to undergo SN2-type displacement when contacted with a sufficient concentration of the acetylene anion. The reaction conditions required to accomplish SN2 displacement of leaving groups by acetylene anions are known to those of ordinary skill in the art.

Purification of the crude product can usually be accomplished by methods known in the art including, but are not limited to, precipitation of the product followed by chromatography, if necessary.

Water soluble polymers can be linked to the bG-CSF polypeptides of the invention. The water soluble polymers may be linked via a non-naturally encoded amino acid incorporated in the bG-CSF polypeptide or any functional group or substituent of a non-naturally encoded or naturally encoded amino acid, or any functional group or substituent added to a non-naturally encoded or naturally encoded amino acid. Alternatively, the water soluble polymers are linked to a bG-CSF polypeptide incorporating a non-naturally encoded amino acid via a naturally-occurring amino acid (including but not limited to, cysteine, lysine or the amine group of the N-terminal residue). In some cases, the bG-CSF polypeptides of the invention comprise 1, 2, 3, 4, 5, 6, 7, 8, 9, 10 non-natural amino acids, wherein one or more non-naturally-encoded amino acid(s) are linked to water soluble polymer(s) (including but not limited to, PEG and/or oligosaccharides). In some cases, the bG-CSF polypeptides of the invention further comprise 1, 2, 3, 4, 5, 6, 7, 8, 9, 10, or more naturally-encoded amino acid(s) linked to water soluble polymers. In some cases, the bG-CSF polypeptides of the invention comprise one or more non-naturally encoded amino acid(s) linked to water soluble polymers and one or more naturally-occurring amino acids linked to water soluble polymers. In some embodiments, the water soluble polymers used in the present invention enhance the serum half-life of the bG-CSF polypeptide relative to the unconjugated form, The number of water soluble polymers linked to a bG-CSF polypeptide (i.e., the extent of PEGylation or glycosylation) of the present invention can be adjusted to provide an altered (including but not limited to, increased or decreased) pharmacologic, pharmacokinetic or pharmacodynamic characteristic such as in vivo half-life. In some embodiments, the half-life of bG-CSF is increased at least about 10, 20, 30, 40, 50, 60, 70, 80, 90 percent, 2-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 50-fold, or at least about 100-fold over an unmodified polypeptide.

PEG Derivatives Containing a Strong Nucleophilic Group (i.e., Hydrazide, Hydrazine, Hydroxylamine or Semicarbazide)

In one embodiment of the present invention, a bG-CSF polypeptide comprising a carbonyl-containing non-naturally encoded amino acid is modified with a PEG derivative that contains a terminal hydrazine, hydroxylamine, hydrazide or semicarbazide moiety that is linked directly to the PEG backbone.

In some embodiments, the hydroxylamine-terminal PEG derivative will have the structure:

$$RO—(CH_2CH_2O)_n—O—(CH_2)_m—O—NH_2$$

where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivative will have the structure:

$$RO—(CH_2CH_2O)_n—O—(CH_2)_m\text{-}X—NH—NH_2$$

where R is a simple alkyl (methyl, ethyl, propyl, etc.), m is 2-10 and n is 100-1,000 and X is optionally a carbonyl group (C═O) that can be present or absent.

In some embodiments, the semicarbazide-containing PEG derivative will have the structure:

$$RO—(CH_2CH_2O)_n—O—(CH_2)_m—NH—C(O)—NH—NH_2$$

where R is a simple alkyl (methyl, ethyl, propyl, etc.), m is 2-10 and n is 100-1,000.

In another embodiment of the invention, a bG-CSF polypeptide comprising a carbonyl-containing amino acid is modified with a PEG derivative that contains a terminal hydroxylamine, hydrazide, hydrazine, or semicarbazide moiety that is linked to the PEG backbone by means of an amide linkage.

In some embodiments, the hydroxylamine-terminal PEG derivatives have the structure:

$$RO—(CH_2CH_2O)_n—O—(CH_2)_2—NH—C(O)(CH_2)_m—O—NH_2$$

where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivatives have the structure:

$$RO—(CH_2CH_2O)_n—O—(CH_2)_2—NH—C(O)(CH_2)_m—X—NH—NH_2$$

where R is a simple alkyl (methyl, ethyl, propyl, etc.), m is 2-10, n is 100-1,000 and X is optionally a carbonyl group (C═O) that can be present or absent.

In some embodiments, the semicarbazide-containing PEG derivatives have the structure:

$$RO—(CH_2CH_2O)_n—O—(CH_2)_2—NH—C(O)(CH_2)_m—NH—C(O)—NH—NH_2$$

where R is a simple alkyl (methyl, ethyl, propyl, etc.), m is 2-10 and n is 100-1,000.

In another embodiment of the invention, a bG-CSF polypeptide comprising a carbonyl-containing amino acid is modified with a branched PEG derivative that contains a terminal hydrazine, hydroxylamine, hydrazide or semicarbazide moiety, with each chain of the branched PEG having a MW ranging from 10-40 kDa and, may be from 5-20 kDa.

In another embodiment of the invention, a bG-CSF polypeptide comprising a non-naturally encoded amino acid is modified with a PEG derivative having a branched structure. For instance, in some embodiments, the hydrazine- or hydrazide-terminal PEG derivative will have the following structure:

$$[RO—(CH_2CH_2O)_n—O—(CH_2)_2—NH—C(O)]_2CH(CH_2)_m—X—NH—NH_2$$

where R is a simple alkyl (methyl, ethyl, propyl, etc.), m is 2-10 and n is 100-1,000, and X is optionally a carbonyl group (C═O) that can be present or absent.

In some embodiments, the PEG derivatives containing a semicarbazide group will have the structure:

$$[RO—(CH_2CH_2O)_n—O—(CH_2)_2—C(O)—NH—CH_2—CH_2]_2CH—X—(CH_2)_m—NH—C(O)—NH—NH_2$$

where Risa simple alkyl (methyl, ethyl, propyl, etc.), X is optionally NH, O, S, C(O) or not present, m is 2-10 and n is 100-1,000.

In some embodiments, the PEG derivatives containing a hydroxylamine group will have the structure:

$$[RO—(CH_2CH_2O)_n—O—(CH_2)_2—C(O)—NH—CH_2—CH_2]_2CH—X—(CH_2)_m—O—NH_2$$

where R is a simple alkyl (methyl, ethyl, propyl, etc.), X is optionally NH, O, S, C(O) or not present, m is 2-10 and n is 100-1,000.

The degree and sites at which the water soluble polymer(s) are linked to the bG-CSF polypeptide can modulate the binding of the bG-CSF polypeptide to a receptor. In some embodiments, the linkages are arranged such that the bG-CSF polypeptide binds the receptor with a $K_d$ of about 400 nM or lower, with a $K_d$ of 150 nM or lower, and in some cases with a $K_d$ of 100 nM or lower, as measured by an equilibrium binding assay, such as that described in Spencer et al., *J Biol. Chem.*, 263:7862-7867 (1988).

Methods and chemistry for activation of polymers as well as for conjugation of peptides are described in the literature and are known in the art. Commonly used methods for activation of polymers include, but are not limited to, activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), PROTEIN IMMOBILISATION. FUNDAMENTAL AND APPLICATIONS, Marcel Dekker, N.Y.; S. S. Wong, (1992), CHEMISTRY OF PROTEIN CONJUGATION AND CROSSLINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Several reviews and monographs on the functionalization and conjugation of PEG are available. See, for example, Harris, *Macromol. Chem. Phys*. C25: 325-373 (1985); Scouten, *Methods in Enzymology* 135:30-65 (1987); Wong et al., *Enzyme Microb. Technol.* 14:866-874 (1992); Delgado et al., Critical Reviews in Therapeutic Drug Carrier Systems 9:249-304 (1992); Zalipsky, *Bioconjugate Chem.* 6:150-165 (1995).

Methods for activation of polymers can also be found in WO 94/17039, U.S. Pat. No. 5,324,844, WO 94/18247, WO 94/04193, U.S. Pat. Nos. 5,219,564, 5,122,614, WO 90/13540, U.S. Pat. No. 5,281,698, and WO 93/15189, and for conjugation between activated polymers and enzymes including but not limited to Coagulation Factor VIII (WO 94/15625), hemoglobin (WO 94/09027), oxygen carrying molecule (U.S. Pat. No. 4,412,989), ribonuclease and superoxide dismutase (Veronese at al., App. Biochem. Biotech. 11:141-52 (1985)). All references and patents cited are incorporated by reference herein.

PEGylation (i.e., addition of any water soluble polymer) of bG-CSF polypeptides containing a non-naturally encoded amino acid, such as p-azido-L-phenylalanine, is carried out by any convenient method. For example, bG-CSF polypeptide is PEGylated with an alkyne-terminated mPEG derivative. Briefly, an excess of solid mPEG(5000)-O—CH2-C≡CH is added, with stirring, to an aqueous solution of p-azido-L-Phe-containing bG-CSF polypeptide at room temperature. Typically, the aqueous solution is buffered with a buffer having a pKa near the pH at which the reaction is to be carried out (generally about pH 4-10). Examples of suitable buffers for PEGylation at pH 7.5, for instance, include, but are not limited to, HEPES, phosphate, borate, TRIS-HCl, EPPS, and TES. The pH is continuously monitored and adjusted if necessary. The reaction is typically allowed to continue for between about 1-48 hours.

The reaction products are subsequently subjected to hydrophobic interaction chromatography to separate the PEGylated bG-CSF polypeptide variants from free mPEG(5000)-O—CH2-C≡CH and any high-molecular weight complexes of the pegylated bG-CSF polypeptide which may form when unblocked PEG is activated at both ends of the molecule, thereby crosslinking bG-CSF polypeptide variant molecules. The conditions during hydrophobic interaction chromatography are such that free mPEG(5000)-O—CH2-C≡CH flows through the column, while any crosslinked PEGylated bG-CSF polypeptide variant complexes elute after the desired forms, which contain one bG-CSF polypeptide variant molecule conjugated to one or more PEG groups. Suitable conditions vary depending on the relative sizes of the cross-linked complexes versus the desired conjugates and are readily determined by those of ordinary skill in the art. The eluent containing the desired conjugates is concentrated by ultra:filtration and desalted by diafiltration.

If necessary, the PEGylated bG-CSF polypeptide obtained from the hydrophobic chromatography can be purified further by one or more procedures known to those of ordinary skill in the art including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; aminonium sulfate precipitation; chromatofocusing; displacement chromatography; electrophoretic procedures (including but not limited to preparative isoelectric focusing), differential solubility (including but not limited to aminonium sulfate precipitation), or extraction. Apparent molecular weight may be estimated by GPC by comparison to globular protein standards (Preneta, A Z in PROTEIN PURIFICATION METHODS, A PRACTICAL APPROACH (Harris & Angal, Eds.) IRL Press 1989, 293-306). The purity of the bG-CSF-PEG conjugate can be assessed by proteolytic degradation (including but not limited to, trypsin cleavage) followed by mass spectromchy analysis. Pepinsky R B., et al., *J. Pharmcol. & Exp. Ther.* 297 (3): 1059-66 (2001).

A water soluble polymer linked to an amino acid of a bG-CSF polypeptide of the invention can be further derivatized or substituted without limitation.

Azide-Containing PEG Derivatives

In another embodiment of the invention, a bG-CSF polypeptide is modified with a PEG derivative that contains an azide moiety that will react with an alkyne moiety present on the side chain of the non-naturally encoded amino acid. In general, the PEG derivatives will have an average molecular weight ranging from 1-100 kDa and, in some embodiments, from 10-40 kDa In some embodiments, the azide-terminal PEG derivative will have the structure:

$$RO—(CH_2CH_2O)_n—O—(CH_2)_m—N_3$$

where R is a simple alkyl (methyl, ethyl, propyl, etc.), m is 2-10 and n is 100-1,000 (i.e., average molecular weight is between 5-40 kDa).

In another embodiment, the azide-terminal PEG derivative will have the structure:

$$RO—(CH_2CH_2O)_n—O—(CH_2)_m—NH—C(O)—(CH_2)_p—N_3$$

where R is a simple alkyl (methyl, ethyl, propyl, etc.), m is 2-10, p is 2-10 and n is 100-1,000 (i.e., average molecular weight is between 5-40 kDa).

In another embodiment of the invention, a bG-CSF polypeptide comprising a alkyne-containing amino acid is modified with a branched PEG derivative that contains a terminal azide moiety, with each chain of the branched PEG having a MW ranging from 10-40 kDa and may be from 5-20 kDa. For instance, in some embodiments, the azide-terminal PEG derivative will have the following structure:

$$[RO—(CH_2CH_2O)_n—O—(CH_2)_2—NH—C(O)]_2CH(CH_2)_m—X—(CH_2)_pN_3$$

where R is a simple alkyl (methyl, ethyl, propyl, etc.), m is 2-10, p is 2-10, and n is 100-1,000, and X is optionally an O, N, S or carbonyl group (C═O), in each case that can be present or absent.

Alkyne-Containing PEG Derivatives

In another embodiment of the invention, a bG-CSF polypeptide is modified with a PEG derivative that contains an alkyne moiety that will react with an azide moiety present on the side chain of the non-naturally encoded amino acid.

In some embodiments, the alkyne-terminal PEG derivative will have the following structure:

$$RO—(CH_2CH_2O)_n—O—(CH_2)_m—C≡CH$$

where R is a simple alkyl (methyl, ethyl, propyl, etc.), m is 2-10 and n is 100-1,000 (i.e., average molecular weight is between 5-40 kDa).

In another embodiment of the invention, a bG-CSF polypeptide comprising an alkyne-containing non-naturally encoded amino acid is modified with a PEG derivative that contains a terminal azide or terminal alkyne moiety that is linked to the PEG backbone by means of an amide linkage.

In some embodiments, the alkyne-terminal PEG derivative will have the following structure:

$$RO—(CH_2CH_2O)_n—O—(CH_2)_m—NH—C(O)—(CH_2)_p—C≡H$$

where R is a simple alkyl (methyl, ethyl, propyl, etc.), m is 2-10, p is 2-10 and n is 100-1,000.

In another embodiment of the invention, a bG-CSF polypeptide comprising an azide-containing amino acid is modified with a branched PEG derivative that contains a terminal alkyne moiety, with each chain of the branched PEG having a MW ranging from 10-40 kDa and may be from 5-20 kDa. For instance, in some embodiments, the alkyne-terminal PEG derivative will have the following structure:

$$[RO—(CH_2CH_2O)_n—O—(CH_2)_2—NH—C(O)]_2CH(CH_2)_m—X—(CH_2)_p C≡CH$$

where R is a simple alkyl (methyl, ethyl, propyl, etc.), m is 2-10, p is 2-10, and n is 100-1,000, and X is optionally an O, N, S or carbonyl group (C═O), or not present.

Phosphine-Containing PEG Derivatives

In another embodiment of the invention, a bG-CSF polypeptide is modified with a PEG derivative that contains an activated functional group (including but not limited to, ester, carbonate) further comprising an aryl phosphine group that will react with an azide moiety present on the side chain of the non-naturally encoded amino acid. In general, the PEG derivatives will have an average molecular weight ranging from 1-100 kDa and, in some embodiments, from 10-40 kDa.

In some embodiments, the PEG derivative will have the structure:

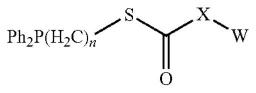

wherein n is 1-10; X can be O, N, S or not present, Ph is phenyl, and W is a water soluble polymer.

In some embodiments, the PEG derivative will have the structure:

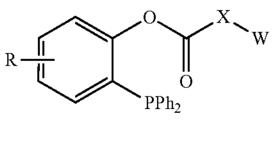

wherein X can be O, N, S or not present, Ph is phenyl, W is a water soluble polymer and R can be H, alkyl, aryl, substituted alkyl and substituted aryl groups. Exemplary R groups include but are not limited to $—CH_2$, $—C(CH_3)_3$, —OR', —NR'R", —SR', -halogen, —C(O)R', —CONR'R", $—S(O)_2R'$, $—S(O)_2NR'R"$, —CN and $—NO_2$. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, $—CF_3$ and $—CH_2CF_3$) and acyl (including but not limited to, $—C(O)CH_3$, $—C(O)CF_3$, $—C(O)CH_2OCH_3$, and the like).

Other PEG Derivatives and General PEGylation Techniques

Other exemplary PEG molecules that may be linked to bG-CSF polypeptides, as well as PEGylation methods include, but are not limited to, those described in, e.g., U.S. Patent Publication No. 2004/0001838; 2002/0052009; 2003/0162949; 2004/0013637; 2003/0228274; 2003/0220447; 2003/0158333; 2003/0143596; 2003/0114647; 2003/0105275; 2003/0105224; 2003/0023023; 2002/0156047; 2002/0099133; 2002/0086939; 2002/0082345; 2002/0072573; 2002/0052430; 2002/0040076; 2002/0037949; 2002/0002250; 2001/0056171; 2001/0044526; 2001/0021763; U.S. Pat. Nos. 6,646,110; 5,824,778; 5,476,653; 5,219,564; 5,629,384; 5,736,625; 4,902,502; 5,281,698; 5,122,614; 5,473,034; 5,516,673; 5,382,657; 6,552,167; 6,610,281; 6,515,100; 6,461,603; 6,436,386; 6,214,966; 5,990,237; 5,900,461; 5,739,208; 5,672,662; 5,446,090; 5,808,096; 5,612,460; 5,324,844; 5,252,714; 6,420,339; 6,201,072; 6,451,346; 6,306,821; 5,559,213; 5,747,646; 5,834,594; 5,849,860; 5,980,948; 6,004,573; 6,129,912; WO 97/32607, EP 229,108, EP 402,378, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, WO 98/05363, EP 809 996, WO 96/41813, WO 96/07670, EP 605 963, EP 510 356, EP 400 472, EP 183 503 and EP 154 316, which are incorporated by reference herein. Any of the PEG molecules described herein may be used in any form, including but not limited to, single chain, branched chain, multiarm chain, single functional, bi-functional, multi-functional, or any combination thereof.

Additional polymer and PEG derivatives including but not limited to, hydroxylamine (aminooxy) PEG derivatives, are described in the following patent applications which are all incorporated by reference in their entirety herein: U.S. Patent Publication No. 2006/0194256, U.S. Patent Publication No. 2006/0217532, U.S. Patent Publication No. 2006/

0217289, U.S. Provisional Patent No. 60/755,338; U.S. Provisional Patent No. 60/755,711; U.S. Provisional Patent No. 60/755,018; International Patent Application No. PCT/US06/49397; WO 2006/069246; U.S. Provisional Patent No. 60/743,041; U.S. Provisional Patent No. 60/743,040; International Patent Application No. PCT/US06/47822; U.S. Provisional Patent No. 60/882,819; U.S. Provisional Patent No. 60/882,500; and U.S. Provisional Patent No. 60/870,594.

Heterologous Fe Fusion Proteins

The bG-CSF compounds described above may be fused directly or via a peptide linker to the Fc portion of an immunoglobulin. Immunoglobulins are molecules containing polypeptide chains held together by disulfide bonds, typically having two light chains and two heavy chains. In each chain, one domain (V) has a variable amino acid sequence depending on the antibody specificity of the molecule. The other domains (C) have a rather constant sequence common to molecules of the same class.

As used herein, the Fc portion of an immunoglobulin has the meaning commonly given to the term in the field of immunology. Specifically, this term refers to an antibody fragment which is obtained by removing the two antigen binding regions (the Fab fragments) from the antibody. One way to remove the Fab fragments is to digest the immunoglobulin with papain protease. Thus, the Fc portion is formed from approximately equal sized fragments of the constant region from both heavy chains, which associate through non-covalent interactions and disulfide bonds. The Fe portion can include the hinge regions and extend through the CH2 and CH3 domains to the C-terminus of the antibody. Representative hinge regions for human and mouse immunoglobulins can be found in Antibody Engineering, A Practical Guide, Borrebaeck, C. A. K., ed., W. H. Freeman and Co., 1992, the teachings of which are herein incorporated by reference. The Fe portion can further include one or more glycosylation sites. The amino acid sequences of numerous representative Fc proteins containing a hinge region, CH2 and CH3 domains, and one N-glycosylation site are well known in the art.

There are five types of human immunoglobulin Fe regions with different effector functions and pharmacokinetic properties: IgG, IgA, IgM, IgD, and IgE. IgG is the most abundant immunoglobulin in serum. IgG also has the longest half-life in serum of any immunoglobulin (23 days). Unlike other immunoglobulins, IgG is efficiently recirculated following binding to an Fe receptor. There are four IgG subclasses G1, G2, G3, and G4, each of which has different effector functions. G1, G2, and G3 can bind C1q and fix complement while G4 cannot. Even though G3 is able to bind C1q more efficiently than G1, G1 is more effective at mediating complement-directed cell lysis. G2 fixes complement very inefficiently. The C1q binding site in IgG is located at the carboxy terminal region of the CH2 domain.

All IgG subclasses are capable of binding to Fe receptors (CD16, CD32, CD64) with G1 and G3 being more effective than G2 and 04. The Fc receptor binding region of IgG is formed by residues located in both the hinge and the carboxy terminal regions of the CH2 domain.

IgA can exist both in a monomeric and dimeric form held together by a J-chain. IgA is the second most abundant Ig in serum, but it has a half-life of only 6 days. IgA has three effector functions. It binds to an IgA specific receptor on macrophages and eosinophils, which lives phagocytosis and degranulation, respectively. It can also fix complement via an unknown alternative pathway.

IgM is expressed as either a pentamer or a hexamer, both of which are held together by a J-chain. IgM has a serum half-life of 5 days. It binds weakly to C1q via a binding site located in its CH3 domain. IgD has a half-life of 3 days in serum. It is unclear what effector functions are attributable to this Ig. IgE is a monomeric Ig and has a serum half-life of 2.5 days. IgE binds to two Fc receptors which drives degranulation and results in the release of proinflammatory agents.

Depending on the desired in vivo effect, the heterologous fusion proteins of the present invention may contain any of the isotypes described above or may contain mutated Fe regions wherein the complement and/or Fc receptor binding functions have been altered. Thus, the heterologous fusion proteins of the present invention may contain the entire Fc portion of an immunoglobulin, fragments of the Fc portion of an immunoglobulin, or analogs thereof fused to a bG-CSF compound.

The fusion proteins of the present invention can consist of single chain proteins or as multi-chain polypeptides. Two or more Fe fusion proteins can be produced such that they interact through disulfide bonds that naturally form between Fe regions. These multimers can be homogeneous with respect to the bG-CSF compound or they may contain different bG-CSF compounds fused at the N-terminus of the Fe portion of the fusion protein.

Regardless of the final structure of the fusion protein, the Fc or Fc-like region may serve to prolong the in vivo plasma half-life of the bG-CSF compound fused at the N-terminus. Also, the bG-CSF component of a fusion protein compound should retain at least one biological activity of bG-CSF. An increase in therapeutic or circulating half-life can be demonstrated using the method described herein or known in the art, wherein the half-life of the fusion protein is compared to the half-life of the bG-CSF compound alone. Biological activity can be determined by in vitro and in vivo methods known in the art.

Since the Fc region of IgG produced by proteolysis has the same in vivo half-life as the intact IgG molecule and Fab fragments are rapidly degraded, it is believed that the relevant sequence for prolonging half-life reside in the CH2 and/or CH3 domains. Further, it has been shown in the literature that the catabolic rates of IgG variants that do not bind the high-affinity Fc receptor or C1q are indistinguishable from the rate of clearance of the parent wild-type antibody, indicating that the catabolic site is distinct from the sites involved in Fc receptor or C1q binding. [Wawrzynczak et al., (1992) Molecular Immunology 29:221]. Site-directed mutagenesis studies using a murine IgG1 Fc region suggested that the site of the IgG1 Fe region that controls the catabolic rate is located at the CH2-CH3 domain interface. F regions can be modified at the catabolic site to optimize the half-life of the fusion proteins. The Fc region used for the fusion proteins of the present invention may be derived from an IgG1 or an IgG4 Fc region, and may contain both the CH2 and CH3 regions including the hinge region.

Heterologous Albumin Fusion Proteins bG-CSF described herein may be fused directly or via a peptide linker, water soluble polymer, or prodrug linker to albumin or an analog, fragment, or derivative thereof. Generally, the albumin proteins that are part of the fusion proteins of the present invention may be derived from albumin cloned from any species, including human. Human serum albumin (HSA) consists of a single non-glycosylated polypeptide chain of 585 amino acids with a formula molecular weight of 66,500. The amino acid sequence of human HSA is known [See Meloun, et al. (1975) FEBS Letters 58:136; Behrens, et al. (1975) Fed. Proc. 34:591; Lawn, et al. (1981) Nucleic Acids Research 9:6102-6114; Minghetti, et al. (1986) J. Biol. Chem. 261:6747, each of which are incorporated by reference herein]. A variety of polymorphic variants as well as analogs and fragments of albumin have been described. [See Weitkamp, et. al., (1973) Ann. Hum. Genet. 37:219]. For example, in EP 322,094, various shorter forms of HSA. Some of these fragments of HSA are disclosed, including HSA (1-373), HSA (1-388), HSA (1-389), HSA (1-369), and HSA (1-419) EP 399,666 discloses albumin fragments that include and fragments between 1-369 and 1-419. HSA (1-177) and HSA (1-200) and fragments between HSA (1-177) and HSA (1-200).

It is understood that the heterologous fusion proteins of the present invention include bG-CSF compounds that are coupled to any albumin protein including fragments, analogs, and derivatives wherein such fusion protein is biologically active and has a longer plasma half-life than the bG-CSF compound alone. Thus, the albumin portion of the fusion protein need not necessarily have a plasma half-life equal to that of native human albumin. Fragments, analogs, and derivatives are known or can be generated that have longer half-lives or have half-lives intermediate to that of native human albumin and the bG-CSF compound of interest.

The heterologous fusion proteins of the present invention encompass proteins having conservative amino acid substitutions in the bG-CSF compound and/or the Fc or albumin portion of the fusion protein. A "conservative substitution" is the replacement of an amino acid with another amino acid that has the same net electronic charge and approximately the same size and shape. Amino acids with aliphatic or substituted aliphatic amino acid side chains have approximately the same size when the total number carbon and heteroatoms in their side chains differs by no more than about four. They have approximately the same shape when the number of branches in their side chains differs by no more than one. Amino acids with phenyl or substituted phenyl groups in their side chains are considered to have about the same size and shape. Except as otherwise specifically provided herein, conservative substitutions are preferably made with naturally occurring amino acids.

Wild-type albumin and immunoglobulin proteins can be obtained from a variety of sources. For example, these proteins can be obtained from a cDNA library prepared from tissue or cells which express the mRNA of interest at a detectable level. Libraries can be screened with probes designed using the published DNA or protein sequence for the particular protein of interest. For example, immunoglobulin light or heavy chain constant regions are described in Adams, et al. (1980) Biochemistry 19:2711-2719; Goughet, et al. (1980) Biochemistry 19:2702-2710; Dolby, et al. (1980) Proc. Natl. Acad. Sci. USA 77:6027-6031; Rice et al. (1982) Proc. Natl. Acad. Sci. USA 79:7862-7862; Falkner, et al. (1982) Nature 298:286-288; and Morrison, et al. (1984) Ann. Rev. hnmunol. 2:239-256. Some references disclosing albumin protein and DNA sequences include Meloun, et al. (1975) FEES Letters 58:136; Behrens, et al. (1975) Fed. Proc. 34:591; Lawn, et al. (1981) Nucleic Acids Research 9:6102-6114; and Minghetti, et al. (1986) J. Biol. Chem. 261:6747.

Characterization of the Heterologous Fusion Proteins of the Present Invention

Numerous methods exist to characterize the fusion proteins of the present invention. Some of these methods include, but are not limited to: SDS-PAGE coupled with protein staining methods or immunoblotting using anti-IgG or anti-RSA antibodies. Other methods include matrix assisted laser desorption/ionization-mass spectrometry (MALDI-MS), liquid chromatography/mass spectrometry, isoelectric focusing, analytical anion exchange, chromatofocusing, and circular dichroism, for example.

Enhancing Affinity for Serum Albumin

Various molecules can also be fused to the bG-CSF polypeptides of the invention to modulate the half-life of bG-CSF polypeptides in serum. In some embodiments, molecules are linked or fused to bG-CSF polypeptides of the invention to enhance affinity for endogenous serum albumin in an animal.

For example, in some cases, a recombinant fusion of a bG-CSF polypeptide and an albumin binding sequence is made. Exemplary albumin binding sequences include, but are not limited to, the albumin binding domain from streptococcal protein G (see. e.g., Makiides et al., *J Pharmacol. Exp. Ther.* 277:534-542 (1996) and Sjolander et al., *J, Immunol. Methods* 201:115-123 (1997)), or albumin-binding peptides such as those described in, e.g., Dennis, et al., *J. Biol. Chem.* 277:35035-35043 (2002).

In other embodiments, the bG-CSF polypeptides of the present invention are acylated with fatty acids. In some cases, the fatty acids promote binding to serum albumin. Sec, e.g., Kurtzhals, et al., *Biochem. J.* 312:725-731 (1995).

In other embodiments, the bG-CSF polypeptides of the invention are fused directly with serum albumin (including but not limited to, human serum albumin). Those of skill in the art will recognize that a wide variety of other molecules can also be linked to bG-CSF in the present invention to modulate binding to serum albumin or other serum components.

X. Glycosylatlon of bG-CSF Polypeptides

The invention includes bG-CSF polypeptides incorporating one or more non-naturally encoded amino acids bearing saccharide residues. The sacchal'ide residues may be either natural (including but not limited to, N-acetylglucosamine) or non-nahrral (including but not limited to, 3-fluorogalactose). The saccharides may be linked to the non-naturally encoded amino acids either by an N- or O-linked glycosidic linkage (including but not limited to, N-acetylgalactose-L-serine) or a non-natural linkage (including but not limited to, an oxirne or the corresponding C- or S-linked glycoside).

The saccharide (including but not limited to, glycosyl) moieties can be added to bG-CSF polypeptides either in vivo or in vitro. In some embodiments of the invention, a bG-CSF polypeptide comprising a carbonyl-containing non-naturally encoded amino acid is modified with a saccharide derivatized with an aminooxy group to generate the corresponding glycosylated polypeptide linked via an mcime linkage. Once attached to the non-naturally encoded amino acid, the saccharide may be further elaborated by treatment with glycosyltransferases and other enzymes to generate an oligosaccharide bound to the bG-CSF. See, e.g., H. Liu, et al. *J. Am. Chem. Soc.* 125:1702-1703 (2003).

In some embodiments of the invention, a bG-CSF polypeptide comprising a carbonyl-containing non-naturally encoded amino acid is modified directly with a glycan with defined structure prepared as an aminooxy derivative. One of ordinary skill in the art will recognize that other functionalities, including azide, alkyne, hydrazide, hydrazine, and semicarbazide, can be used to link the saccharide to the non-naturally encoded amino acid.

In some embodiments of the invention, a bG-CSF polypeptide comprising an azide or alkynyl-containing non-naturally encoded amino acid can then be modified by, including but not limited to, a Huisgen [3+2] cycloaddition reaction with, including but not limited to, alkynyl or azide derivatives, respectively. This method allows for proteins to be modified with extremely high selectivity.

XI. bG-CSF Dimers and Multimers

The present invention also provides for bG-CSF and bG-CSF analog combinations such as homodimers, heterodimers, homomultimers, or heteromultimers (i.e., trimers, tebramers, etc.) where bG-CSF containing one or more non-naturally encoded amino acids is bound to another bG-CSF or bG-CSF variant thereof or any other polypeptide that is not bG-CSF or bG-CSF variant thereof, either directly to the polypeptide backbone or via a linker. Due to its increased molecular weight compared to monomers, the bG-CSF dimer or multimer conjugates may exhibit new or desirable properties, including but not limited to different pharmacological, pharmacokinetic, pharmacodynamic, modulated therapeutic half-life, or modulated plasma half-life relative to the monomeric bG-CSF. In some embodiments, bG-CSF dimers of the invention will modulate signal transduction of the G-CSF receptor. In other embodiments, the bG-CSF dimers or multimers of the present invention will act as a receptor antagonist, agonist, or modulator.

In some embodiments, one or more of the bG-CSF molecules present in a bG-CSF containing dimer or multimer comprises a non-naturally encoded amino acid linked to a water soluble polymer.

In some embodiments, the bG-CSF polypeptides are linked directly, including but not limited to, via an Asn-Lys amide linkage or Cys-Cys disulfide linkage. In some embodiments, the bG-CSF polypeptides, and/or the linked non-bG-CSF molecule, will comprise different non-naturally encoded amino acids to facilitate dimerization, including but not limited to, an alkyne in one non-naturally encoded amino acid of a first bG-CSF polypeptide and an azide in a second non-naturally encoded amino acid of a second molecule will be conjugated via a Huisgen (3+2] cycloaddition. Alternatively, bG-CSF, and/or the linked non-bG-CSF molecule comprising a ketone-containing non-naturally encoded amino acid can be conjugated to a second polypeptide comprising a hydroxylamine-containing non-naturally encoded amino acid and the polypeptides are reacted via formation of the corresponding oxime.

Alternatively, the two bG-CSF polypeptides, and/or the linked non-bG-CSF molecule, are linked via a linker. Any hetero- or homo-bifunctional linker can be used to link the two molecules, and/or the linked non-bG-CSF molecules, which can have the same or different primary sequence. In some cases, the linker used to tether the bG-CSF, and/or the linked non-bG-CSF molecules together can be a bifunctional PEG reagent. The linker may have a wide range of molecular weight or molecular length. Larger or smaller molecular weight linkers may be used to provide a desired spatial relationship or conformation between bG-CSF and the linked entity or between bG-CSF and its receptor, or between the linked entity and its binding partner, if any. Linkers having longer or shorter molecular length may also be used to provide a desired space or flexibility between bG-CSF and the linked entity, or between the linked entity and its binding partner, if any.

In some embodiments, the invention provides water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. The invention provides, in some embodiments, water-soluble compounds that comprise at least one arm of a branched molecular structure. For example, the branched molecular structure can be dendritic.

In some embodiments, the invention provides multimers comprising one or more bG-CSF polypeptide, formed by reactions with water soluble activated polymers that have the structure:

$$R—(CH_2CH_2O)_n—O—(CH_2)_m—X$$

wherein n is from about 5 to 3,000, m is 2-10, X can be an azide, an alkyne, a hydrazine, a hydrazide, an aminooxy group, a hydroxylamine, an acetyl, or carbonyl-containing moiety, and R is a capping group, a functional group, or a leaving group that can be the same or different as X. R can be, for example, a functional group selected from the group consisting of hydroxyl, protected hydroxyl, alkoxyl, N-hydroxysuccinimidyl ester, 1-benzotriazolyl ester, N-hydroxysuccinimidyl carbonate, 1-benzotriazolyl carbonate, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, and ketone.

XII. Measurement of bG-CSF Polypeptide Activity and Affinity of hG-CSF for a Receptor bG-CSF polypeptide activity can be determined using standard or known in vitro or in vivo assays. bG-CSF polypeptides may be analyzed for biological activity by suitable methods known in the art. Such assays include, but are not limited to, those described in Hedari et al. Veterinary Immunology and Immunopathology (2001) 81:45-57 and assays that assess biological activities of hG-CSF.

bG-CSF polypeptides may be analyzed for their ability to upregulate CDI1a, CD11b, CD11c, and/or CD18 in neutrophils. Measurement of this activity may be measured by FACS as described by Hedai et al (supra). Additional assays known to those of ordinary skill in the art measure activation of neutrophils, including but not limited to, assays that measure L-selectin. Other assays that may be performed assess the proliferation and/or differentiation of cells by bG-CSF polypeptides of the invention.

bG-CSF polypeptides may be analyzed for their ability to bind to a receptor. A G-CSF receptor can be prepared using techniques and methods that are known to one of ordinary skill in the art. The hG-CSF receptor can be prepared as described in U.S. Pat. No. 5,574,136, which is incorporated by reference herein. For example, cells or cell lines that act in response to G-CSF or bind G-CSF (including but not limited to, cells containing active G-CSF receptors such as recombinant G-CSF receptor producing cells) can be used to monitor bG-CSF receptor binding. For a non-PEGylated or PEGylated bG-CSF polypeptide comprising a non-natural amino acid, the affinity of bG-CSF for its receptor or for another G-CSF receptor can be measured by using a BIAcore™ biosensor (Pharmacia). Suitable binding assays include, but are not limited to, BIAcore assays (Pearce et al., Biochemistry 38:81-89 (1999)) and AlphaScreen™ assays (PerkinElmer). AlphaScreen™ is a bead-based non-radioactive luminescent proximity assay where the donor beads are excited by a laser at ~680 nm to release singlet oxygen. The singlet oxygen diffuses and reacts with the thioxene derivative on the surface of acceptor beads leading to fluorescence emission at ~600 nm. The fluorescence emission occurs only when the donor and acceptor beads are brought into close proximity by molecular interactions occurring when each is linked to ligand and receptor respectively. This ligand-receptor interaction can be competed away using receptor-binding variants while non-binding variants will not compete.

bG-CSF polypeptide activity can be determined using standard or known in vitro or in vivo assays. For example, cells or cell lines that proliferate in the presence of hG-CSF or bind hG-CSF (including but not limited to, cells containing active G-CSF receptors such as mouse bone marrow cells, WEHI-3B (D+), AML-193 (ATCC), or recombinant G-CSF receptor producing cells) can be used to monitor bG-CSF receptor binding. Sec, e.g., King et al., Exp. Hematol. 20:223 (1992); U.S. Pat. No. 6,385,505, which are incorporated by reference herein. In vivo animal models as well as human clinical trials for testing hG-CSF activity include those described in, e.g., U.S. Pat. Nos. 6,166,183; 6,565,841; 6,162,426; 5,718,893, which are incorporated by reference herein. Such models may be used to evaluate bG-CSF activity.

Regardless of which methods are used to create the present bG-CSF analogs, the analogs are subject to assays for biological activity. Tritiated thymidine assays may be conducted to ascertain the degree of cell division. Other biological assays, however, may be used to ascertain the desired activity. Biological assays such as assaying for the ability to induce terminal differentiation in mouse WEID-3B (D+) leukemic cell line, also provides indication of G-CSF activity. See Nicola, et al. Blood 54:614-27 (1979). Other in vitro assays may be used to ascertain biological activity. See Nicola, Ann. Rev. Biochem. 58:45-77 (1989). In general, the test for biological activity should provide analysis for the desired result, such as increase or decrease in biological activity (as compared to non-altered G-CSF), different biological activity (as compared to non-altered G-CSF), receptor or binding partner affinity analysis, conformational or structural changes of the bG-CSF itself or its receptor (as compared to the modified bG-CSF), or serum half-life analysis.

It was previously reported that WEHI-3BD$^+$ cells and human leukemic cells from newly diagnosed leukemias will bind$^{125}$ I-labeled murine G-CSF and that this binding can be competed for by addition of unlabeled G-CSF or human CSF-ß. The ability of natural G-CSF and bG-CSF to compete for binding of $^{125}$I-G-CSF to human and murine leukemic cells is tested. Highly purified natural G-CSF (>95% pure; 1 μg) is iodinated [Tejedor, et al., Anal. Biochem., 127, 143 (1982)], and is separated from reactants by gel filtration and ion exchange chromatography. The specific activity of the natural $^{125}$I-G-CSF is approximately 100 μCi/μg protein.

The above compilation of references for assay methodologies is not exhaustive, and those of ordinary skill in the art will recognize other assays useful for testing for the desired end result. Alterations to such assays are known to those of ordinary skill in the art.

XIIL Measurement of Potency, Functional In Vivo Half-Life, and Pharmacokinetic Parameters An important aspect of the invention is the prolonged biological half-life that is obtained by construction of the b-GCSF polypeptide with or without conjugation of the polypeptide to a water soluble polymer moiety. The rapid post administration decrease of bG-CSF polypeptide serum concentrations has made it important to evaluate biological responses to treatment with conjugated and non-conjugated bG-CSF polypeptide and variants thereof. The conjugated and non-conjugated bG-CSF polypeptide and variants thereof of the present invention may have prolonged serum half-lives also after administration via, e.g. subcutaneous or i.v. administration, making it possible to measure by, e.g. ELISA method or by a primary screening assay. ELISA or RIA kits from commercial sources may be used. Another example of an assay for the measurement of in vivo half-life of hG-CSF or variants thereof is described in U.S. Pat. No. 5,824,778, which is incorporated by reference herein. Measurement of in vivo biological half-life is carried out as described herein.

The potency and functional in vivo half-life of a hG-CSF polypeptide comprising a non-naturally encoded amino acid can be determined according to the protocol described in U.S. Pat. Nos. 6,646,110; 6,555,660; 6,166,183; 5,985,265; 5,824,778; 5,773,581, which are incorporated by reference herein. These protocols may be used for bG-CSF as well.

Pharmacokinetic parameters for a bG-CSF polypeptide comprising a non-naturally encoded amino acid can be evaluated in normal Sprague-Dawley male rats (N=5 animals per treatment group). Animals will receive either a single dose of 25 uglrat iv or 50 uglrat sc, and approximately 5-7 blood samples will be taken according to a pre-defined time course, generally covering about 6 hours for a bG-CSF polypeptide comprising a non-naturally encoded amino acid not conjugated to a water soluble polymer and about 4 days for a bG-CSF polypeptide comprising a non-naturally encoded amino acid and conjugated to a water soluble polymer. Pharmacokinetic data for bG-CSF without a non-naturally encoded amino acid can be compared directly to the data obtained for bG-CSF polypeptides comprising a non-naturally encoded amino acid.

Pharmacokinetic studies of bG-CSF polypeptides may be performed in mice, rats, or in a primate, e.g., cynomolgus monkeys. Typically, a single injection is administered either subcutaneously or intravenously, and semm bG-CSF levels are monitored over time.

U.S. Pat. No. 5,849,883 and WO 89/10932, which are incorporated by reference herein, describe a number of animal models that may be used to evaluate bG-CSF polypeptides of the invention. Animal studies that may be performed involve cattle challenged with *Pasteurella* haemolytica, cattle with bacterial challenge of the mammary gland/mastitis challenge (*Klebsiella pneumonia*). Other studies that may be performed evaluate the control, incidence, and duration of bovine respiratory disease, or prevention of coliform mastitis. Methods to evaluate the health of animals, milk production, neutrophil count, and other parameters are known to one of ordinary skill in the art. Other models that may be used to evaluate bG-CSF polypeptides of the invention include but are not limited to, animal models of infection or exposure to infection such as a hamster model of *Pseudomonas aeruginosa* pneumonia, a rat model of *Candida albicans* pyelonephritis, models involving neonatal foals, and models involving growing pigs. Some of these models are described in U.S. Pat. No. 5,849,883 and WO 89/10932. Models such as these are known to those of ordinary skill in the art.

Further examples of assays for the measurement of in vivo biological activity of hG-CSF or variants thereof are described in U.S. Pat. Nos. 5,681,720; 5,795,968; 5,824,778; 5,985,265; and Bowen et al., Experimental Hematology 27:425-432 (1999), each of which is incorporated by reference herein.

XIV. Administration and Pharmaceutical Compositions

The polypeptides or proteins of the invention (including but not limited to, bG-CSF, synthetases, proteins comprising one or more unnatural amino acid, etc.) are optionally employed for therapeutic uses, including but not limited to, in combination with a suitable pharmaceutical carrier. Such compositions, for example, comprise a therapeutically effective amount of the compound, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are known to those of ordinary skill in the art and can be applied to administration of the polypeptides of the invention. Compositions may be in a water-soluble form, such as being present as pharmaceutically acceptable salts, which is meant to include both acid and base addition salts. U.S. Pat. No. 6,497,869, which is incorporated by reference herein, discusses formulations and administration of G-CSF polypeptides, including but not limited to, hG-CSF and bG-CSF. Salts comprising sulfate ions such as aminonium sulfate, sodium sulfate, magnesium sulfate, and mixtures thereof as well as buffering agents such as acetate, citrate, phosphate, HEPES, BES, TAPS, EPPS, TES, and mixtures thereof were discussed.

Therapeutic compositions comprising one or more polypeptide of the invention are optionally tested in one or more appropriate in vitro and/or in vivo animal models of disease, to confirm efficacy, tissue metabolism, and to estimate dosages, according to methods known to those of ordinary skill in the art. In particular, dosages can be initially determined by activity, stability or other suitable measures of unnatural herein to natural amino acid homologues (including but not limited to, comparison of a bG-CSF polypeptide modified to include one or more unnatural amino acids to a natural amino acid bG-CSF polypeptide and comparison of a bG-CSF polypeptide modified to include one or more unnatural amino acids to a currently available bG-CSF treatment), i.e., in a relevant assay.

Administration is by any of the routes normally used for introducing a molecule into ultimate contact with blood or tissue cells. The unnatural amino acid polypeptides of the invention are administered in any suitable manner, optionally with one or more pharmaceutically acceptable carriers. Suitable methods of administering such polypeptides in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

bG-CSF polypeptides of the invention may be administered by any conventional route suitable for proteins or peptides, including, but not limited to parenterally, e.g. injections including, but not limited to, subcutaneously or intravenously or any other form of injections or infusions. Polypeptide compositions can be administered by a number of routes including, but not limited to oral, intravenous, intraperitoneal, intramuscular, transdermal, subcutaneous, topical, sublingual, intravascular, intramammary, or rectal means. Compositions comprising non-natural amino acid polypeptides, modified or unmodified, can also be administered via liposomes. Such administration routes and appropriate formulations are generally known to those of skill in the art. The bG-CSF polypeptide, may be used alone or in combination with other suitable components such as a pharmaceutical carrier. The bG-CSF polypeptide may be used in combination with other agents or therapeutics.

The bG-CSF polypeptide comprising a non-natural amino acid, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of bG-CSF can be presented in unit-dose or multi-dose sealed containers, such as ampules and vials.

Parenteral administration and intravenous administration are preferred methods of administration. In particular, the routes of administration already in use for natural amino acid homologue therapeutics (including but not limited to, those typically used for EPO, GH, G-CSF, GM-CSF, IFNs, interleukins, antibodies, FGFs, and/or any other pharmaceutically delivered protein), along with formulations in current use, provide preferred routes of administration and formulation for the polypeptides of the invention.

The dose administered to an animal, in the context of the present invention, is sufficient to have a beneficial therapeutic response in the animal over time, or other appropriate activity, depending on the application. The dose is determined by the efficacy of the particular vector, or formulation, and the activity, stability or serum half-life of the unnatural amino acid polypeptide employed and the condition of the animal, as well as the body weight or surface area of the animal to be treated. The size of the dose is also determined by the existence, nature, and extent of any adverse side-effects that accompany the administration of a particular vector, formulation, or the like in a particular animal.

In determining the effective amount of the vector or formulation to be administered in the treatment or prophylaxis of disease, the veterinarian evaluates circulating plasma levels, formulation toxicities, progression of the disease, and/or where relevant, the production of anti-unnatural amino acid polypeptide antibodies.

The dose administered is typically in the range equivalent to dosages of currently-used therapeutic proteins, adjusted for the altered activity or serum half-life of the relevant composition. The vectors or pharmaceutical formulations of this invention can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, formulations of the present invention are administered at a rate determined by the LD-50 or ED-50 of the relevant formulation, and/or observation of any side-effects of the unnatural amino acid polypeptides at various concentrations, including but not limited to, as applied to the mass and overall health of the animal. Administration can be accomplished via single or divided doses.

If an animal undergoing infusion of a formulation develops fevers, chills, or muscle aches, it may receive the appropriate dose of aspirin, ibuprofen, acetaminophen or other pain/fever controlling drug appropriate for animals. Animals that experience reactions to the infusion such as fever, muscle aches, and chills are premedicated 30 minutes prior to the future infusions with either aspirin, acetaminophen, or, including but not limited to, diphenhydramine, or another drug appropriate for animals. Meperidine may be used used for more severe chills and muscle aches that do not quickly respond to antipyretics and antihistamines. Cell infusion is slowed or discontinued depending upon the severity of the reaction.

bG-CSF polypeptides of the invention can be administered directly to a animal subject. Administration is by any of the routes normally used for introducing bG-CSF polypeptide to a subject. The bG-CSF polypeptide compositions according to embodiments of the present invention include those suitable for oral, rectal, topical, inhalation (including but not limited to, via an aerosol), buccal (including but not limited to, sub-lingual), vaginal, parenteral (including but not limited to, subcutaneous, intramuscular, intradermal, intraarticular, intrapleural, intraperitoneal, intracerebral, intraarterial, or intravenous), topical (i.e., both skin and mucosa} surfaces, including airway surfaces), pulmonary, intraocular, intranasal, and transdermal administration, although the most suitable route in any given case will depend on the nature and severity of the condition being treated. Administration can be either local or systemic. The formulations of compounds can be presented in unit-dose or multi-dose sealed containers, such as ampoules and vials. bG-CSF polypeptides of the invention can be prepared in a mixture in a unit dosage injectable form (including but not limited to, solution, suspension, or emulsion) with a pharmaceutically acceptable carrier. bG-CSF polypeptides of the invention can also be administered by continuous infusion (using, including but not limited to, minipumps such as osmotic pumps), single bolus or slow-release depot formulations.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. Solutions and suspensions can be prepared from sterile powders, granules, and tablets of the kind previously described.

Freeze-drying is a commonly employed technique for presenting proteins which serves to remove water from the protein preparation of interest. Freeze-drying, or lyophilization, is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. Pikal, M. Biopharm. 3 (9) 26-30 (1990) and Arakawa et al. Phann. Res. 8 (3): 285-291 (1991).

The spray drying of pharmaceuticals is also known to those of ordinary skill in the art. For example, see Broadhead, J. et al., "The Spray Drying of Pharmaceuticals," in Drug Dev. Ind. Pharm, 18 (11 & 12), 1169-1206 (1992). In addition to small molecule pharmaceuticals, a variety of biological materials have been spray dried and these include: enzymes, sera, plasma, micro-organisms and yeasts. Spray drying is a useful technique because it can convert a liquid pharmaceutical preparation into a fine, dustless or agglomerated powder in a one-step process. The basic technique comprises the following four steps: a) atomization of the feed solution into a spray; b) spray-air contact; c) drying of the spray; and d) separation of the dried product from the drying air. U.S. Pat. Nos. 6,235,710 and 6,001,800, which are incorporated by reference herein, describe the preparation of recombinant erythropoietin by spray drying.

The pharmaceutical compositions and formulations of the invention may comprise a pharmaceutically acceptable carrier, excipient, or stabilizer. Pharmaceutically acceptable carriers are determined in part by the particular composition being administered, as well as by the particular method used to administer the composition. Accordingly, there is a wide variety of suitable formulations of pharmaceutical compositions (including optional pharmaceutically acceptable carriers, excipients, or stabilizers) of the present invention (see, e.g., *Remington's Pharmaceutical Sciences*, $17^{th}$ ed. 1985)).

Suitable carriers include but are not limited to, buffers containing succinate, phosphate, borate, HEPES, citrate, histidine, imidazole, acetate, bicarbonate, and other organic acids; antioxidants including but not limited to, ascorbic acid; low molecular weight polypeptides including but not limited to those less than about 10 residues; proteins, including but not limited to, serum albumin, gelatin, or immunoglobulins; hydrophilic polymers including but not limited to, polyvinylpyrrolidone; amino acids including but not limited to, glycine, glutamine, asparagine, arginine, histidine or histidine derivatives, methionine, glutamate, or lysine; monosaccharides, disaccharides, and other carbohydrates, including but not limited to, trehalose, sucrose, glucose, mannose, or dextrins; chelating agents including but not limited to, EDTA and edentate disodium; divalent metal ions including but not limited to, zinc, cobalt, or copper; sugar alcohols including but not limited to, mannitol or sorbitol; salt-forming counter ions including but not limited to, sodium and sodium chloride; fillers such as microcrystalline cellulose, lactose, corn and other starches; binding agents; sweeteners and other flavoring agents; coloring agents; and/or nonionic surfactants including but not limited to Tween™ (including but not limited to, Tween 80 (polysorbate 80) and Tween 20 (polysorbate 20), Pluronics™ and other pluronic acids, including but not limited to, pluronic acid F68 (poloxarner 188), or PEG. Suitable surfactants include for example but are not limited to polyethers based upon poly(ethylene oxide)-poly(propylene oxide)-poly(ethylene oxide), i.e., (PEO-PPO-PEO), or poly(propylene oxide)-poly(ethylene oxide)-poly(propylene oxide), i.e., (PPO-PEO-PPO), or a combination thereof. PEO-PPO-PEO and PPO-PEO-PPO are commercially available under the trade names Pluronics™, R-Pluronics™, Tetronics™ and R-Tetronics™ (BASF Wyandotte Corp., Wyandotte, Mich.) and are further described in U.S. Pat. No. 4,820,352 incorporated herein in its entirety by reference. Other ethylene/polypropylene block polymers may be suitable surfactants. A surfactant or a combination of surfactants may be used to stabilize PEGylated bG-CSF against one or more stresses including but not limited to stress that results from agitation. Some of the above may be referred to as "bulking agents." Some may also be referred to as "tonicity modifiers." Antimicrobial preservatives may also be applied for product stability and antimicrobial effectiveness; suitable preservatives include but are not limited to, benzyl alcohol, benzalkonium chloride, metacresol, methyl/propyl parabene, cresol, and phenol, or a combination thereof. U.S. Pat. No. 7,144,574, which is incorporated by reference herein, describe additional materials that may be suitable in pharmaceutical compositions and formulations of the invention and other delivery preparations.

bG-CSF polypeptides of the invention, including those linked to water soluble polymers such as PEG can also be administered by or as part of sustained-release systems. Sustained-release compositions include, including but not limited to, semi-permeable polymer matrices in the form of shaped articles, including but not limited to, films, or microcapsules. Sustained-release matrices include from biocompatible materials such as poly(2-hydroxyethyl methacrylate) (Langer et al., *J Biomed. Mater. Res.,* 15:267-277 (1981); Langer, Chem. Tech., 12:98-105 (1982), ethylene vinyl acetate (Langer et al., supra) or poly-D-(−)-3-hydroxybutyric acid (EP 133,988), polylactides (polylactic acid) (U.S. Pat. No. 3,773,919; EP 58,481), polyglycolide (polymer of glycolic acid), polylactide co-glycolide (copolymers of lactic acid and glycolic acid) polyanhydrides, copolymers of L-glutamic acid and gamma-ethyl-L-glutamate (Sidman et al., *Biopolymers,* 22, 547-556 (1983), poly(ortho) esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Sustained-release compositions also include a liposomally entrapped compound. Liposomes containing the compound are prepared by methods known per se: DE 3,218, 121; Eppstein et al., *Proc. Natl. Acad. Sci. U.S.A.,* 82:3688-3692 (1985); Hwang et al., *Proc. Natl. Acad. Sci. U.S.A.,* 77:4030-4034 (1980); EP 52,322; EP 36,676; U.S. Pat. No. 4,619, 794; EP 143,949; U.S. Pat. No. 5,021,234; Japanese Pat. Appln, 83-118008; U.S. Pat. Nos. 4,485,045 and 4,544,545; and EP 102,324. All references and patents cited are incorporated by reference herein.

Liposomally entrapped bG-CSF polypeptides can be prepared by methods described in, e.g., DE 3,218,121; Eppstein et al., *Proc. Natl. Acad. Sci. U.S.A.,* 82:3688-3692 (1985); Hwang et al., *Proc. Natl. Acad. Sci. U.S.A.,* 77:4030-4034 (1980); EP 52,322; EP 36,676; U.S. Pat. No. 4,619,794; EP 143,949; U.S. Pat. No. 5,021,234; Japanese Pat. Appln. 83-118008; U.S. Pat. Nos. 4,485,045 and 4,544,545; and EP 102,324. Composition and size of liposomes are well known or able to be readily determined empirically by one of ordinary skill in the art. Some examples of liposomes as described in, e.g., Park J W, et al., *Proc. Natl. Acad. Sci. USA* 92:1327-1331 (1995); Lasic D and Papahadjopoulos D (eds): MEDICAL APPLICATIONS OF LIPOSOMES (1998); Drummond D C, et al., Liposomal drug delivery systems for cancer therapy, in Teicher B (ed): CANCER DRUG DISCOVERY AND DEVELOPMENT (2002); Park J W, et al., Clin. Cancer Res. 8:1172-1181 (2002); Nielsen U B, et al., Biochim. Biophys. Acta 1591 (1-3): 109-118 (2002); Mamot C, et al., *Cancer Res.* 63:3154-3161 (2003). All references and patents cited are incorporated by reference herein. A number of formulations of hG-CSF have been described and are known to those of ordinary skill in the art.

The dose administered to an animal in the context of the present invention should be sufficient to cause a beneficial response in the subject over time. Generally, the total pharmaceutically effective amount of the bG-CSF polypeptide of the present invention administered parenterally per dose is in the range of about 0.01 μg/kg/day to about 100 μg/kg, or about 0.05 mg/kg to about 1 mg/kg, of animal body weight, although this is subject to therapeutic discretion. The frequency of dosing is also subject to therapeutic discretion, and may be more frequent or less frequent than the commercially available bG-CSF polypeptide products approved for use in animals. Generally, a PEGylated bG-CSF polypeptide of the invention can be administered by any of the routes of administration described above.

XV. Therapeutic Uses of bG-CSF Polypeptides of the Invention

The b-GCSF polypeptides of the invention are useful for treating a wide range of disorders. Administration of hG-CSF products results in white blood cell formation in humans. Thus, administration of bG-CSF polypeptides of the present invention may be useful to prevent infection in animals that are at risk of infection. bG-CSF polypeptides of the present invention may be administered to animals that have an infection. Infections that may be treated with bG-CSF polypeptides of the invention include but are not limited to, mastitis and shipping fever. In one embodiment of the present invention, a PEGylated bG-CSF polypeptide of the present invention is administered to an animal between two weeks and one day before calving. In one embodiment of the present invention, a PEGylated bG-CSF polypeptide of the present invention is administered to an animal between two weeks and one day before calving, and additionally administered on the day of calving or up to one week following calving. In one embodiment of the present invention, a bG-CSF polypeptide of the present invention is administered to an animal between two weeks and one day before calving. In one embodiment of the present invention, a bG-CSF polypeptide of the present invention is administered to an animal between two weeks and one day before calving, and additionally administered on the day of calving or up to one week following calving. In one embodiment of the present invention, a PEGylated bG-CSF polypeptide of the present invention is administered to an animal between one week and one day before calving. In one embodiment of the present invention, a PEGylated bG-CSF polypeptide of the present invention is administered to an animal between one week and one day before calving, and additionally administered on the day of calving or up to one week following calving. In one embodiment of the present invention, a bG-CSF polypeptide of the present invention is administered to an animal between one week and one day before calving. In one embodiment of the present invention, a bG-CSF polypeptide of the present invention is administered to an animal between one week and one day before calving, and additionally administered on the day of calving or up to one week following calving.

In one embodiment of the present invention, a bG-CSF polypeptide of the present invention is administered to an animal between two weeks before and on the day of shipping. In one embodiment of the present invention, a bG-CSF polypeptide of the present invention is administered to an animal between one week and one day before shipping. In one embodiment of the present invention, a bG-CSF polypeptide of the present invention is administered to an animal between one week and one day before shipping, and additionally administered on the day of shipping or up to one week following shipping.

In one embodiment of the present invention, a PEGylated bG-CSF polypeptide of the present invention is administered to an animal seven days before calving. In one embodiment of the present invention, a PEGylated bG-CSF polypeptide of the present invention is administered to an animal seven days before calving, and additionally administered on the day of calving or up to one week following calving. In one embodiment of the present invention, a PEGylated bG-CSF polypeptide of the present invention is administered to an animal seven days before calving, and additionally administered on the day of calving. In one embodiment of the present invention, a bG-CSF polypeptide of the present invention is administered to an animal seven days before calving. In one embodiment of the present invention, a bG-CSF polypeptide of the present invention is administered to an animal one week before calving, and additionally administered on the day of calving or up to one week following calving. In one embodiment of the present invention, a bG-CSF polypeptide of the present invention is administered to an animal one week before calving, and additionally administered on the day of calving. In one embodiment of the present invention, a bG-CSF polypeptide of the present invention is administered to a cow prior to or on the day of calving to prevent disease in the calf. In one embodiment of the present invention, a PEGylated bG-CSF polypeptide of the present invention is administered to a cow prior to or on the day of calving to prevent disease in the calf. In one embodiment of the present invention, a bG-CSF polypeptide of the present invention is administered to a cow prior to the day of calving to prevent disease in the calf. In one embodiment of the present invention, a PEGylated bG-CSF polypeptide of the present invention is administered to a cow prior to the day of calving to prevent disease in the calf. In one embodiment, the bG-CSF polypeptide of the present invention is administered in a dose of 0.01; 0.02; 0.03; 0.04; 0.05; 0.06; 0.07; 0.08; 0.09; 0.10; 0.11; 0.12; 0.13; 0.14; 0.15; 0.16; 0.17; 0.18; 0.19; 0.20; 0.21; 0.22; 0.23; 0.24; 0.25; 0.26; 0.27; 0.28; 0.29; 0.30; 0.31; 0.32; 0.33; 0.34; 0.35; 0.36; 0.37; 0.38; 0.39; 0.40; 0.41; 0.42; 0.43; 0.44; 0.45; 0.46; 0.47; 0.48; 0.49; or 0.50 μg/kg. In one embodiment, the PEGylated bG-CSF polypeptide of the present invention is administered in a dose of 0.01; 0.02; 0.03; 0.04; 0.05; 0.06; 0.07; 0.08; 0.09; 0.10; 0.11; 0.12; 0.13; 0.14; 0.15; 0.16; 0.17; 0.18; 0.19; 0.20; 0.21; 0.22; 0.23; 0.24; 0.25; 0.26; 0.27; 0.28; 0.29; 0.30; 0.31; 0.32; 0.33; 0.34; 0.35; 0.36; 0.37; 0.38; 0.39; 0.40; 0.41; 0.42; 0.43; 0.44; 0.45; 0.46; 0.47; 0.48; 0.49; or 0.50 μg/kg. In one embodiment, the bG-CSF polypeptide of the present invention is PEGylated and is administered in a dose of 0.01; 0.02; 0.03; 0.04; 0.05; 0.06; 0.07; 0.08; 0.09; 0.10; 0.11; 0.12; 0.13; 0.14; 0.15; 0.16; 0.17; 0.18; 0.19; 0.20; 0.21; 0.22; 0.23; 0.24; 0.25; 0.26; 0.27; 0.28; 0.29; 0.30; 0.31; 0.32; 0.33; 0.34; 0.35; 0.36; 0.37; 0.38; 0.39; 0.40; 0.41; 0.42; 0.43; 0.44; 0.45; 0.46; 0.47; 0.48; 0.49; or 0.50 μg/kg. In one embodiment, the PEGylated bG-CSF polypeptide of the present invention is PEGylated and is administered in a dose of 0.01; 0.02; 0.03; 0.04; 0.05; 0.06; 0.07; 0.08; 0.09; 0.10; 0.11; 0.12; 0.13; 0.14; 0.15; 0.16; 0.17; 0.18; 0.19; 0.20; 0.21; 0.22; 0.23; 0.24; 0.25; 0.26; 0.27; 0.28; 0.29; 0.30; 0.31; 0.32; 0.33; 0.34; 0.35; 0.36; 0.37; 0.38; 0.39; 0.40; 0.41; 0.42; 0.43; 0.44; 0.45; 0.46; 0.47; 0.48; 0.49; or 0.50 μg/kg. In one embodiment, the bG-CSF polypeptide of the present invention is administered in a dose of 0.01 μg/kg. In one embodiment, the PEGylated bG-CSF polypeptide of the present invention is administered in a dose of 0.01 μg/kg.

In one embodiment, the bG-CSF polypeptide of the present invention is administered in a dose of 0.1; 0.2; 0.3; 0.4; 0.5; 0.6; 0.7; 0.8; or 1.0 μg/kg. In one embodiment, the PEGylated bG-CSF polypeptide of the present invention is administered in a dose of 0.1; 0.2; 0.3; 0.4; 0.5; 0.6; 0.7; 0.8; or 1.0 μg/kg. In one embodiment, the bG-CSF polypeptide of the present invention is PEGylated and is administered in a dose of 0.1; 0.2; 0.3; 0.4; 0.5; 0.6; 0.7; 0.8; or 1.0 μg/kg. In one embodiment, the PEGylated bG-CSF polypeptide of the present invention is PEGylated and is administered in a dose of 0.1; 0.2; 0.3; 0.4; 0.5; 0.6; 0.7; 0.8; or 1.0 μg/kg. In one embodiment, the bG-CSF polypeptide of the present invention is administered in a dose of 0.1 μg/k.g. In one embodiment, the PEGylated bG-CSF polypeptide of the present invention is administered in a dose of 0.1 μg/kg. In one embodiment, the bG-CSF polypeptide of the present invention is administered in a dose of 0.2 μg/kg. In one embodiment, the PEGylated bG-CSF polypeptide of the present invention is administered in a dose of 0.2 μg/kg. In one embodiment, the bG-CSF polypeptide of the present invention is administered in a dose of 0.3 μg/kg. In one embodiment, the PEGylated bG-CSF polypeptide of the present invention is administered in a dose of 0.3 μg/kg. In one embodiment, the bG-CSF polypeptide of the present invention is administered in a dose of 0.4 μg/kg. In one embodiment, the PEGylated bG-CSF polypeptide of the present invention is administered in a dose of 0.4 μg/kg. In one embodiment, the bG-CSF polypeptide of the present invention is administered in a dose of 0.5 μg/kg. In one embodiment, the PEGylated bG-CSF polypeptide of the present invention is administered in a dose of 0.5 μg/kg.

In one embodiment, the bG-CSF polypeptide of the present invention is administered in a dose of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 μg/kg. In one embodiment, the PEGylated bG-CSF polypeptide of the present invention is administered in a dose of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 4 41, 42, 43, 44 45, 46, 47, 48, 49, 50, 51, 52, 53, 54, 55, 56, 57, 58, 59, 60 μg/kg. In one embodiment, the bG-CSF polypeptide of the present invention is administered in a dose of 10 μg/kg. In one embodiment, the PEGylated bG-CSF polypeptide of the present invention is administered in a dose of 10 μg/kg. In one embodiment, the bG-CSF polypeptide of the present invention is administered in a dose of 20 μg/kg. In one embodiment, the PEGylated bG-CSF polypeptide of the present invention is administered in a dose of 20 μg/kg. In one embodiment, the bG-CSF polypeptide of the present invention is administered in a dose of 30 μg/kg. In one embodiment, the PEGylated bG-CSF polypeptide of the present invention is administered in a dose of 30 μg/kg. In one embodiment, the bG-CSF polypeptide of the present invention is administered in a dose of 40 μg/kg. In one embodiment, the PEGylated bG-CSF polypeptide of the present invention is administered in a dose of 40 μg/kg. In one embodiment, the bG-CSF polypeptide of the present invention is administered in a dose of 50 μg/kg. In one embodiment, the PEGylated bG-CSF polypeptide of the present invention is administered in a dose of 50 μg/kg. In one embodiment, the bG-CSF polypeptide of the present invention is administered in a dose greater than 0.5 μg/kg. In one embodiment, the PEGylated bG-CSF polypeptide of the present invention is administered in a dose greater than 0.5 μg/kg.

The pharmaceutical compositions containing bG-CSF may be formulated at a strength effective for administration by various means to an animal experiencing disorders characterized by low or defective white blood cell production, either alone or as part of a condition or disease. Average quantities of the bG-CSF may vary and in particular should be based upon the recommendations and prescription of a qualified veterinarian. The exact amount of bG-CSF is a matter of preference subject to such factors as the exact type of condition being treated, the condition of the animal being treated, as well as the other ingredients in the composition. The invention also provides for administration of a therapeutically effective amount of another active agent. The amount to be given may be readily determined by one of ordinary skill in the art based upon therapy with bG-CSF. The bG-CSF of the present invention may thus be used to stimulate white blood cell production and correct depressed red cell levels. Most commonly, white cell levels are decreased due to cancer, infection or chemotherapy. Also treatable are conditions which may lead to neutropenia in an otherwise healthy animal, such as an anticipated treatment with anti-cancer agents. In general, any condition treatable with hG-CSF may also be treated with the bG-CSF and/or PEG:bG-CSF conjugates of the present invention. The invention also provides for administration of a therapeutically effective amount of another active agent such as an anti-cancer chemotherapeutic agent. The amount to be given may be readily determined by one skilled in the art based upon therapy with bG-CSF.

Pharmaceutical compositions of the invention may be manufactured in a conventional manner.

EXAMPLES

The following examples are offered to illustrate, but do not to limit the claimed invention.

Example 1

Site Selection for the Incorporation of Non-Naturally Encoded Amino Acids into bG-CSF This example describes some of the many potential sets of criteria for the selection of sites of incorporation of non-naturally encoded amino acids into bG-CSF.

A theoretical model of bovine GCSF was generated using the crystal structure of human GCSF bound to receptors (PDB ID No. 2D9Q). The coordinates for this human GCSF structure are available from the Protein Data Bank (PDB) (Bernstein et al. *J. Mal. Biol.* 1997, 112, pp 535). Potential residues for substitution include but are not limited to conservative substitution sites and residues with the greatest solvent accessibility using the Cx program (Pintar et al. (2002) *Bioinformatics,* 18 (7): 980-4). Conservative substitution sites identified for substitution with para-acetylphenylalanine include, but are not limited to, tyrosine, phenylalanine, and arginine residues that contain a hydrophobic core with or without charge. Residues that may be structurally relevant were not selected for substitution, including but not limited to, glycines, prolines, and residues involved in helical end capping. Residues in known receptor binding regions were also not selected for substitution. Position 123 (Asp) and 141 (Thr) of SEQ ID NO: 1 may be critical for interaction with a receptor. Position 7 (Arg) may be critical for folding of the polypeptide. Position 133 (Thr) is the O-linked glycosylation site in human G-CSF.

In some embodiments, one or more non-naturally encoded amino acids are incorporated in one or more of the following positions in bG-CSF: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 6 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175 (i.e., at the carboxyl terminus of the protein), and any combination thereof (SEQ ID NO: 1 or the corresponding amino acids in SEQ ID NO: 2 or the corresponding amino acids in another bG-CSF polypeptide).

In some embodiments, one or more non-naturally encoded amino acids are incorporated at one or more of the following positions of bG-CSF: 3, 7, 11, 33, 43, 58, 62, 67, 69, 98, 99, 123, 124, 125, 133, 134, 136, 141, 159, 166, 169, 170, 173, and any combination thereof of SEQ ID NO: 1 or the corresponding amino acids in SEQ ID NO: 2. In some embodiments, one or more non-naturally encoded amino acids are incorporated at one or more of the following positions of bG-CSF: 3, 7, 33, 43, 58, 62, 67, 69, 99, 123, 124, 133, 134, 141, 166, and any combination thereof (SEQ ID NO: 1 or the corresponding amino acids in SEQ ID NO: 2). In some embodiments, one or more non-naturally encoded amino acids are incorporated at one or more of the following positions of bG-CSF: 3, 7, 62, 133, 166, and any combination thereof of SEQ ID NO: 1 or the corresponding amino acids in SEQ ID NO: 2. In some embodiments, one or more non-naturally encoded amino acids are incorporated at one or more of the following positions of bG-CSF: 62, 133, and a combination thereof (SEQ ID NO: 1 or the corresponding amino acids in SEQ ID NO: 2). In some embodiments, one or more non-naturally encoded amino acids are incorporated at position 62 of bG-CSF (SEQ ID NO: 1 or the corresponding amino acid in SEQ ID NO: 2). In some embodiments, one or more non-naturally encoded amino acids are incorporated at position 133 of bG-CSF (SEQ ID NO: 1 or the corresponding amino acid in SEQ ID NO: 2). In some embodiments, the polypeptide of the invention comprises one or more natural amino acid substitution, addition, or deletion. In some embodiments, one or more non-natural amino acids are incorporated in a leader or signal sequence that is N or C terminal to SEQ ID NO: 1, 2, or other bG-CSF sequence.

In some embodiments, the non-naturally occurring amino acid at one or more of these positions is linked to a water soluble polymer, including but not limited to, positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 6 7 71, 72, 73, 74, 75, 76, 77, 78, 79, 8 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165,166, 167, 168, 169, 170, 171, 172, 173, 174, 175 (i.e., at the carboxyl terminus of the protein), and any combination thereof (SEQ ID NO: 1 or the corresponding amino acids in SEQ ID NO: 2 or the corresponding amino acids in another bG-CSF polypeptide).

In some embodiments, the non-naturally occurring amino acid at one or more of these positions is linked to a water soluble polymer, including but not limited to, positions: 3, 7, 11, 33, 43, 58, 62, 67, 69, 98, 99, 123, 124, 125, 133, 134, 136, 141, 159, 166, 169, 170, 173, and any combination thereof (SEQ ID NO: 1 or the corresponding amino acids in SEQ ID NO: 2). In some embodiments, the non-naturally occurring amino acid at one or more of these positions is linked to a water soluble polymer, including but not limited to, positions: 3, 7, 33, 43, 58, 62, 67, 69, 99, 123, 124, 133, 134, 141, 166, and any combination thereof (SEQ ID NO: 1 or the corresponding amino acids in SEQ ID NO: 2). In some embodiments, the non-naturally occurring amino acid at one or more of these positions is linked to a water soluble polymer, including but not limited to, positions: 3, 7, 62, 133, 166, and any combination thereof (SEQ ID NO: 1 or the corresponding amino acids in SEQ ID NO: 2). In some embodiments, the non-naturally encoded amino acid at one or more of these positions is linked to a water soluble polymer, including but not limited to, 62, 133, and a combination thereof (SEQ ID NO: 1 or the corresponding amino acids in SEQ ID NO: 2). In some embodiments, the non-naturally encoded amino acid at position 62 is linked to a water soluble polymer (SEQ ID NO: 1 or the corresponding amino acid in SEQ ID NO: 2). In some embodiments, the non-naturally encoded amino acid at position 133 is linked to a water soluble polymer (SEQ ID NO: 1 or the corresponding amino acid in SEQ ID NO: 2). In some embodiments, the non-naturally occurring amino acid in the signal or leader sequence N or C terminal to SEQ ID NO: 1, 2, or other bG-CSF sequence is linked to a water soluble polymer.

Example 2

Cloning and Expression of a bG-CSF Polypeptide Containing a Non-Naturally Encoded Amino Acid and Produced in *E. coli*

This example details the cloning and expression of a bG-CSF polypeptide including a non-naturally encoded amino acid in *E. coli* and the methods to assess the biological activity of modified bG-CSF polypeptides.

Methods for cloning bG-CSF are known to those of ordinary skill in the art. Polypeptide and polynucleotide sequences for bG-CSF and cloning of bG-CSF into host cells as well as purification of bG-CSF are detailed in U.S. Pat. No. 5,849,883, which is incorporated by reference in its entirety herein, and Heidari et al. Veterinary Immunology and Immunopathology (2001) 81:45-57.

cDNA encoding mature bG-CSF is shown as SEQ ID NO: 3. The polypeptide encoded by this sequence is shown as SEQ ID NO: 1.

cDNA encoding mature bG-CSF with a methionine at the N terminus is shown as SEQ ID NO: 4. The polypeptide encoded by this sequence is shown as SEQ ID NO: 2.

An introduced translation system that comprises an orthogonal tRNA (O-tRNA) and an orthogonal aminoacyl tRNA synthetase (O-RS) is used to express bG-CSF containing a non-naturally encoded amino acid. The O-RS preferentially aminoacylates the O-tRNA with a non-naturally encoded amino acid. In turn the translation system inserts the non-naturally encoded amino acid into bG-CSF, in response to an encoded selector codon. Suitable O-RS and O-tRNA sequences are described in WO 2006/068802 entitled "Compositions of Aminoacyl-tRNA Synthetase and Uses Thereof" (E9—SEQ ID NO: 22 & D286R mutant of E9—SEQ ID NO: 24 in this application) and WO 2007/021297 entitled "Compositions of tRNA and Uses Thereof" (F13; SEQ ID NO: 23 in this application), which are incorporated by reference in their entirety herein.

TABLE 2

| O-RS and O-tRNA sequences. | | |
|---|---|---|
| SEQID NO: 5 | *M. jannaschii* mtRNA $_{CUA}^{Tyr}$ | tRNA |
| SEQID NO: 6 | HLADO3; an optimized amber supressor tRNA | tRNA |
| SEQID NO: 7 | HL325A; an optimized AGGA frameshift supressor tRNA | tRNA |
| SEQID NO: 8 | Aminoacyl tRNA synthetase for the incorporation of p-azido-L-phenylalanine p-Az-PheRS(6) | RS |
| SEQID NO: 9 | Aminoacyl tRNA synthetase jor the incorporation of p-benzoyl-L-phenylalanine p-BpaRS(l) | RS |
| SEQID NO: 10 | Aminoacyl tRNA synthetase for the incorporation of propargyl-phenylalanine Propargyl-PheRS | RS |
| SEQID NO: 11 | Aminoacyl tRNA synthetasefor the incorporation of propargyl-phenylalanine Propargyl-PheRS | RS |
| SEQID NO: 12 | Aminoacyl tRNA synthetase for the incorporation of propargyl-phenylalanine Propargyl-PheRS | RS |
| SEQID NO: 13 | Aminoacyl tRNA synthetase for the incorporation of p-azido-phenylalanine p-Az-PheRS(1) | RS |
| SEQID NO: 14 | Aminoacyl tRNA synthetase for the incorporation of p-azido-phenylalanine p-Az-PheRS(3) | RS |
| SEQ ID NO: 15 | Aminoacyl IRNA synthetase for the incorporation of p-azido-phenylalanine p-Az-PheRS(4) | RS |
| SEQID NO: 16 | Aminoacyl tRNA synthetase for the incorporation of p-azido-phenylalanine p-Az-PheRS(2) | RS |
| SEQID NO: 17 | Aminoacyl tRNA synthetase for the incorporation of p-acetyl-phenylalanine (LWI) | RS |
| SEQID NO: 18 | Aminoacyl tRNA synthetase for the incorporation of p-acetyl-phenylalnnine (LW5) | RS |
| SEQ ID NO: 19 | Aminoacyl IRNA synthetase for the incorporation of p-acetyl-phenylalanine (LW6) | RS |
| SEQID NO: 20 | Aminoacyl tRNA synthetase for the incorporation of p-azido-phenylalanine (AzPheRS-5) | RS |
| SEQID NO: 21 | Aminoacyl tRNA synthetase for the incorporation of p-azido-phenylalanine (AzPheRS-6) | RS |

The transformation of *E. coli* with plasmids containing the modified bG-CSF polynucleotide sequence and the orthogonal aminoacyl tRNA synthetase/tRNA pair (specific for the desired non-naturally encoded amino acid) allows the site-specific incorporation of non-naturally encoded amino acid into the bG-CSF polypeptide. The plasmid used for expression of bG-CSF is shown as FIG. 1. The gene of interest shown as an example is bG-CSF with a selector codon (amber) replacing the codon encoding T133. The polypeptide with para-acetylphenylalanine at position 133 is referred to as bG-CSF T133pAF. Plpp-constitutive *E. coli* promoter; Pro cluster-tandem copies of *E. coli* proline tRNA; Fl 3 cluster-tandem copies of a modified *Methanococcus jannaschii* tyrosine tRNA from WO 2007/021297; E9 RS (D286R) *Methanococcus jannaschii* tyrosyl tRNA synthetase from WO 2006/068802; T7 pro-T7 promoter; T7 terminator; ori-origin of replication; bla (ap) sequence-ampicillin resistance gene.

Figure 3:
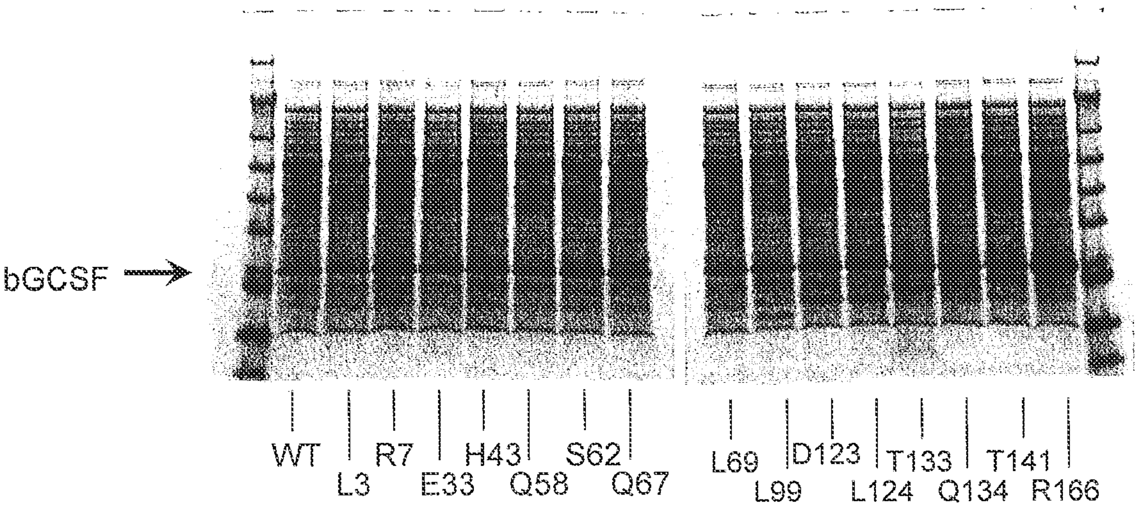
FIG. 3—SDS PAGE analysis of the expression of bG-CSF polypeptides of the present invention is shown.

Polynucleotides encoding wild-type bG-CSF or one of 15 mutant polypeptides were cloned and subsequently sub-cloned into the pVK.6 vector by Codon Devices, Inc. Each construct generated had a selector codon, an amber codon, at different position. The resulting bG-CSF polypeptides had the non-naturally encoded amino acid, para-acetylphenylalanine (pAF; pAcF), substituted for the naturally encoded amino acid at the one of the following positions: L3, R7, E33, H43, Q58, S62, Q67, L69, L99, D123, L124, T133, Q134, T141, and R166 (position numbers refer to SEQ ID NO: 1). Since each of the mutant b-GCSF polypeptides generated each had a methionine at the N-terminus (see SEQ ID NO: 2 for the wild-type sequence of bovine G-CSF with the methionine at the N terminus), the expressed b-GCSF polypeptides had non-natural amino acid substitutions at position number+1 (for example, one mutant had the leucine at position 4 of SEQ ID NO: 2 substituted with pAF). After sequence verification, the plasmids were transformed into W3110 B2 cells, and the colonies grown on ampicillin plates. The *E. coli* cell line information is shown as FIG. 2. These colonies were used to inoculate 5 mL LB with 1:1000 dilution of ampicillin cultures, which were grown at 37° C. to an O.D.600=0.8. pAF (para-acetylphenylalanine) was then added to the 15 different cultures to a final concentration of 4 mM. After approximately 30 minutes, the cultures were induced with L-arabinose to a final concentration of 0.2%, and the cultures were incubated at 37° C. for another 5 hours. At this time, a 500 μL sample was taken of each culture and spun down at 13,000 rpm for 4 minutes. The supernatant was discarded and the pellet was resuspended in 150 μL B-PER with 1 μL DNAse and incubated at room temperature overnight. The next morning, 4×LDS Sample Buffer (Invitrogen, Carlsbad, CA) was added, the samples were heated to 95° C. for 5 minutes, and 1OX Sample Reducing Agent (Invitrogen, Carlsbad, CA) was added. The samples were then resolved by SDS-PAGE on 4-12% gradient gels (Invitrogen, Carlsbad, CA) in MES buffer and visualized using Simply Blue SafeStain (Invitrogen, Carlsbad, CA). FIG. 3 shows the samples generated from the wild-type and bG-CSF mutant cultures after analysis on 4-12% gradient gels and Coomassic staining.

Inclusion Body Prep Solubilization

The cell paste was resuspended by mixing to a final 10% solid in 4° C. inclusion body (IB) Buffer I (50 mM Tris pH 8.0; 100 mM NaCl; 1 mM EDTA; 1% Triton X-100; 4° C.). The cells were lysed by passing resuspended material through a microfluidizer a total of two times. The samples were centrifuged at 10,000 g for 15 minutes as 4° C., and the supernatant was decanted. The inclusion body (IB) pellet was washed by resuspending in an additional volume of IB buffer I (50 mM Tris pH 8.0; 100 mM NaCl; 1 mM EDTA; 1% Triton X-100; 4° C.,) and the resuspended material was passed through a microfluidizer a total of two times. The samples were then centrifuged at 10,000 g for 15 minutes at 4° C., and the supernatant was decanted. The IB pellet was resuspended in one volume of buffer II (50 mM Tris pH 8.0; 100 mM NaCl; 1 mM EDTA; 4° C.). After resuspension, the samples were centrifuged at 10,000 g for 15 minutes at 4° C., and the supernatant was decanted. The IB pellet was then resuspended in ½ volume of buffer II (50 mM Tris pH 8.0; 100 mM NaCl; 1 mM EDTA; 4° C.). The IB was then aliquoted into appropriate containers. The samples were centrifuged at 10,000 g for 15 minutes at 4° C., and the supernatant was decanted. The inclusion bodies were then solubilized or stored at −80° C. until further use.

Inclusion Body Solubilization

The inclusion bodies were solubilized to a final concentration between 10-15 mg/mL in solubilization buffer (20 mM Tris, pH 8.0; 8M Guanidine; 100 mM B-ME). The solubilized IB were incubated at room temperature under constant mixing for 1 hour or until they were fully solubilized. The protein concentration was adjusted by dilution with additional solubilization buffer if protein concentration was high.

Refolding

Refolding was performed by diluting the samples to a final protein concentration of 0.5 mg/mL in 0.5M Arginine, pH 8.0; 4° C. The samples were allowed to refold for 48 to 72 hours at 4° C.

Purification

Figure 4:
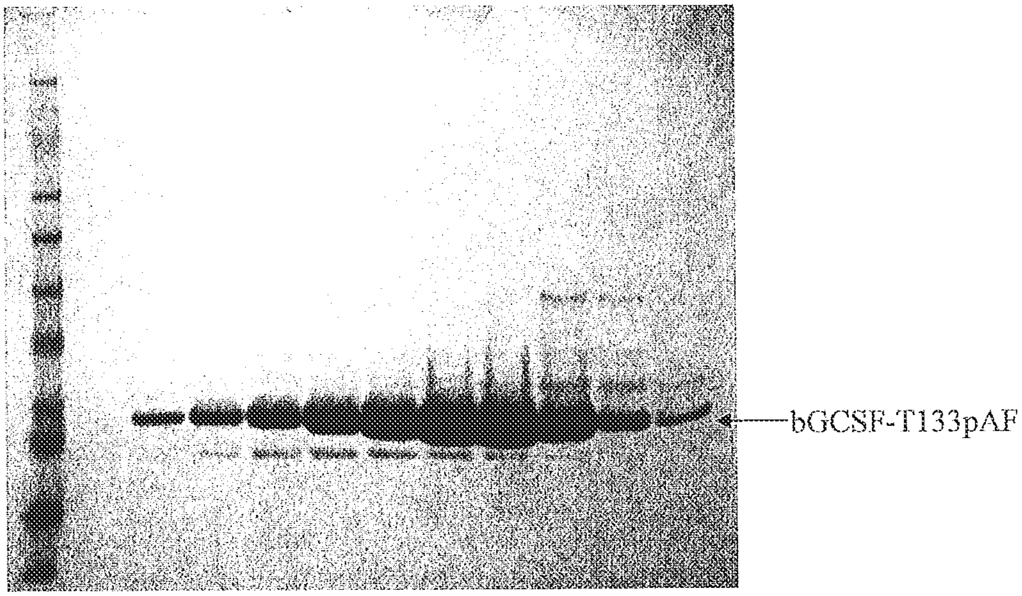
FIG. 4—SDS PAGE analysis of CM FF column peak fractions of bG-CSF prior to PEGylation is shown.

Solid $(NH_4)_2SO_4$ was added to the samples to a final concentration of 20% under gentile mixing. The samples were mixed gently at 4° C. for 30 minutes. Precipitated protein (containing bG-CSF) was pelled by centrifugation at 12,000 g for 15 minutes. The supernatant was removed, and the pellet was resuspended in ½ refold volume 20 mM NaAc, pH 4.5. All of pellet did not go back into solution. Only bG-CSF did go back into solution. Unsolubilized material was pelleted by centrifugation at 12,000 g for 15 minutes. The samples were decanted, and the supernatant was saved. The bG-CSF material was filtered through a 0.45 μm filter. The material was then loaded over a CM FF column (GE Healthcare) equilibrated in Buffer A (20 mM NaAc, pH 4.5). The material was <10m/S before loading onto column. bG-CSF was eluted from the column with a linear gradient over 10 column volumes to 100% Buffer B (20 mM NaAc, pH 4.5; 500 mM NaCl). FIG. 4 shows Coomassie-stained SDS-PAGE analysis of peak fractions from the CM FF column run with bG-CSF-T133pAF.

PEGylation and Purification

Figure 5:
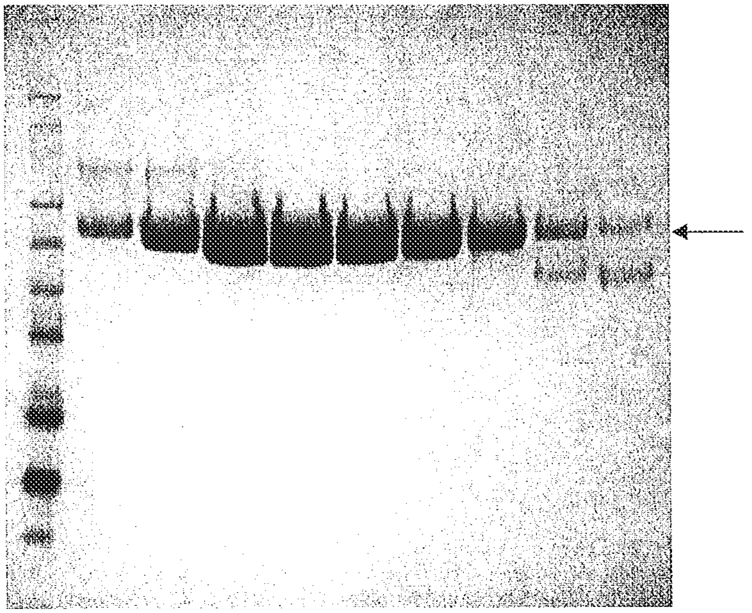
FIG. 5—SDS-PAGE analysis of SP HP column peak fractions of PEGylated bG-CSF-T133pAF is shown.

The pH of the CM pool was adjusted to pH 4.0 with 50% glacial acetic acid. The pool was then concentrated to approximately 4.0 mg/mL protein. 12:1 or 8:1 molar excess hydroxylamine PEG:bG-CSF was added to the pool. The mixture was incubated at 28° C. for 48-72 hours. The mixture were then diluted 8-10 fold with water (<8 rn/S) and then was loaded over a SP HP column (GE Healthcare) equilibrated in Buffer A (20 mM NaAc, pH 4.5). The PEGylated bG-CSF was eluted with a linear gradient over 40 column volumes to 100% Buffer B (20 mM NaAc, pH 4.5; 500 mM NaCl). FIG. 5 shows SDS-PAGE analysis of peak fractions from the SP HP column for PEGylated bG-CSF-T133pAF. 5% ethylene glycol, for example, may be used in the elution buffer as well.

Figure 6:
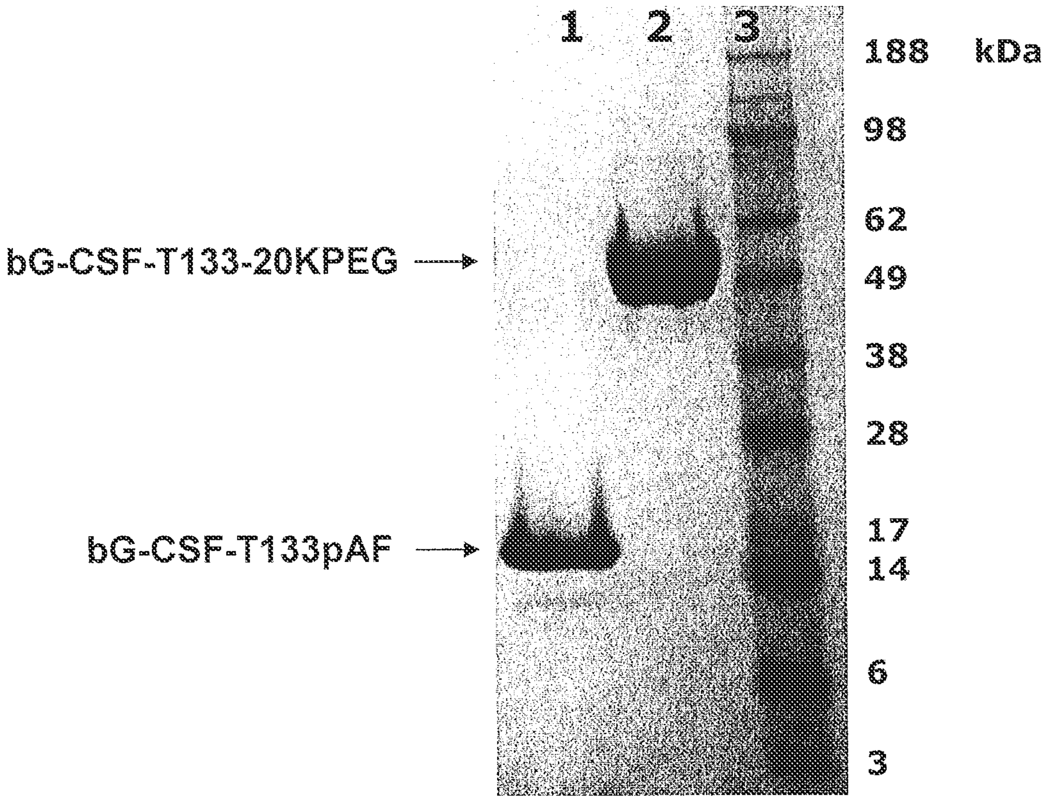
FIG. 6—SDS-PAGE analysis of b-GCSF before and after PEGylation is shown.

PEGylated bG-CSF fractions were pooled and dialyzed against bG-CSF formulation Buffer (4.26 mM NaAc, pH 4.0; 0.565 mM NaCl; 0.0033% Tween 20; 5% Sorbitol). The PEG material was concentrated to between 6-8 mg/mL protein and was filter sterilized using 0.22 μm PES filter. The protein was stored at 4° C. or flash frozen and stored at −80° C. for prolonged storage. FIG. 6 shows SDS-PAGE analysis of b-GCSF before and after PEGylation. Lane 1: bG-CSF-T133pAF; Lane 2: bG-CSF-T133pAF-20KPEG; Lane 3: SeeBlue Plus 2 molecular weight marker.

Peptide Mapping (Trypsin/Endoproteinase Glu-C) of bG-CSF

Peptide mapping was performed to confirm incorporation of para-acetylphenylalanine (pAF) into a bG-CSF polypeptide. Purified bG-CSF T133pAF before PEGylation and wild-type bG-CSF was diluted to a final 6M guanidine-HCl, 50 mM Tris pH 7.8 and reduced with 10 mM DTT at 37° C. for one hour. The sample was alkylated with 20 mM IAA for 40 minutes in the dark at room temperature, and the reaction was quenched with the addition of final 20 mM DTT. The material was dialyzed into 100 mM aminonium bicarbonate pH 7.7 and treated with trypsin 1:50 (protein:enzyme) for four hours at 37° C. This reaction was followed with the addition of Glu-C 1:20 overnight at 25° C. The digestion was quenched with the addition of TFA for a final concentration of 0.1%. The sample was applied onto a Grace Vydac C8 reversed phase column in tandem with a ThermoFinnigan LCQ Deca ion-trap mass spectrometer. The gradient started at 98% mobile phase A (0.05% TFA in water) isocratically for eight minutes and then ramped to 60% mobile phase B (0.05% TFA in acetonitrile) over 90 minutes with detection at 214 nm and 250 nm. A flow rate of 0.2 mL/min and column temperature of 40° C. were applied.

Capillary voltage was set to 15V with full scan range 100-2000 m/z. Collision voltage for MS/MS was 42% of normalized.

Figure 7A:
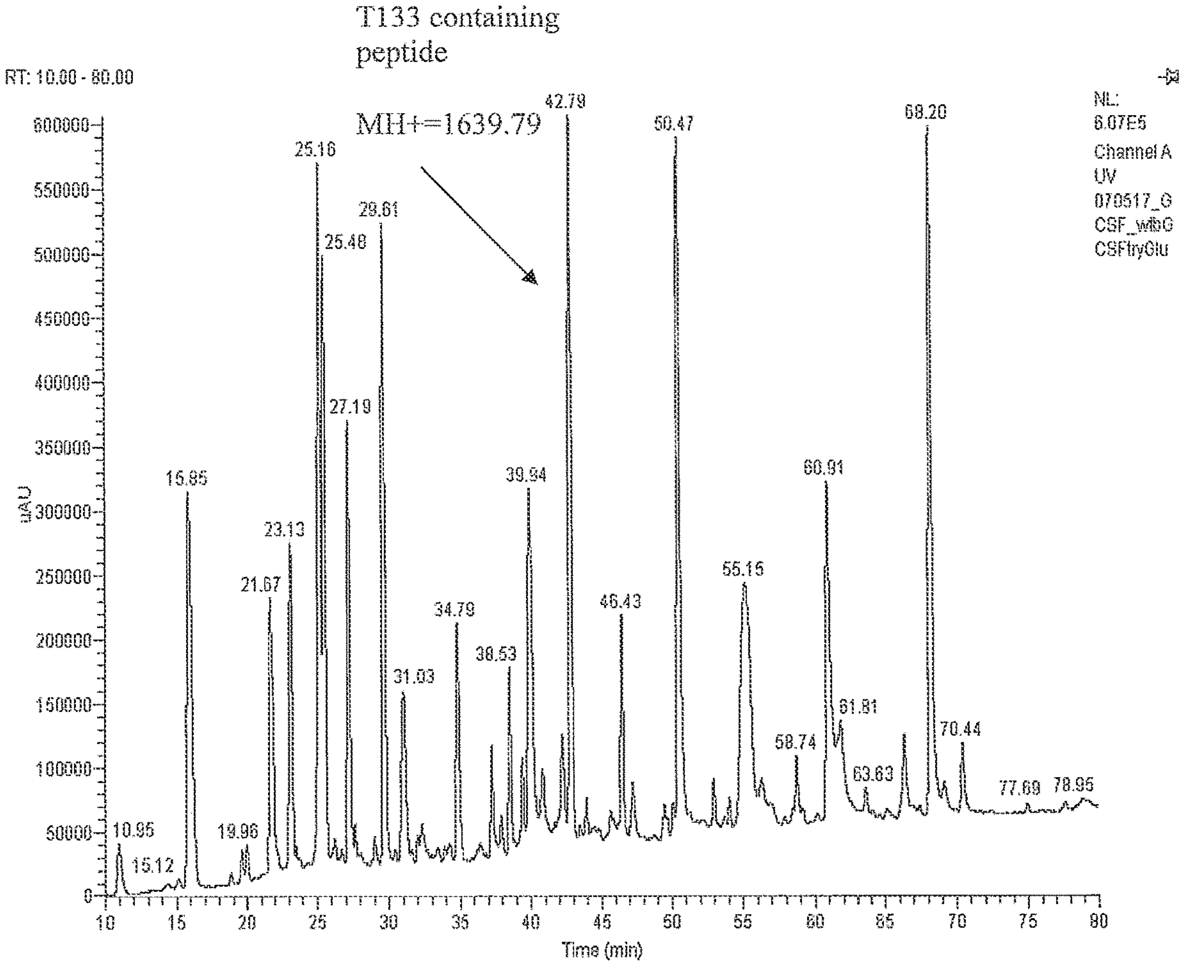
FIG. 7*a*—Trypsin/Glu-C digest of wild-type bG-CSF (214 nm Detection) is shown.
Figure 7B:
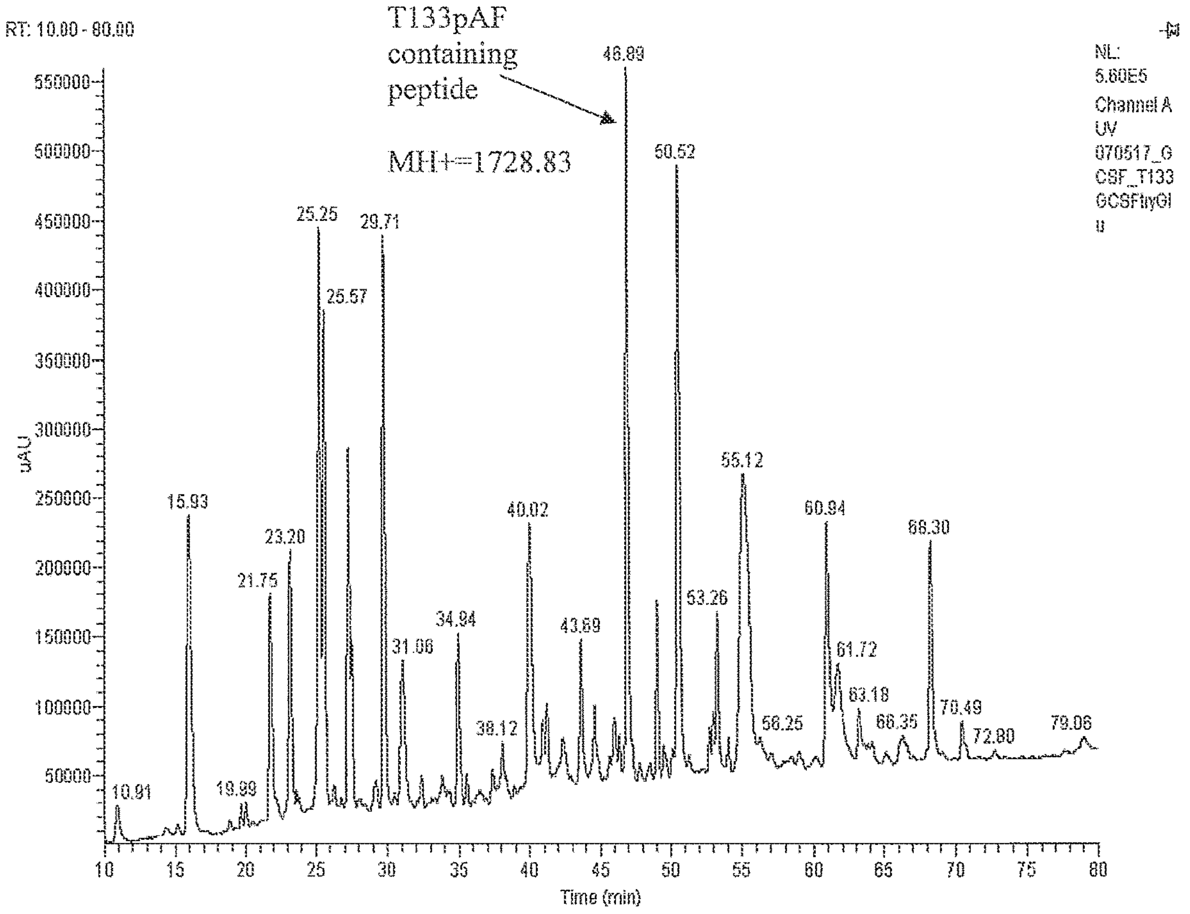
FIG. 7*b*—Trypsin/Glu-C digest of bG-CSF T133pAF (214 nm Detection) is shown.

FIG. 7*a* shows the trypsin/Glu-C digest of wild-type bG-CSF (214 nm Detection). FIG. 7*b* shows the trypsin/Glu-C digest of bG-CSF T133pAF (214 mn Detection). The increased hydrophobicity from the threonine to pAF (para-acetylphenylalanine) substitution is shown. For wild-type bG-CSF, the retention time of the T133 containing peptide was 42.79 minutes; for bG-CSF T133pAF, the T133pAF containing peptide was shifted and had a retention time of 46.89 minutes.

Figure 8A:
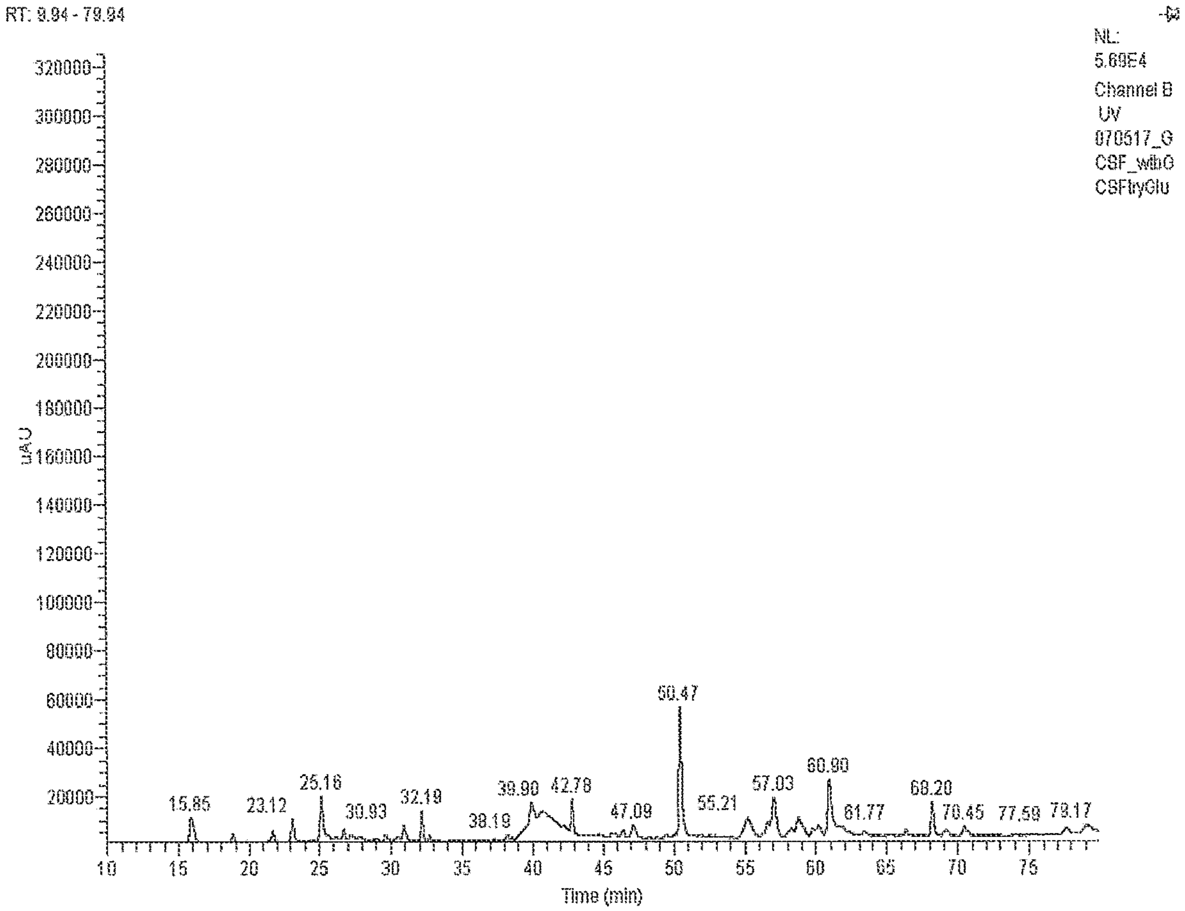
FIG. 8*a*—Trypsin/Glu-C digest of wild-type bG-CSF (250 nm Detection) is shown.
Figure 8B:
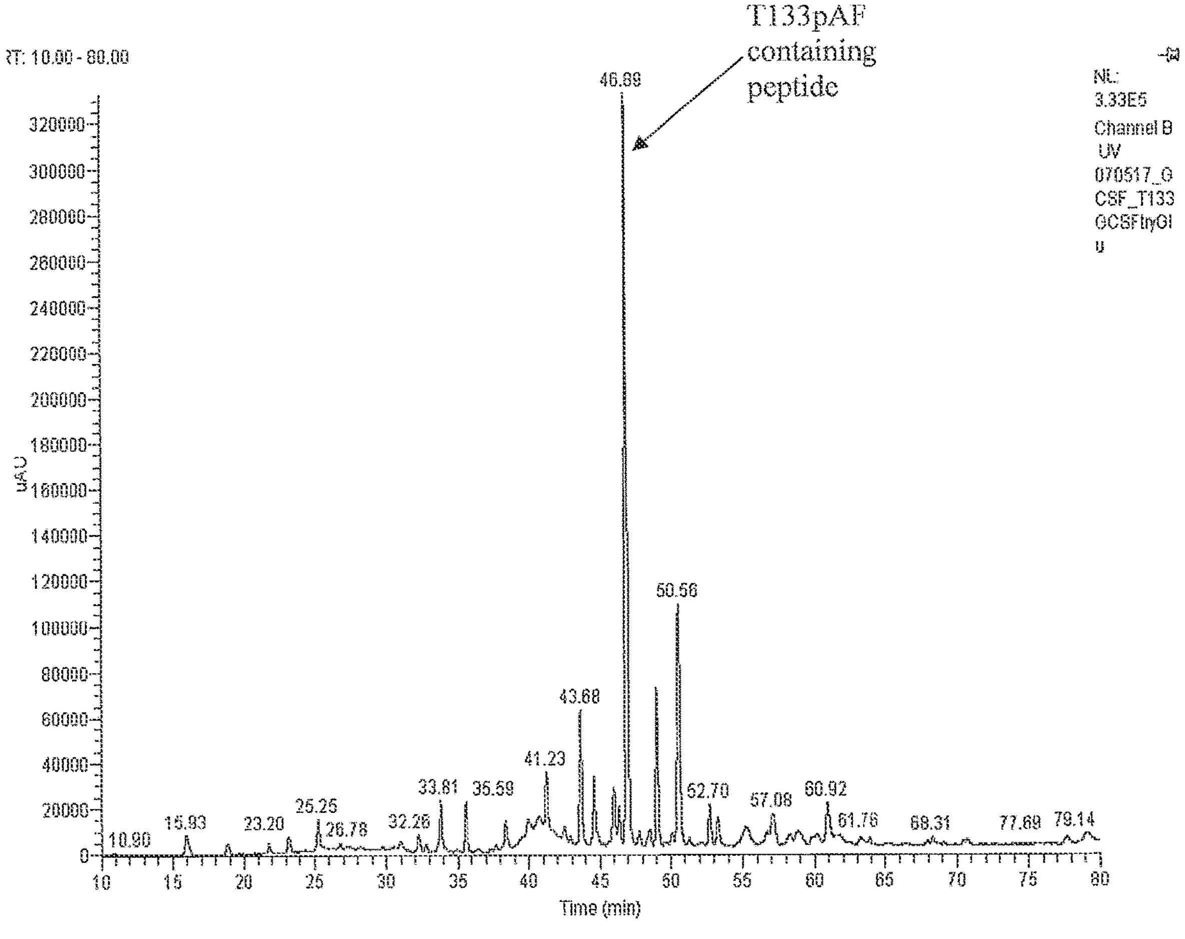
FIG. 8*b*—Trypsin/Glu-C digest of bG-CSF T133pAF (250 run Detection) is shown.

FIG. 8*a* shows the trypsin/Glu-C digest of wild-type bG-CSF (250 nm Detection). FIG. 8*b* shows the trypsin/Glu-C digest of bG-CSF T133pAF (250 nm Detection). With analysis at 250 nm, the protein/peptide signals are low, but the signal due to pAF is strong. The Tl 33 pAF containing peptide is indicated in FIG. 8*b* with a retention time of 46.89 minutes.

Peptide Mapping (Endoproteinase Glu-C) of bG-CSF

Purified bG-CSF T133pAF prior to PEGylation was diluted to a final 6M guanidine-HCl, 50 mM Tris pH 7.8 and reduced with 10 mM DTT at 37° C. for one hour. The sample was alkylated with 20 mM IAA for 40 minutes in the dark at room temperature, and the reaction was quenched with the addition of final 20 mM DTT. The material was dialyzed into 100 mM aminonium bicarbonate pH 7.7 and treated with Glu-C 1:20 (protein:enzyme) overnight at 25° C. Digestion was quenched with the addition of TFA for a final concentration of 0.1%. The sample was applied onto a Grace Vydac CS reversed phase column in tandem with a ThermoFinnigan LCQ Deca ion-trap mass spectrometer. The gradient started at 98% mobile phase A (0.05% TFA in water) isocratically for eight minutes and then ramped to 60% mobile phase B (0.05% TFA in acetonitrile) over 90 minutes with detection at 214 nm and 250 nm. A flow rate of 0.2 mL/min and column temperature of 40° C. were applied. Capillary voltage was set to 15V with full scan range 100-2000 m/z. Collision voltage for MS/MS was 42% of normalized.

Figure 9A:
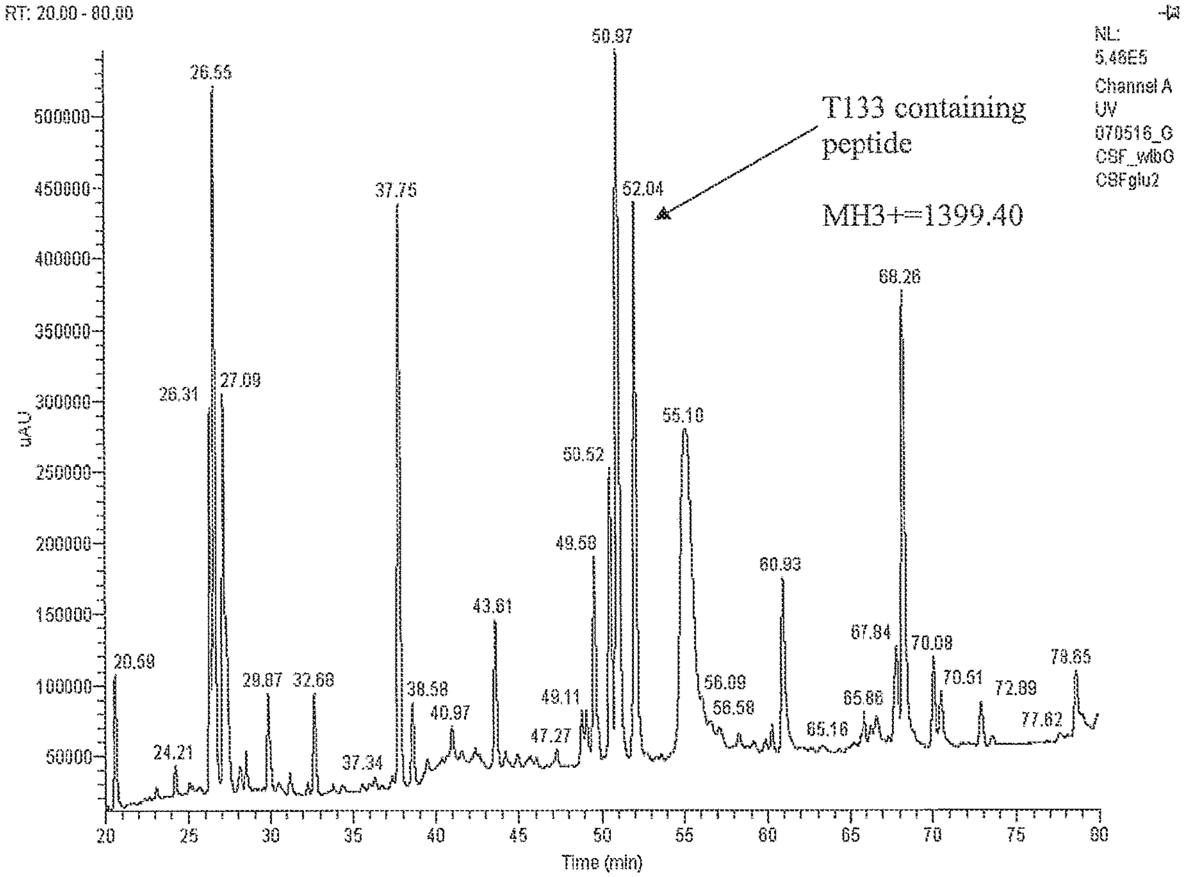
FIG. 9*a*—Glu-C digest of wild-type bG-CSF (214 nm Detection) is shown.
Figure 9B:
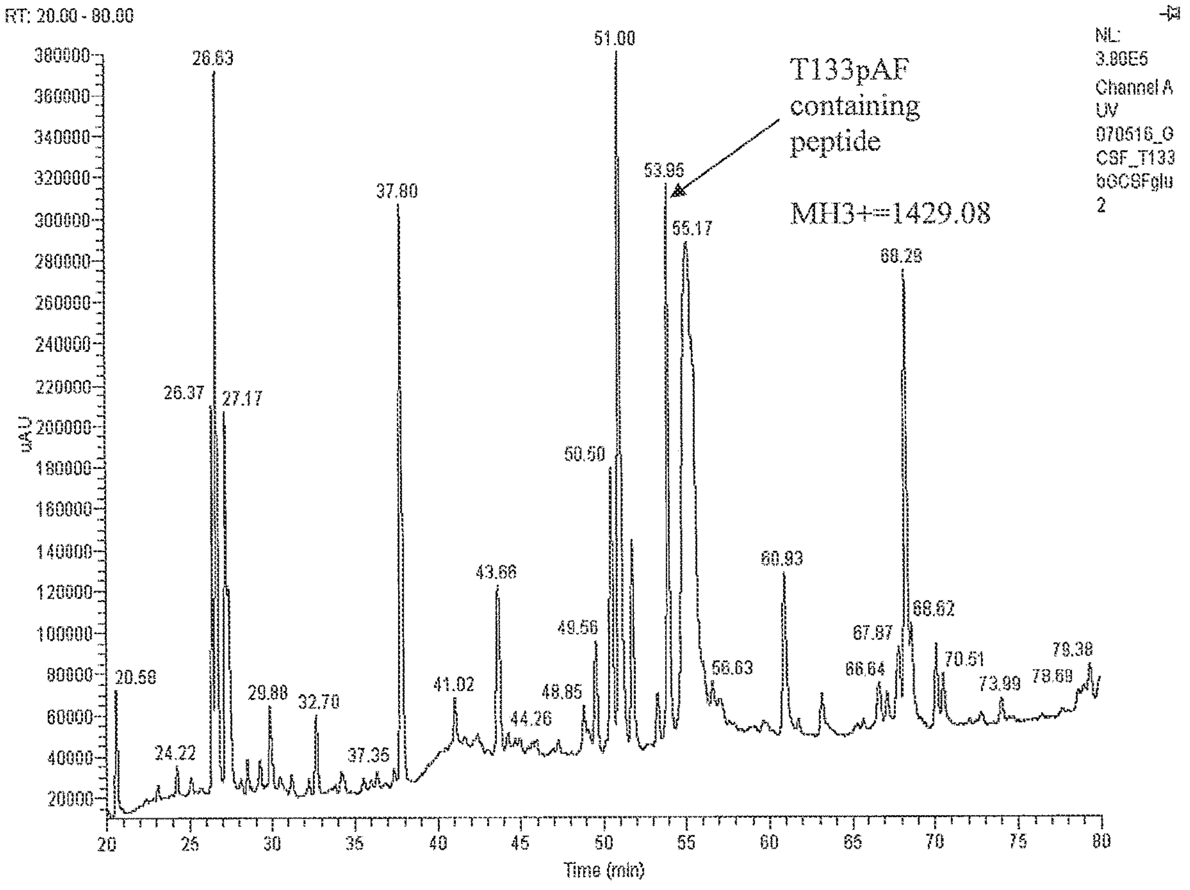
FIG. 9*b*—Glu-C digest of bG-CSF T133pAF (214 nm Detection) is shown.

FIG. 9*a* shows the Glu-C digest of wild-type bG-CSF (214 nm Detection). FIG. 9*b* shows the Glu-C digest of bG-CSF T133pAF (214 nm Detection). For wild-type bG-CSF, the T133 containing peptide had a retention time of 52.04 minutes; for T133pAF bG-CSF, the T133pAF containing peptide had a retention time of 53.95 minutes.

Figure 10A:
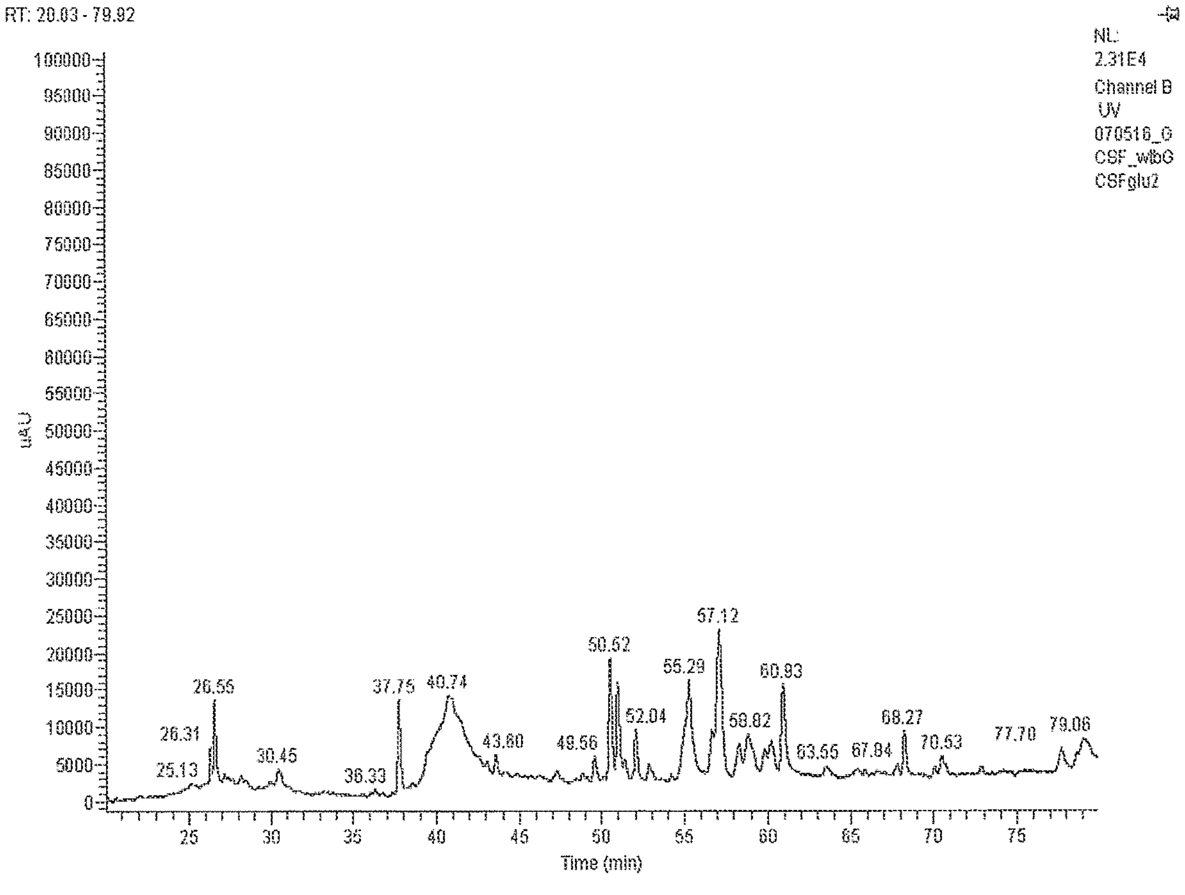
FIG. 10*a*—Glu-C digest of wild-type bG-CSF (250 nm Detection) is shown.
Figure 10B:
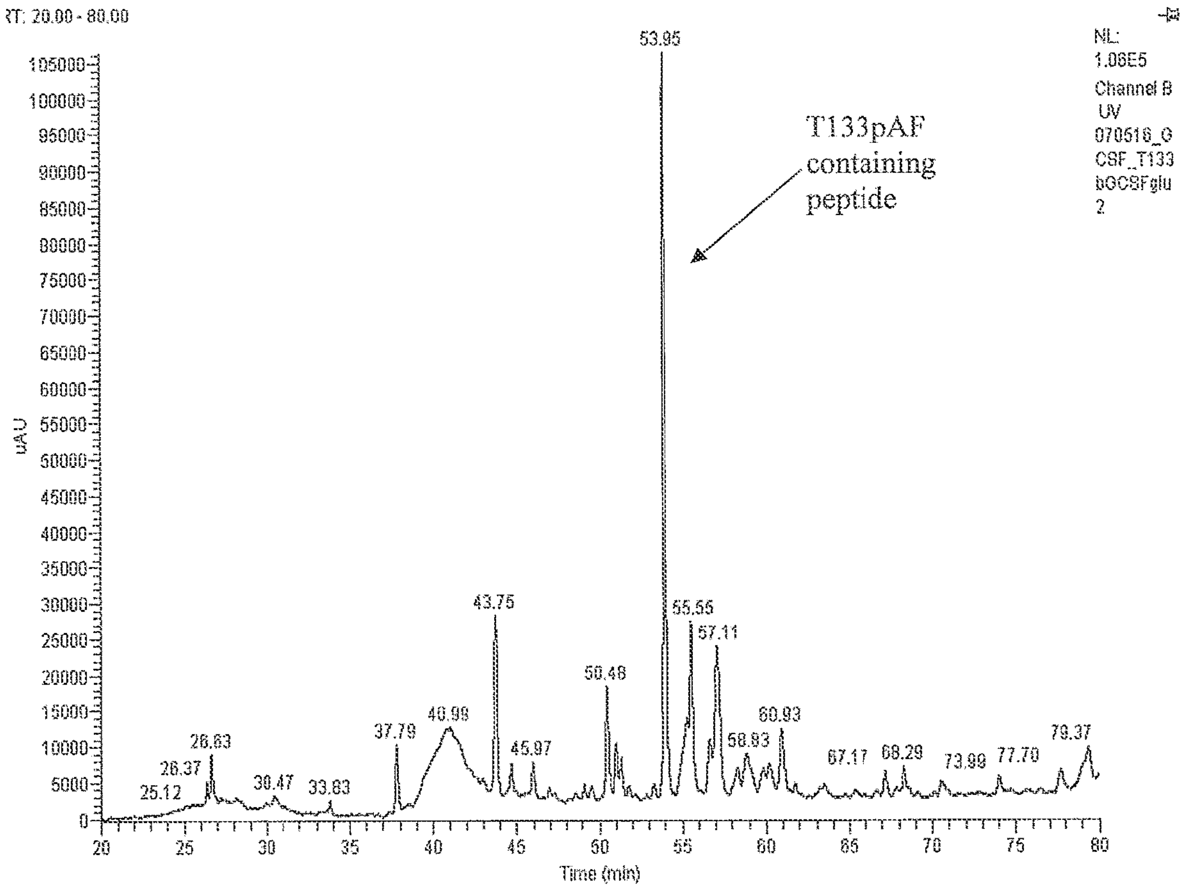
FIG. 10*b*—Glu-C digest of bG-CSF T133pAF (250 nm Detection) is shown.

FIG. 10*a* shows the Glu-C digest of wild-type bG-CSF (250 nm Detection). FIG. 10*b* shows the Glu-C digest of bG-CSF T133pAF (250 nm Detection). With analysis at 250 run, the protein/peptide signals are low, but the signal due to pAF is strong. The T133 pAF containing peptide is indicated in FIG. 10*b* with a retention time of 53.95 minutes.

RP-HPLC and SEC-HPLC Analysis of bG-CSF Polypeptides

RP-HPLC and SEC-HPLC were used to analyze purity and determine identity of the samples after purification. Purified 20K PEG-bG-CSF T133pAF was diluted to 1 mg/mL with formulation buffer (4.26 mM sodium acetate pH 4.0, 0.565 mM sodium chloride, 0.0033% Tween-20 and 5% sorbitol) and 10 μL was injected onto a J. T. Baker wide pore Octyl (C8) reversed phase column (4.6×100 mm, 5 μm). The gradient started with 50% of mobile phase A (0.1% TFA in water) and ramped up to 70% of mobile phase B (0.1% TFA in acetonitrile) over 26 minutes. The column was regenerated with 90% mobile phase B for 4 minutes and reequilibrated with 50% mobile phase A over 5 minutes. A flow rate of 1.5 mL/min and column temperature of 60° C. were applied with detection at 214 nm. Analysis was performed using Agilent Chemstation software. Table 3 shows the main peak (20K PEG-bG-CSF T133pAF) with a retention time of 8.50 minutes. By Area % calculation, 91.2% of the sample was PEGylated-b-GCSF.

TABLE 3

| Time (minutes) | Area | Area % |
|---|---|---|
| 4.2 | 50.6 | 0.6 |
| 5.0 | 20.0 | 0.3 |
| 6.8 | 155.2 | 2.0 |
| 7.3 | 99.7 | 1.3 |
| 8.0 | 121.2 | 1.5 |
| 8.5 | 7245.0 | 91.2 |
| 9.3 | 87.9 | 1.1 |
| 9.7 | 31.9 | 0.4 |
| 10.1 | 135.5 | 1.7 |

bG-CSF that was not PEGylated was also analyzed by RP-HPLC. Table 4 shows the main peak (bG-CSF T133pAF) with a retention time of 8.893 minutes. By Area % calculation, 64.3% of the sample was bG-CSF Tl 33pAF.

TABLE 4

| Time (minutes) | Area | Area % |
|---|---|---|
| 5.6 | 114.3 | 1.6 |
| 7.4 | 17.4 | 0.2 |
| 8.1 | 12.2 | 0.2 |
| 8.2 | 13.6 | 0.2 |
| 8.3 | 13.7 | 0.2 |
| 8.9 | 4622.1 | 64.3 |
| 9.3 | 930.8 | 13.0 |
| 10.2 | 13.9 | 0.2 |
| 10.3 | 12.9 | 0.2 |
| 10.8 | 1151.5 | 16.0 |
| 11.1 | 273.9 | 3.8 |
| 11.8 | 10.0 | 0.1 |

Figure 11:
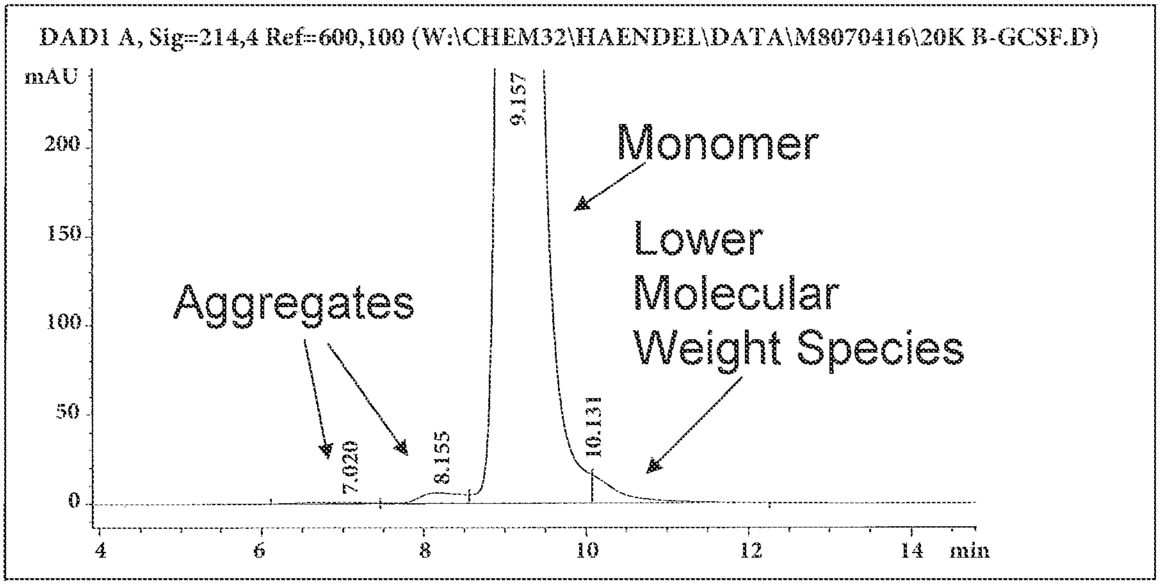
FIG. 11—SEC-HPLC analysis of the PEGylated bG-CSF polypeptide is shown.

Purified 20K PEG-bG-CSF T133pAF was also analyzed by SEC-HPLC. The sample was injected neat (2 μL) onto a Tosohaas TSK Super SW3000 (4.6×300 mm, 4 μm 250A) sizing column using a 25 minute isocratic gradient. The mobile phase contains 97% of 63 mM sodium phosphate pH 7.0 and 3% 2-propanol. A flow rate of 0.3 mL/min and column temperature of 25° C. was applied with detection at 214 mn. Analysis was performed using Agilent Chemstation software. Table 5 shows the main peak with a retention time of 9.157 minutes. By Area % calculation, 98.3% of the sample was monomeric PEG-bG-CSF. See FIG. 11 for the SEC-HPLC analysis of the PEGylated polypeptide.

TABLE 5

Figure 12:
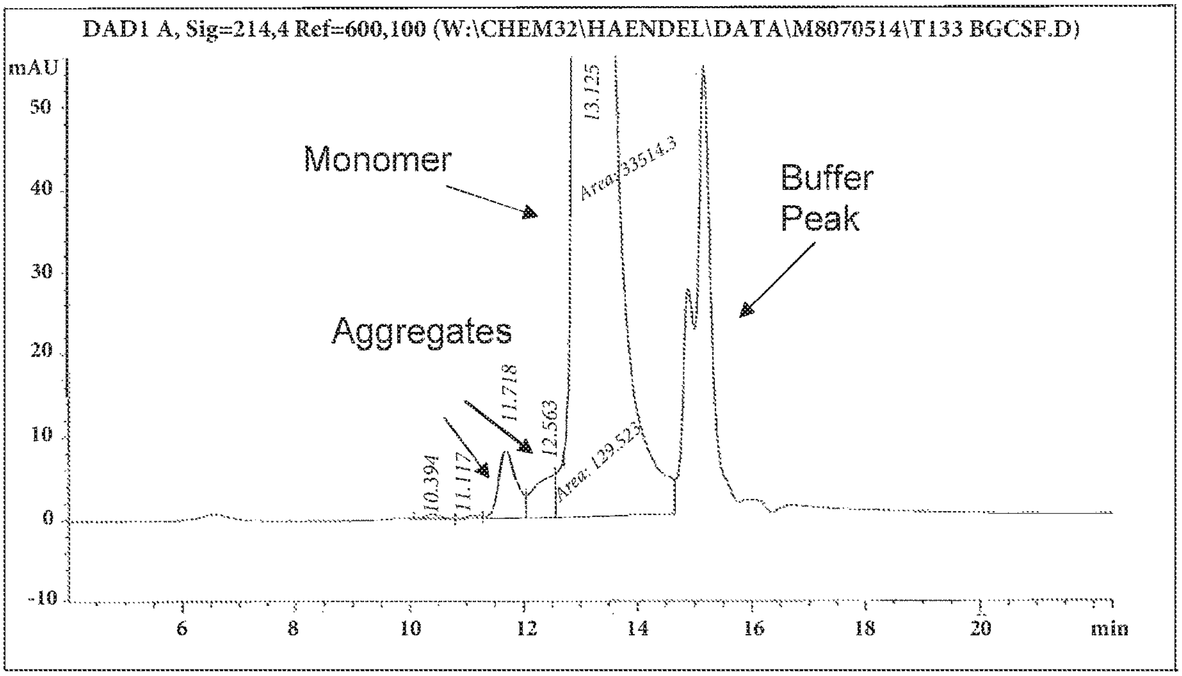
FIG. 12—SEC-HPLC analysis of the bG-CSF polypeptide is shown.

| Time (minutes) | Area | Area % |
|---|---|---|
| 7.0 | 50.3 | 0.1 |
| 8.2 | 228.0 | 0.6 |
| 9.2 | 36454.5 | 98.3 |
| 10.1 | 361.4 | 1.0 |

bG-CSF that was not PEGylated was also analyzed by SEC-HPLC. Table 6 shows the main peak with a retention time of 13.125 minutes. By Area % calculation, 99.0% of the sample was monomeric bG-CSF T133pAF. See FIG. 12 for the SEC-HPLC analysis of the polypeptide.

TABLE 6

| Time (minutes) | Area | Area % |
|---|---|---|
| 10.4 | 10.0 | 0.0 |
| 11.1 | 6.8 | 0.0 |
| 11.7 | 178.2 | 0.5 |
| 12.6 | 129.5 | 0.4 |
| 13.1 | 33514.3 | 99.0 |

ESI-TOF high-accuracy analysis (Agilent Technology) of bG-CSF polypeptide was also performed to confirm identity of the bG-CSF polypeptide. Purified bG-CSF T133pAF was dialyzed into 0.1% formic acid. The sample was applied onto a C-18 cartridge for one minute with water and then eluted with 50% acetonitrile in water. The total run time was three minutes with a flow rate of 0.3 ml/min. ESI capillary voltage was set to 4 kV, and the MSTOF fragmentor voltage was set at 300V. The charge state envelope scanned was deconvoluted to provide an MH+ value. The Expected MHI+ MW was 19145. The observed MH+MW was 19146.

M-NFS60 Proliferation Assay

To evaluate the potency of the bG-CSF molecules, a proliferation assay was performed with the M-NFS60 cell line. The cell line was purchased from ATCC (catalog #CRL-1838). The cells were thawed and maintained in RPMI 1640+10% FBS+penicillin/streptomycin+50 μM 2-mercaptoethanol+20 ng/ml mIL-3 (Invitrogen, Carlsbad, CA; mIL3 from BD Pharmingen cat #554579). The cells were split every two days and seeded at $0.02\times10^6$ cells/mL.

The day before the assay, the cells were split to $0.1\times10^6$ cells/mL. After 16-24 hours, the cells were seeded in assay medium into black, flat-bottom 96 well plates at 10,000 cells/well and serial dilutions of the bG-CSF compounds were added in duplicate. The total volume per well was 100 μL, and the Assay Medium was RPMI 1640+10% FBS+P/S. Standards, such as Neupogen® and WT bG-CSF, were added in duplicate for every plate as well. The plates were then incubated at 37° C., 5% $CO_2$ for 42 hours. After this 42 hour incubation, 10 μL/well of Alamar Blue (Biosource cat #: DAL1100) was added, and the plates were incubated for another 6 hours at 37° C., 5% $CO_2$. The plates were then spun down at 4000 rpm for 2 minutes at room temperature to get rid of any air bubbles. The plates were read on the Tecan fluorometer with excitation at 535 nm, and emission at 590 nm settings. The plates were wrapped in foil to avoid light exposure to the light-sensitive Alamar Blue dye.

Figure 13:
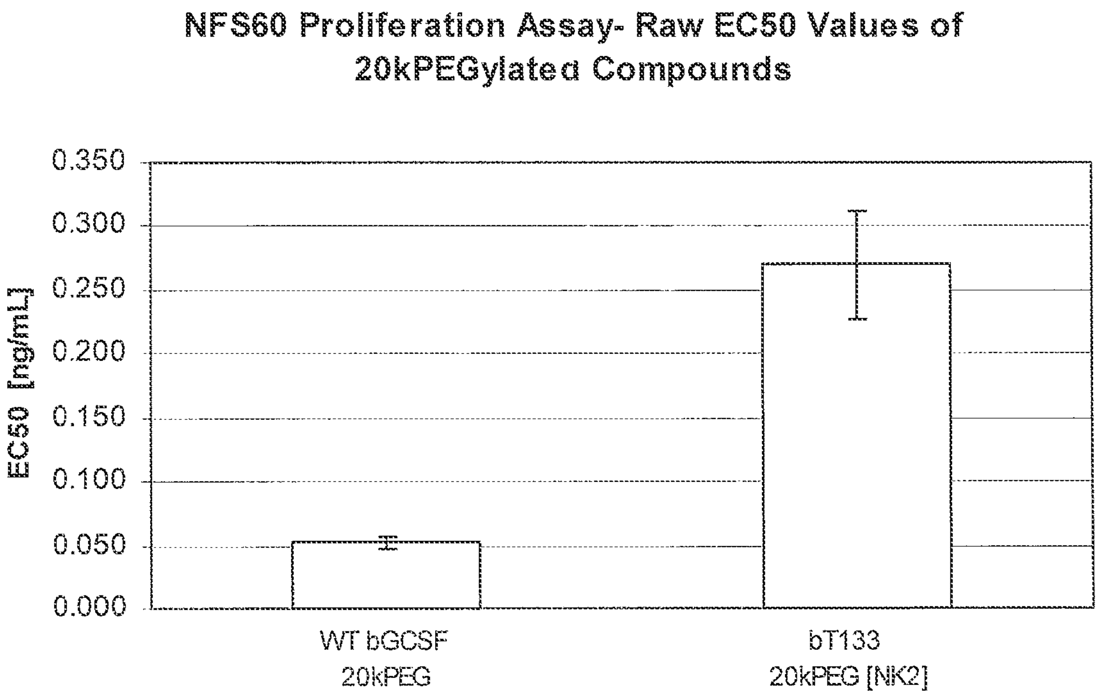
FIG. 13—Raw EC50 values from the M-NFS60 proliferation assay of 20K PEGylated bovine G-CSF T133pAF and wild-type are shown.
Figure 14:
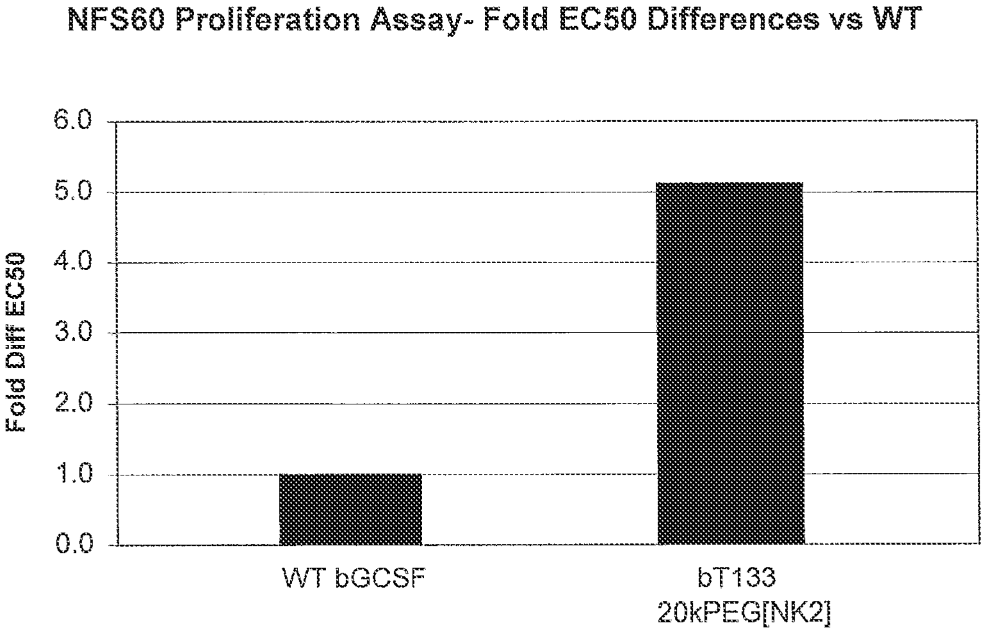
FIG. 14—Fold EC50 differences in the M-NFS60 proliferation assay of 20K PEGylated bovine G-CSF T133pAF vs. wild-type are shown.

For data analysis, duplicate serial dilutions for each compound were averaged, and the ECSO values were calculated in SigmaPlot. Raw EC50 values were listed for all compounds, and the fold differences were calculated (PEGylated bovine GCSF compounds were compared to WT bG-CSF). The experiments were run multiple times to establish an intra-assay CV<20% and an inter-assay CV<30%. FIG. 13/Table 7=M-NFS60 proliferation assay-raw EC50 values of 20K PEGylated bovine G-CSF T133pAF and wild-type. FIG. 14/Table 8=M-NFS60 proliferation assay-fold EC50 differences of 20K PEGylated bovine G-CSF T133pAF vs. wild-type.

Other bG-CSF molecules comprising a non-naturally encoded amino acid substitution were assayed. Table 9 shows the average EC50 values obtained.

TABLE 7

| | | Neupoaen | Neulasta | WTbG-CSF | 20K PEG-bT133 batch NK2] |
|---|---|---|---|---|---|
| Summary | Avg EC50 [ng/ml] | 0.025 | 0.077 | 0.053 | 0.270 |
| | SD | 0.005 | 0.004 | 0.005 | 0.042 |
| | CV | 18% | 5% | 9% | 16% |
| | N | 14 | 5 | 16 | 2 |

TABLE 8

| | | Neupoaen | Neulasta | WTbG-CSF | 20K PEG-bT133 [batch NK21 |
|---|---|---|---|---|---|
| Summary | Fold Diff EC50 [X] | 1.0 | 3.2 | 1 | 5.1 |
| | SD | 0.0 | 0.7 | 0 | 0.5 |
| | CV | 0% | 23% | 0% | 9% |
| | N | 14 | 5 | 12 | 2 |

TABLE 9

| | Avg EC50 Values | SD | CV |
|---|---|---|---|
| Neupogen | 0.025 | 0.005 | 18% |
| WTbG-CSF | 0.053 | 0.005 | 9% |
| Neulasta | 0.077 | 0.004 | 5% |
| 20kPEG-bS62 | 0.150 | 0.008 | 5% |
| 20kPEG-bT133 [NK1] | 0.258 | 0.045 | 17% |
| 20kPEG-bT133 [NK2] | 0.270 | 0.042 | 16% |
| 20kPEG-bR7 | 0.348 | 0.073 | 21% |
| 20kPEG-bR166 | 0.363 | 0.033 | 9% |
| 20kPEG-bL3 | 0.477 | 0.081 | 17% |

CD11b Staining of Bovine Neutrophils 50 ul of bovine blood was added to a non-treated polystyrene, 96-well plate (Cal Poly Pomona). Cells were stimulated by adding 50 ul of Neupogen®, Neulasta®, or bG-CSF-T133pAcF-20K PEG diluted in PBS (200 ng/ml to 0.001 ng/ml final). The solution was gently mixed and incubated for 30 minutes at 39° C. in a $CO_2$ incubator. 20 μg/ml of primary antibody was added to the cells (Mouse anti-bovine CD11b: MM12A, VMRD). Cells were incubated at 4° C. for 30 minutes. The assay plate was centrifuged at 800×g for 2 minutes, and the supernatant was discarded. The erythrocytes were lysed for 1 minute by adding 150 ul of cold lysis solution (0.15M phosphate, pH7.2), and the isotonicity was restored by adding 50 ul of restoring solution (0.15M phosphate, 0.5M NaCl, pH7.4). The plate was centrifuged again, and the supernatant was discarded. The lysis procedure was repeated until all red blood cells that were visible were removed. The cells were washed with 200 ul FACS buffer twice (1×PBS, 2.5 mM HEPES, 0.1% sodium azide, 2.0% FBS) and resuspended in 100 ul FACS buffer. 20 ug/ml of secondary antibody (Goat anti-mouse IgGl, Human ads-PE) was added and incubated at 4° C. for 30 minutes in the dark. The cells were pelleted and washed twice and resuspended in 200 ul FACS buffer. The BD FACS Array instrument was used to acquire 50,000 events and count CD11b positive cells.

Figure 15:
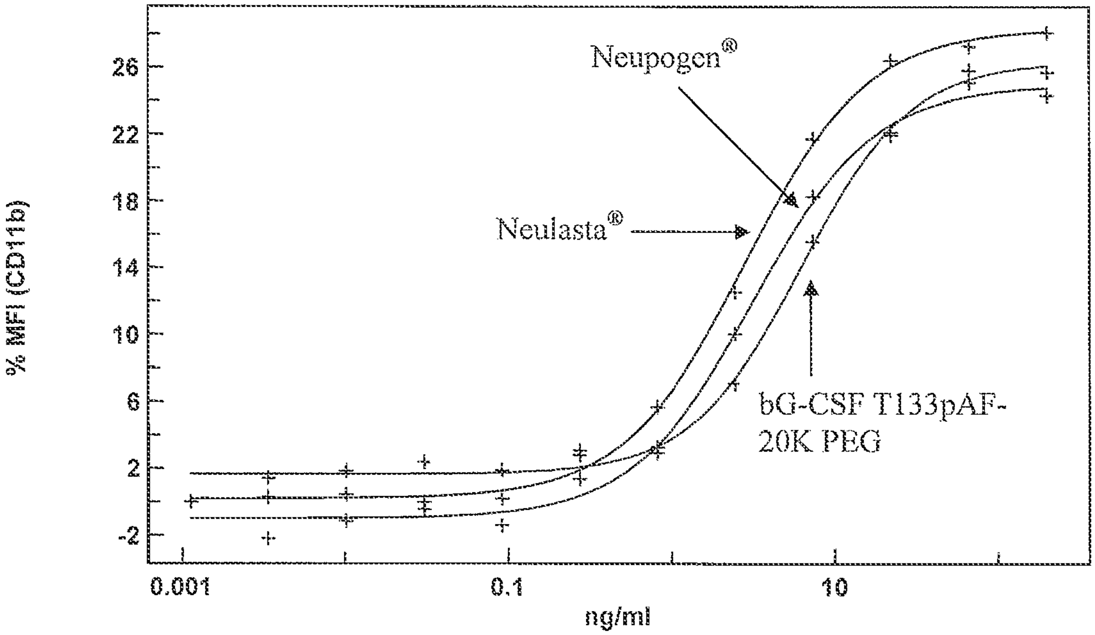
FIG. 15—Results from an experiment analyzing bovine neutrophils stained with CD11b antibody are shown.

FIG. 15 shows the results of the experiment in which bovine neutrophils were stained with CD11b antibody to assess their responsiveness to various molecules. The Mean Fluorescent Intensity (MFI) for granulocytes was used to determine the level of CD11b presentation on the cell surface. The % MFI is a normalized value relative to an unstimulated control group. Dose response curves and EC50 values were generated for Neupogen, Neulasta, and bG-CSF T133pAF-20K PEG based on a 4-parameter fit. The EC50 value for Neupogen® was 3.18 ng/ml. For Neulasta®, the EC50 value was 2.84 ng/ml, and for bG-CSF T133pAF-20K PEG the EC50 value was 6.23 ng/ml.

Example 3

Introduction of a Carbonyl-Containing Amino Acid and Subsequent Reaction with an Aminooxy-Containing PEG This Example demonstrates a method for the generation of a bG-CSF polypeptide that incorporates a ketone-containing non-naturally encoded amino acid that is subsequently reacted with an aminooxy-containing PEG of approximately 5,000 MW. Each of the residues before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175 (i.e., at the carboxyl terminus of the protein), and any combination thereof (SEQ ID NO: 1 or the corresponding amino acids in SEQ ID NO: 2 or the corresponding amino acids in another bG-CSF polypeptide) is separately substituted with a non-naturally encoded amino acid having the following structure:

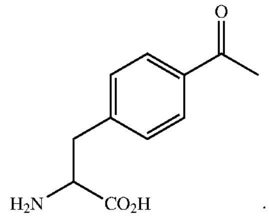

The sequences utilized for site-specific incorporation of p-acetyl-phenylalanine into bG-CSF are SEQ ID NO: 3 or 4 (bG-CSF), and SEQ ID NO: 23 or 5

$$\left(muttRNA,\ M\ jannaschii\ mtRNA\ A_{CUA}^{Tyr}\right),$$

and SEQ ID NOs: 22, 24, 17, 18, 19 (TyrRS LW1, 5, or 6) described in Example 2 above.

Once modified, the bG-CSF polypeptide variant comprising the carbonyl-containing amino acid is reacted with an aminooxy-containing PEG derivative of the form:

$$\text{R-PEG(N)—O—(CH}_2\text{)n-O—NH}_2$$

where R is methyl, n is 3 and N is approximately 5,000 MW. The purified b-GCSF containing p-acetylphenylalanine dissolved at 10 mg/mL in 25 mM MES (Sigma Chemical, St. Louis, MO) pH 6.0, 25 mM Hepes (Sigma Chemical, St. Louis, MO) pH 7.0, or in 10 mM Sodium Acetate (Sigma Chemical, St. Louis, MO) pH 4.5, is reacted with a 10 to 100-fold excess of aminooxy-containing PEG, and then stirred for 10-16 hours at room temperature (Jencks, W. J. Am. Chem. Soc. 1959, 81, pp 475). The PEG-b-GCSF is then diluted into appropriate buffer for immediate purification and analysis.

Example 4

Conjugation with a PEG Consisting of a Hydroxylamine Group Linked to the PEG Via an Amide Linkage A PEG reagent having the following structure is coupled to a ketone-containing non-naturally encoded amino acid using the procedure described in Example 3:

$$\text{R-PEG(N)—O—(CH}_2\text{)}_2\text{—NH—C(O)(CH}_2\text{)}_n\text{—O—NH}_2$$

where R=methyl, n=4 and N is approximately 20,000 MW. The reaction, purification, and analysis conditions are as described in Example 3.

Example 5

Introduction of Two Distinct Non-Naturally Encoded Amino Acids into bG-CSF Polypeptides This example demonstrates a method for the generation of a bG-CSF polypeptide that incorporates non-naturally encoded amino acid comprising a ketone functionality at two positions among the following residues: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175 (i.e., at the carboxyl terminus of the protein), and any combination thereof (SEQ ID NO: 1 or the corresponding amino acids in SEQ ID NO: 2 or the corresponding amino acids in another bG-CSF polypeptide). The bG-CSF polypeptide is prepared as described in Examples 1 and 2, except that the selector codon is introduced at two distinct sites within the nucleic acid.

Example 6

Conjugation of bG-CSF Polypeptide to a Hydrazide-Containing PEG and Subsequent In Situ Reduction A bG-CSF polypeptide incorporating a carbonyl-containing amino acid is prepared according to the procedure described in Examples 2 and 3. Once modified, a hydrazide-containing PEG having the following structure is conjugated to the bG-CSF polypeptide:

$$\text{R-PEG(N)—O—(CH}_2\text{)}_2\text{—NH—C(O)(CH}_2\text{)}_n\text{—X—NH—NH}_2$$

where R=methyl, n=2 and N=10,000 MW and X is a carbonyl (C═O) group. The purified b-GCSF containing p-acetylphenylalanine is dissolved at between 0.1-10 mg/mL in 25 mM MES (Sigma Chemical, St. Louis, MO) pH 6.0, 25 mM Hepes (Sigma Chemical, St. Louis, MO) pH 7.0, or in 10 mM Sodium Acetate (Sigma Chemical, St. Louis, MO) pH 4.5, is reacted with a 1 to 100-fold excess of hydrazide-containing PEG, and the corresponding hydrazone is reduced in situ by addition of stock 1M $NaCNBH_3$ (Sigma Chemical, St. Louis, MO), dissolved in $H_2O$, to a final concentration of 10-50 mM. Reactions are carried out in the dark at 4° C. to RT for 18-24 hours. Reactions are stopped by addition of 1 M Tris (Sigma Chemical, St. Louis, MO) at about pH 7.6 to a final Tris concentration of 50 mM or diluted into appropriate buffer for immediate purification.

Example 7

Introduction of an Alkyne-Containing Amino Acid into a bG-CSF Polypeptide and Derivatization with mPEG-Azide The following residues, before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 3 38, 39, 4 41, 42, 43, 4 45, 46, 47, 48, 4 50, 51, 52, 53, 54, 55, 5 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175 (i.e., at the carboxyl terminus of the protein), and any combination thereof (SEQ ID NO: 1 or the corresponding amino acids in SEQ ID NO: 2 or the corresponding amino acids in another bG-CSF polypeptide), are each substituted with the following non-naturally encoded amino acid:

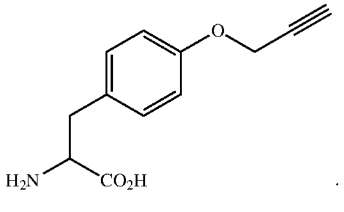 [SMILES: C#CCOc1ccc(CC(N)C(=O)O)cc1]

.

The sequences utilized for site-specific incorporation of p-propargyl-tyrosine into bG-CSF are SEQ ID NO: 3 or 4, SEQ ID NO: 5

$$\left(muttRNA, M\ jannaschii\ mtRNA_{CUA}^{Tyr}\right),$$

and 10, 11, 12 described in Example 2 above. The bG-CSF polypeptide containing the propargyl tyrosine is expressed in *E. coli* and purified using the conditions described in Example 3.

The purified bG-CSF containing propargyl-tyrosine dissolved at between 0.1-10 mg/mL in PB buffer (100 mM sodium phosphate, 0.15 M NaCl, pH=8) and a 10 to 1000-fold excess of an azide-containing PEG is added to the reaction mixture. A catalytic amount of $CuSO_4$ and Cu wire are then added to the reaction mixture. After the mixture is incubated (including but not limited to, about 4 hours at room temperature or 37° C., or overnight at 4° C.), $H_2O$ is added and the mixture is filtered through a dialysis membrane. The sample can be analyzed for the addition, including but not limited to, by similar procedures described in Example 3.

In this Example, the PEG will have the following structure:

$$R\text{-}PEG(N)—O—(CH_2)_2—NH—C(O)(CH_2)_n\text{-}N_3$$

where R is methyl, n is 4 and N is 10,000 MW.

Example 8

Substitution of a Large, Hydrophobic Amino Acid in a bG-CSF Polypeptide with Propargyl Tyrosine A Phe, Trp or Tyr residue present within one the following regions of bG-CSF: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175 (i.e., at the carboxyl terminus of the protein), and any combination thereof (SEQ ID NO: 1 or the corresponding amino acids in SEQ ID NO: 2 or the corresponding amino acids in another bG-CSF polypeptide) is substituted with the following non-naturally encoded amino acid as described in Example 7:

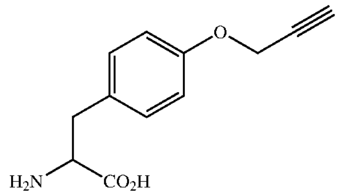 [SMILES: C#CCOc1ccc(CC(N)C(=O)O)cc1]

Once modified, a PEG is attached to the bG-CSF polypeptide variant comprising the alkyne-containing amino acid. The PEG will have the following structure:

$$Me\text{-}PEG(N)—O—(CH_2)_2—N_3$$

and coupling procedures would follow those in Example 7. This will generate a bG-CSF polypeptide variant comprising a non-naturally encoded amino acid that is approximately isosteric with one of the naturally-occurring, large hydrophobic amino acids and which is modified with a PEG derivative at a distinct site within the polypeptide.

Example 9

Generation of a hG-CSF Polypeptide Homodimer, Heterodimer, Homomultimer, or Heteromultimer Separated by One or More PEG Linkers The alkyne-containing bG-CSF polypeptide variant produced in Example 7 is reacted with a bifunctional PEG derivative of the form:

$N_3$—$(CH_2)_n$—C(O)—NH—$(CH_2)_2$—O-PEG(N)—O—$(CH_2)_2$—NH—C(O)—$(CH_2)_n$—$N_3$ where n is 4 and the PEG has an average MW of approximately 5,000, to generate the corresponding bG-CSF polypeptide homodimer where the two bG-CSF molecules are physically separated by PEG. In an analogous manner a bG-CSF polypeptide may be coupled to one or more other polypeptides to form heterodimers, homomultimers, or heteromultimers. Coupling, purification, and analyses will be performed as in Examples 7 and 3.

Example 10

Coupling of a Saccharide Moiety to a bG-CSF Polypeptide

One residue of the following is substituted with the non-naturally encoded amino acid below: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175 (i.e., at the carboxyl terminus of the protein), and any combination thereof (SEQ ID NO: 1 or the corresponding amino acids in SEQ ID NO: 2 or the corresponding amino acids in another bG-CSF polypeptide) as described in Example 3.

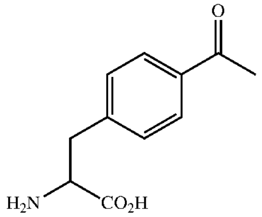

Once modified, the bG-CSF polypeptide variant comprising the carbonyl-containing amino acid is reacted with a β-linked aminooxy analogue of N-acetylglucosamine (GlcNAc). The bG-CSF polypeptide variant (10 mg/mL) and the aminooxy saccharide (21 mM) are mixed in aqueous 100 mM sodium acetate buffer (pH 5.5) and incubated at 37° C. for 7 to 26 hours. A second saccharide is coupled to the first enzymatically by incubating the saccharide-conjugated bG-CSF polypeptide (5 mg/mL) with UDP-galactose (16 mM) and β-1,4-galactosyltransferase (0.4 units/mL) in 150 mM HEPES buffer (pH 7.4) for 48 hours at ambient temperature (Schanbacher et al. *J. Biol. Chem.* 1970, 245, 5057-5061).

Example 11

Generation of a PEGylated bG-CSF Polypeptide Antagonism

A residue, including but not limited to, those involved in bG-CSF receptor binding is substituted with the following non-naturally encoded amino acid as described in Example 3.

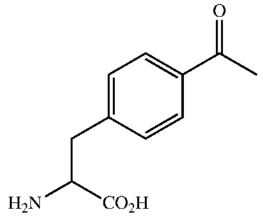

Once modified, the bG-CSF polypeptide variant comprising the carbonyl-containing amino acid will be reacted with an aminooxy-containing PEG derivative of the form:

R-PEG(N)—O—$(CH_2)_n$—O—$NH_2$ where R is methyl, n is 4 and N is 20,000 MW to generate a b-GCSF polypeptide antagonist comprising a non-naturally encoded amino acid that is modified with a PEG derivative at a single site within the polypeptide. Coupling, purification, and analyses are performed as in Example 3.

Example 12

Generation of a bG-CSF Polypeptide Homodimer, Heterodimer, Homomultimer, or Heteromultimer in which the bG-CSF Molecules are Linked Directly A bG-CSF polypeptide variant comprising the alkyne-containing amino acid can be directly coupled to another bG-CSF polypeptide variant comprising the azido-containing amino acid. In an analogous manner a bG-CSF polypeptide polypeptide may be coupled to one or more other polypeptides to form heterodimers, homomultimers, or heteromultimers. Coupling, purification, and analyses are performed as in Examples 3, 6, and 7.

Example 13

$$\frac{\textit{PEG-OH} + \textit{Br-}(CH_2)_n\textit{-}C \equiv CR' \rightarrow \textit{PEG-O-}(CH_2)_n\textit{-}C \equiv CR'}{A \quad B}$$

The polyalkylene glycol (P-OH) is reacted with the alkyl halide (A) to form the ether (B). In these compounds, n is an integer from one to nine and R' can be a straight- or branched-chain, saturated or unsaturated C1, to C20 alkyl or heteroalkyl group. R' can also be a C3 to C7 saturated or unsaturated cyclic alkyl or cyclic heteroalkyl, a substituted or unsubstituted aryl or heteroaryl group, or a substituted or unsubstituted alkaryl (the alkyl is a C1 to C20 saturated or unsaturated alkyl) or heteroalkaryl group. Typically, PEG-OH is polyethylene glycol (PEG) or monomethoxy polyethylene glycol (mPEG) having a molecular weight of 800 to 40,000 Daltons (Da).

Example 14 mPEG-OH+Br—$CH_2$—C≡CH→mPEG-O—$CH_2$—C≡CH mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). A solution of propargyl bromide, dissolved as an 80% weight solution in xylene (0.56 mL, 5 mmol, 50 equiv., Aldrich), and a catalytic amount of KI were then added to the solution and the resulting mixture was heated to reflux for 2 hours. Water (1 mL) was then added and the solvent was removed under vacuum. To the residue was added $CH_2Cl_2$ (25 mL) and the organic layer was separated, dried over anhydrous $Na_2SO_4$, and the volume was reduced to approximately 2 mL. This $CH_2Cl_2$ solution was added to diethyl ether (150 mL) drop-wise. The resulting precipitate was collected, washed with several portions of cold diethyl ether, and dried to afford propargyl-O-PEG.

Example 15 mPEG-OH+Br—$(CH_2)_3$—C≡CH→mPEG-O—$(CH_2)_3$—C≡CH

The mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). Fifty equivalents of 5-bromo-1-pentyne (0.53 mL, 5 mmol, Aldrich) and a catalytic amount of KI were then added to the mixture. The resulting mixture was heated to reflux for 16 hours. Water (1 mL) was then added and the solvent was removed under vacuum. To the residue was added $CH_2Cl_2$ (25 mL) and the organic layer was separated, dried over anhydrous $Na_2SO_4$, and the volume was reduced to approximately 2 mL. This $CH_2Cl_2$ solution was added to diethyl ether (150 mL) drop-wise. The resulting precipitate was collected, washed with several portions of cold diethyl ether, and dried to afford the corresponding alkyne. 5-chloro-1-pentyne may be used in a similar reaction.

Example 16

Production of mPEG-O-CH2-C6H40-CH2-C□CH (1) m-$HOCH_2C_6H_4OH$+NaOH+Br—$CH_2$—C≡CH→m-$HOCH_2C_6H_4O$—$CH_2C$≡CH (2) m-$HOCH_2C_6H_4O$—$CH_2$—C≡CH+MsCl+N$(Et)_3$→m-$MsOCH_2C_6H_4O$—$CH_2$—C≡CH (3) m-$MsOCH_2C_6H_4O$—$CH_2$—C≡CH+LiBr→m-Br—$CH_2C_6H_4O$—$CH_2$—C≡CH (4) mPEG-OH+m-Br—$CH_2C_6H_4O$—$CH_2$—O≡CH→mPEG-O—$CH_2$—$C_6H_4O$—$CH_2$—C≡CH To a solution of 3-hydroxybenzylalcohol (2.4 g, 20 mmol) in THF (50 mL) and water (2.5 mL) was first added powdered sodium hydroxide (1.5 g, 37.5 mmol) and then a solution of propargyl bromide, dissolved as an 80% weight solution in xylene (3.36 mL, 30 mmol). The reaction mixture was heated at reflux for 6 hours. To the mixture was added 10% citric acid (2.5 mL) and the solvent was removed under vacuum. The residue was extracted with ethyl acetate (3×15 mL) and the combined organic layers were washed with saturated NaCl solution (10 mL), dried over $MgSO_4$ and concentrated to give the 3-propargyloxybenzyl alcohol.

Methanesulfonyl chloride (2.5 g, 15.7 mmol) and triethylamine (2.8 mL, 20 mmol) were added to a solution of compound 3 (2.0 g, 11.0 mmol) in $CH_2Cl_2$ at 0° C. and the reaction was placed in the refrigerator for 16 hours. A usual work-up afforded the mesylate as a pale yellow oil. This oil (2.4 g, 9.2 mmol) was dissolved in THF (20 mL) and LiBr (2.0 g, 23.0 mmol) was added. The reaction mixture was heated to reflux for 1 hour and was then cooled to room temperature. To the mixture was added water (2.5 mL) and the solvent was removed under vacuum. The residue was extracted with ethyl acetate (3×15 mL) and the combined organic layers were washed with saturated NaCl solution (10 mL), dried over anhydrous $Na_2SO_4$, and concentrated to give the desired bromide.

mPEG-OH 20 kDa (1.0 g, 0.05 mmol, Sunbio) was dissolved in THF (20 mL) and the solution was cooled in an ice bath. NaH (6 mg, 0.25 mmol) was added with vigorous stirring over a period of several minutes followed by addition of the bromide obtained from above (2.55 g, 11.4 mmol) and a catalytic amount of KI. The cooling bath was removed and the resulting mixture was heated to reflux for 12 hours. Water (1.0 mL) was added to the mixture and the solvent was removed under vacuum. To the residue was added $CH_2Cl_2$ (25 mL) and the organic layer was separated, dried over anhydrous $Na_2SO_4$, and the volume was reduced to approximately 2 mL. Dropwise addition to an ether solution (150 mL) resulted in a white precipitate, which was collected to yield the PEG derivative.

Example 17 mPEG-$NH_2$+X—C(O)—$(CH_2)_n$—C═CR'→mPEG-NH—C(O)—$(CH_2)_n$C≡R'

The terminal alkyne-containing poly(ethylene glycol) polymers can also be obtained by coupling a poly(ethylene glycol) polymer containing a terminal functional group to a reactive molecule containing the alkyne functionality as shown above. n is between 1 and 10. R' can be H or a small alkyl group from C1 to C4.

Example 18

Production of mPEG-NH—C(O)—$(CH_2)_2$—C≡CH (1) $HO_2C$—$(CH_2)_2$—C≡CH+NHS+DCC→NHSO—C(O)—$(CH_2)_2$—C≡CH (2) mPEG-$NH_2$+NHSO—C(O)—$(CH_2)_2$—C≡CH→mPEG-NH—C(O)—$(CH_2)_2$—C≡CH 4-pentynoic acid (2.943 g, 3.0 mmol) was dissolved in $CH_2Cl_2$ (25 mL). N-hydroxysuccinimide (3.80 g, 3.3 mmol) and DCC (4.66 g, 3.0 mmol) were added and the solution was stirred overnight at room temperature. The resulting crude NHS ester 7 was used in the following reaction without further purification.

mPEG-$NH_2$ with a molecular weight of 5,000 Da (mPEG-$NH_2$, 1 g, Sunbio) was dissolved in THF (50 mL) and the mixture was cooled to 4° C. NHS ester 7 (400 mg, 0.4 mmol) was added portion-wise with vigorous stirring. The mixture was allowed to stir for 3 hours while warming to room temperature. Water (2 mL) was then added and the solvent was removed under vacuum. To the residue was added $CH_2Cl_2$ (50 mL) and the organic layer was separated, dried over anhydrous $Na_2SO_4$, and the volume was reduced to approximately 2 mL. This $CH_2Cl_2$ solution was added to ether (150 mL) drop-wise. The resulting precipitate was collected and dried in vacuo.

Example 19

Preparation of Methanesulfonate or Mesylate of Poly(Ethylene Glycol)

This Example represents the preparation of the methane sulfonyl ester of poly(ethylene glycol), which can also be referred to as the methanesulfonate or mesylate of poly (ethylene glycol). The corresponding tosylate and the halides can be prepared by similar procedures.

mPEG-OH+$CH_3SO_2Cl$+N$(Et)_3$→mPEG-O—$SO_2CH_3$→mPEG-$N_3$

The mPEG-OH (MW=3,400, 25 g, 10 mmol) in 150 mL of toluene was azeotropically distilled for 2 hours under nitrogen and the solution was cooled to room temperature. 40 mL of dry $CH_2Cl_2$ and 2.1 mL of dry triethylamine (15 mmol) were added to the solution. The solution was cooled in an ice bath and 1.2 mL of distilled methanesulfonyl chloride (15 mmol) was added dropwise. The solution was stirred at room temperature under nitrogen overnight, and the reaction was quenched by adding 2 mL of absolute ethanol. The mixture was evaporated under vacuum to remove solvents, primarily those other than toluene, filtered, concentrated again under vacuum, and then precipitated into 100 mL of diethyl ether. The filtrate was washed with several portions of cold diethyl ether and died in vacuo to afford the mesylate.

The mesylate (20 g, 8 mmol) was dissolved in 75 ml of THF and the solution was cooled to 4° C. To the cooled solution was added sodium azide (1.56 g, 24 mmol). The reaction was heated to reflux under nitrogen for 2 hours. The solvents were then evaporated and the residue diluted with $CH_2Cl_2$ (50 mL). The organic fraction was washed with NaCl solution and dried over anhydrous $MgSO_4$. The volume was reduced to 20 ml and the product was precipitated by addition to 150 ml of cold dry ether.

Example 20

Production of mPEG-O—$CH_2$—$C_6H_4$—$N_3$ (1) $N_3$—$C_6H_4CO_2H$→$N_3$—$C_6H_4CH_2OH$ (2) $N_3$—$C_6H_4CH_2OH$→Br—$CH_2$—$C_6H_4$—$N_3$ (3) mPEG-OH+BR—$CH_2$—$C_6H_4$—$N_3$→mPEG-O—$CH_2$—$C_6H_4$—$N_3$ 4-azidobenzyl alcohol can be produced using the method described in U.S. Pat. No. 5,998,595, which is incorporated by reference herein. Methanesulfonyl chloride (2.5 g, 15.7 mmol) and triethylamine (2.8 mL, 20 mmol) were added to a solution of 4-azidobenzyl alcohol (1.75 g, 11.0 mmol) in $CH_2Cl_2$ at 0° C. and the reaction was placed in the refrigerator for 16 hours. A usual work-up afforded the mesylate as a pale yellow oil. This oil (9.2 mmol) was dissolved in THF (20 mL) and LiBr (2.0 g, 23.0 mmol) was added. The reaction mixture was heated to reflux for 1 hour and was then cooled to room temperature. To the mixture was added water (2.5 mL) and the solvent was removed under vacuum. The residue was extracted with ethyl acetate (3×15 mL) and the combined organic layers were washed with saturated NaCl solution (10 mL), dried over anhydrous $Na_2SO_4$, and concentrated to give the desired bromide.

mPEG-OH 20 kDa (2.0 g, 0.1 mmol, Sunbio) was treated with NaH (12 mg, 0.5 mmol) in THF (35 mL) and the bromide (3.32 g, 15 mmol) was added to the mixture along with a catalytic amount of K1. The resulting mixture was heated to reflux for 12 hours. Water (1.0 mL) was added to the mixture and the solvent was removed under vacuum. To the residue was added $CH_2Cl_2$ (25 mL) and the organic layer was separated, dried over anhydrous $Na_2SO_4$, and the volume was reduced to approximately 2 mL. Dropwise addition to an ether solution (150 mL) resulted in a precipitate, which was collected to yield mPEG-O-CH2-$C_6H_4$—N3.

Example 21

$NH_2$—PEG-O—$CH_2CH_2CO_2H$+$N_3$—$CH_2CH_2CO_2$—NHS→$N_3$—$CH_2CH_2C(O)NH$-PEG-O—$CH_2CH_2CO_2H$ $NH_2$-PEG-O—$CH_2CH_2CO_2H$ (MW 3,400 Da, 2.0 g) was dissolved in a saturated aqueous solution of NaHCO3 (10 mL) and the solution was cooled to 0° C. 3-azido-1-N-hydroxysuccinimido propionate (5 equiv.) was added with vigorous stirring. After 3 hours, 20 mL of $H_2O$ was added and the mixture was stirred for an additional 45 minutes at room temperature. The pH was adjusted to 3 with 0.5 N $H_2SO_4$ and NaCl was added to a concentration of approximately 15 wt %. The reaction mixture was extracted with $CH_2Cl_2$ (100 mL×3), dried over $Na_2SO_4$ and concentrated. After precipitation with cold diethyl ether, the product was collected by filtration and dried under vacuum to yield the omega-carboxy-azide PEG derivative.

Example 22 mPEG-OMs+HC≡CLi→mPEG-O—$CH_2$—$CH_2C$≡C—H

To a solution of lithium acetylide (4 equiv.), prepared as known in the art and cooled to −78° C. in THF, is added dropwise a solution of mPEG-OMs dissolved in THF with vigorous stirring. After 3 hours, the reaction is permitted to warm to room temperature and quenched with the addition of 1 mL of butanol. 20 mL of $H_2O$ is then added and the mixture was stirred for an additional 45 minutes at room temperature. The pH was adjusted to 3 with 0.5 N $H_2SO_4$ and NaCl was added to a concentration of approximately 15 wt %. The reaction mixture was extracted with $CH_2Cl_2$ (100 mL×3), dried over $Na_2SO_4$ and concentrated. After precipitation with cold diethyl ether, the product was collected by filtration and dried under vacuum to yield the 1-(but-3-ynyloxy)-methoxypolyethylene glycol (mPEG).

Example 23

Incorporation of Azide- and Acetylene-Containing Amino Aicds

Azide- and acetylene-containing amino acids can be incorporated site-selectively into proteins using the methods described in L. Wang, et al., (2001) *Science* 292:498-500, J. W. Chin et al., *Science* 301:964-7 (2003)), J. W. Chin et al., (2002), *Journal of the American Chemical Society* 124: 9026-9027; J. W. Chin, & P. G. Schultz, (2002), *Chem Bio Chem* 3 (11): 1135-1137; J. W. Chin, et al., (2002), *PNAS United States of America* 99:11020-11024; and, L. Wang, & P. G. Schultz, (2002), *Chem. Comm.,* 1:1-11. Once the amino acids were incorporated, the cycloaddition reaction is carried out with 0.01 mM protein in phosphate buffer (PB), pH 8, in the presence of 2 mM PEG derivative, 1 mM $CuSO_4$, and ~1 mg Cu-wire for 4 hours at 37° C.

Example 24

Synthesis of p-Acetyl-D,L-Phenylalanine (pAF) and m-PEG-Hydroxylamine Derivatives The racemic pAF is synthesized using the previously described procedure in Zhang, Z., Smith, B. A. C., Wang, L., Brock, A., Cho, C. & Schultz, P. G., Biochemistry, (2003) 42, 6735-6746.

To synthesize the m-PEG-hydroxylamine derivative, the following procedures are completed. To a solution of (N-t-Boc-aminooxy) acetic acid (0.382 g, 2.0 mmol) and 1,3-Diisopropylcarbodiimide (0.16 mL, 1.0 mmol) in dichloromethane (DCM, 70 mL), which is stirred at room temperature (RT) for 1 hour, methoxy-polyethylene glycol amine (m-PEG-$NH_2$, 7.5 g, 0.25 mmol, Mt. 30 K, from BioVectra) and Diisopropylethylamine (0.1 mL, 0.5 mmol) is added. The reaction is stirred at RT for 48 hours, and then is concentrated to about 100 mL. The mixture is added dropwise to cold ether (800 mL). The t-Boc-protected product precipitated out and is collected by filtering, washed by ether 3×100 mL. It is further purified by re-dissolving in DCM (100 mL) and precipitating in ether (800 mL) twice. The product is dried in vacuum yielding 7.2 g (96%), confirmed by NMR and Nihydrin test.

The deBoc of the protected product (7.0 g) obtained above is carried out in 50% TFA/DCM (40 mL) at 0° C. for 1 hour and then at RT for 1.5 hour. After removing most of TFA in vacuum, the TFA salt of the hydroxylamine derivative is converted to the HCl salt by adding 4N HCl in dioxane (1 mL) to the residue. The precipitate is dissolved in DCM (50 mL) and re-precipitated in ether (800 mL). The final product (6.8 g, 97%) is collected by filtering, washed with ether 3×100 mL, dried in vacuum, stored under nitrogen. Other PEG (5K, 20K) hydroxylamine derivatives are synthesized using the same procedure.

Example 25

In Vitro and In Vivo Activity of PEGylated bG-CSF

PEG-bG-CSF, unmodified bG-CSF and buffer solution are administered to mice or rats. The results will show superior activity and prolonged half life of the PEGylated bG-CSF of the present invention compared to unmodified bG-CSF which is indicated by significantly increased amounts of neutrophils and a shift of white blood cell count maximum using the same dose per mouse.

Pharmacokinetic Analysis

A bG-CSF polypeptide of the invention is administered by intravenous or subcutaneous routes to mice. The animals are bled prior to and at time points after dosing. Plasma is collected from each sample and analyzed by radioimmunoassay. Elimination half-life can be calculated and compared between bG-CSF polypeptides comprising a non-naturally encoded amino acid and wild-type bG-CSF or various forms of bG-CSF polypeptides of the invention. Similarly, bG-CSF polypeptides of the invention may be administered to cynomolgus monkeys. The animals are bled prior to and at time points after dosing. Plasma is collected from each sample and analyzed by radioimmunoassay.

Polypeptides of the invention may be administered to an animal model of disease. Animal studies that may be performed involve cattle challenged with *Pasteurella haemolytica*, cattle with bacterial challenge of the mammary gland/mastitis challenge (*Klebsiella pneumonia*). Other studies that may be performed evaluate the control, incidence, and duration of bovine respiratory disease, or prevention of coliform mastitis. Methods to evaluate the health of animals, milk production, neutrophil count, and other parameters are known to one of ordinary skill in the art. Other models that may be used to evaluate bG-CSF polypeptides of the invention include but are not limited to, animal models of infection or exposure to infection such as a hamster model of *Pseudomonas aeruginosa* pneumonia, a rat model of *Candida albicans* pyelonephritis, models involving neonatal foals, and models involving growing pigs. Some of these models are described in U.S. Pat. No. 5,849,883 and WO 89/10932. Models such as these are known to those of ordinary skill in the art.

$^3$H-thymidine Assay. The $^3$H-thymidine assay is performed using standard methods. Bone marrow is obtained from sacrificed female Balb C mice or from other animals. Bone marrow cells are briefly suspended, centrifuged, and resuspended in a growth medium. A 160 μl aliquot containing approximately 10,000 cells is placed into each well of a 96 well micro-titer plate. Samples of the purified G-CSF analog (as prepared above) are added to each well, and incubated for 68 hours. Tritiated thymidine is added to the wells and allowed to incubate for five additional hours. After the five hour incubation time, the cells are harvested, filtered, and thoroughly rinsed. The filters are added-to a vial containing scintillation fluid. The beta emissions are counted (LKB Betaplate scintillation counter). Standards and analogs are analyzed in triplicate, and samples which fell substantially above or below the standard curve are re-assayed with the proper dilution. The results are reported as the average of the triplicate analog data relative to the unaltered bG-CSF standard results.

Proliferation induction of human bone marrow cells is assayed on the basis of increased incorporation of $^3$H-thymidine. Human bone marrow from healthy donors is subjected to a density cut with Ficoll-Hypaque (1.077 g/ml, Pharmacia) and low density cells are suspended in Iscove's medium (GIBCO) containing 10% fetal bovine serum and glutamine pen-strep. Subsequently, $2\times10^4$ human bone marrow cells are incubated with either control medium or the recombinant *E. coli*-derived bG-CSF material in 96 flat bottom well plates at 37° C. in 5% $CO_2$ in air for 2 days. The samples are assayed in duplicate and the concentration varied over a 10,000 fold range. Cultures are then pulsed for 4 hours with 0.5 μCi/well of $^3$H-Thymidine (New England Nuclear, Boston, Mass.). $^3$H-Thymidine uptake is measured as described in Venuta, et al., Blood, 61, 781 (1983).

WEHI-3B $D^+$ Differentiation Induction. The ability of bG-CSF polypeptides of the present invention to induce differentiation of the murine myelomonocytic leukemic cell line WEHI-3B D+ is assayed in semi-solid agar medium as described in Metcalf, Int. J. Cancer, 25, 225 (1980). The recombinant bG-CSF product and media controls are incubated with about 60 WEHI-3B $D^+$ cells/well at 37° C. in 5% $CO_2$ in air for 7 days. The samples are incubated in 24 flat bottom well plates and the concentration varied over a 2000-fold range. Colonies are classified as undifferentiated, partially differentiated or wholly differentiated and colony cell counts are counted microscopically.

CFU-GM, BFU-E and CFU-GEMM Assays. Natural isolates of human G-CSF and hG-CSF are found to cause human bone marrow cells to proliferate and differentiate. These activities are measured in CFU-GM [Broxmeyer, et al., Exp. Hematol., 5, 87, (1971)], BFU-E and CFU-GEMM assays [Lu, et al., Blood, 61, 250 (1983)] using low density, non-adherent bone marrow cells from healthy human volunteers. Cells from other sources may be used. A comparison of CFU-GM, BFU-E and CFU-GEMM biological activities using either 500 units of G-CSF or bG-CSF polypeptides of the invention are performed.

Colony assays are performed with low density non-adherent bone marrow cells. Human bone marrow cells are subject to a density cut with Ficoll-Hypaque (density, 1.077 g/cm$^3$; Pharmacia). The low density cells are then resuspended in Iscove's modified Dulbecco's medium containing fetal calf serum and placed for adherence on Falcon tissue culture dishes (No. 3003, Becton Dickinson, Cockeysville, Md.) for 1½ hours at 37° C.

Medium control consists of Iscove's modified Dulbecco medium plus 10% FCS, 0.2 mM hemin and 1 unit of a recombinant erythropoietin. For the CFU-GM assay target cells are plated at $1\times10^5$ in 1 ml of 0.3% agar culture medium that includes supplemented McCoy's 5A medium and 10% heat inactivated fetal calf serum. Cultures are scored for colonies (greater than 40 cells per aggregate) and morphology is assessed on day 7 of culture. The number of colonies is shown as the mean±SEM as determined from quadruplicate plates.

For the BFU-E and CFU-GEMM assays, cells ($1\times10^5$) are added to a 1 ml mixture of Iscove's modified Dulbecco medium (Gibco), 0.8% methylcellulose, 30% fetal calf serum 0.05 nM 2-mercaptoethanol, 0.2 mM hemin and 1 unit of recombinant erythropoietin. Dishes are incubated in a humidified atmosphere of 5% $CO_2$ and 5% $O_2$. Low oxygen tension is obtained using an oxyreducer from Reming Bioinstruments (Syracuse, N.Y.). Colonies are scored after 14 days of incubation. The number of colonies is determined as the mean±SEM, as determined from duplicate plates.

Colonies formed in the CFU GM assay are all expected to be chloroacetate esterase positive and non-specific esterase (alpha-naphthyl acetate esterase) negative, consistent with the colonies being granulocyte in type. Both natural G-CSF and bG CSF polypeptides of the invention are expected to have a specific activity of an approximately $1\times10^8$ U/mg pure protein, when assayed by serial dilution in a CFU-GM assay. It is important to note that the bG-CSF of the invention may be extremely pure and free of other potential mammalian growth factors by virtue of its production in *E. coli*. Thus bG-CSF may be capable of supporting mixed colony formation (CFU-GEMM) and BFU-E when added in the presence of recombinant erythropoietin.

Measurement of the in vivo Half-life of Conjugated and Non-conjugated bG-CSF and Variants Thereof. Male Sprague Dawley rats (about 7 weeks old) are used. On the day of administration, the weight of each animal is measured. 100 μg per kg body weight of the non-conjugated and conjugated bG-CSF samples are each injected intravenously into the tail vein of three rats. At 1 minute, 30 minutes, 1, 2, 4, 6, and 24 hours after the injection, 500 μl of blood is withdrawn from each rat while under $CO_2$-anesthesia. The blood samples are stored at room temperature for 1.5 hours followed by isolation of serum by centrifugation (4° C., 18000×g for 5 minutes). The serum samples are stored at −80° C. until the day of analysis. The amount of active bG-CSF in the serum samples is quantified by the bG-CSF in vitro activity assay after thawing the samples on ice.

Measurement of the in vivo Biological Activity in Healthy Rats of Conjugated and Non-conjugated bG-CSF and Variants Thereof. Measurement of the in vivo biological effects of bG-CSF in SPF Sprague Dawley rats is used to evaluate the biological efficacy of conjugated and non-conjugated bG-CSF and variants thereof. On the day of arrival the rats are randomly allocated into groups of 6. The animals are rested for a period of 7 days wherein individuals in poor condition or at extreme weights are rejected. The weight range of the rats at the start of the resting period is 250-270 g.

On the day of administration the rats are fasted for 16 hours followed by subcutaneous injection of 100 μg per kg body weight of bG-CSF or a variant thereof. Each bG-CSF sample is injected into a group of 6 randomized rats. Blood samples of 300 μg EDTA stabilized blood are drawn from a tail vein of the rats prior to dosing and at 6, 12, 24, 36, 48, 72, 96, 120 and 144 hours after dosing. The blood samples are analyzed for the following hematological parameters: hemoglobin, red blood cell count, hematocrit, mean cell volume, mean cell hemoglobin concentration, mean cell hemoglobin, white blood cell count, differential leukocyte count (neutrophils, lymphocytes, eosinophils, basophils, monocytes). On the basis of these measurements the biological efficacy of conjugated and non-conjugated bG-CSF and variants thereof is evaluated.

Measurement of the in Vivo Biological Activity in Rats with Chemotherapy-induced Neutropenia of Conjugated and Non-conjugated bG-CSF and Variants Thereof. SPF Sprague Dawley rats are utilized for this analysis. On the day of arrival the rats are randomly allocated into groups of 6. The animals are rested for a period of 7 days wherein individuals in poor condition or at extreme weights are rejected. The weight range of the rats at the start of the resting period is 250-270 g.

24 hours before administration of the bG-CSF samples the rats are injected i.p. with 50 mg per kg body weight of cyclophosphamide (CPA) to induce neutropenia that mimics neutropenia resulting from anti-cancer chemotherapy. At day 0, 100 μg per kg body weight of bG-CSF or a variant thereof is injected s.c. Each bG-CSF sample is injected into a group of 6 randomized rats. Blood samples of 300 μl EDTA stabilized blood are drawn from a tail vein of the rats prior to dosing and at 6, 12, 24, 36, 48, 72, 96, 120, 144 and 168 hours after dosing. The blood samples are analyzed for the following hematological parameters: hemoglobin, red blood cell count, hematocrit, mean cell volume, mean cell hemoglobin concentration, mean cell hemoglobin, white blood cell count, differential leukocyte count (neutrophils, lymphocytes, eosinophils, basophils, monocytes). On the basis of these measurements the biological efficacy of conjugated and non-conjugated bG-CSF and variants thereof is evaluated.

Example 26

An In Vivo Study Assessing the Impact of bG-CSF-T133pAF 20K PEG Variant on the Hematological Responses of Cattle Recombinant bG-CSF containing a single pAF substitution at position T133 (bG-CSF T133pAF-20K PEG) was produced in *E. coli*. This protein had an N terminal methionine (SEQ ID NO: 2) and the threonine at position 134 of SEQ ID NO: 2 was substituted with para-acetylphenylalanine. The protein was PEGylated at the pAF incorporation site using 20 KD oxyamino PEG and purified by cation exchange liquid chromatography to >98% purity. The final formulation contained 7.377 mg/ml of PEGylated bG-CSF in formulation buffer composed of 4.26 mM NaAc; 5% sorbitol; 0.0033% Tween 20; 0.565 mM NaCl; pH 4.0.

Commercial English or Continental crossbred beef steers weighing approximately 150 kg were purchased and transported to the research facility where they were individually identified with cartages and acclimated for 7 days prior to enrollment in the study. No antibiotics or vaccines were administered to the animals during the acquisition or acclimation periods. No concomitant medications were administered to the animals during the study. Animals were housed in pens with concrete slotted floors and were exposed to ambient temperatures. Animals were fed once daily to appetite with a complete, pelleted ration (Rumilab® 5508).

The study was conducted using a randomized complete block design where calves were blocked by pen. Twelve animals were assigned to either treated or negative control (formulation buffer without protein) groups (6 animals/treatment). Animals were randomly assigned to blocks and treatments within blocks.

On day −1 calves were evaluated by a veterinarian for clinical signs of disease. Evaluations included pulse rate, respiration rate and rectal temperatures as well as overall condition. Body weights and rectal temperatures were determined and anti-coagulated blood samples were collected for hematology evaluations (pre-treatment sample). Animals within the specified weight range with normal hematological profiles based on literature reference ranges and no clinical signs of disease were selected for inclusion in the study.

On day 0, calves were treated with either a single subcutaneous injection of PEGylated bG-CSF T133pAF (40 μg/kg) or formulation buffer (1 ml/125 kg). Injections were administered in the pre-scapular region an the left side of the neck.

Venous whole blood samples (~30 ml) were collected into sterile tubes containing either EDTA (ethylenediaminetetraacetic acid) for absolute leukocyte counts or ACD (acid-citrate-dextrose) for determination of absolute neutrophil counts. Absolute leukocyte counts were determined using a using a Beckman Coulter $ACT_{10}$™ blood analyzer. Absolute neutrophil counts (ANC) were determined by flow cytometric evaluation of the percentage of neutrophils in CD45-stained whole blood samples using a Becton Dickinson FACSarray™ bioanalyzer. Absolute neutrophil counts were calculated by multiplying the absolute leukocyte count by the percentage of neutrophils.

In addition to the pre-treatment samples collected on day-1, samples were collected at 4, 8 and 12 hours on day 0, 24, and 36 hours post-treatment, and once daily on days 3-14.

Figure 16:
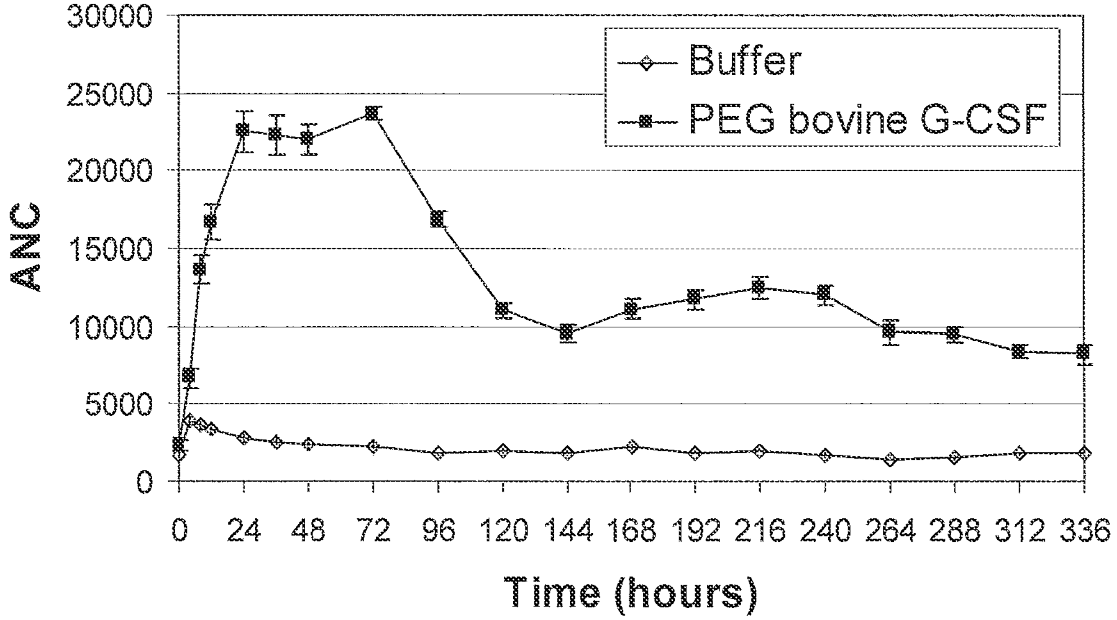
FIG. 16—Results of PEGylated bG-CSF administration on ANC are shown.

The results of PEGylated bG-CSF administration on ANC are presented in FIG. 16. Animals treated with formulation buffer alone exhibited relatively constant ANC values throughout the duration of the study. In contrast, animals receiving PEGylated bG-CSF exhibited a marked increase in ANC within 8 hours post-treatment. Maximal ANC values (approximately 10-fold over pre-treatment levels) were observed at 72 hours post-treatment. Absolute neutrophil counts declined to approximately 4 to 5-fold over the pre-treatment level by day 5 post-treatment and remained at this level through day 10. Values declined further to about 3.5 fold over the pre-treatment level from day 11 through day 14.

These results indicate site-specific PEGylation of bG-CSF at position T133 enabled us to obtain potent hematopoetic activity which persisted for at least two weeks in calves treated with a single injection of protein.

Example 27 bG-CSF T-133 PEGylated Variant Hematology Study Summary

An in vivo study was performed to assess the impact of bG-CSF-T133pAF 20K PEG variant on the hematological responses of cattle.

Recombinant bG-CSF containing a single pAF substitution at position T133 was produced in *E. coli*. The protein was PEGylated at the pAF incorporation site using 20 KD oxyamino PEG and purified by size exclusion high performance liquid chromatography to >98% purity. The final formulation contained 7.377 mg/ml of PEGylated bG-CSF in formulation buffer composed of 4.26 mM NaAc; 5% sorbitol; 0.0033% Tween 20; 0.565 mM NaCl; pH 4.0.

Commercial English or Continental crossbred beef steers weighing approximately 150 kg were purchased and transported to the research facility where they were individually identified with eaiiags and acclimated for 7 days prior to enrolment in the study. No antibiotics or vaccines were administered to the animals during the acquisition or acclimation periods. No concomitant medications were administered to the animals during the study. Animals were housed in pens with concrete slotted floors and were exposed to ambient temperatures. Animals were fed once daily to appetite with a complete, pelleted ration (Rurnilab® 5508).

The study was conducted using a randomized complete block design where calves were blocked by pen. Twelve animals were assigned to either treated or negative control (formulation buffer without protein) groups (6 animals/treatment group.). Animals were randomly assigned to blocks and treatments within blocks.

On day −1 calves were evaluated by a veterinarian for clinical signs of disease. Evaluations included pulse rate, respiration rate and rectal temperatures as well as overall condition. Body weights and rectal temperatures were determined and anti-coagulated blood samples were collected for hematology evaluations (pre-treatment sample). Animals within the specified weight range with normal hematological profiles based on literature reference ranges and no clinical signs of disease were selected for inclusion in the study.

On day 0, calves were treated with either a single subcutaneous injection of PEGylated bG-CSF (40 μg/kg) or formulation buffer (1 ml/125 kg). Injections were administered in the pre-scapular region on the left side of the neck.

Venous whole blood samples (~30 ml) were collected into sterile tubes containing cither EDTA (ethylenediaminetetraacetic acid) for absolute leukocyte counts or ACD (acid-citrate-dextrose) for determination of absolute neutrophil counts. Absolute leukocyte counts were determined using a using a Beckman Coulter ACT10™ blood analyzer. Absolute neuh•ophil counts (ANC) were determined by flow cytometric evaluation of the percentage of neutrophils in CD45-stained whole blood samples using a Becton Dickinson FACSarray™ bioanalyzer. Absolute neutrophil counts were calculated by multiplying the absolute leukocyte count by the percentage of neutrophils.

In addition to the pre-treatment samples collected on day-1, samples were collected at 4, 8 and 12 hours on day 0, 24 and 36 hours on day 1 and once daily on days 3-14.

Figure 17:
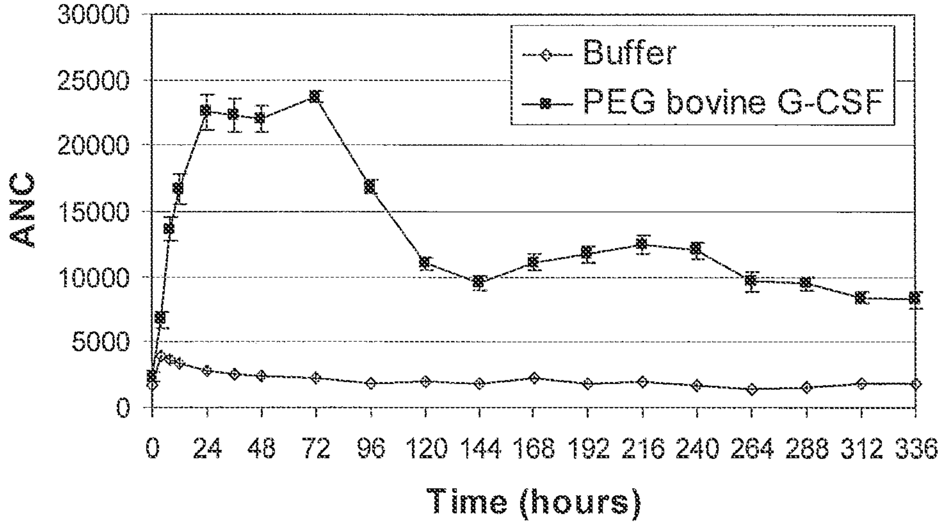
FIG. 17—A line graph showing absolute neutrophil counts (mean±std. error) in calves treated with either formulation buffer of PEGylated bG-CSF following a single subcutaneous injection at 40 μg/kg.

The results of PEGylated bG-CSF administration on ANC are presented in FIG. 17. Animals treated with formulation buffer alone exhibited relatively constant ANC values throughout the duration of the study. In contrast, animals receiving PEGylated bG-CSF exhibited a marked increase in ANC within 8 hours post-treatment. Maximal ANC values (approximately 10-fold over pre-treatment levels) were observed at 72 hours post-treatment. Absolute neutrophil counts declined to approximately 4 to 5-fold over the pre-treatment level by day 5 post-treatment and remained at this level through day 10. Values declined further to about 3.5 fold over the pre-treatment level from day 11 through day 14 (see FIG. 17).

These results indicate site-specific PEGylation of bG-CSF at position T133 enabled us to obtain potent hematopoetic activity which persisted for at least two weeks in calves treated with a single injection of protein.

It is understood that the examples and embodiments described herein are for illustrative purposes only and that various modifications or changes in light thereof will be suggested to those of ordinary skill in the art and are to be included within the spirit and purview of this application and scope of the appended claims. All publications, patents, patent applications, and/or other documents cited in this application are incorporated by reference in their entirety for all purposes to the same extent as if each individual publication, patent, patent application, and/or other document were individually indicated to be incorporated by reference for all purposes.

Example 28 bG-CSF T-133 PEGylated Variant Mastitis Efficacy Study Summary

The metaphylactic efficacy of bG-CSF-T133pAF 20K PEG variant against naturally occurring intramammary infections associated with key mastitis pathogens was assessed using an induced mastitis infection model.

Recombinant bG-CSF containing a single pAF substitution at position T133 was produced in *E. coli*. The protein was PEGylated at the pAF incorporation site using 20 KO oxyamino PEG and purified by size exclusion high performance liquid chromatography. The final formulation contained PEGylated bG-CSF in formulation buffer composed of 10 mM NaAc; 5% sorbitol and 0.0033% Tween 20 at pH 4.0.

Multiparous Holstein-Friesian periparturient cows weighing approximately 600-800 kg are were selected from the commercial production herds. No antibacterial treatments are administered to the cows within 30 days prior to enrollment in the study. Animals were fed an appropriate dry cow ration prior to calving and a transition cow ration beginning on the day of calving and continuing for the duration of the study. Animals were allowed ad libitum access to fresh water. Routine dairy husbandry procedures were followed and cows were milked twice daily.

Healthy cows were enrolled in the study approximately seven days prior to their anticipated calving date based on breeding records and an evaluation of their readiness to calve by the herdsmen. Cows were allotted to treatment groups using a completely randomized design. Each treatment group contained approximately fifty cows.

Cows were treated with either sterile saline (negative control), daily injections (day −7 to day 6) of non-PEGylated bG-CSF-T133pAF or various doses of bG-CSF-T133pAF 20K PEG variant on the day of enrollment and the day of calving. Treatments were administered via subcutaneous injection in the pre-scapular region of the neck.

Animals were observed for clinical signs of mastitis at each milking on days 0-28 by an individual blinded to treatment groups. Specific observations included assignment of a clinical score based on the appearance of the milk and condition of the mammary gland. If any abnormality was observed, a California Mastitis Test was performed on the affected quarter(s) and the animal's rectal temperature was recorded. Any animals which died during the course of the study were necropsied to determine the cause of death if possible.

Milk yield was recorded at each milking on days 0-28, and composite milk samples were collected from healthy quarters on days 3, 5, 7 and 10 for milk composition analyses including: somatic cell counts, milk fat, milk protein, lactose and solids. Additional milk samples were also collected from quarters exhibiting clinical abnormalities for the identification of bacterial pathogens.

The percentages of live births and first service conception rates following rebreeding by artificial insemination were collected for all cows enrolled in the study to assess the impact of treatments on reproductive health. Daily health observations were also recorded for all calves during their first 30 days of life and any abnormalities were documented to assess the impact of treatments on the health of the calves.

Efficacy was assessed by comparing morbidity rates between treatment groups for both cows and individual quarters. Secondary endpoints included evaluation of the impact of the treatments on the incidence of mortalities, milk production, milk composition and first service conception rates.

The impact of the various treatments on the incidence of clinical mastitis and mortalities are summarized in Table 10.

TABLE 10

| Treatment Description | Morbidity | Mortality |
|---|---|---|
| Sterile Saline (SIDx2 Day −7 and Day 0) | 26/50 (52%) | 4 |
| bG-CSF T133-QAF (3 μg/kg1 SIDx141 Day −7-Day 6) | 16/49 (33%) | 6 |
| bG-CSF T133- AF 20K PEG (40 μg/kg1 SIDx2, Day −7 & Day 0) | 6/53 (11%) | 2 |
| bG-CSF T133- AF 20K PEG (20 gg/kg1 SIDx2, Day −7 & Day 0) | 7/52 (13%) | 3 |

Administration of daily doses of non-PEGylated bG-CSF T-133 pAF significantly reduced the incidence of new clinical mastitis infections relative to the saline controls. Administration of either dose of bG-CSF T133-pAF 20K PEG significantly reduced the incidence of new clinical mastitis infections relative to either the saline controls or the daily injections of non-PEGylated bG-CSF T133-pAF. Administration of either dose of bG-CSF T133-pAF 20K PEG provided a small numerical reduction in the number of mortalities relative to the saline controls.

Figure 18:
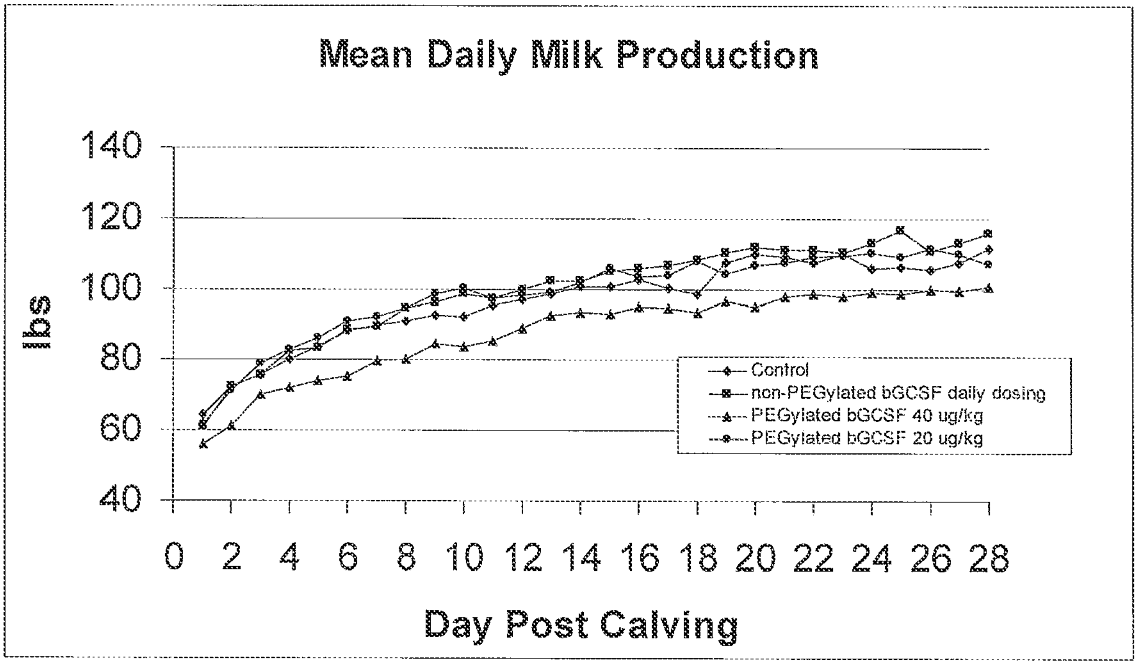
FIG. 18—A line graph showing the mean daily milk production of cows from example 40 μg/kg.

The impact of the treatments upon daily milk production by healthy cows is summarized in FIG. 18. Milk production levels were similar for cows treated with either sterile saline, non-PEGylated bG-CSF T133 pAF and the lower dose of bG-CSF T133-pAF 20K PEG. These animals exhibited increases in milk production over the duration of the study typical of those normally observed during the first month of lactation. Animals treated with the higher dose of bG-CSF T133-pAF 20K PEG exhibited a significantly reduced daily milk production relative to the other treatments throughout the duration of the study.

Figure 19:
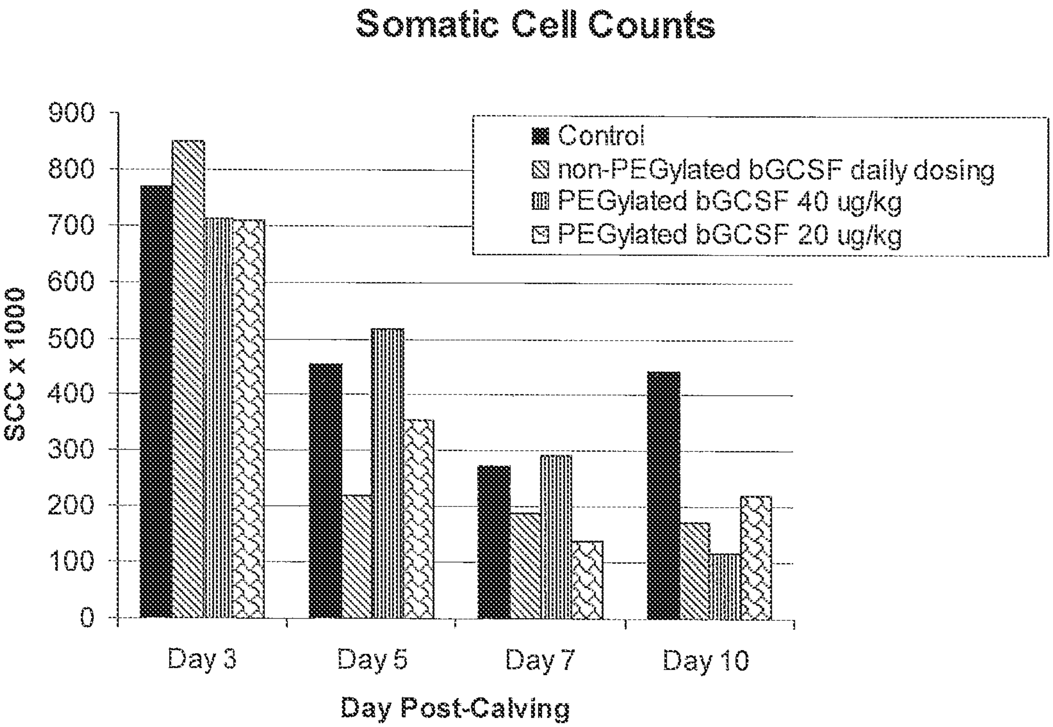
FIG. 19—A bar graph showing the differences in somatic cell counts at days 3, 5, 7, and 10 post-calving between four groups of cows including a control group, a group treated with non-PEGylated bG-CSF daily treated, a group injected with PEGylated bG-CSF 40 μg/kg, and a group injected with PEGylated bG-CSF 20 μg/kg

The impact of the treatments upon somatic cell counts is summarized in FIG. 19. Animals treated with either non-PEGylated bG-CSF T133-pAF or bG-CSF T133 pAF 20K PEG exhibited somatic cell counts which were either similar to or lower than those observed in the saline controls on Days 3, 5 and 7 post-calving. By Day 10 post-calving, the somatic cell counts for animals treated with non-PEGylated bG-CSF T133-pAF or bG-CSF T133 pAF 20K PEG were significantly lower than those of the saline controls suggesting these treatments were likely reducing the incidence of non-clinical mastitis in addition to clinical mastitis.

Results of microbiological analyses indicated morbid cows exhibited a typical range of bacterial pathogens including coliforms, *Streptococcus* species, *Staphylococcus* species and *Bacillus* species. These results suggest administration of bG-CSF T133-pAF 20K PEG was effective in reducing disease against both Gram positive and Gram negative species of bacteria.

The impact of the treatments upon live births and first service conception rates are summarized in Table 11. There were no significant differences in the percentages of live births between treatments suggesting the experimental treatments had no impact on the viability of the calves in utero. There was a numeric improvement in first service conception rates among animals treated with either non-PEGylated bG-CSF T133-pAF or bG-CSF T133 pAF 20K PEG and the saline controls. These results suggest the experimental treatments had no negative impact on reproductive health.

TABLE 11

| Treatment Description | % Live Births | First Serv ice Conception Rate |
|---|---|---|
| Sterile Saline (SIDx2 Day −7 and Day 0) | 94% | 25.6% |
| bG-CSF T133-pAF (3 µg/kg, SIDx14, Day −7-Day 6) | 98% | 41.2% |
| bG-CSF T133-pAF 20K PEG (40 µg/kg, SIDx2, Day −7 & Day 0) | 92% | 34.2% |
| bG-CSF T133-pAF 20K PEG (20 µg/kg, SIDx2, Day −7 & Day 0) | 93% | 34.2% |

The impact in utero exposure to the treatments on the health of calves born to animals enrolled in the study is summarized in Table 12. These results indicate none of the experimental treatments reduced the incidence of enteric or respiratory disease relative to the saline controls during the first thirty days of life. However, both non-PEGylated bG-CSF T133-pAF and bG-CSF T133 pAF 20K PEG significantly reduced the number of mmtalities relative to the saline controls. These results suggest the experimental treatments had a positive impact on the severity of disease.

TABLE 12

| Treatment Description | Incidence of Enteric Disease | Incidence of Respiratory Disease | Mortalities |
|---|---|---|---|
| Sterile Saline (SIDx2 Day −7 and Day 0) | 28 | 1 | 6 |
| bG-CSF T133-pAF (3 µg/kg, SIDx14, Day −7-Day 6) | 32 | 1 | 1 |
| bG-CSF T133-pAF 20K PEG (40 µg/kg, SIDx2, Day −7 & Day 0) | 30 | 2 | 0 |
| bG-CSF T133-pAF 20K PEG (20 µg/kg, SIDx2, Day −7 & Day 0) | 34 | 2 | 1 |

Example 29 bG-CSF T-133 PEGylated Variant Respiratory Disease Efficacy Study Summary

The metaphylactic efficacy of various doses of bG-CSF-T133 pAF 20K PEG variant against naturally occurring bovine respiratory disease is assessed under commercial feedyard conditions.

Recombinant bG-CSF containing a single pAF substitution at position T133 is produced in *E. coli*. The protein is PEGylated at the pAF incorporation site using 20 KD oxyamino PEG and purified by size exclusion high performance liquid chromatography. The final formulation contains PEGylated bG-CSF in formulation buffer composed of 10 mM NaAc; 5% sorbitol and 0.0033% Tween 20 at pH 4.0.

Commercial English or Continental crossbred steers weighing approximately 500 lbs. and typical of commercial feeder calves are purchased at one or more sale barns in the Southeastern US. Upon arrival at the commingling site, animals are individually identified and examined by a veterinarian for clinical abnormalities. Rectal temperatures are also recorded and animals which are free of clinical signs of disease and have rectal temperatures <104° F. are selected for enrollment in the study. Blood samples for total and differential white blood cell counts are obtained prior to treatment.

Calves are randomly allotted to treatment groups as outlined in Table 13.

TABLE 13

| Treatment | Dose Regimen | # of Animals |
|---|---|---|
| 1) Sterile Saline | SIDX1 | 40 |
| 2) bG-CSF-T133 20K PEG (20 µg/kg) | SIDX1 | 40 |
| 3) bG-CSF-T133 20K PEG (10 µg/kg) | SIDX1 | 40 |
| 4) bG-CSF-T133 20K PEG (5 µg/kg) | SIDX1 | 40 |

Sterile saline or bG-CSF-T133 pAF 20K PEG is administered by subcutaneous injection in the pre-scapular region of the neck.

The following morning, calves are loaded onto trucks and shipped approximately 1400 miles to a commercial feedyard in Northern Colorado. Upon arrival, the calves are unloaded into am.val pens and provided access to feed and water. Within four hours after arrival, the animals are moved to a processing area where they are weighed and the first ten calves assigned to each treatment group are bled to obtain samples for total and differential white blood cell counts. These counts are used to confirm animals are responding to treatment as evidenced by an increase in absolute neutrophil numbers. Calves are randomly distributed into study pens containing five animals from each treatment group for a total of 20 animals per pen.

Calves are observed daily for 14 days after arrival by a veterinarian blinded to treatment assignments for clinical signs of disease. Each animal receives an illness score ranging from 0 (healthy) to 4 (moribund). Animals which exhibit illness scores >0 are moved to a processing area and their rectal temperature is recorded. Animals which exhibit illness scores >0 and rectal temperatures >104° F. are identified as morbid and are treated with an approved antibiotic and returned to their study pen. The identities of animals which die during the course of the study are recorded and the animal is necropsied to determine a cause of death.

The primary endpoint for determining efficacy is the relative morbidity rates between treatment groups. Secondary efficacy endpoints include mortality rates, mean daily weight gains and mean daily illness scores for each treatment group.

It is understood that the examples and embodiments described herein are for illustrative purposes only and that various modifications or changes in light thereof will be suggested to those of ordinary skill in the art and are to be included within the spirit and purview of this application and scope of the appended claims. All publications, patents, patent applications, and/or other documents cited in this application are incorporated by reference in their entirety for all purposes to the same extent as if each individual publication, patent, patent application, and/or other document were individually indicated to be incorporated by reference for all purposes.

TABLE 14

| Sequences Cited. | | |
|---|---|---|
| SEQ ID # | Sequence Type and Name | Sequence |
| 1 | Amino acid sequence of bovine G-CSF | TPLGPARSLPQSFLLKCLEQVRKIQADGAELQ ERLCAAHKLCHPEELMLLRHSLGIPQAPLSSC SSQSLQLTSCLNQLHGGLFLYQGLLQALAGIS PELAPTLDTLQLDVTDFATNIWLQMEDLGAAP AVQPTQGAMPTFTSAFQRRAGGVLVASQLHR FLELAYRGLRYLAEP |
| 2 | Amino acid sequence of bovine G-CSF with methionine at N terminus | MTPLGPARSLPQSFLLKCLEQVRKIQADGAEL QERLCAAHKLCHPEELMLLRHSLGIPQAPLSS CSSQSLQLTSCLNQLHGGLFLYQGLLQALAGI SPELAPTLDTLQLDVTDFATNIWLQMEDLGAA PAVQPTQGAMPTFTSAFQRRAGGVLVASQLH RFLELAYRGLRYLAEP |
| 3 | Nucleotide sequence of bovine G-CSF | actccattaggtcctgcacgtagcctgcctcaaagttttctgctgaaatgcctggagcaggtccgcaaa attcaagctgatggtgcggaactgcaggagcgtctgtgtgccgcacataaactgtgccacccggaag aactgatgctgctgcgccattcactgggaatcccacaggctcctctgtcacgtgtagctctcaaagtct gcagctgacttcatgcctgaatcaactgcacggaggcctgacctgtatcagggtctgctgcaggcgc tggccgggatttccccggagctggcaccgacactggacaccctgcaactggatgtaacggactttgc tactaacatctggctgcagatggaagatctgggagcggccccagcagtgcaacctacacagggcgc tatgccgaccttcacgtcggcgtttcagcgtcgcgccggtggcgttctggtcgcaagccaactgcatc gtttcctggagctggcgtaccgcggtctgcgttatctggctgaaccgtaa |
| 4 | Nucleotide sequence of bovine G-CSF with methionine at N terminus | atgactccattaggtcctgcacgtagcctgcctcaaagttttctgctgaaatgcctggagcaggtccgc aaaattcaagctgatggtgcggaactgcaggagcgtctgtgtgccgcacataaactgtgccacccgg aagaactgatgctgctgcgccattcactgggaatcccacaggctcctctgtcctcgtgtagctctcaaa gtctgcagctgacttcatgcctgaatcaactgcacggaggcctgttcctgtatcagggtctgctgcagg cgctggccgggatttccccggagctggcaccgacactggacaccctgcaactggatgtaacggactt tgctactaacatctggctgcagatggaagatctgggagcggccccagcagtgcaacctacacaggg cgctatgccgaccttcacgtcggcgtttcagcgtcgcgccggtggcgttctggtcgcaagccaactgc atcgtttcctggagctggcgtaccgcggtctgcgttatctggctgaaccgtaa |

SEQUENCE LISTING

```
Sequence total quantity: 24
SEQ ID NO: 1            moltype = AA  length = 174
FEATURE                 Location/Qualifiers
source                  1..174
                        mol_type = protein
                        organism = Bos taurus
SEQUENCE: 1
TPLGPARSLP QSFLLKCLEQ VRKIQADGAE LQERLCAAHK LCHPEELMLL RHSLGIPQAP  60
LSSCSSQSLQ LTSCLNQLHG GLFLYQGLLQ ALAGISPELA PTLDTLQLDV TDFATNIWLQ  120
MEDLGAAPAV QPTQGAMPTF TSAFQRRAGG VLVASQLHRF LELAYRGLRY LAEP        174

SEQ ID NO: 2            moltype = AA  length = 175
FEATURE                 Location/Qualifiers
source                  1..175
                        mol_type = protein
                        organism = Bos taurus
SEQUENCE: 2
MTPLGPARSL PQSFLLKCLE QVRKIQADGA ELQERLCAAH KLCHPEELML LRHSLGIPQA  60
PLSSCSSQSL QLTSCLNQLH GGLFLYQGLL QALAGISPEL APTLDTLQLD VTDFATNIWL  120
QMEDLGAAPA VQPTQGAMPT FTSAFQRRAG GVLVASQLHR FLELAYRGLR YLAEP       175

SEQ ID NO: 3            moltype = DNA  length = 525
FEATURE                 Location/Qualifiers
source                  1..525
                        mol_type = genomic DNA
                        organism = Bos taurus
SEQUENCE: 3
actccattag gtcctgcacg tagcctgcct caaagttttc tgctgaaatg cctggagcag  60
gtccgcaaaa ttcaagctga tggtgcggaa ctgcaggagc gtctgtgtgc cgcacataaa  120
ctgtgccacc cggaagaact gatgctgctg cgccattcac tgggaatccc acaggctcct  180
ctgtcctcgt gtagctctca aagtctgcag ctgacttcat gcctgaatca actgcacgga  240
ggcctgttcc tgtatcaggg tctgctgcag gcgctggccg ggatttcccc ggagctggca  300
ccgacactgg acaccctgca actggatgta acggactttg ctactaacat ctggctgcag  360
atggaagatc tgggagcggc cccagcagtg caacctacac agggcgctat gccgaccttc  420
acgtcggcgt ttcagcgtcg cgccggtggc gttctggtcg caagccaact gcatcgtttc  480
ctggagctgg cgtaccgcgg tctgcgttat ctggctgaac cgtaa                  525
```

```
SEQ ID NO: 4            moltype = DNA  length = 528
FEATURE                 Location/Qualifiers
source                  1..528
                        mol_type = genomic DNA
                        organism = Bos taurus
SEQUENCE: 4
atgactccat taggtcctgc acgtagcctg cctcaaagtt ttctgctgaa atgcctggag  60
caggtccgca aaattcaagc tgatggtgcg gaactgcagg agcgtctgtg tgccgcacat  120
aaactgtgcc acccggaaga actgatgctg ctgcgccatt cactgggaat cccacaggct  180
cctctgtcct cgtgtagctc tcaaagtctg cagctgactt catgcctgaa tcaactgcac  240
ggaggcctgt tcctgtatca gggtctgctg caggcgctgg ccgggatttc cccggagctg  300
gcaccgacac tggacaccct gcaactggat gtaacggact ttgctactaa catctggctg  360
cagatggaag atctgggagc ggccccagca gtgcaaccta cacagggcgc tatgccgacc  420
ttcacgtcgg cgtttcagcg tcgcgccggt ggcgttctgg tcgcaagcca actgcatcgt  480
ttcctggagc tggcgtaccg cggtctgcgt tatctggctg aaccgtaa              528

SEQ ID NO: 5            moltype = DNA  length = 77
FEATURE                 Location/Qualifiers
source                  1..77
                        mol_type = other DNA
                        organism = Methanococcus jannaschii
SEQUENCE: 5
ccggcggtag ttcagcaggg cagaacggcg gactctaaat ccgcatggcg ctggttcaaa  60
tccggcccgc cggacca                                                77

SEQ ID NO: 6            moltype = DNA  length = 88
FEATURE                 Location/Qualifiers
misc_feature            1..88
                        note = An optimized amber supressor tRNA
source                  1..88
                        mol_type = other DNA
                        organism = synthetic construct
SEQUENCE: 6
cccagggtag ccaagctcgg ccaacggcga cggactctaa atccgttctc gtaggagttc  60
gagggttcga atcccttccc tgggacca                                    88

SEQ ID NO: 7            moltype = DNA  length = 89
FEATURE                 Location/Qualifiers
misc_feature            1..89
                        note = An optimized AGGA frameshift supressor tRNA
source                  1..89
                        mol_type = other DNA
                        organism = synthetic construct
SEQUENCE: 7
gcgagggtag ccaagctcgg ccaacggcga cggacttcct aatccgttct cgtaggagtt  60
cgagggttcg aatccctccc ctcgcacca                                   89

SEQ ID NO: 8            moltype = AA  length = 307
FEATURE                 Location/Qualifiers
REGION                  1..307
                        note = Aminoacyl tRNA synthetase for the incorporation of
                         p-azido-L-phenylalanine
source                  1..307
                        mol_type = protein
                        organism = synthetic construct
SEQUENCE: 8
GMDEFEMIKR NTSEIISEEE LREVLKKDEK SAGIGFEPSG KIHLGHYLQI KKMIDLQNAG  60
FDIIILLADL HAYLNQKGEL DEIRKIGDYN KKVFEAMGLK AKYVYGSTFQ LDKDYTLNVY  120
RLALKTTLKR ARRSMELIAR EDENPKVAEV IYPIMQVNTY YYLGVDVAVG GMEQRKIHML  180
ARELLPKKVV CIHNPVLTGL DGEGKMSSSK GNFIAVDDSP EEIRAKIKKA YCPAGVVEGN  240
PIMEIAKYFL EYPLTIKRPE KFGGDLTVNS YEELESLFKN KELHPMDLKN AVAEELIKIL  300
EPIRKRL                                                           307

SEQ ID NO: 9            moltype = AA  length = 306
FEATURE                 Location/Qualifiers
REGION                  1..306
                        note = Aminoacyl tRNA synthetase for the incorporation of
                         p-benzoyl-L-phenylalanine
source                  1..306
                        mol_type = protein
                        organism = synthetic construct
SEQUENCE: 9
MDEFEMIKRN TSEIISEEEL REVLKKDEKS AGIGFEPSGK IHLGHYLQIK KMIDLQNAGF  60
DIIILLADLH AYLNQKGELD EIRKIGDYNK KVFEAMGLKA KYVYGSSFQL DKDYTLNVYR  120
LALKTTLKRA RRSMELIARE DENPKVAEVI YPIMQVNTSH YLGVDVAVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKRPEK FGGDLTVNSY EELESLFKNK ELHPMDLKNA VAEELIKILE  300
PIRKRL                                                            306
```

-continued

```
SEQ ID NO: 10          moltype = AA  length = 305
FEATURE                Location/Qualifiers
REGION                 1..305
                       note = Aminoacyl tRNA synthetase for the incorporation of
                        propargyl-phenylalanine
source                 1..305
                       mol_type = protein
                       organism = synthetic construct
SEQUENCE: 10
MDEFEMIKRN TSEIISEEEL REVLKKDEKS AAIGFEPSGK IHLGHYLQIK KMIDLQNAGF  60
DIIILLADLH AYLNQKGELD EIRKIGDYNK KVFEAMGLKA KYVYGSPFQL DKDYTLNVYR  120
LALKTTLKRA RRSMELIARE DENPKVAEVI YPIMQVNAIY LAVDVAVGGM EQRKIHMLAR  180
ELLPKKVVCI HNPVLTGLDG EGKMSSSKGN FIAVDDSPEE IRAKIKKAYC PAGVVEGNPI  240
MEIAKYFLEY PLTIKRPEKF GGDLTVNSYE ELESLFKNKE LHPMDLKNAV AEELIKILEP  300
IRKRL                                                              305

SEQ ID NO: 11          moltype = AA  length = 305
FEATURE                Location/Qualifiers
REGION                 1..305
                       note = Aminoacyl tRNA synthetase for the incorporation of
                        propargyl-phenylalanine
source                 1..305
                       mol_type = protein
                       organism = synthetic construct
SEQUENCE: 11
MDEFEMIKRN TSEIISEEEL REVLKKDEKS AAIGFEPSGK IHLGHYLQIK KMIDLQNAGF  60
DIIILLADLH AYLNQKGELD EIRKIGDYNK KVFEAMGLKA KYVYGSPFQL DKDYTLNVYR  120
LALKTTLKRA RRSMELIARE DENPKVAEVI YPIMQVNIPY LPVDVAVGGM EQRKIHMLAR  180
ELLPKKVVCI HNPVLTGLDG EGKMSSSKGN FIAVDDSPEE IRAKIKKAYC PAGVVEGNPI  240
MEIAKYFLEY PLTIKRPEKF GGDLTVNSYE ELESLFKNKE LHPMDLKNAV AEELIKILEP  300
IRKRL                                                              305

SEQ ID NO: 12          moltype = AA  length = 305
FEATURE                Location/Qualifiers
REGION                 1..305
                       note = Aminoacyl tRNA synthetase for the incorporation of
                        propargyl-phenylalanine
source                 1..305
                       mol_type = protein
                       organism = synthetic construct
SEQUENCE: 12
MDEFEMIKRN TSEIISEEEL REVLKKDEKS AAIGFEPSGK IHLGHYLQIK KMIDLQNAGF  60
DIIILLADLH AYLNQKGELD EIRKIGDYNK KVFEAMGLKA KYVYGSKFQL DKDYTLNVYR  120
LALKTTLKRA RRSMELIARE DENPKVAEVI YPIMQVNAIY LAVDVAVGGM EQRKIHMLAR  180
ELLPKKVVCI HNPVLTGLDG EGKMSSSKGN FIAVDDSPEE IRAKIKKAYC PAGVVEGNPI  240
MEIAKYFLEY PLTIKRPEKF GGDLTVNSYE ELESLFKNKE LHPMDLKNAV AEELIKILEP  300
IRKRL                                                              305

SEQ ID NO: 13          moltype = AA  length = 306
FEATURE                Location/Qualifiers
REGION                 1..306
                       note = Aminoacyl tRNA synthetase for the incorporation of
                        p-azido-phenylalanine
source                 1..306
                       mol_type = protein
                       organism = synthetic construct
SEQUENCE: 13
MDEFEMIKRN TSEIISEEEL REVLKKDEKS ATIGFEPSGK IHLGHYLQIK KMIDLQNAGF  60
DIIILLADLH AYLNQKGELD EIRKIGDYNK KVFEAMGLKA KYVYGSNFQL DKDYTLNVYR  120
LALKTTLKRA RRSMELIARE DENPKVAEVI YPIMQVNPLH YQGVDVAVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKRPEK FGGDLTVNSY EELESLFKNK ELHPMDLKNA VAEELIKILE  300
PIRKRL                                                             306

SEQ ID NO: 14          moltype = AA  length = 306
FEATURE                Location/Qualifiers
REGION                 1..306
                       note = Aminoacyl tRNA synthetase for the incorporation of
                        p-azido-phenylalanine
source                 1..306
                       mol_type = protein
                       organism = synthetic construct
SEQUENCE: 14
MDEFEMIKRN TSEIISEEEL REVLKKDEKS ATIGFEPSGK IHLGHYLQIK KMIDLQNAGF  60
DIIILLADLH AYLNQKGELD EIRKIGDYNK KVFEAMGLKA KYVYGSSFQL DKDYTLNVYR  120
LALKTTLKRA RRSMELIARE DENPKVAEVI YPIMQVNPLH YQGVDVAVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKRPEK FGGDLTVNSY EELESLFKNK ELHPMDLKNA VAEELIKILE  300
```

```
PIRKRL                                                     306

SEQ ID NO: 15          moltype = AA  length = 306
FEATURE                Location/Qualifiers
REGION                 1..306
                       note = Aminoacyl tRNA synthetase for the incorporation of
                        p-azido-phenylalanine
source                 1..306
                       mol_type = protein
                       organism = synthetic construct
SEQUENCE: 15
MDEFEMIKRN TSEIISEEEL REVLKKDEKS ALIGFEPSGK IHLGHYLQIK KMIDLQNAGF  60
DIIILLADLH AYLNQKGELD EIRKIGDYNK KVFEAMGLKA KYVYGSTFQL DKDYTLNVYR  120
LALKTTLKRA RRSMELIARE DENPKVAEVI YPIMQVNPVH YQGVDVAVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKRPEK FGGDLTVNSY EELESLFKNK ELHPMDLKNA VAEELIKILE  300
PIRKRL                                                     306

SEQ ID NO: 16          moltype = AA  length = 306
FEATURE                Location/Qualifiers
REGION                 1..306
                       note = Aminoacyl tRNA synthetase for the incorporation of
                        p-azido-phenylalanine
source                 1..306
                       mol_type = protein
                       organism = synthetic construct
SEQUENCE: 16
MDEFEMIKRN TSEIISEEEL REVLKKDEKS ATIGFEPSGK IHLGHYLQIK KMIDLQNAGF  60
DIIILLADLH AYLNQKGELD EIRKIGDYNK KVFEAMGLKA KYVYGSSFQL DKDYTLNVYR  120
LALKTTLKRA RRSMELIARE DENPKVAEVI YPIMQVNPSH YQGVDVAVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKRPEK FGGDLTVNSY EELESLFKNK ELHPMDLKNA VAEELIKILE  300
PIRKRL                                                     306

SEQ ID NO: 17          moltype = AA  length = 306
FEATURE                Location/Qualifiers
REGION                 1..306
                       note = Aminoacyl tRNA synthetase for the incorporation of
                        p-acetyl-phenylalanine
source                 1..306
                       mol_type = protein
                       organism = synthetic construct
SEQUENCE: 17
MDEFEMIKRN TSEIISEEEL REVLKKDEKS ALIGFEPSGK IHLGHYLQIK KMIDLQNAGF  60
DIIILLADLH AYLNQKGELD EIRKIGDYNK KVFEAMGLKA KYVYGSEFQL DKDYTLNVYR  120
LALKTTLKRA RRSMELIARE DENPKVAEVI YPIMQVNGCH YRGVDVAVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKRPEK FGGDLTVNSY EELESLFKNK ELHPMDLKNA VAEELIKILE  300
PIRKRL                                                     306

SEQ ID NO: 18          moltype = AA  length = 306
FEATURE                Location/Qualifiers
REGION                 1..306
                       note = Aminoacyl tRNA synthetase for the incorporation of
                        p-acetyl -phenylalanine
source                 1..306
                       mol_type = protein
                       organism = synthetic construct
SEQUENCE: 18
MDEFEMIKRN TSEIISEEEL REVLKKDEKS ALIGFEPSGK IHLGHYLQIK KMIDLQNAGF  60
DIIILLADLH AYLNQKGELD EIRKIGDYNK KVFEAMGLKA KYVYGSEFQL DKDYTLNVYR  120
LALKTTLKRA RRSMELIARE DENPKVAEVI YPIMQVNGTH YRGVDVAVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKRPEK FGGDLTVNSY EELESLFKNK ELHPMDLKNA VAEELIKILE  300
PIRKRL                                                     306

SEQ ID NO: 19          moltype = AA  length = 306
FEATURE                Location/Qualifiers
REGION                 1..306
                       note = Aminoacyl tRNA synthetase for the incorporation of
                        p-acetyl-phenylalanine
source                 1..306
                       mol_type = protein
                       organism = synthetic construct
SEQUENCE: 19
MDEFEMIKRN TSEIISEEEL REVLKKDEKS AAIGFEPSGK IHLGHYLQIK KMIDLQNAGF  60
DIIILLADLH AYLNQKGELD EIRKIGDYNK KVFEAMGLKA KYVYGSEFQL DKDYTLNVYR  120
LALKTTLKRA RRSMELIARE DENPKVAEVI YPIMQVNGGH YLGVDVIVGG MEQRKIHMLA  180
RELLPKKVVC IHNPVLTGLD GEGKMSSSKG NFIAVDDSPE EIRAKIKKAY CPAGVVEGNP  240
```

-continued

```
IMEIAKYFLE YPLTIKRPEK FGGDLTVNSY EELESLFKNK ELHPMDLKNA VAEELIKILE  300
PIRKRL                                                             306

SEQ ID NO: 20          moltype = AA  length = 306
FEATURE                Location/Qualifiers
REGION                 1..306
                       note = Aminoacyl tRNA synthetase for the incorporation of
                        p-azido-phenylalanine
source                 1..306
                       mol_type = protein
                       organism = synthetic construct
SEQUENCE: 20
MDEFEMIKRN TSEIISEEEL REVLKKDEKS AAIGFEPSGK IHLGHYLQIK KMIDLQNAGF  60
DIIILLADLH AYLNQKGELD EIRKIGDYNK KVFEAMGLKA KYVYGSRFQL DKDYTLNVYR  120
LALKTTLKRA RRSMELIARE DENPKVAEVI YPIMQVNVIH YDGVDVAVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKRPEK FGGDLTVNSY EELESLFKNK ELHPMDLKNA VAEELIKILE  300
PIRKRL                                                             306

SEQ ID NO: 21          moltype = AA  length = 306
FEATURE                Location/Qualifiers
REGION                 1..306
                       note = Aminoacyl tRNA synthetase for the incorporation of
                        p-azido-phenylalanine
source                 1..306
                       mol_type = protein
                       organism = synthetic construct
SEQUENCE: 21
MDEFEMIKRN TSEIISEEEL REVLKKDEKS AGIGFEPSGK IHLGHYLQIK KMIDLQNAGF  60
DIIILLADLH AYLNQKGELD EIRKIGDYNK KVFEAMGLKA KYVYGSTFQL DKDYTLNVYR  120
LALKTTLKRA RRSMELIARE DENPKVAEVI YPIMQVNTYY YLGVDVAVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKRPEK FGGDLTVNSY EELESLFKNK ELHPMDLKNA VAEELIKILE  300
PIRKRL                                                             306

SEQ ID NO: 22          moltype = DNA  length = 921
FEATURE                Location/Qualifiers
misc_feature           1..921
                       note = Mutant synthetase derived from Methanococcus
                        jannaschii synthetase
source                 1..921
                       mol_type = other DNA
                       organism = synthetic construct
SEQUENCE: 22
atggacgaat ttgaaatgat aaagagaaac acatctgaaa ttatcagcga ggaagagtta  60
agagaggttt taaaaaaaga tgaaaaatct gctgttatag gttttgaacc aagtggtaaa  120
atacatttag ggcattatct ccaaataaaa aagatgattg atttacaaaa tgctggattt  180
gatataatta tatatttggc tgatttacac gcctatttaa accagaaagg agagttggat  240
gagattagaa aaataggaga ttataacaaa aaagtttttg aagcaatggg gttaaaggca  300
aaatatgttt atggaagtga acatggtctt gataaggatt atacactgaa tgtctataga  360
ttggctttaa aaactacctt aaaaagagca agaaggagta tggaacttat agcaagagag  420
gatgaaaatc caaaggttgc tgaagttatc tatccaataa tgcaggttaa tgggattcat  480
tatgagggcg ttgatgttgc agttggaggg atggagcaga gaaaaataca catgttagca  540
agggagcttt taccaaaaaa ggttgtttgt attcacaacc ctgtcttaac gggtttggat  600
ggagaaggaa agatgagttc ttcaaaaggg aattttatag ctgttgatga ctctccagaa  660
gagattaggg ctaagataaa gaaagcatac tgcccagctg gagttgttga aggaaatcca  720
ataatggaga tagctaaata cttccttgaa tatcctttaa ccataaaaag gccagaaaaa  780
tttggtggag atttgacagt taatagctat gaggagttag agagtttatt taaaaataag  840
gaattgcatc caatggattt aaaaaatgct gtagctgaag aacttataaa gattttagag  900
ccaattagaa agagattata a                                            921

SEQ ID NO: 23          moltype = DNA  length = 77
FEATURE                Location/Qualifiers
misc_feature           1..77
                       note = Mutant tRNA derived from Methanococcus jannaschii
                        tRNA
source                 1..77
                       mol_type = other DNA
                       organism = synthetic construct
SEQUENCE: 23
ccggcggtag ttcagcaggg cagaacggcg gactctaaat ccgcatggcg ctggttcaaa  60
tccagcccgc cggacca                                                 77

SEQ ID NO: 24          moltype = AA  length = 306
FEATURE                Location/Qualifiers
REGION                 1..306
                       note = Mutant synthetase derived from Methanococcus
                        jannaschii synthetase
source                 1..306
```

-continued

```
                        mol_type = protein
                        organism = synthetic construct
SEQUENCE: 24
MDEFEMIKRN TSEIISEEEL REVLKKDEKS AVIGFEPSGK IHLGHYLQIK KMIDLQNAGF  60
DIIIYLADLH AYLNQKGELD EIRKIGDYNK KVFEAMGLKA KYVYGSEHGL DKDYTLNVYR  120
LALKTTLKRA RRSMELIARE DENPKVAEVI YPIMQVNGIH YEGVDVAVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKRPEK FGGDLTVNSY EELESLFKNK ELHPMRLKNA VAEELIKILE  300
PIRKRL                                                            306
```

What is claimed is:

1. An isolated nucleic acid comprising at least 95% sequence identity to SEQ ID NO: 3, wherein the isolated nucleic acid encodes a polypeptide of SEQ ID NO: 1, except wherein nucleotides 397-399 of SEQ ID NO: 3 are substituted for an amber codon, that, when expressed with a translation system comprising an orthogonal tRNA and an orthogonal aminoacyl tRNA synthetase pair selectively incorporates a non-naturally encoded amino acid at position 133 of SEQ ID NO: 1.

2. A cell comprising the nucleic acid of claim 1.

3. A method of making a bG-CSF polypeptide comprising para-acetylphenylalanine, the method comprising:

a) culturing cells comprising a polynucleotide sequence comprising at least 95% sequence identity to (i) SEQ ID NO: 3 except at nucleotides 397-399, wherein nucleotides 397-399 of SEQ ID NO: 3 are substituted for an amber codon, or (ii) SEQ ID NO: 4 except at nucleotides 400-402, wherein nucleotides 400-402 of SEQ ID NO: 4 are substituted for an amber codon;

in the presence of (i) para-acetylphenylalanine and, (ii) an orthogonal tRNA and aminoacyl tRNA synthetase pair capable of efficient incorporation of para-acetylphenylalanine;

to produce a modified bG-CSF polypeptide having a para-acetylphenylalanine incorporated; and b) purifying the bG-CSF polypeptide.

4. The method of claim 3, wherein the polynucleotide sequence comprises 95% sequence identity to SEQ ID NO: 3, except at nucleotides 397-399 which are substituted with an amber codon.

5. The method of claim 4, wherein the modified bG-CSF polypeptide of step b) is linked to a water soluble polymer comprising a poly(ethylene)glycol moiety at the incorporated para-acetylphenylalanine.

6. The method of claim 3, wherein the modified bG-CSF polypeptide of step b) is linked to a water soluble polymer comprising a poly(ethylene)glycol moiety at the incorporated para-acetylphenylalanine.

7. The method of claim 3, wherein the polynucleotide sequence comprises 95% sequence identity to SEQ ID NO: 4, except at nucleotides 400-402 which are substituted with an amber codon.

8. The method of claim 7, wherein the modified bG-CSF polypeptide of step b) is linked to a water soluble polymer comprising a poly(ethylene)glycol moiety at the incorporated para-acetylphenylalanine.

9. An isolated nucleic acid comprising at least 95% sequence identity to SEQ ID NO: 4, wherein the isolated nucleic acid encodes a polypeptide of SEQ ID NO: 2, except wherein nucleotides 400-402 are substituted for an amber codon, that when expressed with a translation system comprising an orthogonal tRNA and orthogonal aminoacyl tRNA synthetase pair selectively incorporates a non-naturally encoded amino acid at position 134 of SEQ ID NO: 2.

10. A cell comprising the nucleic acid of claim 9.

* * * * *